United States Patent
Amari et al.

(10) Patent No.: US 12,404,270 B2
(45) Date of Patent: Sep. 2, 2025

(54) QUINAZOLINE DERIVATIVES AS LPA RECEPTOR 2 INHIBITORS

(71) Applicant: CHIESI FARMACEUTICI S.P.A., Parma (IT)

(72) Inventors: Gabriele Amari, Parma (IT); Elisabetta Armani, Parma (IT); Mafalda Pagano, Parma (IT); Luca Raveglia, Parma (IT); Marta Giuliani, Parma (IT); Claudia Beato, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 597 days.

(21) Appl. No.: 17/784,557

(22) PCT Filed: Dec. 10, 2020

(86) PCT No.: PCT/EP2020/085460
§ 371 (c)(1),
(2) Date: Jun. 10, 2022

(87) PCT Pub. No.: WO2021/116260
PCT Pub. Date: Jun. 17, 2021

(65) Prior Publication Data
US 2023/0063121 A1  Mar. 2, 2023

(30) Foreign Application Priority Data
Dec. 12, 2019 (EP) .................................. 19215719

(51) Int. Cl.
| C07D 417/12 | (2006.01) |
|---|---|
| C07D 239/94 | (2006.01) |
| C07D 409/12 | (2006.01) |
| C07D 413/12 | (2006.01) |
| C07D 413/14 | (2006.01) |
| C07D 417/14 | (2006.01) |

(52) U.S. Cl.
CPC ......... *C07D 417/12* (2013.01); *C07D 239/94* (2013.01); *C07D 409/12* (2013.01); *C07D 413/12* (2013.01); *C07D 413/14* (2013.01); *C07D 417/14* (2013.01)

(58) Field of Classification Search
CPC .. C07D 417/12; C07D 239/94; C07D 413/12; C07D 413/14; C07D 409/12
See application file for complete search history.

(56) References Cited

FOREIGN PATENT DOCUMENTS

| CN | 103347510 A | 10/2013 |
|---|---|---|
| WO | WO 2012028243 A1 | 3/2012 |
| WO | WO-2012078593 A2 | 6/2012 |
| WO | WO 2017223016 A1 | 12/2017 |
| WO | WO 2019126086 A1 | 6/2019 |
| WO | WO 2019126087 A1 | 6/2019 |
| WO | WO 2019126090 A1 | 6/2019 |
| WO | WO 2019126099 A1 | 6/2019 |

OTHER PUBLICATIONS

Beck, H.P., et al., "Discovery of potent LPA2 (EDG4) antagonists as potential anticancer agents," Bioorg Med Chem Lett. 18(3):1037-1041, Elsevier, Netherlands (Feb. 2008).
Choi, J.W., et al., "LPA Receptors: Subtypes and Biological Actions," Annu Rev Pharmacol Toxicol. 50:157-86, Annual Reviews, United States (2010).
Gan, L., et al., "Blockade of lysophosphatidic acid receptors LPAR1/3 ameliorates lung fibrosis induced by irradiation," Biochem Biophys Res Commun 409(1):7-13, Elsevier, Netherlands (2011).
Huang, L.S., et al., "Lysophosphatidic Acid Receptor-2 Deficiency Confers Protection against Bleomycin-Induced Lung Injury and Fibrosis in Mice," Am J Respir Cell Mol Biol. 49(6):912-922, the American Thoracic Society, United States (Dec. 2013).
Ishii, I., et al., "Functional Comparisons of the Lysophosphatidic Acid Receptors, $LP_{A1}$/VZG-1/EDG-2, $LP_{A2}$/EDG-4, and $LP_{A3}$/EDG-7 in Neuronal Cell Lines Using a Retrovirus Expression System," Mol Pharmacol 58(5):895-902, The American Society for Pharmacology and Experimental Therapeutics, United States (2000).
International Search Report and Written Opinion for International Application No. PCT/EP2020/085460, European Patent Office, Netherlands, mailed on Mar. 10, 2021, 7 pages.
Lai, Y.J., et al., "c-Src-mediated phosphorylation of TRIP6 regulates its function in lysophosphatidic acid-induced cell migration," Mol. Cell. Biol. 25(14):5859-5868, American Society for Microbiology (2005).
Lin, F-T., "Regulation of the LPA2 receptor signaling through the carboxyl-terminal tail-mediated protein-protein interactions," Biochim. Biophys.Acta (BBA)—Molecular and Cell Biology of Lipids 1781(9):558-562, Elsevier, Netherlands (Sep. 2008).
Mio, T., et al., "Lysophosphatidic acid augments fibroblast-mediated contraction of released collagen gels," Journal of Laboratory and Clinical Medicine, 139(1):20-27, Elsevier, Netherlands (Jan. 2002).
Pradere, J-P., et al., "LPA1 Receptor Activation Promotes Renal Interstitial Fibrosis," J Am Soc Nephrol 18:3110-3118 (2007).
Riaz, A., et al., "G-Protein-Coupled Lysophosphatidic Acid Receptors and Their Regulation of AKT Signaling," Int J Mol Sci. 17(2):215, MDPI, Switzerland (Feb. 2016).
Sano, T., et al., J Biol Chem. 277(50):21197-206 (Dec. 2002).
Shiomi, T., et al., "Lysophosphatidic acid stimulates EGF-family ectodomain shedding and paracrine signaling from human lung fibroblasts," Wound Repair Regen. 19(2): 229-240 (Mar.-Apr. 2011).
Stoddard, N.C. and Chun, J., "Promising Pharmacological Directions in the World of Lysophosphatidic Acid Signaling," Biomol Ther 23(1):1-11, The Korean Society of Applied Pharmacology, Korea (Jan. 2015).

(Continued)

*Primary Examiner* — Rebecca L Anderson
(74) *Attorney, Agent, or Firm* — Sterne, Kessler, Goldstein & Fox P.L.L.C.

(57) ABSTRACT

The present invention relates to a compounds of general formula (I) inhibiting lysophosphatidic acid receptor 2 (LPA2), particularly the invention relates to compounds that are quinazoline derivatives, methods of preparing such compounds, pharmaceutical compositions containing them and therapeutic use thereof. The compounds of the invention may be useful in the treatment of diseases or conditions associated with a dysregulation of LPA receptors, in particular fibrosis.

16 Claims, No Drawings

(56) References Cited

OTHER PUBLICATIONS

Swaney, J.S., et al., "A novel, orally active LPA(1) receptor antagonist inhibits lung fibrosis in the mouse bleomycin model," Br J Pharmacol. 160(7):1699-1713, The British Pharmacological Society, United Kingdom (Aug. 2010).

Tager, A.M., at al. "The lysophosphatidic acid receptor LPA1 links pulmonary fibrosis to lung injury by mediating fibroblast recruitment and vascular leak," Nat Med. 14(1):45-54, Springer Nature Limited, Germany (Jan. 2008).

Wilson, M.S. and Wynn, T.A., "Pulmonary fibrosis: pathogenesis, etiology and regulation," Mucosal Immunol 2(2):103-121, Nature Publishing Group, Germany (2009).

Xu, M.Y., et al., "Lysophosphatidic Acid Induces αvβ6 Integrin-Mediated TGF-β Activation via the LPA2 Receptor and the Small G Protein Gαq," Am J Pathol. 174(4):1264-79, (Apr. 2009).

Ye, X., et al., "Lysophosphatidic acid in neural signaling," Neuroreport. 13(17):2169-75, Lippincott Williams & Wilkins, Inc. United States (Dec. 2002).

Yung, Y.C., et al., "LPA receptor signaling: pharmacology, physiology, and Pathophysiology," J Lipid Res. 55(7):1192-1214, Elsevier, Netherlands (Jul. 2014).

QUINAZOLINE DERIVATIVES AS LPA RECEPTOR 2 INHIBITORS

FIELD OF THE INVENTION

The present invention generally relates to compounds inhibiting lysophosphatidic acid receptors (hereinafter LPA inhibitors); the invention relates to compounds that are quinazoline derivatives, methods of preparing such compounds, pharmaceutical compositions containing them and therapeutic use thereof.

The compounds of the invention may be useful for instance in the treatment of many disorders associated with LPA receptors mechanisms.

BACKGROUND OF THE INVENTION

Lysophosphatidic acid (LPA) is a phospholipid mediator concentrated in serum that acts as a potent extracellular signalling molecule through at least six cognate G protein-coupled receptors (GPCRs) in numerous developmental and adult processes including cell survival, proliferation, migration, differentiation, vascular regulation, and cytokine release.

These LPA-mediated processes involve nervous system function, vascular development, immune system function, cancer, reproduction, fibrosis, and obesity (see e.g. Yung et al., *J Lipid Res.* 2014 July; 55(7):1192-214). The formation of an LPA species depends on its precursor phospholipid, which can vary typically by acyl chain length and degree of saturation. The term LPA generally refers to 18:1 oleoyl-LPA (1-acyl-2-hydroxy-sn-glycero3-phosphate), that is the most quantitatively abundant forms of LPA in human plasma with 16:0-, 18:2-, and 18:1-LPA (see e.g. Sano et al., *J Biol Chem.* 2002 Dec. 13; 277(50):21197-206). All LPA species are produced from membrane phospholipids via two major metabolic routes. Depending upon the site of synthesis, membrane phospholipids get converted to the corresponding lysophospholipids by the action of phospholipase A1 (PLA1), phospholipase A2 (PLA2), or PLA1 and lecithin-cholesterol acyltransferase (LCAT). Autotaxin (ATX) then acts on the lysophospholipids and converts them into LPA species. The second pathway first converts the phospholipids into phosphatidic acid by the action of phospholipase D. Then PLA1 or PLA2 metabolize phosphatidic acid to the lysophosphatidic acids (see e.g. Riaz et al., *Int J Mol Sci.* 2016 February; 17(2): 215).

ATX activity is the major source of plasma extracellular LPA but the source of tissue LPA that contributes to signalling pools likely involves not only ATX but other enzymes as well. The biological functions of LPA are mediated by at least six recognized cell-surface receptors.

All LPA receptors are rhodopsin-like 7-TM proteins that signal through at least two of the four Gα subunit families (Gα12/13, Gαq/11, Gαi/o and GαS). LPA receptors usually trigger response from multiple heterotrimeric G-proteins, resulting in diverse outcomes in a context and cell type dependent manner. Gα12/13-mediated LPA signalling regulates cell migration, invasion and cytoskeletal re-adjustments through activation of RHO pathway proteins. RAC activation downstream of Gαi/o-PI3K also regulates similar processes, but the most notable function of LPA-induced Gαi/o is mitogenic signalling through the RAF-MEK-MAPK cascade and survival signalling through the PI3K-AKT pathway. The LPA-coupled Gαq/11 protein primarily regulates Ca2+ homeostasis through PLC and the second messengers IP3 and DAG. Lastly, GαS can activate adenylyl cyclase and increase cAMP concentration upon LPA stimulation (see e.g. Riaz et al., *Int J Mol Sci.* 2016 February; 17(2): 215).

LPA, especially LPA1, LPA2 and LPA3, have been implicated in migration, invasion, metastasis, proliferation and survival and differ in their tissue distribution and downstream signalling pathways.

LPA1 is a 41-kD protein that is widely expressed, albeit at different levels, in all human adult tissues examined and the importance of LPA1 signalling during development and adult life has been demonstrated through numerous approaches (see e.g. Ye at al., 2002, *Neuroreport.* December 3; 13(17):2169-75). Wide expression of LPA1 is observed in adult mice, with clear presence in at least brain, uterus, testis, lung, small intestine, heart, stomach, kidney, spleen, thymus, placenta, and skeletal muscle. LPA1 is also widely expressed in humans where the expression is more spatially restricted during embryonic development. LPA1 couples with and activates three types of G proteins: Gαi/o, Gαq/11, and Gα12/13. LPA1 activation induces a range of cellular responses: cell proliferation and survival, cell migration, cytoskeletal changes, Ca2+ mobilization, adenylyl cyclase inhibition and activation of mitogen-activated protein kinase, phospholipase C, Akt, and Rho pathways (see e.g. Choi et al., *Annu Rev Pharmacol Toxicol.* 2010; 50:157-86).

LPA2 in humans is a 39-kD protein and shares ~55% amino acid sequence homology with LPA1 (see e.g. Yung et al., *J Lipid Res.* 2014 July; 55(7):1192-214). In mouse, LPA2 is highly expressed in kidney, uterus, and testis and moderately expressed in lung; in human tissues, high expression of LPA2 is detected in testis and leukocytes, with moderate expression found in prostate, spleen, thymus, and pancreas.

In terms of signalling activity, LPA2 mostly activates the same pathways as triggered by LPA1 with some exceptions that regards its unique cross-talk behaviour. For example, LPA2 promotes cell migration through interactions with focal adhesion molecule TRIPE (see e.g. Lai Y J, 2005, *Mol. Cell. Biol.* 25:5859-68), and several PDZ proteins and zinc finger proteins are also reported to interact directly with the carboxyl-terminal tail of LPA2 (see e.g. Lin F T, 2008, *Biochim. Biophys. Acta* 1781:558-62).

Human LPA3 is a 40-kD protein and shares sequence homology with LPA1 (~54%) and LPA2 (~49%). In adult humans LPA3 is highly expressed in heart, pancreas, prostate and testis. Moderate levels of expression are also found in brain, lungs and ovary. Like LPA1 and LPA2 the signalling activity of LPA3 results from its coupling to Gαi/o and Gαq/11 (see e.g Ishii et al., *Mol Pharmacol* 58:895-902, 2000). Each LPA has multiple important regulatory functions throughout the body.

As LPA signalling has been strongly implicated in many disease states, great interest has been expressed in developing specific LPA inhibitors (see e.g. Stoddard et el., *Biomol Ther (Seoul)* 2015 January; 23(1): 1-11). Different studies have demonstrated a positive role for LPA in the pathogenesis of pulmonary fibrosis (PF), a devastating disease characterized by alveolar epithelial cell injury, accumulation of myofibroblasts and deposition of extracellular matrix proteins leading to a loss of lung function and death (see e.g. Wilson M S, Wynn T A (2009), *Mucosal Immunol* 2: 103-121).

Evidences showed that lysophosphatidic acid levels dramatically increase in bronchoalveolar lavage fluid of PF patients where it mediates fibroblast migration in the injured lung acting through LPA1 (see e.g. Tager et al., *Nat Med.* 2008 January; 14(1):45-54). In addition, mice lacking LPA1 or LPA2 are markedly protected from fibrosis and mortality in a mouse model of the bleomycin induced pulmonary fibrosis (see e.g. Huang et al., *Am J Respir Cell Mol Biol.* 2013 December; 49(6): 912-922 and Tager et al., *Nat Med.* 2008 January; 14(1):45-54).

In vitro, LPA1 is known to induce the proliferation and differentiation of lung fibroblasts (see e.g. Shiomi et al., *Wound Repair Regen.* 2011 March-April; 19(2): 229-240), and to augment the fibroblast-mediated contraction of released collagen gels (see e.g. Mio et al., *Journal of Laboratory and Clinical Medicine, Volume* 139, *Issue* 1, January 2002, Pages 20-27). In human lung fibroblasts, the knockdown of LPA2 attenuated the LPA-induced expression of TGF-β1 and the differentiation of lung fibroblasts to myofibroblasts, resulting in the decreased expression of different profibrotic markers such as FN, α-SMA, and collagen, as well as decreased activation of extracellular regulated kinase ½, Akt, Smad3, and p38 mitogen-activated protein kinase (see e.g. Huang et al., *Am J Respir Cell Mol Biol.* 2013 December; 49(6): 912-922). Moreover Xu et al., confirmed that the expression of LPA2 was also up-regulated in lungs from bleomycin-challenged mice where it is able to induce the activation of TGF-β pathway, a key cytokine that play an essential role during the development of the disease, via a RhoA and Rho kinase pathway (see e.g. Xu et al., *Am J Pathol.* 2009 April; 174(4): 1264-79). In in vivo preclinical model, the oral administration of an LPA1 antagonist significantly reduced bleomycin-induced pulmonary fibrosis in mice (Tager et al., *Nat Med.* 2008 January; 14(1):45-54; Swaney et al., *Br J Pharmacol.* 2010 August; 160(7): 1699-1713), and the intraperitoneal injection of an LPA1/3 antagonist ameliorated irradiation-induced lung fibrosis (see e.g. Gan et al., 2011, *Biochem Biophys Res Commun* 409: 7-13). In a renal fibrosis model, LPA1 administration of an LPA1 antagonist suppressed renal interstitial fibrosis (see e.g Pradere et al., *J Am Soc Nephrol* 2007; 18:3110-3118).

Various compounds have been described in the literature as LPA1 or LPA2 antagonist.

WO2019126086 and WO2019126087 (Bristol-Myers Squibb) disclose cyclohexyl acid isoxazole azines as LPA1 antagonist, useful for the treatment of disorder or condition associated with dysregulation of lysophosphatidic acid receptor 1.

WO2019126099 (Bristol-Myers Squibb) discloses isoxazole N-linked carbamoyl cyclohexyl acid as LPA1 antagonist for the treatment of disorder or condition associated with dysregulation of lysophosphatidic acid receptor 1.

WO2019126090 (Bristol-Myers Squibb) discloses triazole N-linked carbamoyl cyclohexyl acids as LPA1 antagonists. The compounds are selective LPA1 receptor inhibitors and are useful for the treatment of disorder or condition associated with dysregulation of lysophosphatidic acid receptor 1.

WO2017223016 (Bristol-Myers Squibb) discloses carbamoyloxymethyl triazole cyclohexyl acids as LPA1 antagonist for the treatment of fibrosis including idiopathic pulmonary fibrosis.

WO2012028243 (Merck) discloses pyrazolopyridinone derivatives according to formula (I) and a process of manufacturing thereof as LPA2 receptor antagonists for the treatment of various diseases.

Amgen Inc. discloses in "Discovery of potent LPA2 (EDG4) antagonists as potential anticancer agents" Bioorg Med Chem Lett. 2008 Feb. 1; 18(3):1037-41, LPA2 antagonists. Key compounds were evaluated in vitro for inhibition of LPA2 mediated Erk activation and proliferation of HCT-116 cells. These compounds could be used as tool compounds to evaluate the anticancer effects of blocking LPA2 signalling.

Of note, antagonizing the LPA receptors may be useful for the treatment of fibrosis and diseases, disorders and conditions that result from fibrosis, and even more antagonizing receptor LPA2 may be particularly efficacious in the treatment of the above-mentioned diseases, disorders and conditions.

Several efforts have been done in the past years to develop novel LPA1 receptor antagonist useful for the treatment of several diseases and some of those compounds have shown efficacy also in humans.

Thus, there remains a potential for developing inhibitors of receptors LPA2 useful for the treatment of diseases or conditions associated with a dysregulation of LPA receptors, in particular fibrosis.

In this respect, the state of the art does not describe or suggest quinazoline derivatives of general formula (I) of the present invention having an antagonist activity on receptor LPA2 which represents a solution to the aforementioned need.

SUMMARY OF THE INVENTION

In a first aspect the invention refers to a compound of formula (I)

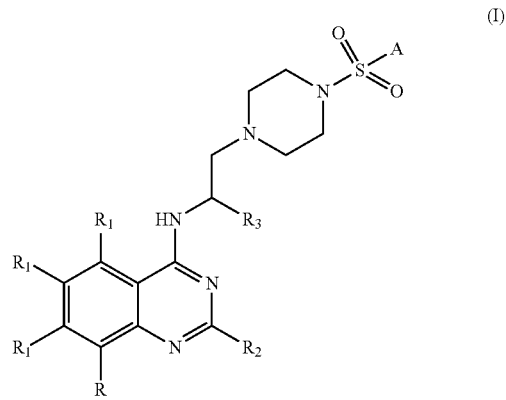

wherein

R is H or selected from the group consisting of $(C_1-C_4)$ alkyl, halo, $(C_1-C_4)$haloalkyl, —$NO_2$, —C(O)$OR_1$, —$OR_1$, —O($C_1-C_4$)haloalkyl, —$NR_AR_B$, —OC(O) $NR_AR_B$, —C(O)$R_C$, —C(O)$NR_AR_B$ and —($C_1-C_4$)alkylene-$NR_AR_B$;

$R_1$ is H or ($C_1-C_4$)alkyl;

$R_2$ is H or selected from the group consisting of $(C_1-C_4)$ alkyl, $(C_1-C_4)$haloalkyl, —$(C_1-C_4)$alkylene-$OR_1$ and $(C_3-C_8)$cycloalkyl;

$R_3$ is H or selected form the group consisting of $(C_1-C_4)$ alkyl;

A is selected from the group consisting of 5-6 membered heteroaryl and aryl wherein each of said heteroaryl and aryl may be optionally substituted by one or more group selected from $(C_1-C_4)$alkyl, —C(O)$R_1$, —C(O) $OR_1$, —C(O)$R_1$, $(C_1-C_4)$haloalkyl, halo, —$NR_AC(O)$ $R_1$, —$NR_AC(O)OR_1$, —$NR_AC(O)$—$(C_1-C_4)$alkylene-$OR_1$, —$NR_AC(O)R_C$, —$NR_AC(O)NR_AR_B$, —$N(C_1-C_4)$ alkylene-$NR_AR_B$, aryl and heteroaryl optionally substituted by one or more $(C_1-C_4)$alkyl and $(C_1-C_4)$ haloalkyl, or when A is aryl it may be fused to a second saturated or unsaturated ring optionally containing one or more heteroatoms selected from N, O and S to form a bicyclic ring system optionally substituted by one or more group selected from —C(O)R$_1$, (C$_1$-C$_4$)alkyl and oxo;

R$_C$ is selected from the group consisting of heteroaryl, aryl, (C$_3$-C$_8$) cycloalkyl and (C$_4$-C$_8$) heterocycloalkyl wherein said heteroaryl, aryl, heterocycloalkyl and cycloalkyl may be optionally substituted by one or more (C$_1$-C$_4$)alkyl and —C(O)OR$_1$;

R$_A$ and R$_B$ are at each occurrence independently H or selected from the group consisting of (C$_1$-C$_4$)alkyl, (C$_3$-C$_8$)cycloalkyl, (C$_1$-C$_6$)haloalkyl and halo, or R$_A$ and R$_B$ may form together with the nitrogen atom to which they are attached a 4-6 membered saturated heterocyclic ring system optionally containing a further heteroatom selected from N, S and O, said heterocyclic ring system may be optionally substituted by one or more groups selected from (C$_1$-C$_4$)alkyl, (C$_1$-C$_4$) haloalkyl and halo, with the proviso that when R$_2$ is H, R is not H.

In a second aspect, the invention refers to pharmaceutical composition comprising a compound of formula (I) in admixture with one or more pharmaceutically acceptable carrier or excipient.

In a third aspect, the invention refers to a compound of formula (I) for use as a medicament.

In a further aspect, the invention refers to a compound of formula (I) for use in treating diseases, disorders, or conditions associated with dysregulation of lysophosphatidic acid receptor 2 (LPA2).

In a further aspect, the invention refers to a compound of formula (I) for use in the prevention and/or treatment of fibrosis and/or diseases, disorders, or conditions that involve fibrosis.

In a further aspect, the invention refers to a compound of formula (I) for use in the prevention and/or treatment idiopathic pulmonary fibrosis (IPF).

DETAILED DESCRIPTION OF THE INVENTION

Unless otherwise specified, the compound of formula (I) of the present invention is intended to include also stereoisomer, tautomer or pharmaceutically acceptable salt or solvate thereof.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "solvate" means a physical association of a compound of this invention with one or more solvent molecules, whether organic or inorganic. This physical association includes hydrogen bonding. In certain instances, the solvate will be capable of isolation, for example, when one or more solvent molecules are incorporated in the crystal lattice of the crystalline solid. The solvate may comprise either a stoichiometric or nonstoichiometric amount of the solvent molecules.

The term "stereoisomer" refers to isomers of identical constitution that differ in the arrangement of their atoms in space. Enantiomers and diastereomers are examples of stereoisomers.

The term "enantiomer" refers to one of a pair of molecular species that are mirror images of each other and are not superimposable.

The term "diastereomer" refers to stereoisomers that are not mirror images.

The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, Pure and Applied Chemistry, 68:2193-2222 (1996)).

The term "tautomer" refers to each of two or more isomers of a compound that exist together in equilibrium and are readily interchanged by migration of an atom or group within the molecule.

The term "halogen" or "halogen atoms" or "halo" as used herein includes fluorine, chlorine, bromine, and iodine atom.

The term "5-membered heterocyclyl" refers to a mono satured or unsatured group containing one or more heteroatoms selected from N and 0.

The term "(C$_x$-C$_y$) alkyl" wherein x and y are integers, refers to a straight or branched chain alkyl group having from x to y carbon atoms. Thus, when x is 1 and y is 6, for example, the term includes methyl, ethyl, n-propyl, isopropyl, n-butyl, isobutyl, sec-butyl, t-butyl, n-pentyl and n-hexyl.

The term "(C$_x$-C$_y$)alkylene" wherein x and y are integers, refers to a C$_x$-C$_y$alkyl radical having in total two unsatisfied valencies, such as a divalent methylene radical.

The expressions "(C$_x$-C$_y$) haloalkyl" wherein x and y are integers, refer to the above defined "C$_x$-C$_y$alkyl" groups wherein one or more hydrogen atoms are replaced by one or more halogen atoms, which can be the same or different.

Examples of said "(C$_x$-C$_y$) haloalkyl" groups may thus include halogenated, poly-halogenated and fully halogenated alkyl groups wherein all hydrogen atoms are replaced by halogen atoms, e.g. trifluoromethyl.

The term "(C$_x$-C$_y$) cycloalkyl" wherein x and y are integers, refers to saturated cyclic hydrocarbon groups containing the indicated number of ring carbon atoms. Examples include cyclopropyl, cyclobutyl, cyclopentyl, cyclohexyl, cycloheptyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic group containing one or more heteroatoms selected from S, N and O, and includes groups having two such monocyclic rings, or one such monocyclic ring and one monocyclic aryl ring, which are fused through a common bond.

The term "($C_x$-$C_y$) heterocycloalkyl" wherein x and y are integers, refers to saturated or partially unsaturated monocyclic ($C_x$-$C_y$) cycloalkyl groups in which at least one ring carbon atom is replaced by at least one heteroatom (e.g. N, S or O) or may bear an -oxo (═O) substituent group. Said heterocycloalkyl may be further optionally substituted on the available positions in the ring, namely on a carbon atom, or on an heteroatom available for substitution. Substitution on a carbon atom includes spiro disubstitution as well as substitution on two adjacent carbon atoms, in both cases thus form additional condensed 5 to 6 membered heterocyclic ring.

The term "($C_x$-$C_y$) aminoalkyl" wherein x and y are integers, refers to the above defined "($C_1$-$C_6$) alkyl" groups wherein one or more hydrogen atoms are replaced by one or more amino group.

The term "($C_x$-$C_y$) hydroxyalkyl" wherein x and y are integers, refers to the above defined "($C_1$-$C_6$) alkyl" groups wherein one or more hydrogen atoms are replaced by one or more hydroxy (OH) group.

The term "($C_x$-$C_y$) alkoxy" or "($C_x$-$C_y$) alkoxyl" wherein x and y are integers, refer to a straight or branched hydrocarbon of the indicated number of carbons, attached to the rest of the molecule through an oxygen bridge.

A dash ("-") that is not between two letters or symbols is meant to represent the point of attachment for a substituent.

The carbonyl group is herein preferably represented as —C(O)— as an alternative to the other common representations such as —CO—, —(CO)— or —C(═O)—.

In general, the bracketed group is a lateral group, not included into the chain, and brackets are used, when deemed useful, to help disambiguating linear chemical formulas; e.g. the sulfonyl group —$SO_2$— might be also represented as —S(O)$_2$— to disambiguate e.g. with respect to the sulfinic group —S(O)O—.

Whenever basic amino or quaternary ammonium groups are present in the compounds of formula I, physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups such as COOH groups, corresponding physiological cation salts may be present as well, for instance including alkaline or alkaline earth metal ions.

As above indicated, the present invention refers to a series of compounds represented by the general formula (I) as herein below described in details, which are endowed with an inhhinitory activity on receptor LPA2.

Advantageously, the antagonist action receptor LPA2 can be effective in the treatment of those diseases where the LPA receptors play a relevant role in the pathogenesis such as fibrosis and disease, disorder and condition from fibrosis.

Differently from similar compounds of the prior art, such as compounds disclosed for example in Merck WO2012028243 and Amgen compounds, the compounds of formula (I) of the present invention are much more acitve on the LPA2 receptor.

The Merck and Amgen compounds show a maximum potency expressed as half maximal inhibitory concentration ($IC_{50}$) on LPA2 around 500 nm.

As indicated in the experimental part, in particular in Table 2, the compounds of formula (I) of the present invention show a notable potency with respect to their inhibitory activity on receptor LPA2 below about 500 nm, confirming that they are able to antagonize the isoform of LPA2 receptor involved in fibrosis and diseases that result from fibrosis with a greater potency respect to the compounds of the prior art.

Advantageously, the compounds of the present invention characterized by a very high potency, could be administered in human at a lower dosage in comparison to the compounds of the prior art, thus reducing the adverse events that typically occur administering higher dosages of drug.

Therefore, the compounds of the present invention are particularly appreciated by the skilled person when looking at a suitable and efficacious compounds useful for the treatment of fibrosis, in particular idiopatic pulmonary fibrosis.

Thus, in one aspect the present invention relates to a compound of general formula (I) as LPA2 antagonist

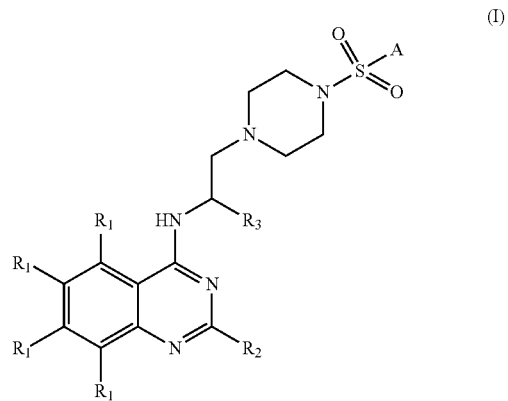

(I)

wherein R is H or selected from the group consisting of ($C_1$-$C_4$)alkyl, halo, ($C_1$-$C_4$)haloalkyl, —$NO_2$, —C(O)O$R_1$, —O$R_1$, —O($C_1$-$C_4$)haloalkyl, —$NR_AR_B$, —OC(O)$NR_AR_B$, —C(O)$R_C$, —C(O)$NR_AR_B$ and —($C_1$-$C_4$) alkylene-$NR_AR_B$;

$R_1$ is H or ($C_1$-$C_4$)alkyl;

$R_2$ is H or selected from the group consisting of ($C_1$-$C_4$) alkyl, ($C_1$-$C_4$)haloalkyl, —($C_1$-$C_4$)alkylene-O$R_1$ and ($C_3$-$C_8$)cycloalkyl;

$R_3$ is H or selected form the group consisting of ($C_1$-$C_4$) alkyl,

A is selected from the group consisting of 5-6 membered heteroaryl and aryl wherein each of said heteroaryl and aryl may be optionally substituted by one or more group selected from ($C_1$-$C_4$)alkyl, —C(O)$R_1$, —C(O)O$R_1$, —C(O)$R_1$, ($C_1$-$C_4$)haloalkyl, halo, —$NR_AC(O)$ $R_1$, —$NR_AC(O)OR_1$, —$NR_AC(O)$—($C_1$-$C_4$)alkylene-O$R_1$, —$NR_AC(O)R_C$, —$NR_AC(O)NR_AR_B$, —N($C_1$-$C_4$) alkylene-$NR_AR_B$, aryl and heteroaryl optionally substituted by one or more ($C_1$-$C_4$)alkyl and ($C_1$-$C_4$) haloalkyl, or when A is aryl it may be fused to a second saturated or unsaturated ring optionally containing one or more heteroatoms selected from N, O and S to form a bicyclic ring system optionally substituted by one or more group selected from —C(O)$R_1$, ($C_1$-$C_4$)alkyl and oxo;

$R_C$ is selected from the group consisting of from heteroaryl, aryl, ($C_3$-$C_8$) cycloalkyl and ($C_4$-$C_8$) heterocycloalkyl wherein said heteroaryl, aryl, heterocycloalkyl and cycloalkyl may be optionally substituted by one or more $(C_1-C_4)$alkyl and —C(O)OR$_1$;

$R_A$ and $R_B$ are at each occurrence independently H or selected from the group consisting of $(C_1-C_4)$alkyl, $(C_3-C_8)$cycloalkyl, $(C_1-C_6)$haloalkyl and halo, or $R_A$ and $R_B$ may form together with the nitrogen atom to which they are attached a 4-6 membered saturated heterocyclic ring system optionally containing a further heteroatom selected from N, S and O, said heterocyclic ring system may be optionally substituted by one or more groups selected from $(C_1-C_4)$alkyl, $(C_1-C_4)$haloalkyl and halo, with the proviso that when $R_2$ is H, R is not H.

In one preferred embodiment A is selected from the group consisting of 5-6 membered heteroaryl and aryl wherein each of said heteroaryl and aryl may be optionally substituted by one or more group selected from $(C_1-C_4)$alkyl, —C(O)R$_1$, —C(O)OR$_1$, —C(O)R$_1$, $(C_1-C_4)$haloalkyl, halo, —NR$_A$C(O)R$_1$, —NR$_A$C(O)OR$_1$, —NR$_A$C(O)—$(C_1-C_4)$alkylene-OR$_1$, —NR$_A$C(O)R$_C$, —NR$_A$C(O)NR$_A$R$_B$, —N$(C_1-C_4)$alkylene-NR$_A$R$_B$, aryl and heteroaryl optionally substituted by one or more $(C_1-C_4)$alkyl and $(C_1-C_4)$haloalkyl selected from the group consisting of isoxazole, pyridine, thiazole, oxazole, 1,2,4-oxadiazole, 1,3,4-oxadiazole and pyrazole; or when A is aryl it may be fused to a second saturated or unsaturated ring optionally containing one or more heteroatoms selected from N, O and S to form a bicyclic ring system optionally substituted by one or more group selected from —C(O)R$_1$, $(C_1-C_4)$alkyl and oxo;

In one preferred embodiment when A is 5-6 membered heteroaryl said 5-6 membered heteroaryl is selected from the group consisting of thiazole, thiophene and furan.

In one preferred embodiment when R$_C$ is heteroaryl said heteroaryl is isoxazole optionally substituted by one or more $(C_1-C_4)$alkyl and —C(O)OR$_1$ In one preferred embodiment, the invention refers to a compound of formula (I) wherein R is H or selected from the group consisting of $(C_1-C_4)$alkyl, halo, $(C_1-C_4)$haloalkyl, —NO$_2$, —C(O)OR$_1$, —OR$_1$, —O$(C_1-C_4)$haloalkyl, —NR$_A$R$_B$, —OC(O)NR$_A$R$_B$, —C(O)R$_C$, —C(O)NR$_A$R$_B$, —$(C_1-C_4)$alkylene-NR$_A$R$_B$;

$R_1$ is H or $(C_1-C_4)$alkyl, $R_2$ is H or selected from the group consisting of $(C_1-C_4)$alkyl, $(C_1-C_4)$haloalkyl, —$(C_1-C_4)$alkylene-OR$_1$ and $(C_3-C_8)$cycloalkyl;

$R_3$ is $(C_1-C_4)$alkyl;

A is selected from the group consisting of 5-6 membered heteroaryl and aryl wherein each of said heteroaryl and aryl may be optionally substituted by one or more group selected from $(C_1-C_4)$alkyl, halo, —NR$_A$C(O)R$_1$, —NR$_A$C(O)OR$_1$, —NR$_A$C(O)—$(C_1-C_4)$alkylene-OR$_1$, —NR$_A$C(O)R$_C$, —NR$_A$C(O)NR$_A$R$_B$, aryl and heteroaryl optionally substituted by one or more $(C_1-C_4)$alkyl, or when A is aryl it may be fused to a second saturated ring optionally containing one or more heteroatoms selected from N, S and O, to form a bicyclic ring system optionally substituted by one or more oxo;

$R_C$ is selected from $(C_3-C_8)$cycloalkyl and 5-6 membered heteroaryl optionally substituted by one or more $(C_1-C_4)$alkyl;

$R_A$ and $R_B$ are at each occurrence independently H or selected from the group consisting of $(C_1-C_4)$alkyl, $(C_3-C_8)$cycloalkyl, $(C_1-C_6)$haloalkyl and halo, or $R_A$ and $R_B$ may form together with the nitrogen atom to which they are attached a 4-6 membered saturated heterocyclic ring system optionally containing a further heteroatom selected from N, S and O, said heterocyclic ring system may be optionally substituted by one or more groups selected from $(C_1-C_4)$alkyl, $(C_1-C_4)$haloalkyl and halo, with the proviso that when $R_2$ is H, R is not H.

According to the preferred embodiment, the invention refers to at least one of the compounds listed in the Table 1 below; those compounds are active on LPA2, as shown in Table 2.

TABLE 1

List of preferred compounds of Formula (I)

| Example | Structure | Chemical name |
|---|---|---|
| 1 | 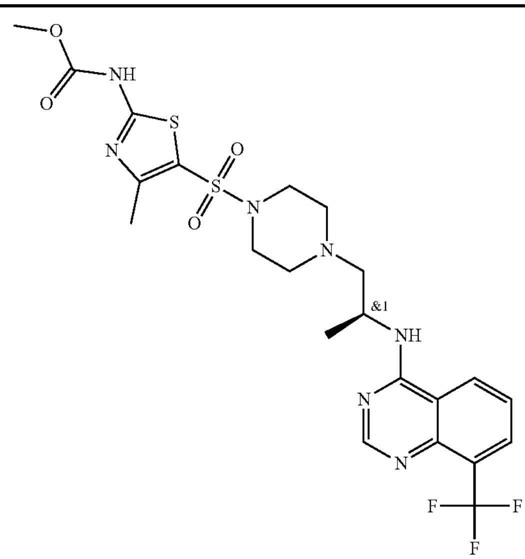 | methyl N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate |

TABLE 1-continued
List of preferred compounds of Formula (I)
| Example | Structure | Chemical name |
|---|---|---|
| 2 | 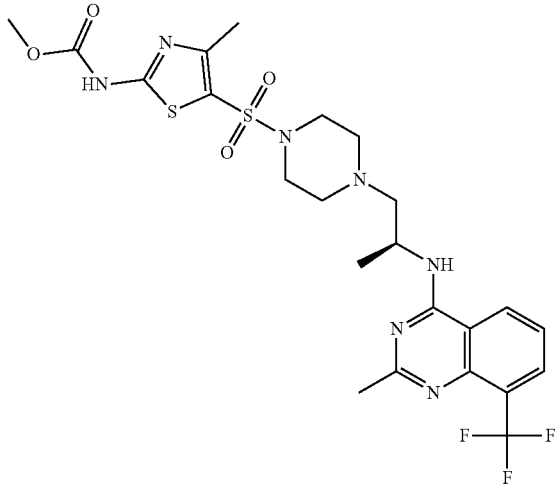 [SMILES: COC(=O)Nc1nc(C)c(S(=O)(=O)N2CCN(C[C@H](C)Nc3nc(C)nc4c(C(F)(F)F)cccc34)CC2)s1] | methyl N-[4-methyl-5-({4-[(2S)-2-{[2-methyl-8-(trifluoromethyl)quinazolin-4-yl]amino}propyl]piperazin-1-yl}sulfonyl)-1,3-thiazol-2-yl]carbamate |
| 3 | 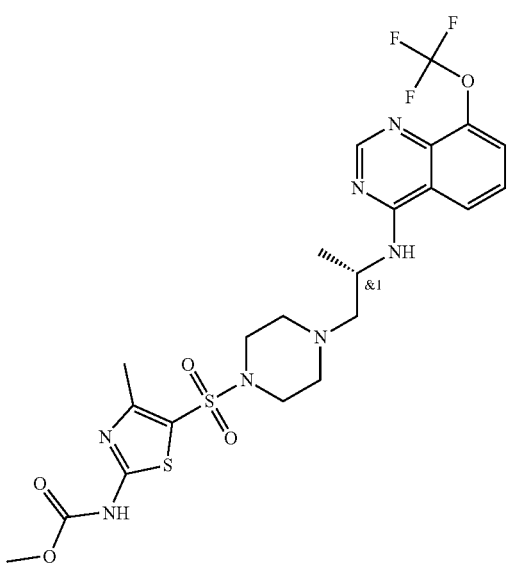 [SMILES: COC(=O)Nc1nc(C)c(S(=O)(=O)N2CCN(C[C@H](C)Nc3ncnc4c(OC(F)(F)F)cccc34)CC2)s1] | methyl N-[4-methyl-5-({4-[(2S)-2-{[8-(trifluoromethoxy)quinazolin-4-yl]amino}propyl]piperazin-1-yl}sulfonyl)-1,3-thiazol-2-yl]carbamate |

TABLE 1-continued

List of preferred compounds of Formula (I)

| Example | Structure | Chemical name |
|---|---|---|
| 4 | 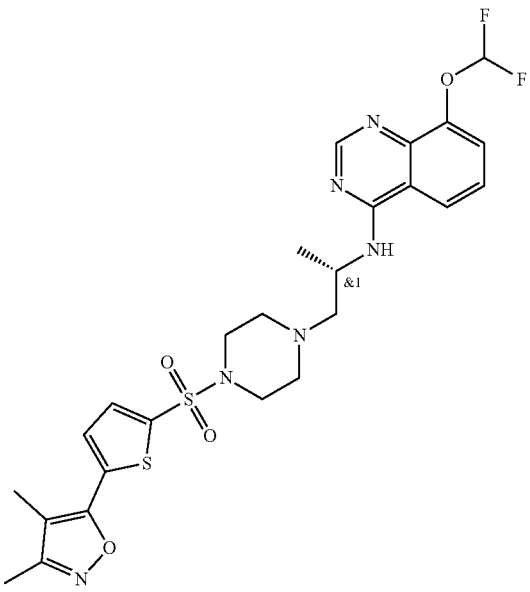 [SMILES: Cc1noc(-c2ccc(S(=O)(=O)N3CCN(C[C@H](C)Nc4ncnc5c(OC(F)F)cccc45)CC3)s2)c1C] | 8-(difluoromethoxy)-N-[(2S)-1-(4-{[5-(3,4-dimethyl-1,2-oxazol-5-yl)thiophen-2-yl]sulfonyl}piperazin-1-yl)propan-2-yl]quinazolin-4-amine |
| 5 | 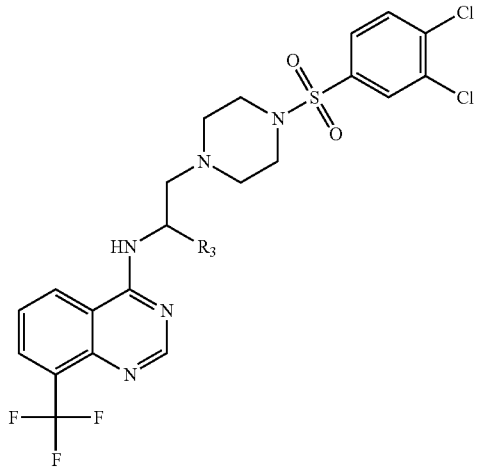 | N-[(2S)-1-[4-(3,4-dichlorobenzenesulfonyl)piperazin-1-yl]propan-2-yl]-8-(trifluoromethyl)quinazolin-4-amine |
| 6 | 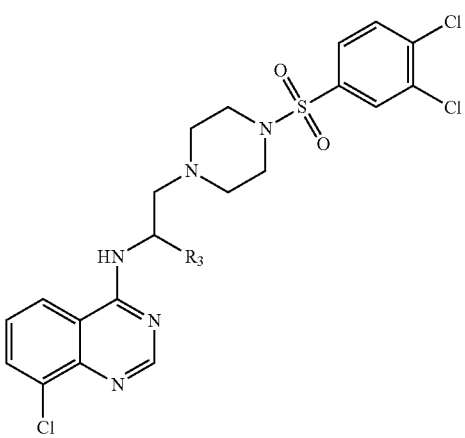 | 8-chloro-N-[(2S)-1-[4-(3,4-dichlorobenzenesulfonyl)piperazin-1-yl]propan-2-yl]quinazolin-4-amine |

TABLE 1-continued

List of preferred compounds of Formula (I)

| Example | Structure | Chemical name |
|---|---|---|
| 7 | 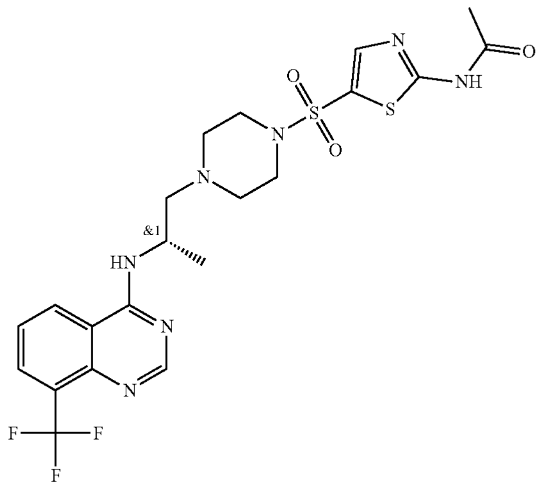 [SMILES: CC(=O)Nc1ncc(S(=O)(=O)N2CCN(C[C@H](C)Nc3ncnc4c(C(F)(F)F)cccc34)CC2)s1] | N-[5-({4-[(2S)-2-{[8-(trifluoromethyl)quinazolin-4-yl]amino}propyl]piperazin-1-yl}sulfonyl)-1,3-thiazol-2-yl]acetamide |
| 8 | 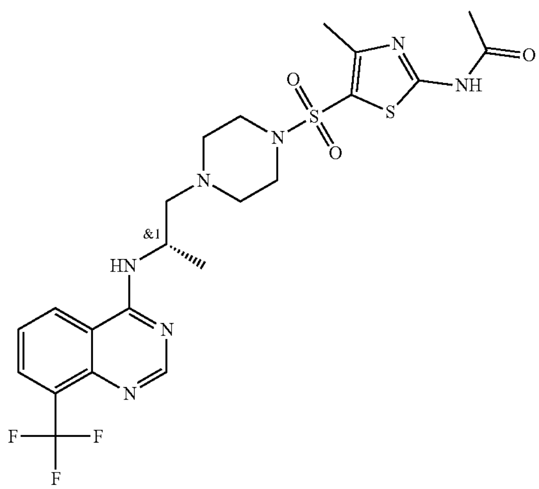 [SMILES: CC(=O)Nc1nc(C)c(S(=O)(=O)N2CCN(C[C@H](C)Nc3ncnc4c(C(F)(F)F)cccc34)CC2)s1] | N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide |
| 9 | 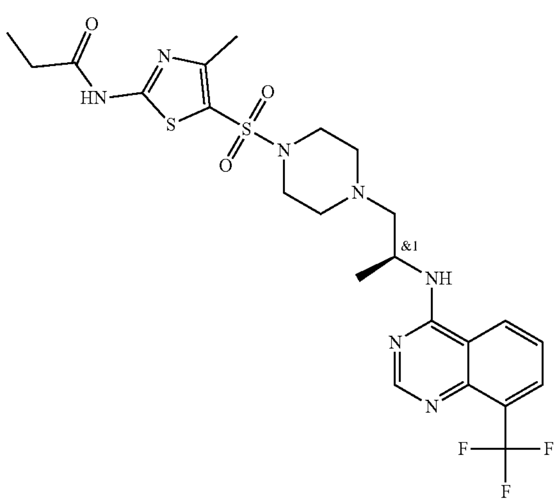 [SMILES: CCC(=O)Nc1nc(C)c(S(=O)(=O)N2CCN(C[C@H](C)Nc3ncnc4c(C(F)(F)F)cccc34)CC2)s1] | N-[4-methyl-5-({4-[(2S)-2-{[8-(trifluoromethyl)quinazolin-4-yl]amino}propyl]piperazin-1-yl}sulfonyl)-1,3-thiazol-2-yl]propanamide |

TABLE 1-continued

List of preferred compounds of Formula (I)

| Example | Structure | Chemical name |
|---|---|---|
| 10 | 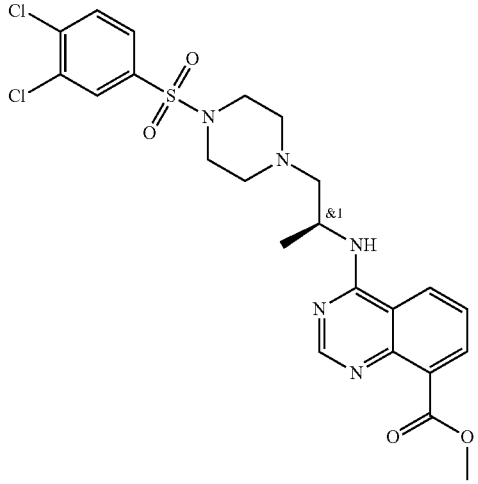 [SMILES: COC(=O)c1cccc2c(N[C@@H](C)CN3CCN(S(=O)(=O)c4ccc(Cl)c(Cl)c4)CC3)ncnc12] | methyl 4-{[(2S)-1-[4-(3,4-dichlorobenzenesulfonyl)piperazin-1-yl]propan-2-yl]amino}quinazoline-8-carboxylate |
| 11 | 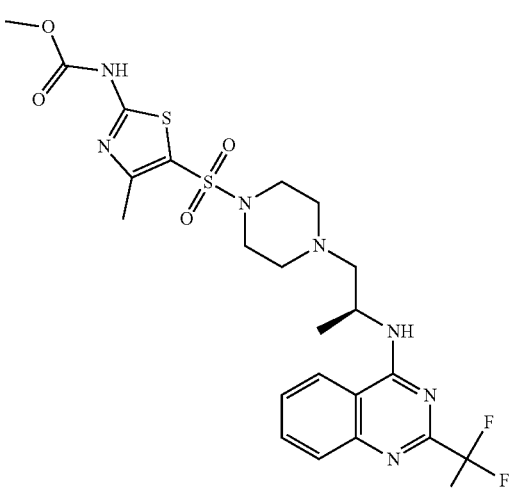 | methyl N-[4-methyl-5-({4-[(2S)-2-{[2-(trifluoromethyl)quinazolin-4-yl]amino}propyl]piperazin-1-yl}sulfonyl)-1,3-thiazol-2-yl]carbamate |
| 12 | 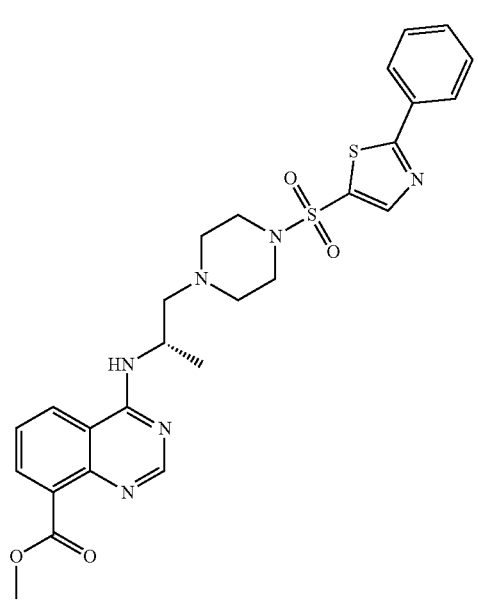 [SMILES: COC(=O)c1cccc2c(N[C@@H](C)CN3CCN(S(=O)(=O)c4cnc(-c5ccccc5)s4)CC3)ncnc12] | methyl 4-{[(2S)-1-{4-[(2-phenyl-1,3-thiazol-5-yl)sulfonyl]piperazin-1-yl}propan-2-yl]amino}quinazoline-8-carboxylate |

TABLE 1-continued

List of preferred compounds of Formula (I)

| Example | Structure | Chemical name |
|---|---|---|
| 13 | 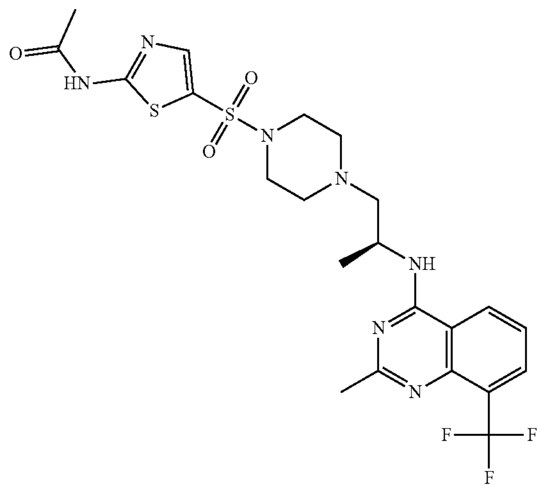 [SMILES: CC(=O)Nc1ncc(S(=O)(=O)N2CCN(C[C@H](C)Nc3nc(C)nc4c(C(F)(F)F)cccc34)CC2)s1] | N-[5-({4-[(2S)-2-{[2-methyl-8-(trifluoromethyl)quinazolin-4-yl]amino}propyl]piperazin-1-yl}sulfonyl)-1,3-thiazol-2-yl]acetamide |
| 14 | 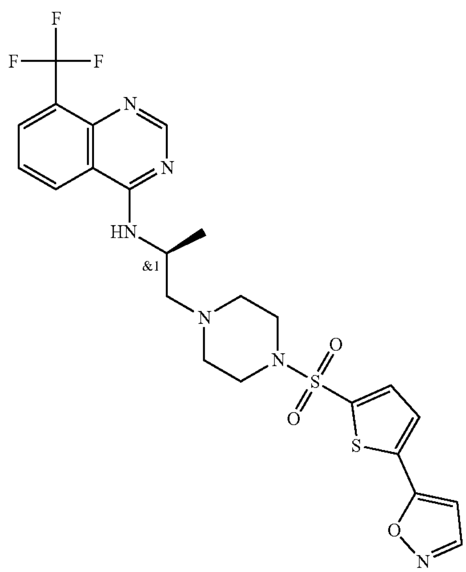 [SMILES: C[C@@H](CN1CCN(S(=O)(=O)c2ccc(-c3ccno3)s2)CC1)Nc1ncnc2c(C(F)(F)F)cccc12] | N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine |
| 15 | 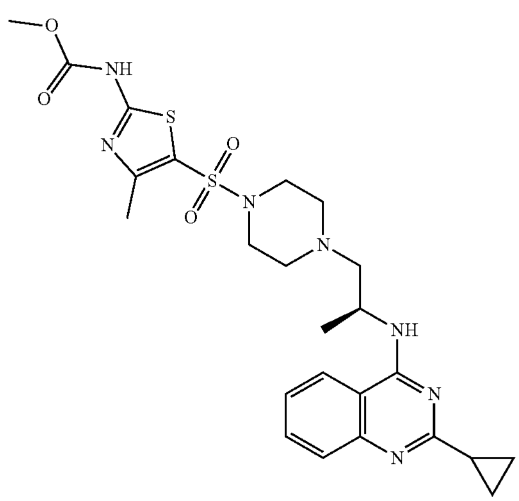 [SMILES: COC(=O)Nc1nc(C)c(S(=O)(=O)N2CCN(C[C@H](C)Nc3nc(C4CC4)nc4ccccc34)CC2)s1] | methyl N-[5-({4-[(2S)-2-[(2-cyclopropylquinazolin-4-yl)amino]propyl]piperazin-1-yl}sulfonyl)-4-methyl-1,3-thiazol-2-yl]carbamate |

TABLE 1-continued

List of preferred compounds of Formula (I)

| Example | Structure | Chemical name |
|---|---|---|
| 16 | 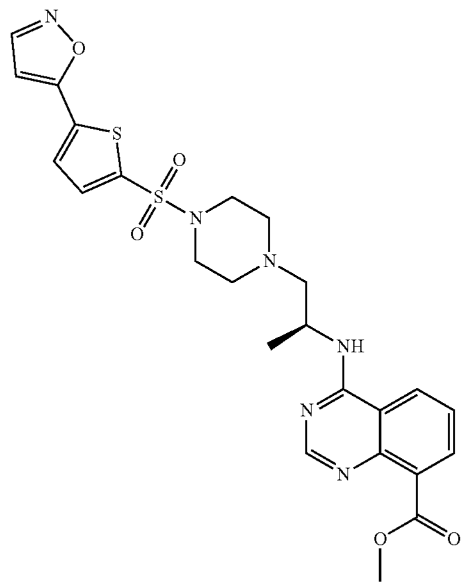 [SMILES: COC(=O)c1cccc2c(N[C@@H](C)CN3CCN(S(=O)(=O)c4ccc(-c5ccno5)s4)CC3)ncnc12] | methyl 4-{[(2S)-1-(4-{[5-(1,2-oxazol-5-yl)thiophen-2-yl]sulfonyl}piperazin-1-yl)propan-2-yl]amino}quinazoline-8-carboxylate |
| 17 | 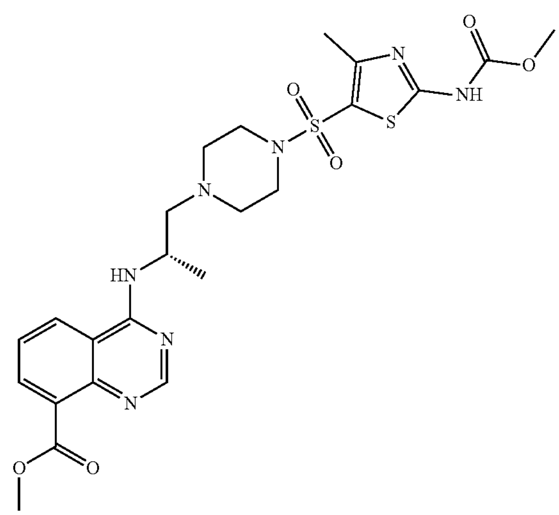 [SMILES: COC(=O)Nc1nc(C)c(S(=O)(=O)N2CCN(C[C@H](C)Nc3ncnc4c(C(=O)OC)cccc34)CC2)s1] | methyl 4-{[(2S)-1-[4-({2-[(methoxycarbonyl)amino]-4-methyl-1,3-thiazol-5-yl}sulfonyl)piperazin-1-yl]propan-2-yl]amino}quinazoline-8-carboxylate |
| 18 | 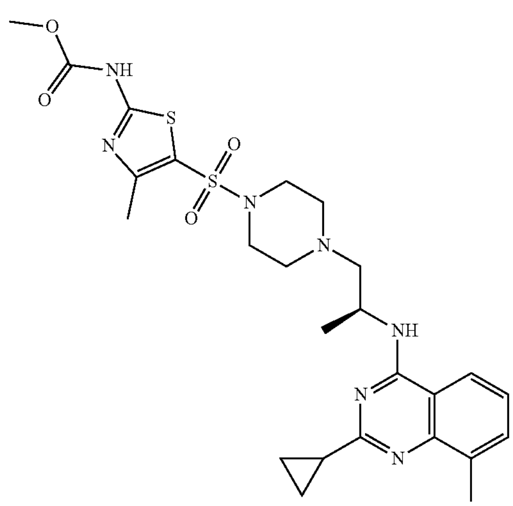 [SMILES: COC(=O)Nc1nc(C)c(S(=O)(=O)N2CCN(C[C@H](C)Nc3nc(C4CC4)nc4c(C)cccc34)CC2)s1] | methyl N-[5-({4-[(2S)-2-[(2-cyclopropyl-8-methylquinazolin-4-yl)amino]propyl]piperazin-1-yl}sulfonyl)-4-methyl-1,3-thiazol-2-yl]carbamate |

TABLE 1-continued
List of preferred compounds of Formula (I)
| Example | Structure | Chemical name |
|---|---|---|
| 19 | 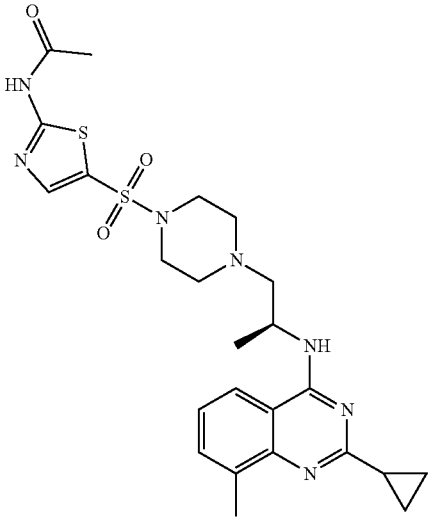 [SMILES: CC(=O)Nc1ncc(S(=O)(=O)N2CCN(C[C@H](C)Nc3nc(C4CC4)nc4c(C)cccc34)CC2)s1] | N-[5-({4-[(2S)-2-[(2-cyclopropyl-8-methylquinazolin-4-yl)amino]propyl]piperazin-1-yl}sulfonyl)-1,3-thiazol-2-yl]acetamide |
| 20 | 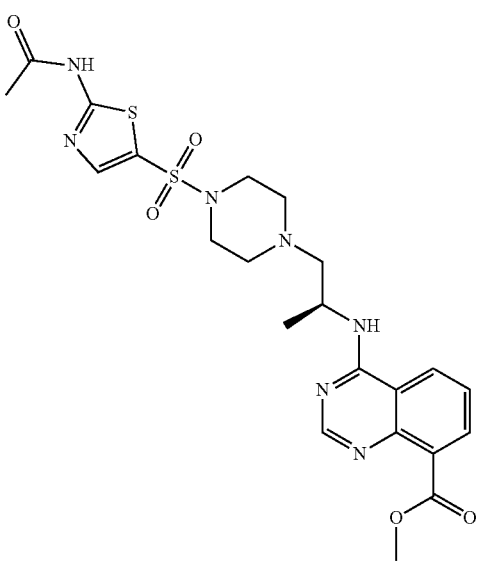 [SMILES: COC(=O)c1cccc2c(N[C@@H](C)CN3CCN(S(=O)(=O)c4cnc(NC(C)=O)s4)CC3)ncnc12] | methyl 4-{[(2S)-1-{4-[(2-acetamido-1,3-thiazol-5-yl)sulfonyl]piperazin-1-yl}propan-2-yl]amino}quinazoline-8-carboxylate |

TABLE 1-continued
List of preferred compounds of Formula (I)
| Example | Structure | Chemical name |
|---|---|---|
| 21 | 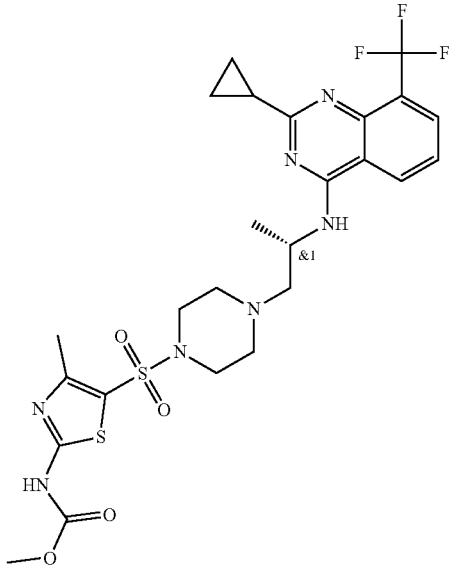 [SMILES: COC(=O)Nc1nc(C)c(S(=O)(=O)N2CCN(C[C@H](C)Nc3nc(C4CC4)nc4c(C(F)(F)F)cccc34)CC2)s1] | methyl N-[5-({4-[(2S)-2-{[2-cyclopropyl-8-(trifluoromethyl)quinazolin-4-yl]amino}propyl]piperazin-1-yl}sulfonyl)-4-methyl-1,3-thiazol-2-yl]carbamate |
| 22 | 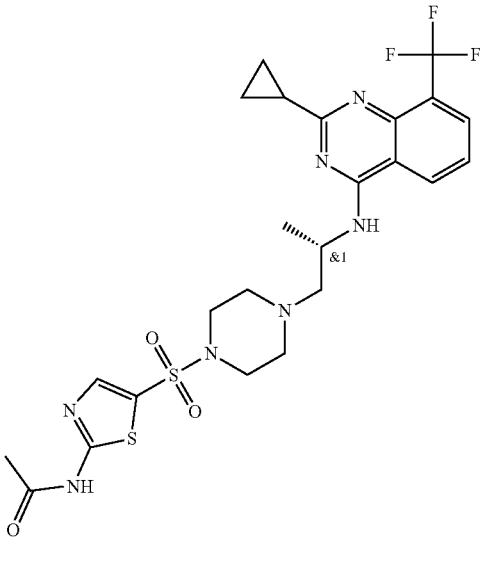 [SMILES: CC(=O)Nc1ncc(S(=O)(=O)N2CCN(C[C@H](C)Nc3nc(C4CC4)nc4c(C(F)(F)F)cccc34)CC2)s1] | N-[5-({4-[(2S)-2-{[2-cyclopropyl-8-(trifluoromethyl)quinazolin-4-yl]amino}propyl]piperazin-1-yl}sulfonyl)-1,3-thiazol-2-yl]acetamide |

TABLE 1-continued

List of preferred compounds of Formula (I)

| Example | Structure | Chemical name |
|---|---|---|
| 23 | 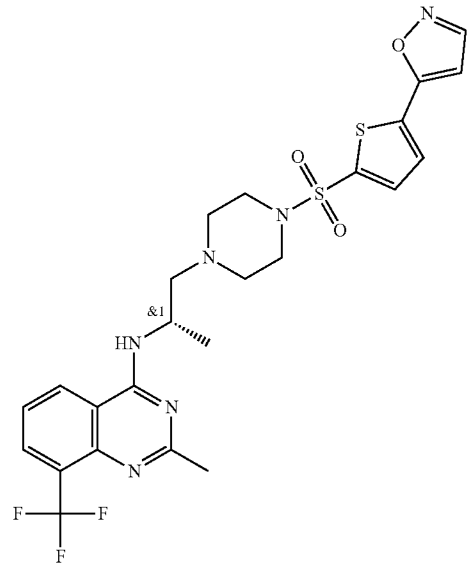 [SMILES: Cc1nc(N[C@@H](C)CN2CCN(S(=O)(=O)c3ccc(-c4ccno4)s3)CC2)c2cccc(C(F)(F)F)c2n1] | 2-methyl-N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine |
| 24 | 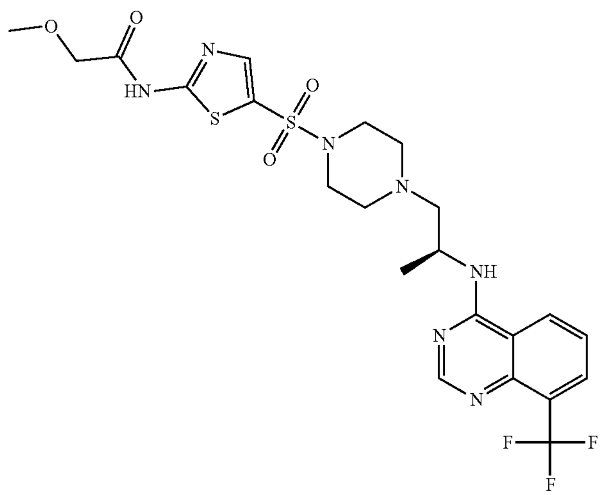 [SMILES: COCC(=O)Nc1ncc(S(=O)(=O)N2CCN(C[C@H](C)Nc3ncnc4c(C(F)(F)F)cccc34)CC2)s1] | 2-methoxy-N-[5-({4-[(2S)-2-{[8-(trifluoromethyl)quinazolin-4-yl]amino}propyl]piperazin-1-yl}sulfonyl)-1,3-thiazol-2-yl]acetamide |
| 25 | 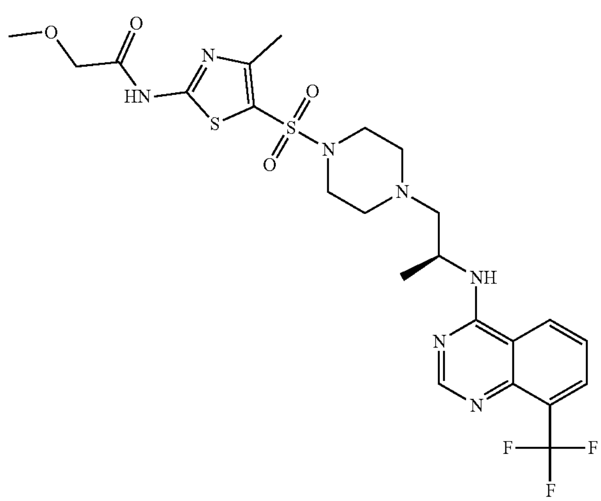 [SMILES: COCC(=O)Nc1nc(C)c(S(=O)(=O)N2CCN(C[C@H](C)Nc3ncnc4c(C(F)(F)F)cccc34)CC2)s1] | 2-methoxy-N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide |

TABLE 1-continued

List of preferred compounds of Formula (I)

| Example | Structure | Chemical name |
|---|---|---|
| 26 | 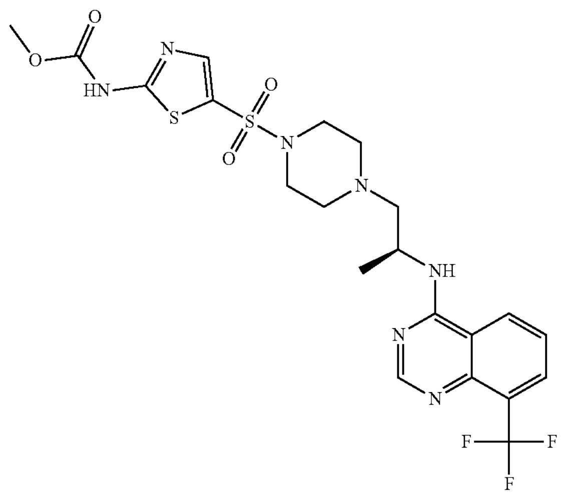 [SMILES: COC(=O)Nc1ncc(S(=O)(=O)N2CCN(C[C@H](C)Nc3ncnc4c(C(F)(F)F)cccc34)CC2)s1] | methyl N-[5-({4-[(2S)-2-{[8-(trifluoromethyl)quinazolin-4-yl]amino}propyl]piperazin-1-yl}sulfonyl)-1,3-thiazol-2-yl]carbamate |
| 27 | 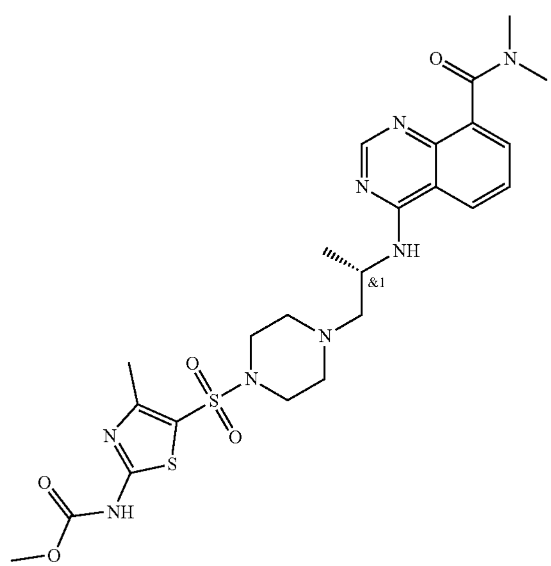 | methyl N-[5-({4-[(2S)-2-{[8-(dimethylcarbamoyl)quinazolin-4-yl]amino}propyl]piperazin-1-yl}sulfonyl)-4-methyl-1,3-thiazol-2-yl]carbamate |
| 28 | 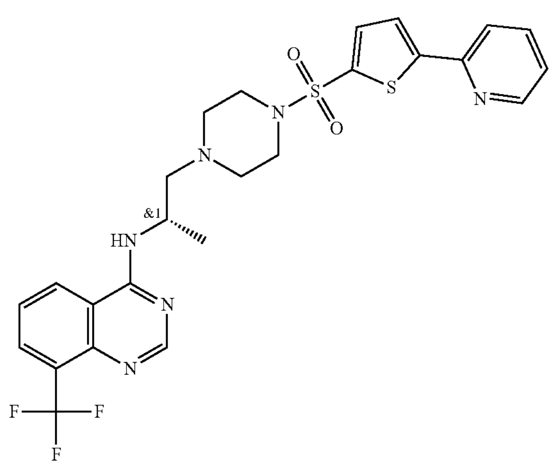 [SMILES: C[C@@H](CN1CCN(S(=O)(=O)c2ccc(-c3ccccn3)s2)CC1)Nc1ncnc2c(C(F)(F)F)cccc12] | N-[(2S)-1-(4-{[5-(pyridin-2-yl)thiophen-2-yl]sulfonyl}piperazin-1-yl)propan-2-yl]-8-(trifluoromethyl)quinazolin-4-amine |

TABLE 1-continued

List of preferred compounds of Formula (I)

| Example | Structure | Chemical name |
|---|---|---|
| 29 | 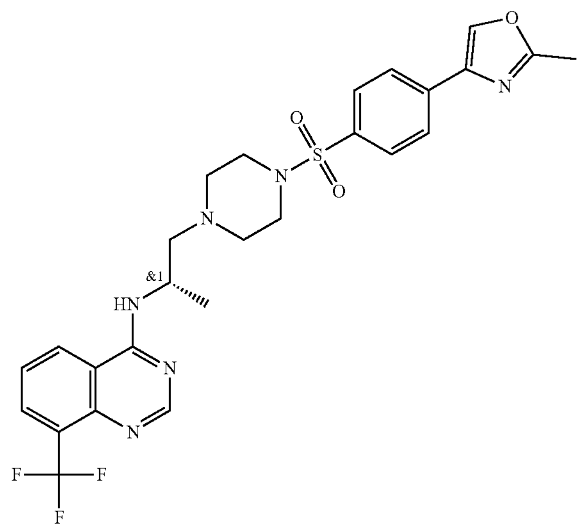 [SMILES: Cc1nc(-c2ccc(S(=O)(=O)N3CCN(C[C@H](C)Nc4ncnc5c(C(F)(F)F)cccc45)CC3)cc2)co1] | N-[(2S)-1-{4-[4-(2-methyl-1,3-oxazol-4-yl)benzenesulfonyl]piperazin-1-yl}propan-2-yl]-8-(trifluoromethyl)quinazolin-4-amine |
| 30 | 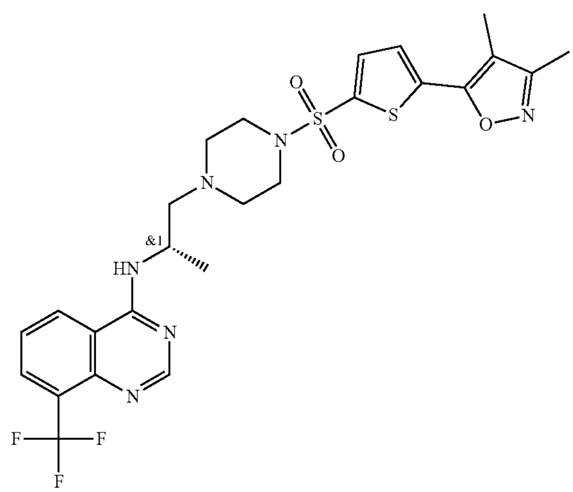 [SMILES: Cc1noc(-c2ccc(S(=O)(=O)N3CCN(C[C@H](C)Nc4ncnc5c(C(F)(F)F)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-(trifluoromethyl)quinazolin-4-amine |
| 31 | 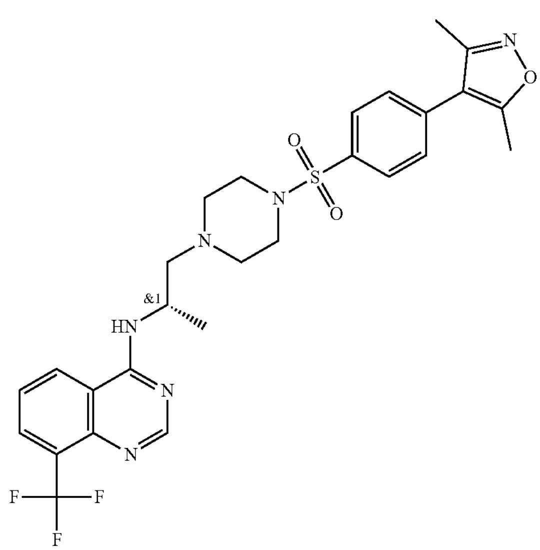 [SMILES: Cc1noc(C)c1-c1ccc(S(=O)(=O)N2CCN(C[C@H](C)Nc3ncnc4c(C(F)(F)F)cccc34)CC2)cc1] | N-[(2S)-1-{4-[4-(3,5-dimethyl-1,2-oxazol-4-yl)benzenesulfonyl]piperazin-1-yl}propan-2-yl]-8-(trifluoromethyl)quinazolin-4-amine |

TABLE 1-continued

List of preferred compounds of Formula (I)

| Example | Structure | Chemical name |
|---|---|---|
| 32 | 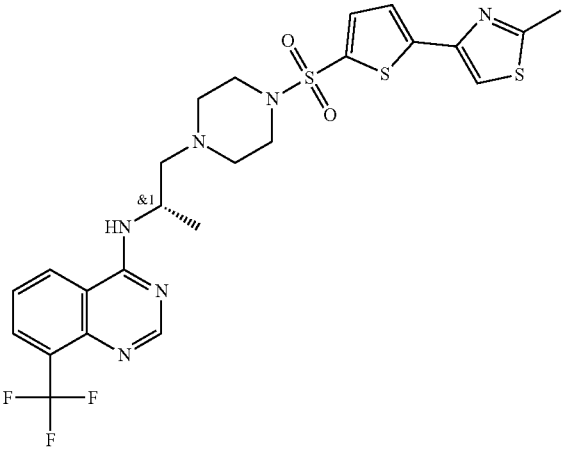 [SMILES: Cc1nc(-c2ccc(S(=O)(=O)N3CCN(C[C@H](C)Nc4ncnc5c(C(F)(F)F)cccc45)CC3)s2)cs1] | N-[(2S)-1-(4-{[5-(2-methyl-1,3-thiazol-4-yl)thiophen-2-yl]sulfonyl}piperazin-1-yl)propan-2-yl]-8-(trifluoromethyl)quinazolin-4-amine |
| 33 | 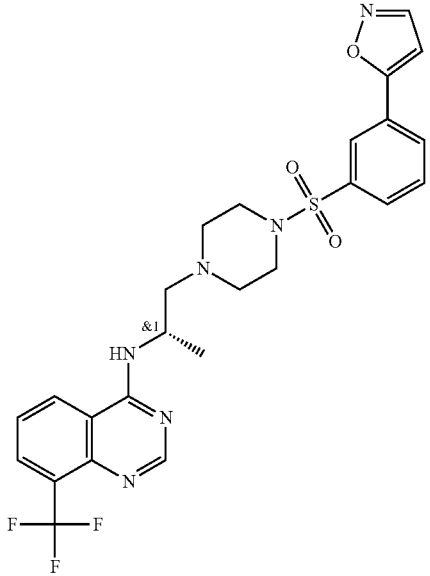 [SMILES: C[C@@H](CN1CCN(S(=O)(=O)c2cccc(-c3ccno3)c2)CC1)Nc1ncnc2c(C(F)(F)F)cccc12] | N-[(2S)-1-{4-[3-(1,2-oxazol-5-yl)benzenesulfonyl]piperazin-1-yl}propan-2-yl]-8-(trifluoromethyl)quinazolin-4-amine |
| 34 | 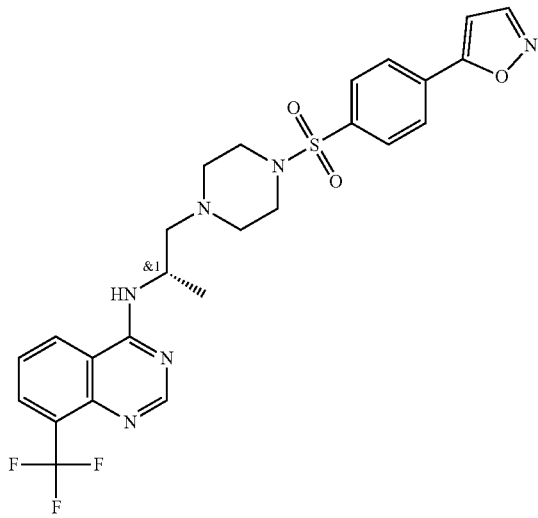 [SMILES: C[C@@H](CN1CCN(S(=O)(=O)c2ccc(-c3ccno3)cc2)CC1)Nc1ncnc2c(C(F)(F)F)cccc12] | N-[(2S)-1-{4-[4-(1,2-oxazol-5-yl)benzenesulfonyl]piperazin-1-yl}propan-2-yl]-8-(trifluoromethyl)quinazolin-4-amine |

TABLE 1-continued

List of preferred compounds of Formula (I)

| Example | Structure | Chemical name |
|---|---|---|
| 35 | 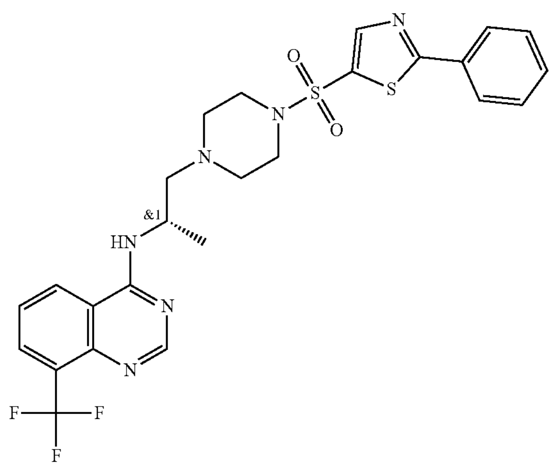 [SMILES: C[C@@H](CN1CCN(S(=O)(=O)c2cnc(-c3ccccc3)s2)CC1)Nc1ncnc2c(C(F)(F)F)cccc12] | N-[(2S)-1-{4-[(2-phenyl-1,3-thiazol-5-yl)sulfonyl]piperazin-1-yl}propan-2-yl]-8-(trifluoromethyl)quinazolin-4-amine |
| 36 | 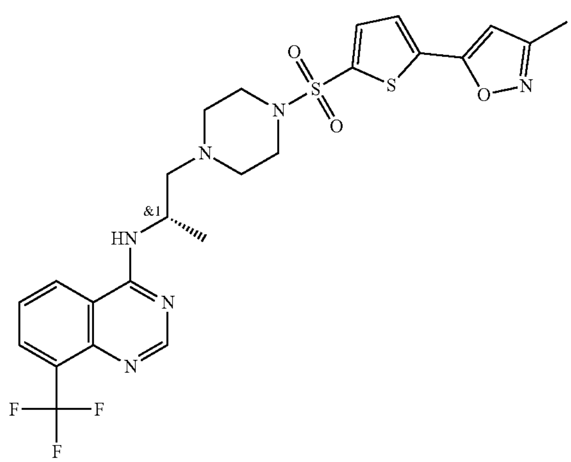 [SMILES: Cc1cc(-c2ccc(S(=O)(=O)N3CCN(C[C@H](C)Nc4ncnc5c(C(F)(F)F)cccc45)CC3)s2)on1] | N-[(2S)-1-(4-{[5-(3-methyl-1,2-oxazol-5-yl)thiophen-2-yl]sulfonyl}piperazin-1-yl)propan-2-yl]-8-(trifluoromethyl)quinazolin-4-amine |
| 37 | 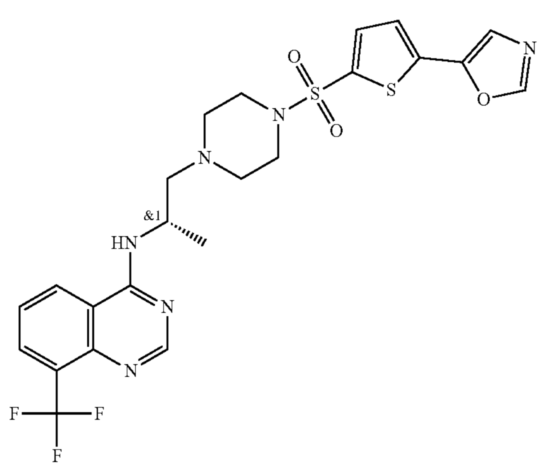 [SMILES: C[C@@H](CN1CCN(S(=O)(=O)c2ccc(-c3cnco3)s2)CC1)Nc1ncnc2c(C(F)(F)F)cccc12] | N-[(2S)-1-(4-{[5-(1,3-oxazol-5-yl)thiophen-2-yl]sulfonyl}piperazin-1-yl)propan-2-yl]-8-(trifluoromethyl)quinazolin-4-amine |

TABLE 1-continued
List of preferred compounds of Formula (I)
| Example | Structure | Chemical name |
|---|---|---|
| 38 | 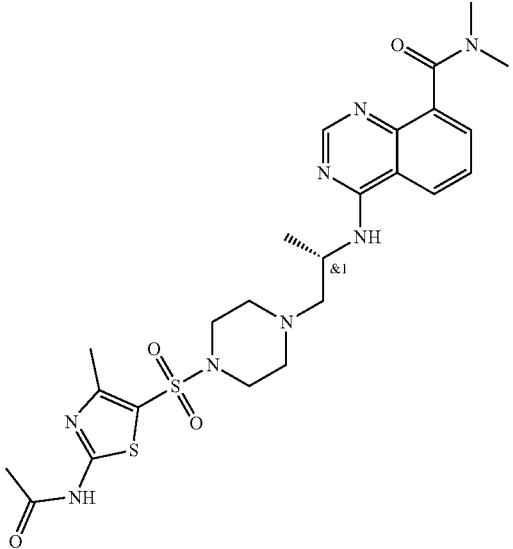 [SMILES: CC(=O)Nc1nc(C)c(S(=O)(=O)N2CCN(C[C@H](C)Nc3ncnc4c(C(=O)N(C)C)cccc34)CC2)s1] | 4-{[(2S)-1-{4-[(2-acetamido-4-methyl-1,3-thiazol-5-yl)sulfonyl]piperazin-1-yl}propan-2-yl]amino}-N,N-dimethylquinazoline-8-carboxamide |
| 39 | 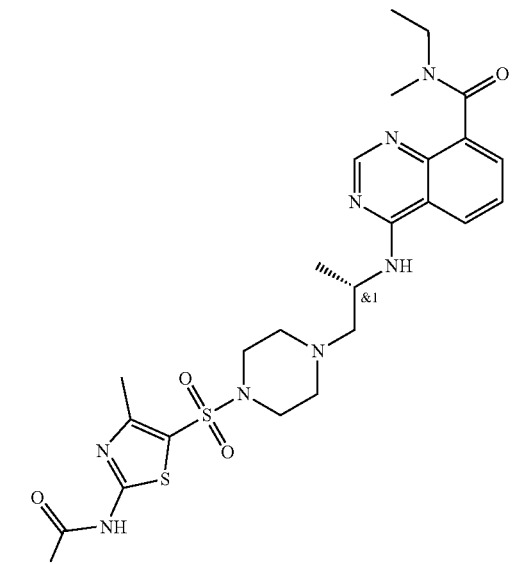 | methyl N-[5-({4-[(2S)-2-({8-[ethyl(methyl)carbamoyl]quinazolin-4-yl}amino)propyl]piperazin-1-yl}sulfonyl)-4-methyl-1,3-thiazol-2-yl]carbamate |

TABLE 1-continued
List of preferred compounds of Formula (I)
| Example | Structure | Chemical name |
|---|---|---|
| 40 | 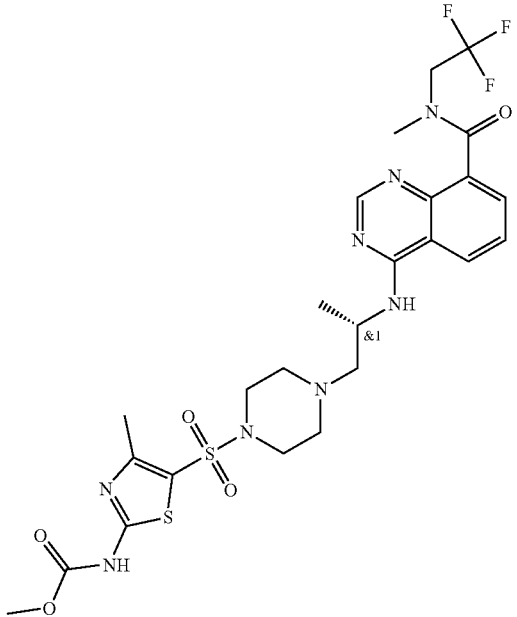 [SMILES: COC(=O)Nc1nc(C)c(S(=O)(=O)N2CCN(C[C@H](C)Nc3ncnc4c(C(=O)N(C)CC(F)(F)F)cccc34)CC2)s1] | methyl N-[4-methyl-5-({4-[(2S)-2-({8-[methyl(2,2,2-trifluoroethyl)carbamoyl]quinazolin-4-yl}amino)propyl]piperazin-1-yl}sulfonyl)-1,3-thiazol-2-yl]carbamate |
| 41 | 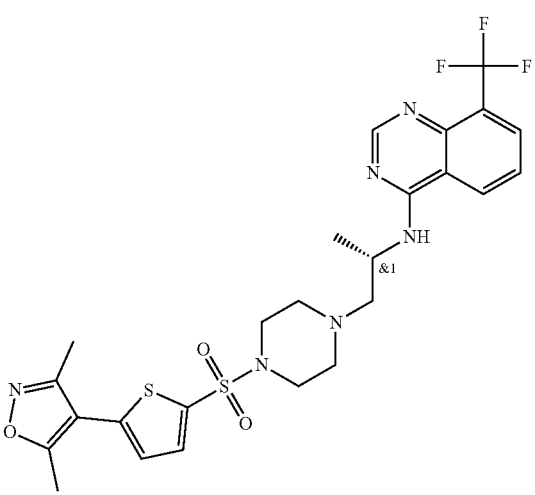 [SMILES: Cc1noc(C)c1-c1ccc(S(=O)(=O)N2CCN(C[C@H](C)Nc3ncnc4c(C(F)(F)F)cccc34)CC2)s1] | N-[(2S)-1-(4-{[5-(3,5-dimethyl-1,2-oxazol-4-yl)thiophen-2-yl]sulfonyl}piperazin-1-yl)propan-2-yl]-8-(trifluoromethyl)quinazolin-4-amine |

TABLE 1-continued
List of preferred compounds of Formula (I)
| Example | Structure | Chemical name |
|---|---|---|
| 42 | 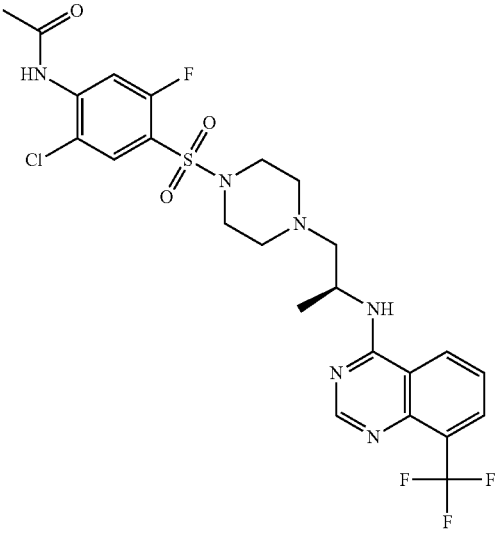 [SMILES: CC(=O)Nc1cc(F)c(S(=O)(=O)N2CCN(C[C@H](C)Nc3ncnc4c(C(F)(F)F)cccc34)CC2)cc1Cl] | N-[2-chloro-5-fluoro-4-({4-[(2S)-2-{[8-(trifluoromethyl)quinazolin-4-yl]amino}propyl]piperazin-1-yl}sulfonyl)phenyl]acetamide |
| 43 | 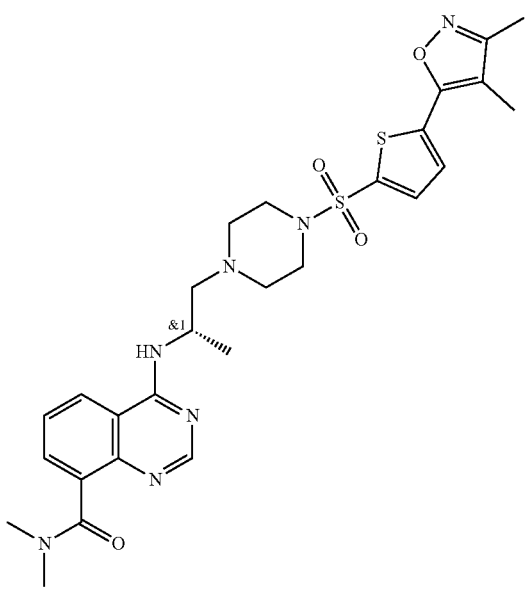 | 4-{[(2S)-1-(4-{[5-(3,4-dimethyl-1,2-oxazol-5-yl)thiophen-2-yl]sulfonyl}piperazin-1-yl)propan-2-yl]amino}-N,N-dimethylquinazoline-8-carboxamide |

TABLE 1-continued
List of preferred compounds of Formula (I)
| Example | Structure | Chemical name |
|---|---|---|
| 44 | 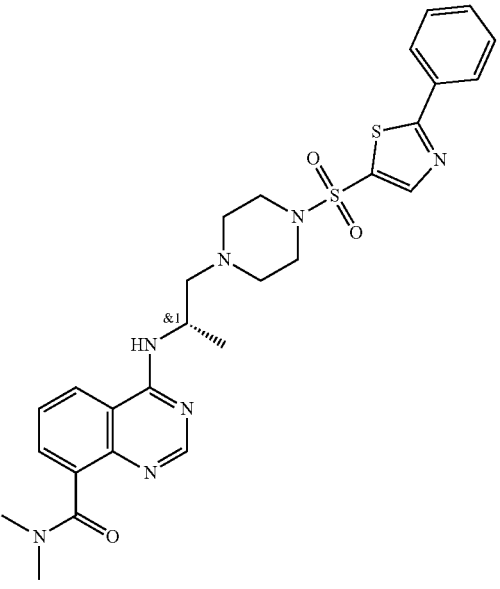 [SMILES: C[C@@H](CN1CCN(S(=O)(=O)c2cnc(-c3ccccc3)s2)CC1)Nc1ncnc2c(C(=O)N(C)C)cccc12] | N,N-dimethyl-4-{[(2S)-1-{4-[(2-phenyl-1,3-thiazol-5-yl)sulfonyl]piperazin-1-yl}propan-2-yl]amino}quinazoline-8-carboxamide |
| 45 | 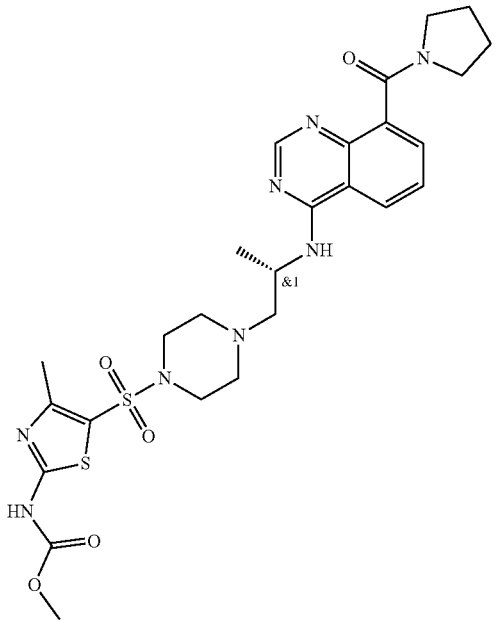 [SMILES: COC(=O)Nc1nc(C)c(S(=O)(=O)N2CCN(C[C@H](C)Nc3ncnc4c(C(=O)N5CCCC5)cccc34)CC2)s1] | methyl N-[4-methyl-5-({4-[(2S)-2-{[8-(pyrrolidine-1-carbonyl)quinazolin-4-yl]amino}propyl]piperazin-1-yl}sulfonyl)-1,3-thiazol-2-yl]carbamate |

TABLE 1-continued
List of preferred compounds of Formula (I)
| Example | Structure | Chemical name |
|---|---|---|
| 46 | 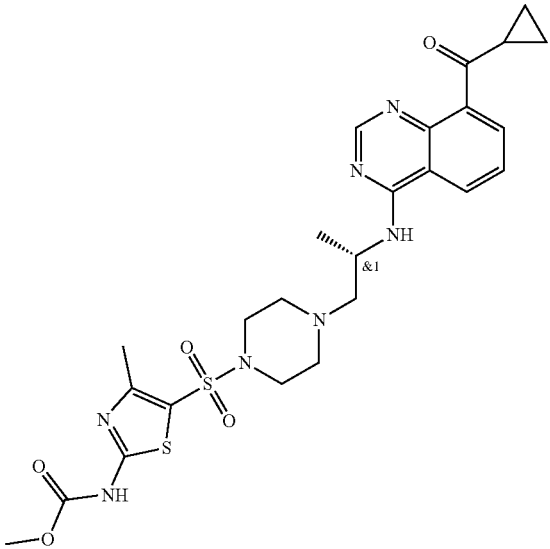 [SMILES: COC(=O)Nc1nc(C)c(S(=O)(=O)N2CCN(C[C@H](C)Nc3ncnc4c(C(=O)C5CC5)cccc34)CC2)s1] | methyl N-[5-({4-[(2S)-2-[(8-cyclopropanecarbonylquinazolin-4-yl)amino]propyl]piperazin-1-yl}sulfonyl)-4-methyl-1,3-thiazol-2-yl]carbamate |
| 47 | 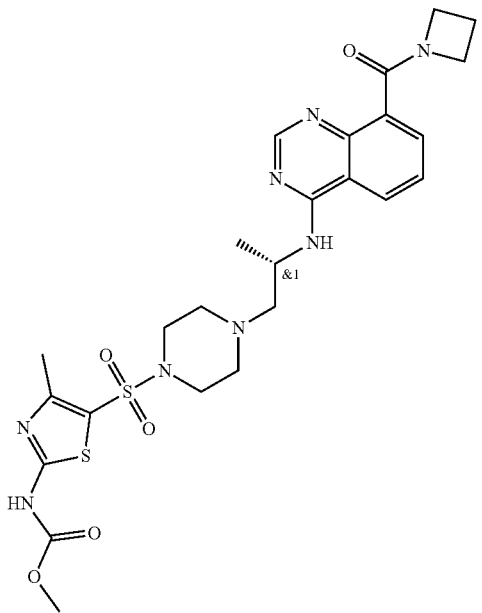 [SMILES: COC(=O)Nc1nc(C)c(S(=O)(=O)N2CCN(C[C@H](C)Nc3ncnc4c(C(=O)N5CCC5)cccc34)CC2)s1] | methyl N-[5-({4-[(2S)-2-{[8-(azetidine-1-carbonyl)quinazolin-4-yl]amino}propyl]piperazin-1-yl}sulfonyl)-4-methyl-1,3-thiazol-2-yl]carbamate |

TABLE 1-continued
List of preferred compounds of Formula (I)
| Example | Structure | Chemical name |
|---|---|---|
| 48 | 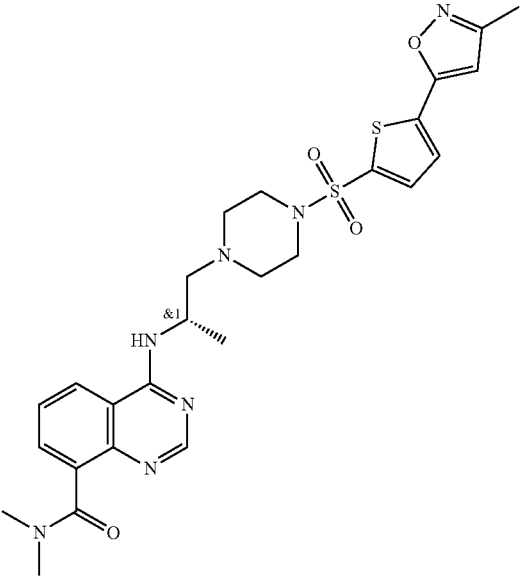 | N,N-dimethyl-4-{[(2S)-1-(4-{[5-(3-methyl-1,2-oxazol-5-yl)thiophen-2-yl]sulfonyl}piperazin-1-yl)propan-2-yl]amino}quinazoline-8-carboxamide |
| 49 | 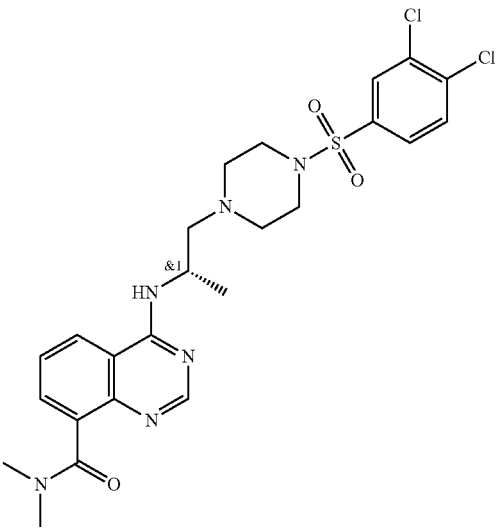 [SMILES: C[C@@H](CN1CCN(S(=O)(=O)c2ccc(Cl)c(Cl)c2)CC1)Nc1ncnc2c(C(=O)N(C)C)cccc12] | 4-{[(2S)-1-[4-(3,4-dichlorobenzenesulfonyl)piperazin-1-yl]propan-2-yl]amino}-N,N-dimethylquinazoline-8-carboxamide |

TABLE 1-continued
List of preferred compounds of Formula (I)
| Example | Structure | Chemical name |
|---|---|---|
| 50 | 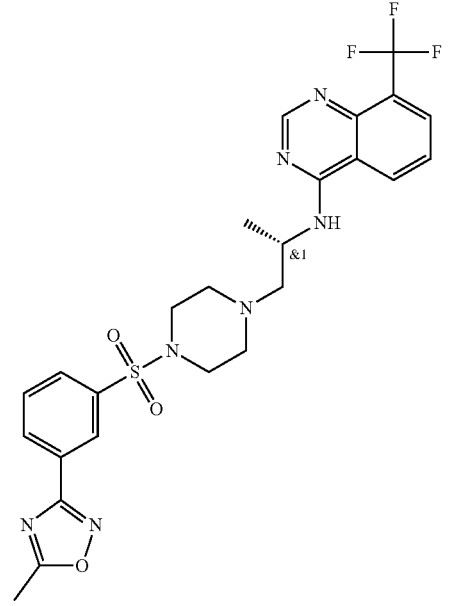 [SMILES: Cc1nc(-c2cccc(S(=O)(=O)N3CCN(C[C@H](C)Nc4ncnc5c(C(F)(F)F)cccc45)CC3)c2)no1] | N-[(2S)-1-{4-[3-(5-methyl-1,2,4-oxadiazol-3-yl)benzenesulfonyl]piperazin-1-yl}propan-2-yl]-8-(trifluoromethyl)quinazolin-4-amine |
| 51 | 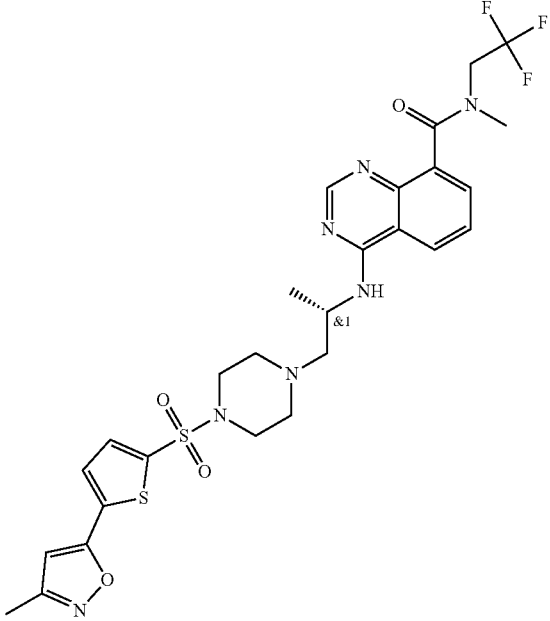 [SMILES: Cc1cc(-c2ccc(S(=O)(=O)N3CCN(C[C@H](C)Nc4ncnc5c(C(=O)N(C)CC(F)(F)F)cccc45)CC3)s2)on1] | N-methyl-4-{[(2S)-1-(4-{[5-(3-methyl-1,2-oxazol-5-yl)thiophen-2-yl]sulfonyl}piperazin-1-yl)propan-2-yl]amino}-N-(2,2,2-trifluoroethyl)quinazoline-8-carboxamide |

TABLE 1-continued

List of preferred compounds of Formula (I)

| Example | Structure | Chemical name |
|---|---|---|
| 52 | 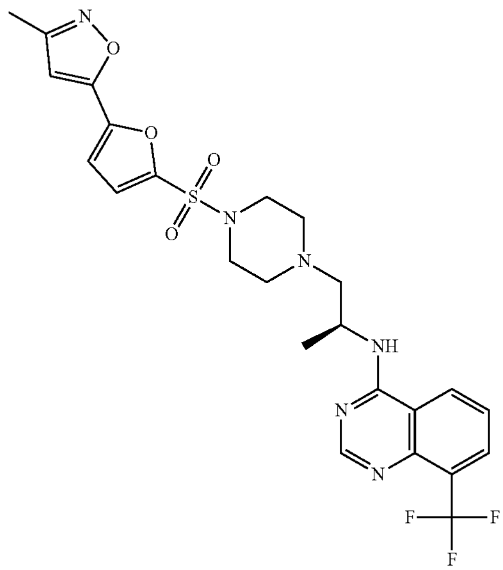 [SMILES: Cc1cc(-c2ccc(S(=O)(=O)N3CCN(C[C@H](C)Nc4ncnc5c(C(F)(F)F)cccc45)CC3)o2)on1] | N-[(2S)-1-(4-{[5-(3-methyl-1,2-oxazol-5-yl)furan-2-yl]sulfonyl}piperazin-1-yl)propan-2-yl]-8-(trifluoromethyl)quinazolin-4-amine |
| 53 | 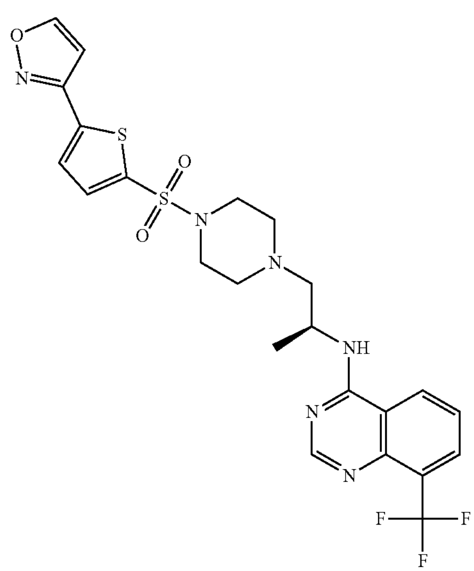 [SMILES: C[C@@H](CN1CCN(S(=O)(=O)c2ccc(-c3ccon3)s2)CC1)Nc1ncnc2c(C(F)(F)F)cccc12] | N-[(2S)-1-(4-{[5-(1,2-oxazol-3-yl)thiophen-2-yl]sulfonyl}piperazin-1-yl)propan-2-yl]-8-(trifluoromethyl)quinazolin-4-amine |

TABLE 1-continued

List of preferred compounds of Formula (I)

| Example | Structure | Chemical name |
| --- | --- | --- |
| 54 | 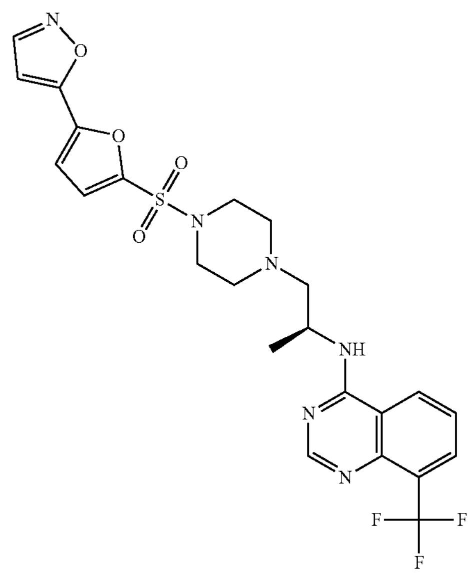 [SMILES: C[C@@H](CN1CCN(S(=O)(=O)c2ccc(-c3ccno3)o2)CC1)Nc1ncnc2c(C(F)(F)F)cccc12] | N-[(2S)-1-(4-{[5-(1,2-oxazol-5-yl)furan-2-yl]sulfonyl}piperazin-1-yl)propan-2-yl]-8-(trifluoromethyl)quinazolin-4-amine |
| 55 | 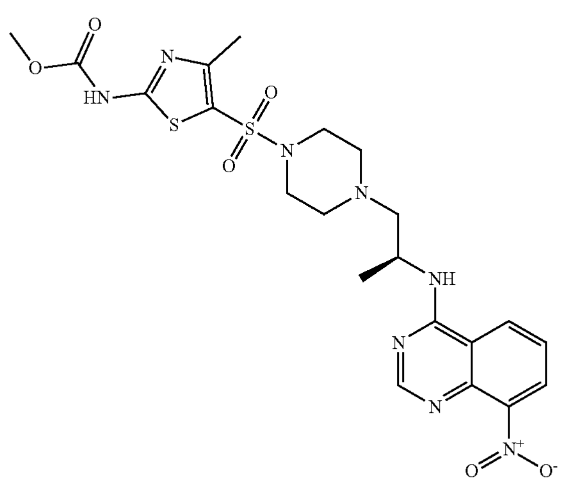 [SMILES: COC(=O)Nc1nc(C)c(S(=O)(=O)N2CCN(C[C@H](C)Nc3ncnc4c([N+](=O)[O-])cccc34)CC2)s1] | methyl N-[4-methyl-5-({4-[(2S)-2-[(8-nitroquinazolin-4-yl)amino]propyl]piperazin-1-yl}sulfonyl)-1,3-thiazol-2-yl]carbamate |

TABLE 1-continued
List of preferred compounds of Formula (I)
| Example | Structure | Chemical name |
|---|---|---|
| 56 | 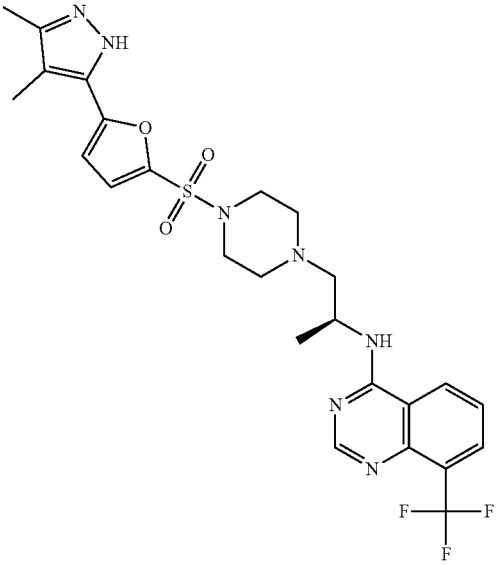 [SMILES: Cc1n[nH]c(-c2ccc(S(=O)(=O)N3CCN(C[C@H](C)Nc4ncnc5c(C(F)(F)F)cccc45)CC3)o2)c1C] | N-[(2S)-1-(4-{[5-(3,4-dimethyl-1H-pyrazol-5-yl)furan-2-yl]sulfonyl}piperazin-1-yl)propan-2-yl]-8-(trifluoromethyl)quinazolin-4-amine |
| 57 | 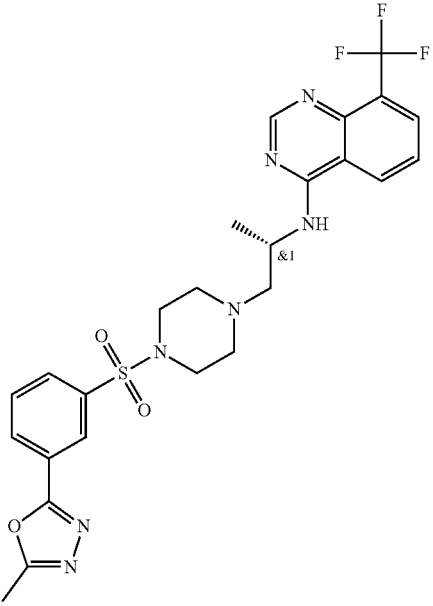 [SMILES: Cc1nnc(-c2cccc(S(=O)(=O)N3CCN(C[C@H](C)Nc4ncnc5c(C(F)(F)F)cccc45)CC3)c2)o1] | N-[(2S)-1-{4-[3-(5-methyl-1,3,4-oxadiazol-2-yl)benzenesulfonyl]piperazin-1-yl}propan-2-yl]-8-(trifluoromethyl)quinazolin-4-amine |

TABLE 1-continued
List of preferred compounds of Formula (I)
| Example | Structure | Chemical name |
|---|---|---|
| 58 | 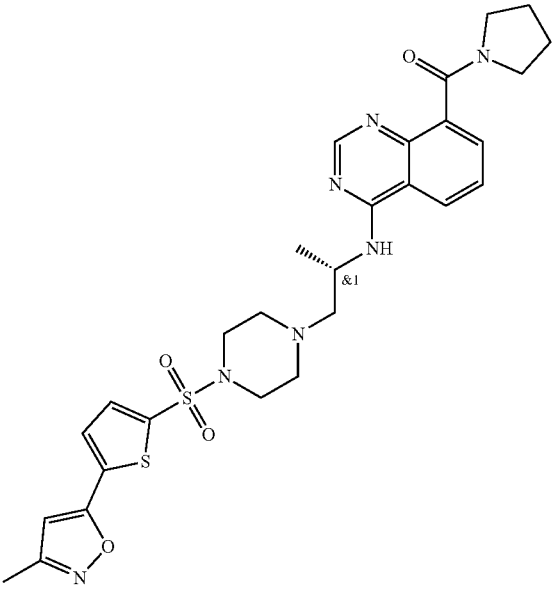 [SMILES: Cc1cc(-c2ccc(S(=O)(=O)N3CCN(C[C@H](C)Nc4ncnc5c(C(=O)N6CCCC6)cccc45)CC3)s2)on1] | N-[(2S)-1-(4-{[5-(3-methyl-1,2-oxazol-5-yl)thiophen-2-yl]sulfonyl}piperazin-1-yl)propan-2-yl]-8-(pyrrolidine-1-carbonyl)quinazolin-4-amine |
| 59 | 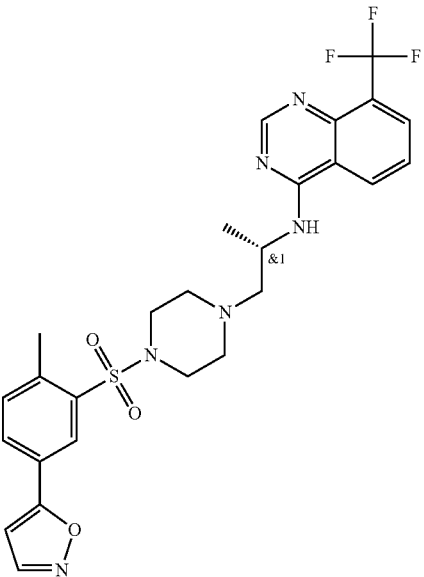 [SMILES: Cc1ccc(-c2ccno2)cc1S(=O)(=O)N1CCN(C[C@H](C)Nc2ncnc3c(C(F)(F)F)cccc23)CC1] | N-[(2S)-1-{4-[2-methyl-5-(1,2-oxazol-5-yl)benzenesulfonyl]piperazin-1-yl}propan-2-yl]-8-(trifluoromethyl)quinazolin-4-amine |

TABLE 1-continued
List of preferred compounds of Formula (I)
| Example | Structure | Chemical name |
|---------|-----------|---------------|
| 60 | 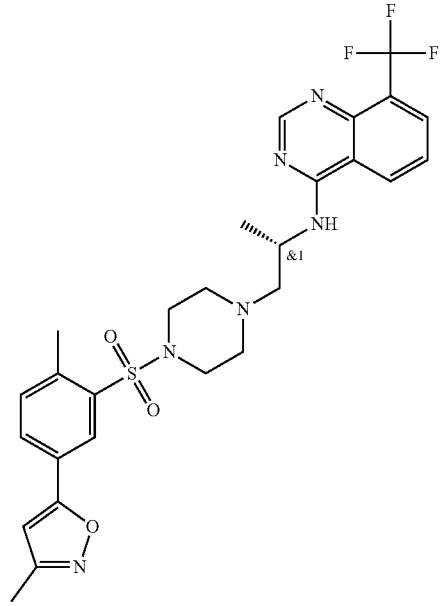 [SMILES: Cc1cc(-c2ccc(C)c(S(=O)(=O)N3CCN(C[C@H](C)Nc4ncnc5c(C(F)(F)F)cccc45)CC3)c2)on1] | N-[(2S)-1-{4-[2-methyl-5-(3-methyl-1,2-oxazol-5-yl)benzenesulfonyl]piperazin-1-yl}propan-2-yl]-8-(trifluoromethyl)quinazolin-4-amine |
| 61 | 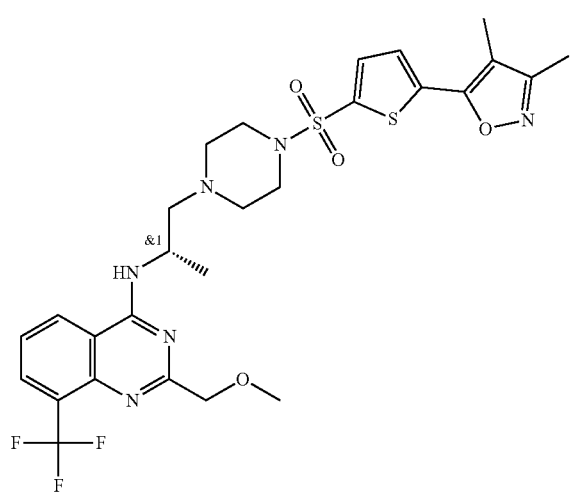 [SMILES: COCc1nc(N[C@@H](C)CN2CCN(S(=O)(=O)c3ccc(-c4onc(C)c4C)s3)CC2)c2cccc(C(F)(F)F)c2n1] | N-[(2S)-1-(4-{[5-(3,4-dimethyl-1,2-oxazol-5-yl)thiophen-2-yl]sulfonyl}piperazin-1-yl)propan-2-yl]-2-(methoxymethyl)-8-(trifluoromethyl)quinazolin-4-amine |

TABLE 1-continued
List of preferred compounds of Formula (I)
| Example | Structure | Chemical name |
|---|---|---|
| 62 | 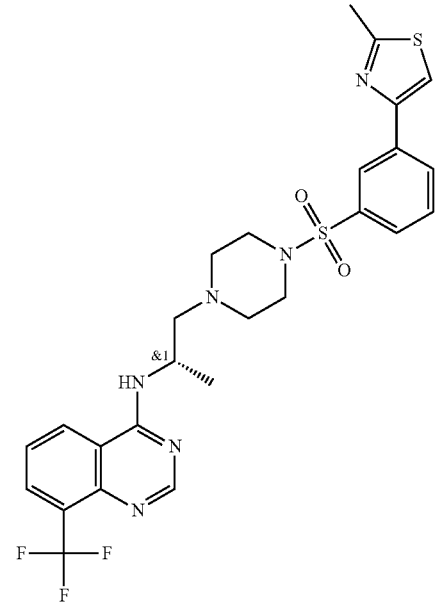 [SMILES: Cc1nc(-c2cccc(S(=O)(=O)N3CCN(C[C@H](C)Nc4ncnc5c(C(F)(F)F)cccc45)CC3)c2)cs1] | N-[(2S)-1-{4-[3-(2-methyl-1,3-thiazol-4-yl)benzenesulfonyl]piperazin-1-yl}propan-2-yl]-8-(trifluoromethyl)quinazolin-4-amine |
| 63 | 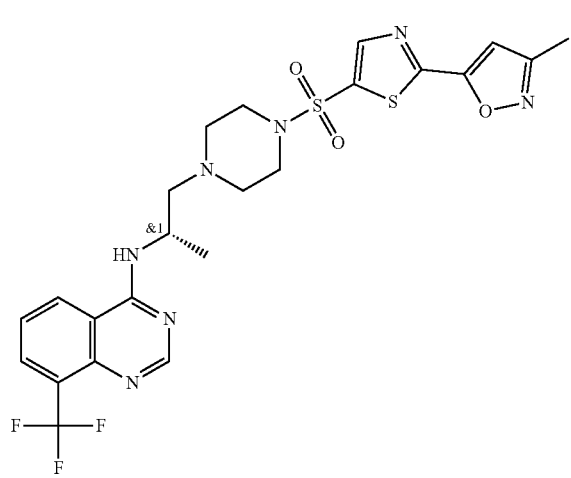 [SMILES: Cc1cc(-c2ncc(S(=O)(=O)N3CCN(C[C@H](C)Nc4ncnc5c(C(F)(F)F)cccc45)CC3)s2)on1] | N-[(2S)-1-(4-{[2-(3-methyl-1,2-oxazol-5-yl)-1,3-thiazol-5-yl]sulfonyl}piperazin-1-yl)propan-2-yl]-8-(trifluoromethyl)quinazolin-4-amine |

TABLE 1-continued

List of preferred compounds of Formula (I)

| Example | Structure | Chemical name |
|---|---|---|
| 64 | 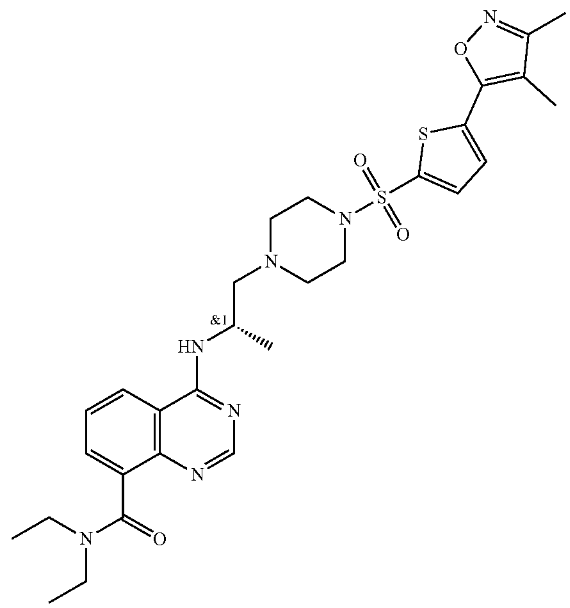 [SMILES: CCN(CC)C(=O)c1cccc2c(N[C@@H](C)CN3CCN(S(=O)(=O)c4ccc(-c5onc(C)c5C)s4)CC3)ncnc12] | 4-{[(2S)-1-(4-{[5-(3,4-dimethyl-1,2-oxazol-5-yl)thiophen-2-yl]sulfonyl}piperazin-1-yl)propan-2-yl]amino}-N,N-diethylquinazoline-8-carboxamide |
| 65 | 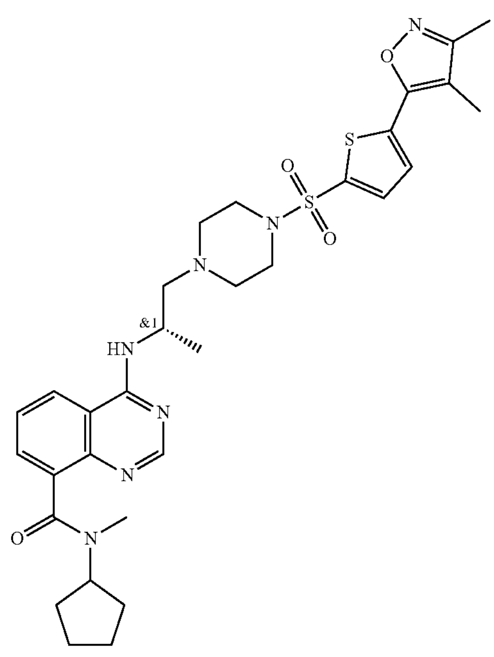 [SMILES: Cc1noc(-c2ccc(S(=O)(=O)N3CCN(C[C@H](C)Nc4ncnc5c(C(=O)N(C)C6CCCC6)cccc45)CC3)s2)c1C] | N-cyclopentyl-4-{[(2S)-1-(4-{[5-(3,4-dimethyl-1,2-oxazol-5-yl)thiophen-2-yl]sulfonyl}piperazin-1-yl)propan-2-yl]amino}-N-methylquinazoline-8-carboxamide |

TABLE 1-continued
List of preferred compounds of Formula (I)
| Example | Structure | Chemical name |
|---|---|---|
| 66 | 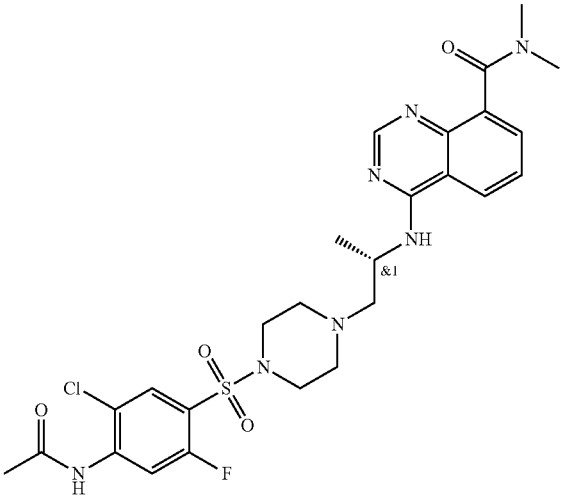 [SMILES: CC(=O)Nc1cc(F)c(S(=O)(=O)N2CCN(C[C@H](C)Nc3ncnc4c(C(=O)N(C)C)cccc34)CC2)cc1Cl] | 4-{[(2S)-1-[4-(5-chloro-4-acetamido-2-fluorobenzenesulfonyl)piperazin-1-yl]propan-2-yl]amino}-N,N-dimethylquinazoline-8-carboxamide |
| 67 | 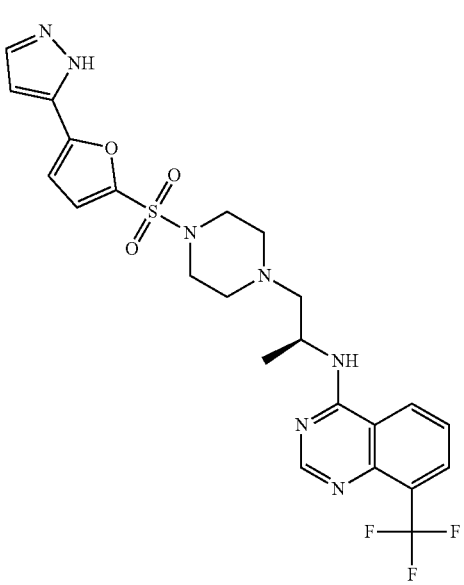 [SMILES: C[C@@H](CN1CCN(S(=O)(=O)c2ccc(-c3ccn[nH]3)o2)CC1)Nc1ncnc2c(C(F)(F)F)cccc12] | N-[(2S)-1-(4-{[5-(1H-pyrazol-5-yl)furan-2-yl]sulfonyl}piperazin-1-yl)propan-2-yl]-8-(trifluoromethyl)quinazolin-4-amine |

TABLE 1-continued
List of preferred compounds of Formula (I)
| Example | Structure | Chemical name |
|---|---|---|
| 68 | 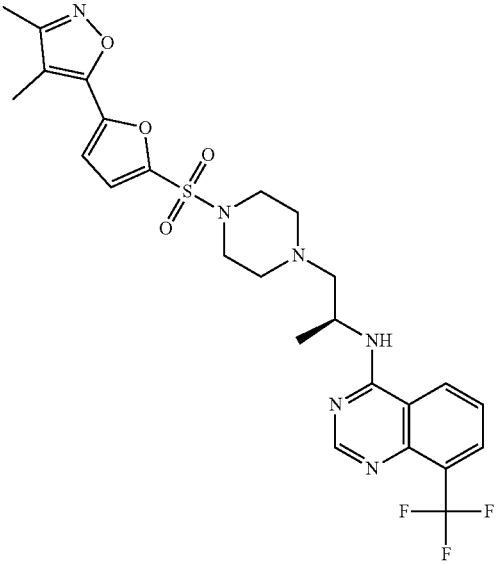 [SMILES: Cc1noc(-c2ccc(S(=O)(=O)N3CCN(C[C@H](C)Nc4ncnc5c(C(F)(F)F)cccc45)CC3)o2)c1C] | N-[(2S)-1-(4-{[5-(3,4-dimethyl-1,2-oxazol-5-yl)furan-2-yl]sulfonyl}piperazin-1-yl)propan-2-yl]-8-(trifluoromethyl)quinazolin-4-amine |
| 69 | 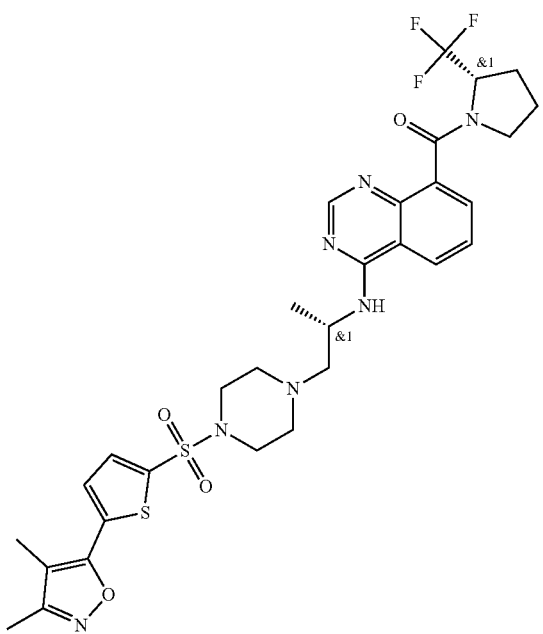 [SMILES: Cc1noc(-c2ccc(S(=O)(=O)N3CCN(C[C@H](C)Nc4ncnc5c(C(=O)N6CCC[C@H]6C(F)(F)F)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-[(2S)-2-(trifluoromethyl)pyrrolidine-1-carbonyl]quinazolin-4-amine |

TABLE 1-continued
List of preferred compounds of Formula (I)
| Example | Structure | Chemical name |
|---|---|---|
| 70 | 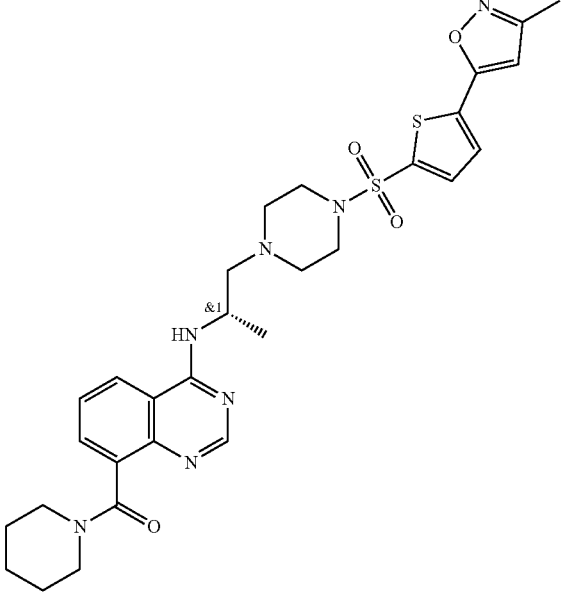 [SMILES: Cc1cc(-c2ccc(S(=O)(=O)N3CCN(C[C@H](C)Nc4ncnc5c(C(=O)N6CCCCC6)cccc45)CC3)s2)on1] | N-[(2S)-1-(4-{[5-(3-methyl-1,2-oxazol-5-yl)thiophen-2-yl]sulfonyl}piperazin-1-yl)propan-2-yl]-8-(piperidine-1-carbonyl)quinazolin-4-amine |
| 71 | 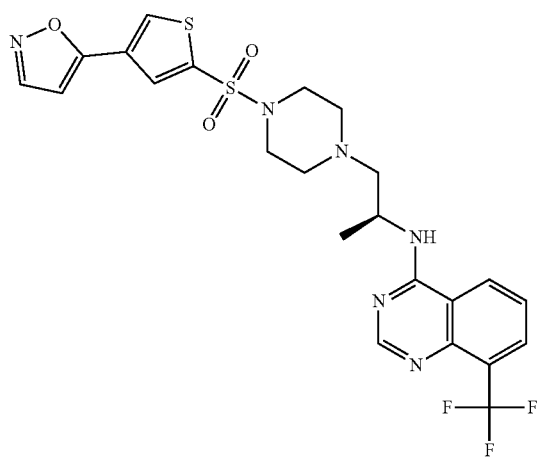 [SMILES: C[C@@H](CN1CCN(S(=O)(=O)c2cc(-c3ccno3)cs2)CC1)Nc1ncnc2c(C(F)(F)F)cccc12] | N-[(2S)-1-(4-{[4-(1,2-oxazol-5-yl)thiophen-2-yl]sulfonyl}piperazin-1-yl)propan-2-yl]-8-(trifluoromethyl)quinazolin-4-amine |

TABLE 1-continued

List of preferred compounds of Formula (I)

| Example | Structure | Chemical name |
|---|---|---|
| 72 | 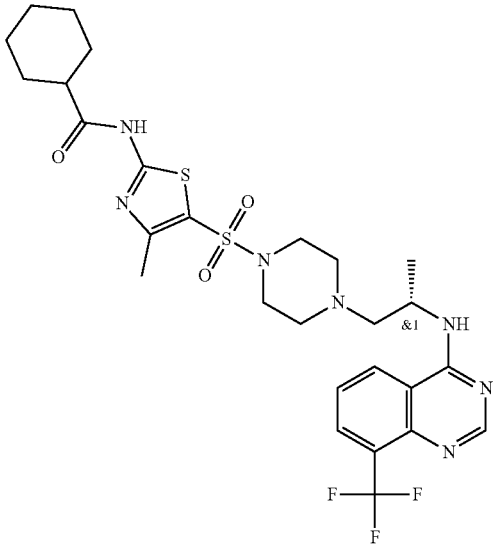 [SMILES: Cc1nc(NC(=O)C2CCCCC2)sc1S(=O)(=O)N1CCN(C[C@H](C)Nc2ncnc3c(C(F)(F)F)cccc23)CC1] | N-[4-methyl-5-({4-[(2S)-2-{[8-(trifluoromethyl)quinazolin-4-yl]amino}propyl]piperazin-1-yl}sulfonyl)-1,3-thiazol-2-yl]cyclohexanecarboxamide |
| 73 | 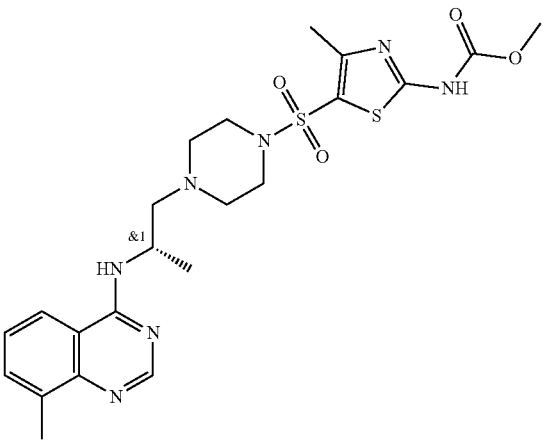 [SMILES: COC(=O)Nc1nc(C)c(S(=O)(=O)N2CCN(C[C@H](C)Nc3ncnc4c(C)cccc34)CC2)s1] | methyl N-[4-methyl-5-({4-[(2S)-2-[(8-methylquinazolin-4-yl)amino]propyl]piperazin-1-yl}sulfonyl)-1,3-thiazol-2-yl]carbamate |
| 74 | 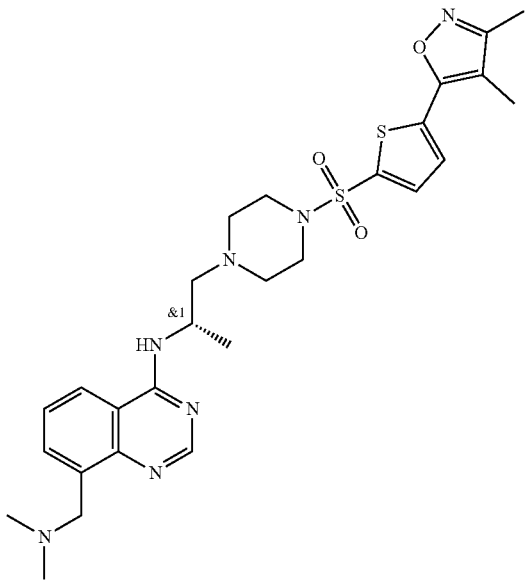 | N-[(2S)-1-(4-{[5-(3,4-dimethyl-1,2-oxazol-5-yl)thiophen-2-yl]sulfonyl}piperazin-1-yl)propan-2-yl]-8-[(dimethylamino)methyl]quinazolin-4-amine |

TABLE 1-continued
List of preferred compounds of Formula (I)
| Example | Structure | Chemical name |
|---------|-----------|---------------|
| 75 | 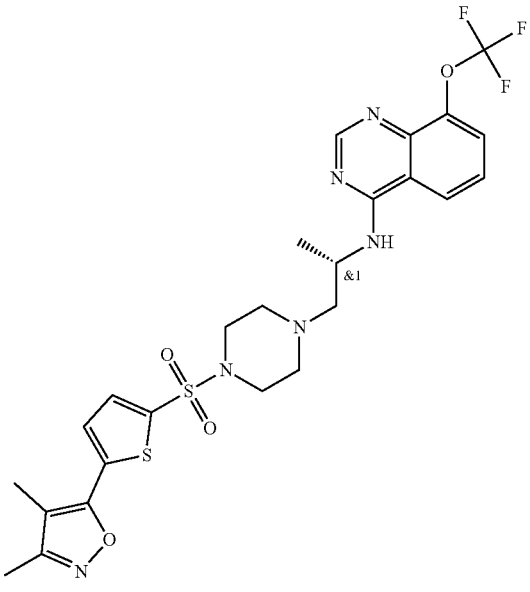 [SMILES: Cc1noc(-c2ccc(S(=O)(=O)N3CCN(C[C@H](C)Nc4ncnc5c(OC(F)(F)F)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-(trifluoromethoxy)quinazolin-4-amine |
| 76 | 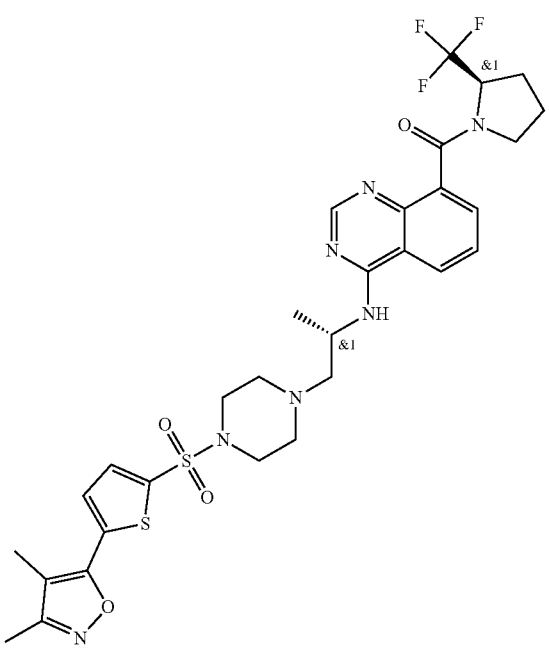 [SMILES: Cc1noc(-c2ccc(S(=O)(=O)N3CCN(C[C@H](C)Nc4ncnc5c(C(=O)N6CCC[C@@H]6C(F)(F)F)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-[(2R)-2-(trifluoromethyl)pyrrolidine-1-carbonyl]quinazolin-4-amine |

TABLE 1-continued
List of preferred compounds of Formula (I)
| Example | Structure | Chemical name |
|---|---|---|
| 77 | 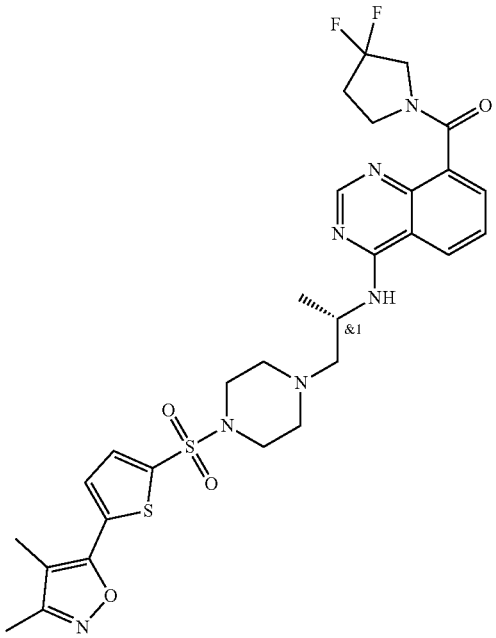 [SMILES: Cc1noc(-c2ccc(S(=O)(=O)N3CCN(C[C@H](C)Nc4ncnc5c(C(=O)N6CCC(F)(F)C6)cccc45)CC3)s2)c1C] | 8-(3,3-difluoropyrrolidine-1-carbonyl)-N-[(2S)-1-(4-{[5-(3,4-dimethyl-1,2-oxazol-5-yl)thiophen-2-yl]sulfonyl}piperazin-1-yl)propan-2-yl]quinazolin-4-amine |
| 78 | 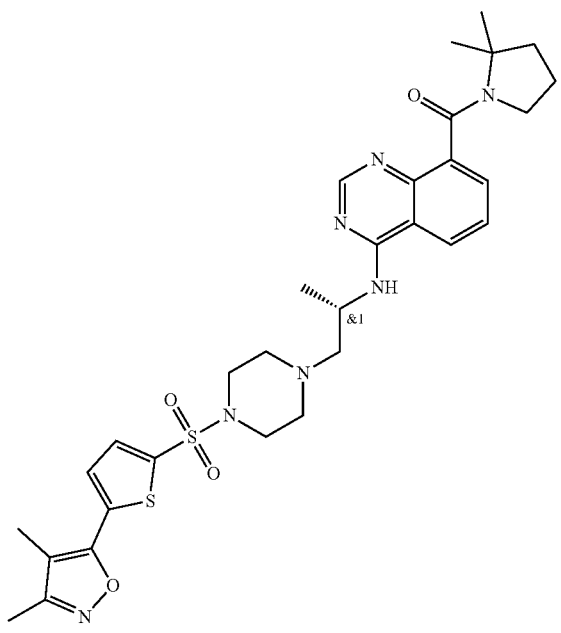 [SMILES: Cc1noc(-c2ccc(S(=O)(=O)N3CCN(C[C@H](C)Nc4ncnc5c(C(=O)N6CCCC6(C)C)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-(2,2-dimethylpyrrolidine-1-carbonyl)quinazolin-4-amine |

TABLE 1-continued
List of preferred compounds of Formula (I)
| Example | Structure | Chemical name |
|---|---|---|
| 79 | 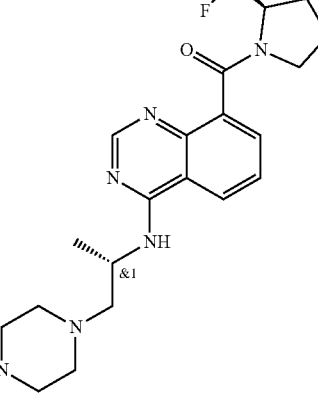 | methyl N-[4-methyl-5-({4-[(2S)-2-({8-[(2R)-2-(trifluoromethyl)pyrrolidine-1-carbonyl]quinazolin-4-yl}amino)propyl]piperazin-1-yl}sulfonyl)-1,3-thiazol-2-yl]carbamate |
| 80 | 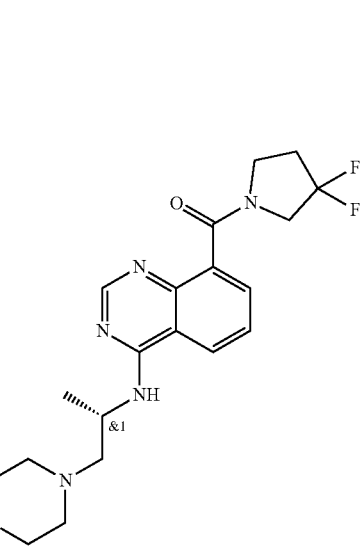 | methyl N-[5-({4-[(2S)-2-{[8-(3,3-difluoropyrrolidine-1-carbonyl)quinazolin-4-yl]amino}propyl]piperazin-1-yl}sulfonyl)-4-methyl-1,3-thiazol-2-yl]carbamate |

TABLE 1-continued
List of preferred compounds of Formula (I)
| Example | Structure | Chemical name |
|---|---|---|
| 81 | 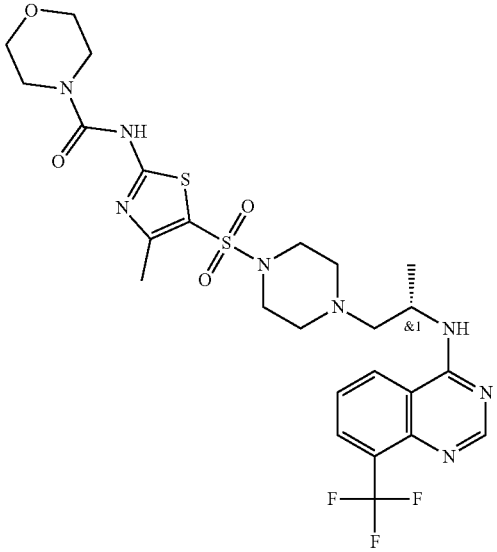 [SMILES: Cc1nc(NC(=O)N2CCOCC2)sc1S(=O)(=O)N1CCN(C[C@H](C)Nc2ncnc3c(C(F)(F)F)cccc23)CC1] | N-[4-methyl-5-({4-[(2S)-2-{[8-(trifluoromethyl)quinazolin-4-yl]amino}propyl]piperazin-1-yl}sulfonyl)-1,3-thiazol-2-yl]morpholine-4-carboxamide |
| 82 | 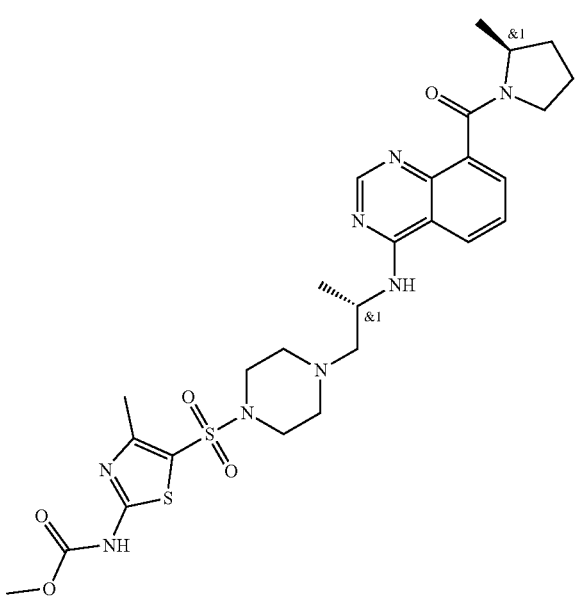 [SMILES: COC(=O)Nc1nc(C)c(S(=O)(=O)N2CCN(C[C@H](C)Nc3ncnc4c(C(=O)N5CCC[C@@H]5C)cccc34)CC2)s1] | methyl N-[4-methyl-5-({4-[(2S)-2-({8-[(2S)-2-methylpyrrolidine-1-carbonyl]quinazolin-4-yl}amino)propyl]piperazin-1-yl}sulfonyl)-1,3-thiazol-2-yl]carbamate |

TABLE 1-continued

List of preferred compounds of Formula (I)

| Example | Structure | Chemical name |
|---|---|---|
| 83 | 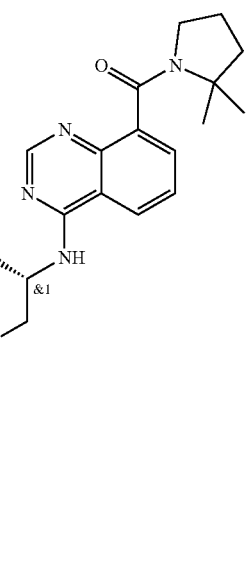 | methyl N-[5-({4-[(2S)-2-{[8-(2,2-dimethylpyrrolidine-1-carbonyl)quinazolin-4-yl]amino}propyl]piperazin-1-yl}sulfonyl)-4-methyl-1,3-thiazol-2-yl]carbamate |
| 84 | 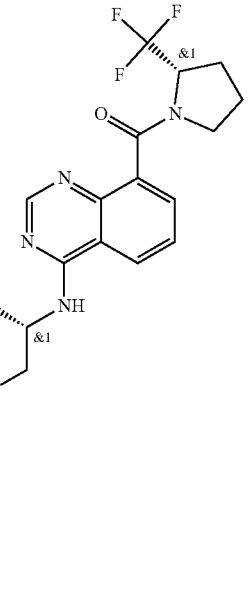 | methyl N-[4-methyl-5-({4-[(2S)-2-({8-[(2S)-2-(trifluoromethyl)pyrrolidine-1-carbonyl]quinazolin-4-yl}amino)propyl]piperazin-1-yl}sulfonyl)-1,3-thiazol-2-yl]carbamate |
| 85 | 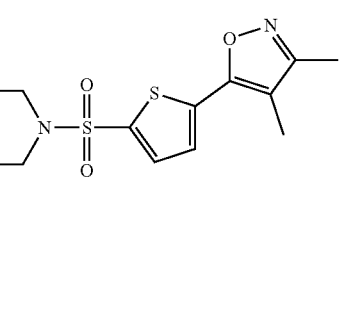 | 8-{3-azabicyclo[3.1.0]hexane-3-carbonyl}-N-[(2S)-1-(4-{[5-(3,4-dimethyl-1,2-oxazol-5-yl)thiophen-2-yl]sulfonyl}piperazin-1-yl)propan-2-yl]quinazolin-4-amine |

TABLE 1-continued

List of preferred compounds of Formula (I)

| Example | Structure | Chemical name |
|---|---|---|
| 86 | 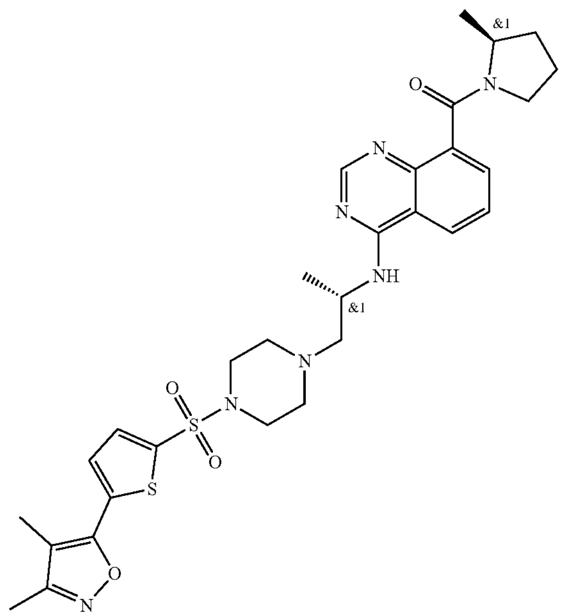 [SMILES: Cc1noc(-c2ccc(S(=O)(=O)N3CCN(C[C@H](C)Nc4ncnc5c(C(=O)N6CCC[C@@H]6C)cccc45)CC3)s2)c1C] | N-[(2S)-1-(4-{[5-(3,4-dimethyl-1,2-oxazol-5-yl)thiophen-2-yl]sulfonyl}piperazin-1-yl)propan-2-yl]-8-[(2S)-2-methylpyrrolidine-1-carbonyl]quinazolin-4-amine |
| 87 | 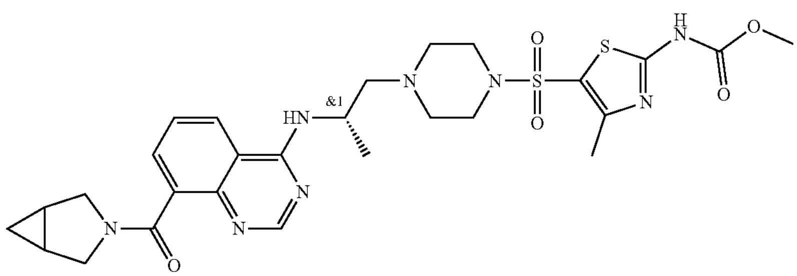 [SMILES: COC(=O)Nc1nc(C)c(S(=O)(=O)N2CCN(C[C@H](C)Nc3ncnc4c(C(=O)N5CC6CC6C5)cccc34)CC2)s1] | methyl N-[5-({4-[(2S)-2-[(8-{3-azabicyclo[3.1.0]hexane-3-carbonyl}quinazolin-4-yl)amino]propyl]piperazin-1-yl}sulfonyl)-4-methyl-1,3-thiazol-2-yl]carbamate |
| 88 | 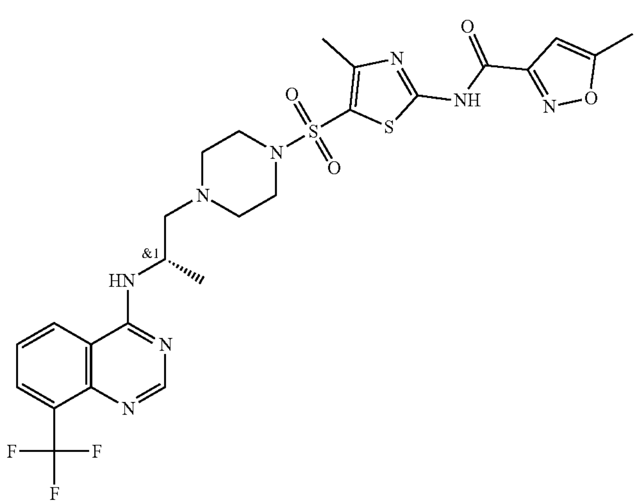 [SMILES: Cc1cc(C(=O)Nc2nc(C)c(S(=O)(=O)N3CCN(C[C@H](C)Nc4ncnc5c(C(F)(F)F)cccc45)CC3)s2)no1] | 5-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]-1,2-oxazole-3-carboxamide |

TABLE 1-continued
List of preferred compounds of Formula (I)
| Example | Structure | Chemical name |
|---|---|---|
| 89 | 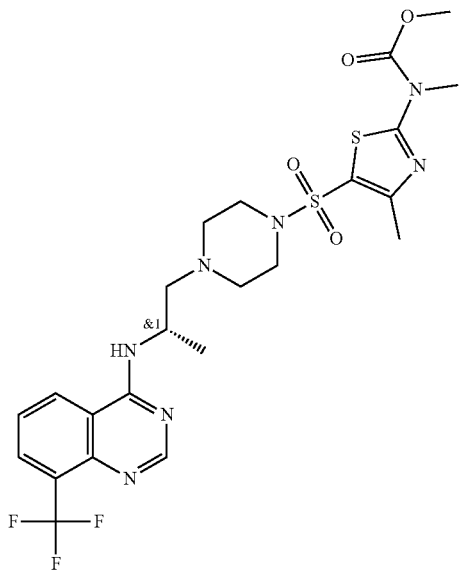 [SMILES: COC(=O)N(C)c1nc(C)c(S(=O)(=O)N2CCN(C[C@H](C)Nc3ncnc4c(C(F)(F)F)cccc34)CC2)s1] | methyl N-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate |
| 90 | 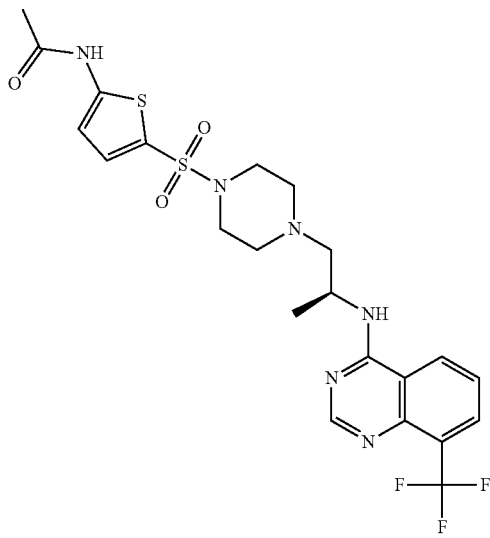 [SMILES: CC(=O)Nc1ccc(S(=O)(=O)N2CCN(C[C@H](C)Nc3ncnc4c(C(F)(F)F)cccc34)CC2)s1] | N-[5-({4-[(2S)-2-{[8-(trifluoromethyl)quinazolin-4-yl]amino}propyl]piperazin-1-yl}sulfonyl)thiophen-2-yl]acetamide |

TABLE 1-continued

List of preferred compounds of Formula (I)

| Example | Structure | Chemical name |
|---|---|---|
| 91 | 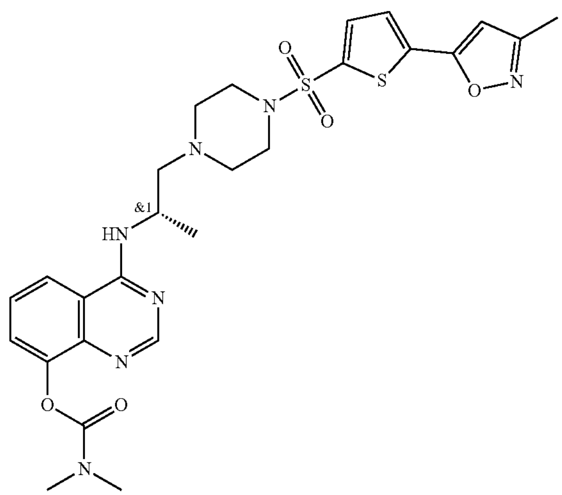 [SMILES: Cc1cc(-c2ccc(S(=O)(=O)N3CCN(C[C@H](C)Nc4ncnc5c(OC(=O)N(C)C)cccc45)CC3)s2)on1] | 4-{[(2S)-1-(4-{[5-(3-methyl-1,2-oxazol-5-yl)thiophen-2-yl]sulfonyl}piperazin-1-yl)propan-2-yl]amino}quinazolin-8-yl N,N-dimethylcarbamate |
| 92 | 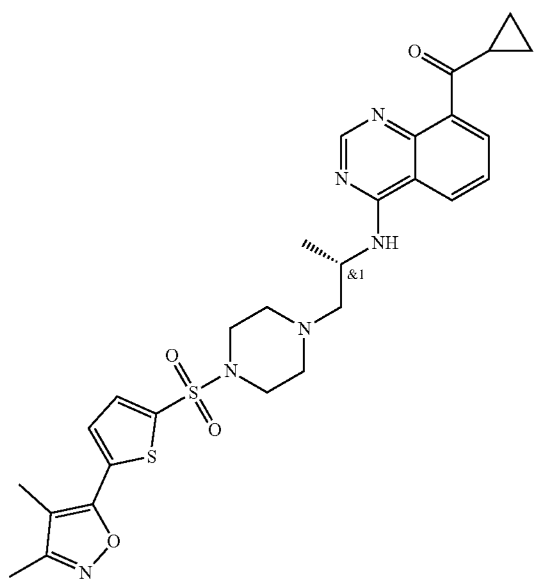 [SMILES: Cc1noc(-c2ccc(S(=O)(=O)N3CCN(C[C@H](C)Nc4ncnc5c(C(=O)C6CC6)cccc45)CC3)s2)c1C] | 8-cyclopropanecarbonyl-N-[(2S)-1-(4-{[5-(3,4-dimethyl-1,2-oxazol-5-yl)thiophen-2-yl]sulfonyl}piperazin-1-yl)propan-2-yl]quinazolin-4-amine |
| 93 | 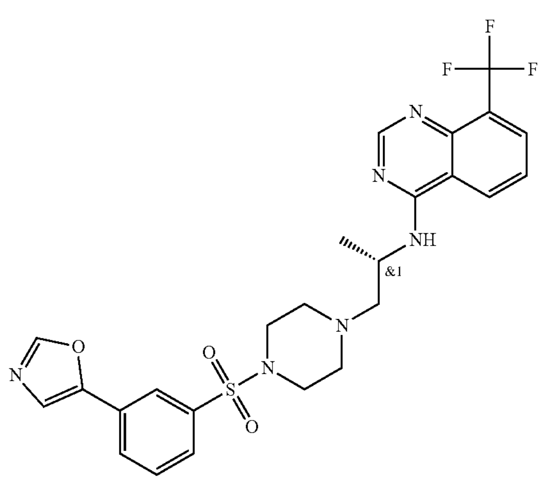 [SMILES: C[C@@H](CN1CCN(S(=O)(=O)c2cccc(-c3cnco3)c2)CC1)Nc1ncnc2c(C(F)(F)F)cccc12] | N-[(2S)-1-{4-[3-(1,3-oxazol-5-yl)benzenesulfonyl]piperazin-1-yl}propan-2-yl]-8-(trifluoromethyl)quinazolin-4-amine |

TABLE 1-continued

List of preferred compounds of Formula (I)

| Example | Structure | Chemical name |
|---|---|---|
| 94 | 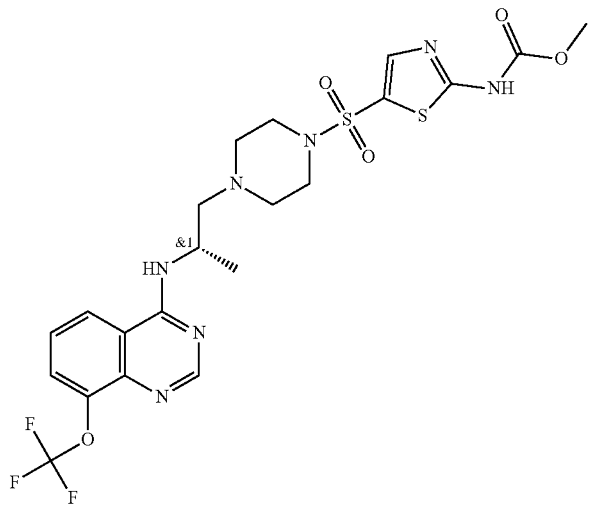 [SMILES: COC(=O)Nc1ncc(S(=O)(=O)N2CCN(C[C@H](C)Nc3ncnc4c(OC(F)(F)F)cccc34)CC2)s1] | methyl N-[5-({4-[(2S)-2-{[8-(trifluoromethoxy)quinazolin-4-yl]amino}propyl]piperazin-1-yl}sulfonyl)-1,3-thiazol-2-yl]carbamate |
| 95 | 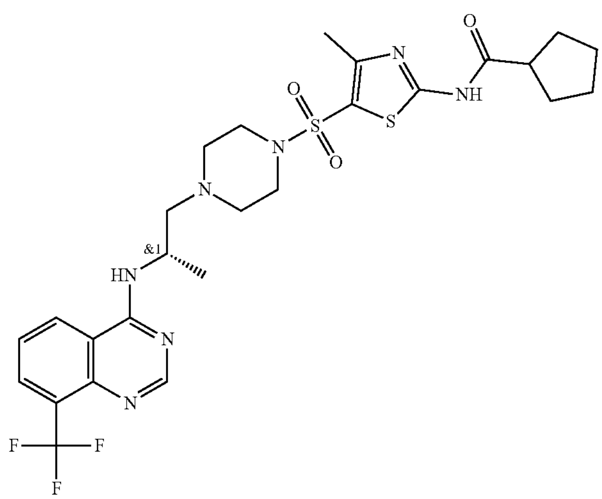 [SMILES: Cc1nc(NC(=O)C2CCCC2)sc1S(=O)(=O)N1CCN(C[C@H](C)Nc2ncnc3c(C(F)(F)F)cccc23)CC1] | N-[4-methyl-5-({4-[(2S)-2-{[8-(trifluoromethyl)quinazolin-4-yl]amino}propyl]piperazin-1-yl}sulfonyl)-1,3-thiazol-2-yl]cyclopentanecarboxamide |
| 96 | 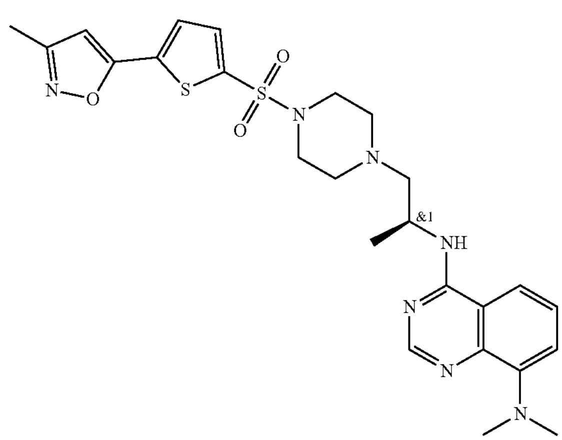 | N8,N8-dimethyl-N4-[(2S)-1-(4-{[5-(3-methyl-1,2-oxazol-5-yl)thiophen-2-yl]sulfonyl}piperazin-1-yl)propan-2-yl]quinazoline-4,8-diamine |

TABLE 1-continued

List of preferred compounds of Formula (I)

| Example | Structure | Chemical name |
|---|---|---|
| 97 | 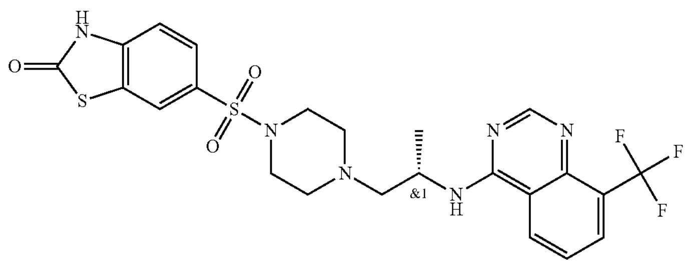 [SMILES: C[C@@H](CN1CCN(S(=O)(=O)c2ccc3[nH]c(=O)sc3c2)CC1)Nc1ncnc2c(C(F)(F)F)cccc12] | 6-({4-[(2S)-2-{[8-(trifluoromethyl)quinazolin-4-yl]amino}propyl]piperazin-1-yl}sulfonyl)-2,3-dihydro-1,3-benzothiazol-2-one |
| 98 | 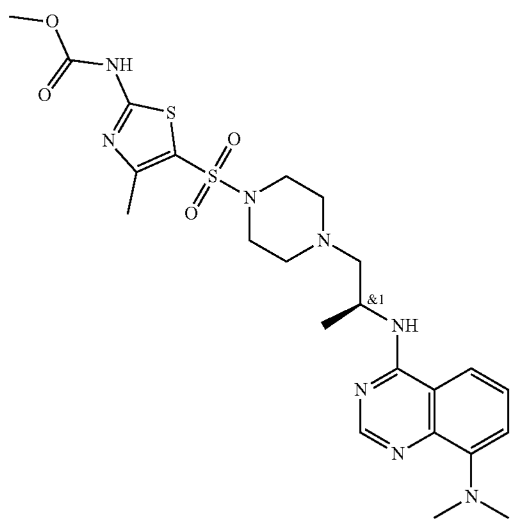 | methyl N-[5-({4-[(2S)-2-{[8-(dimethylamino)quinazolin-4-yl]amino}propyl]piperazin-1-yl}sulfonyl)-4-methyl-1,3-thiazol-2-yl]carbamate |
| 99 | 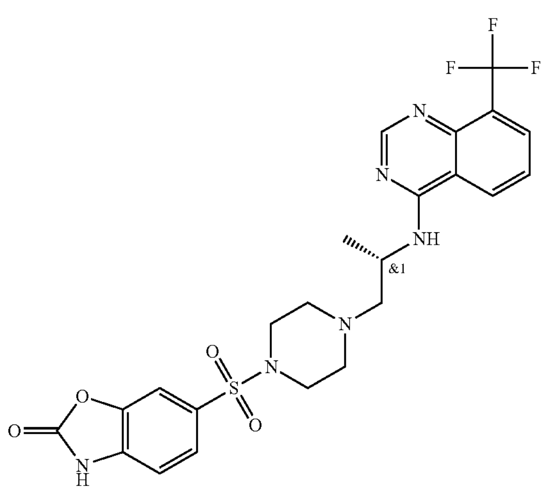 [SMILES: C[C@@H](CN1CCN(S(=O)(=O)c2ccc3[nH]c(=O)oc3c2)CC1)Nc1ncnc2c(C(F)(F)F)cccc12] | 6-({4-[(2S)-2-{[8-(trifluoromethyl)quinazolin-4-yl]amino}propyl]piperazin-1-yl}sulfonyl)-2,3-dihydro-1,3-benzoxazol-2-one |

TABLE 1-continued
List of preferred compounds of Formula (I)
| Example | Structure | Chemical name |
|---|---|---|
| 100 | 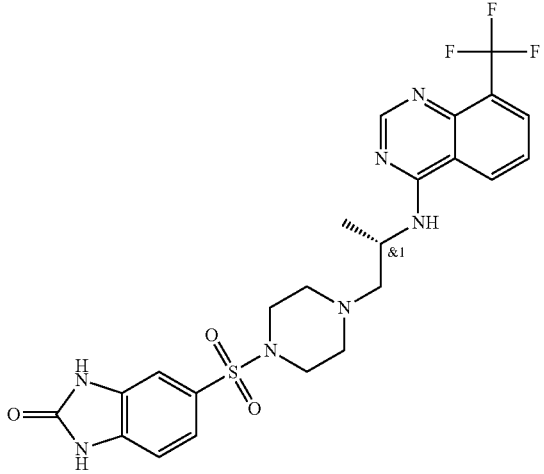 [SMILES: C[C@@H](CN1CCN(S(=O)(=O)c2ccc3[nH]c(=O)[nH]c3c2)CC1)Nc1ncnc2c(C(F)(F)F)cccc12] | 5-({4-[(2S)-2-{[8-(trifluoromethyl)quinazolin-4-yl]amino}propyl]piperazin-1-yl}sulfonyl)-2,3-dihydro-1H-1,3-benzodiazol-2-one |
| 101 | 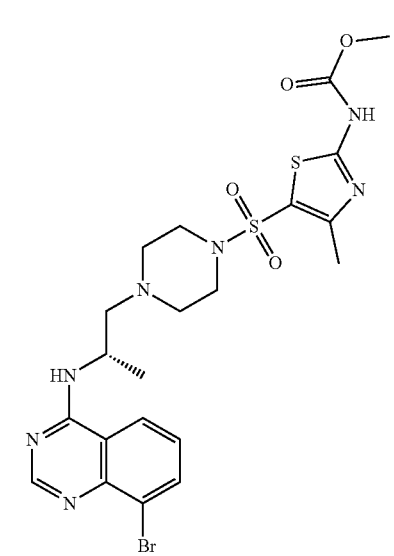 [SMILES: COC(=O)Nc1nc(C)c(S(=O)(=O)N2CCN(C[C@H](C)Nc3ncnc4c(Br)cccc34)CC2)s1] | methyl N-[5-({4-[(2S)-2-[(8-bromoquinazolin-4-yl)amino]propyl]piperazin-1-yl}sulfonyl)-4-methyl-1,3-thiazol-2-yl]carbamate |

The compounds of the present invention can be prepared in a number of ways known to one skilled in the art of organic synthesis. It will be understood by those skilled in the art of organic synthesis that the functionality present on the molecule should be consistent with the transformation proposed. This will sometimes require a modification of the order of synthetic steps in order to obtain a desired compound of the invention. The compounds of formula (I), including all the compounds here above listed, can be generally prepared according to the procedure outlined in Schemes shown below using generally known methods.

SCHEME 1

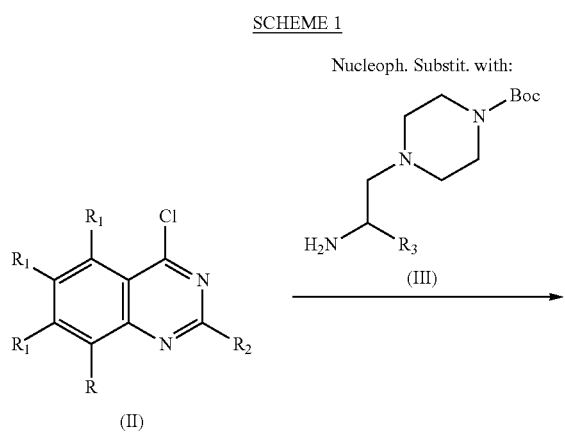

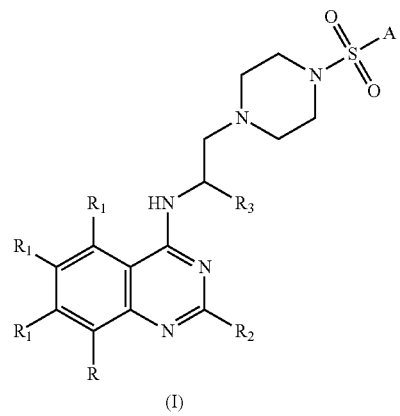

Compound of formula (II) can be reacted with a nitrogen based nucleophile of formula (III), in the presence of a suitable base e.g. N,N-diisopropylethylamine in a suitable solvent such as Acetonitrile, to provide compound (IV), containing a Boc-protected amino group. Deprotection under well-known procedures gives compound (V) and final reaction with a suitable sulphonyl halide (VI) leads to compound of formula (I).

In another embodiment of the present invention, compound (II) can be synthesized as reported in Scheme 2.

SCHEME 2

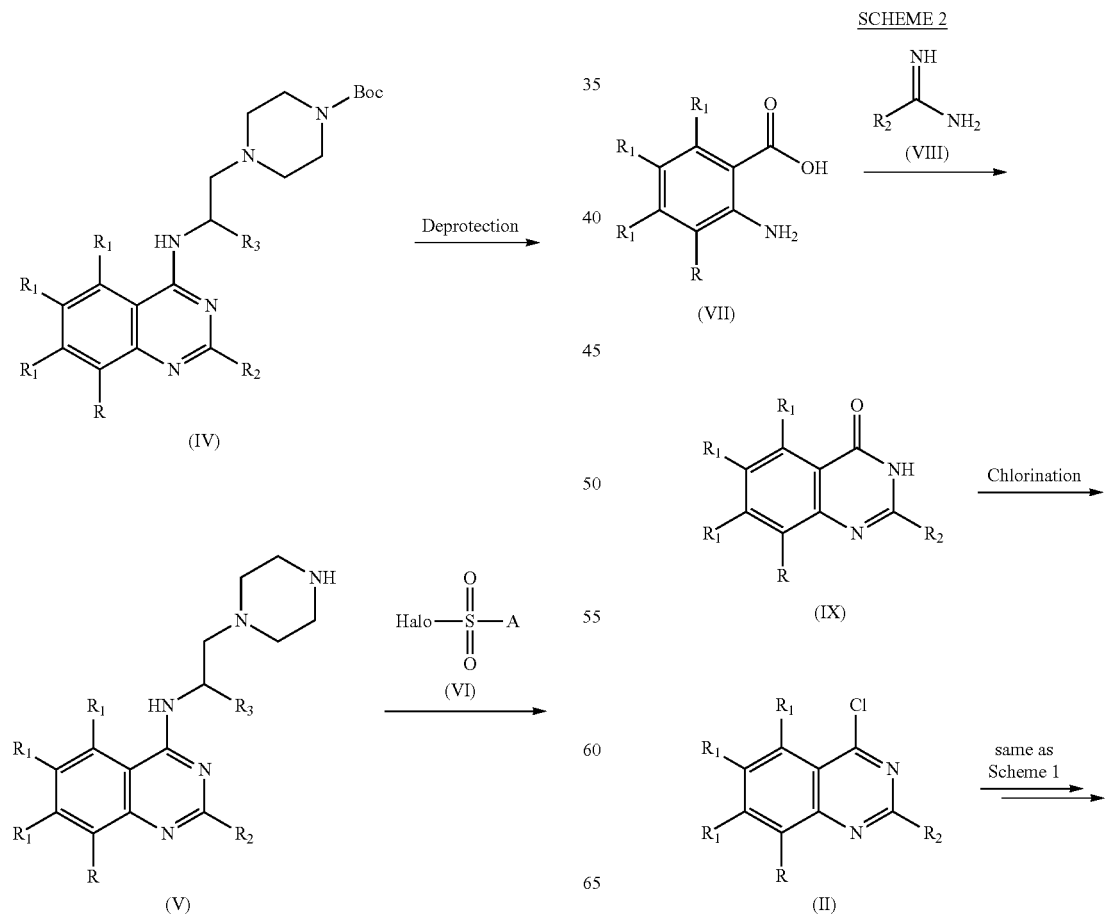

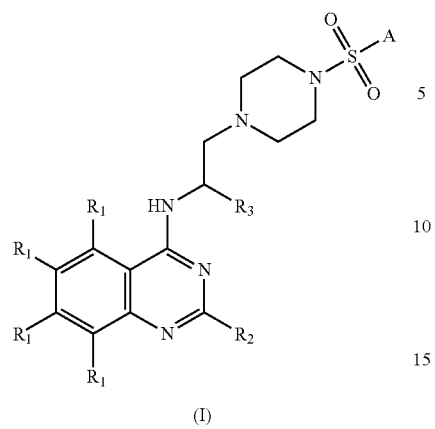

(I)

(XII)

Cyclization of commercially available compound (VII) with the appropriate carboximidamide (VIII) and subsequent chlorination with a suitable chlorinating agent such as POCl$_3$ provides intermediate (II). Compound (II) is then converted to the final compound (I) by following the synthetic sequence previously outlined in Scheme 1.

Alternatively, for compounds where R2=CH$_3$, compound (XII) can be synthesized as reported in Scheme 3.

In another embodiment of the present invention, wherein A is an N-acylated aminothiazole with R4 and R5=H, CH$_3$, compound (XVIII) may be obtained according to Scheme 4. Reaction of intermediate (V) with N-acetyl thiazole sulfonyl chloride (XIII) followed by deacetylation under acidic conditions provides intermediate (XV). Final acetylation with a suitable acyl chloride in presence of a base, such as N,N-dimethyl-4-pyridinamine, leads to final compound (XVIII).

SCHEME 3

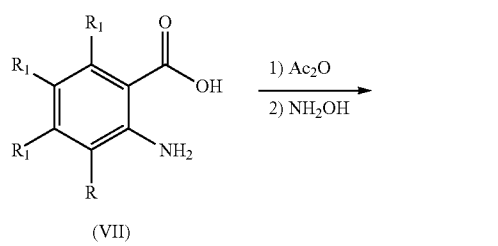

SCHEME 4

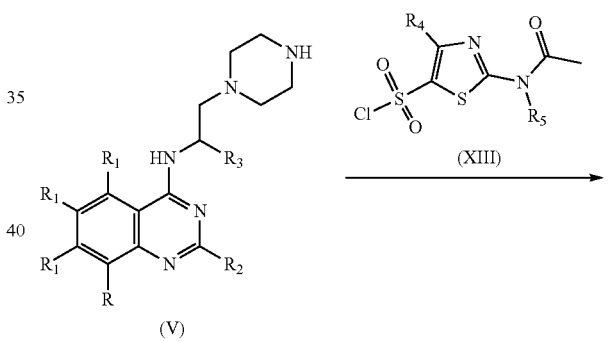

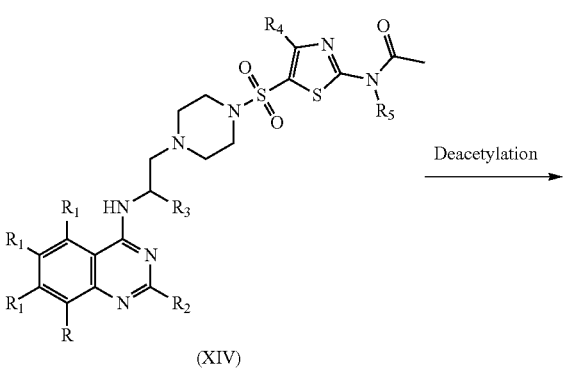

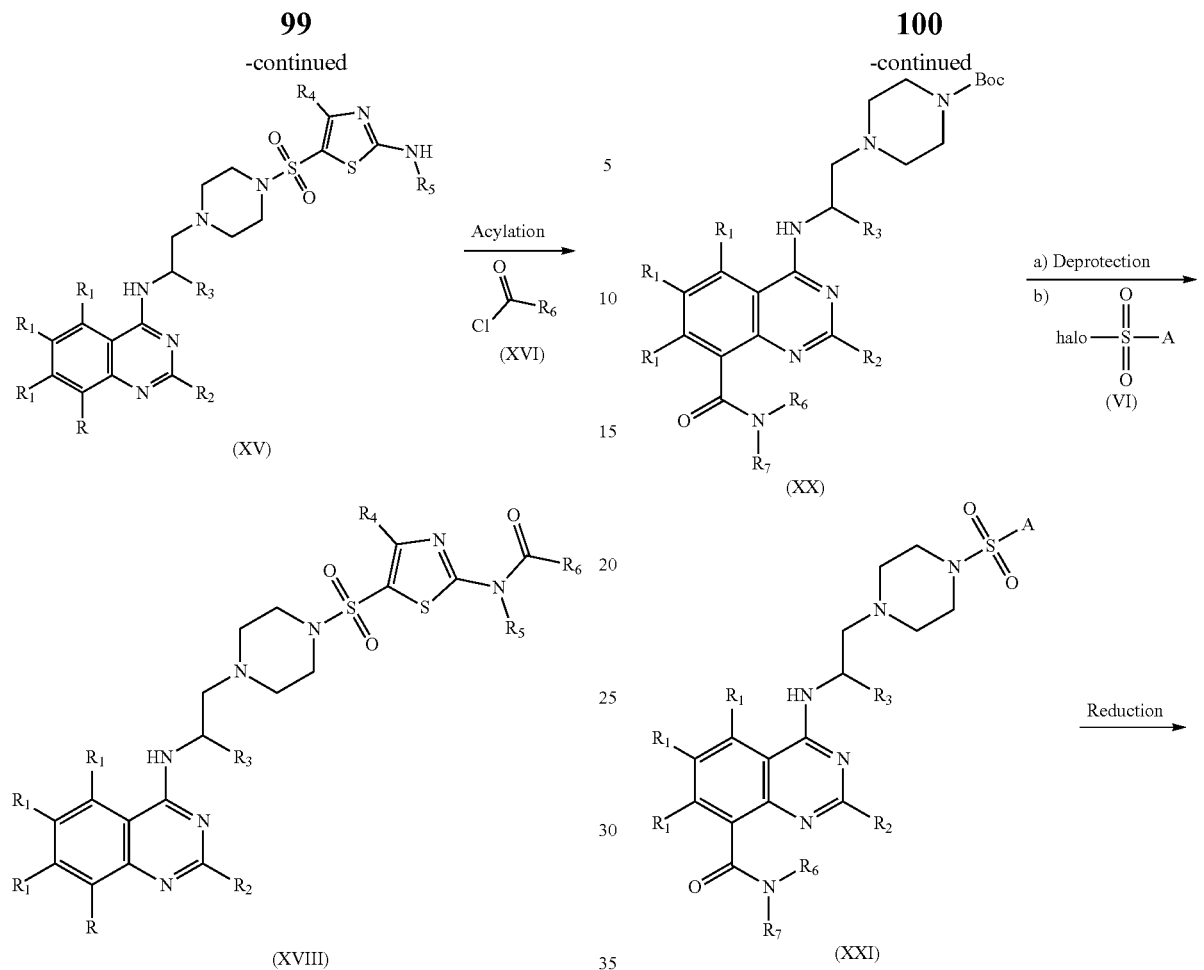

For compounds wherein R is an amide or an aminomethyl group, compounds (XXI) and (XXII) can be synthesized as outlined in Scheme 5.

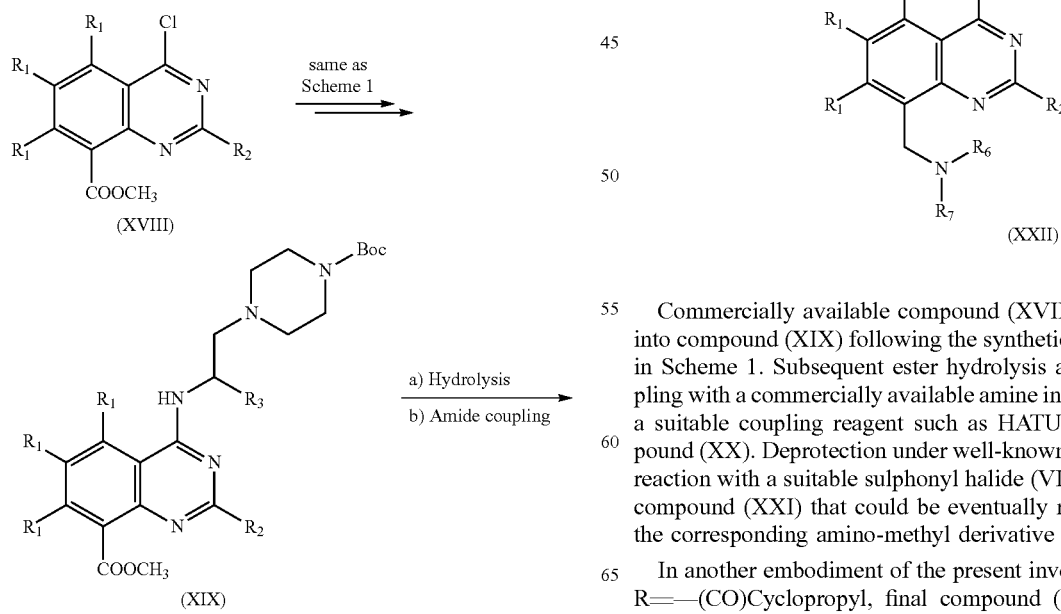

Commercially available compound (XVIII) is converted into compound (XIX) following the synthetic route outlined in Scheme 1. Subsequent ester hydrolysis and amide coupling with a commercially available amine in the presence of a suitable coupling reagent such as HATU leads to compound (XX). Deprotection under well-known procedure and reaction with a suitable sulphonyl halide (VI) provides final compound (XXI) that could be eventually reduced to give the corresponding amino-methyl derivative (XXII).

In another embodiment of the present invention, wherein R=—(CO)Cyclopropyl, final compound (XXXI) can be obtained ad highlighted in Scheme 6.

Cyclization of commercially available compound (XXIII) with formamidine (XXIV) and subsequent Weinreb amidation in the presence of a suitable coupling reagent leads to intermediate (XXVII). Chlorination using well-known procedures provides intermediate (XXVIII) that is then reacted with Cyclopropylmagnesium bromide to obtain the desired ketone intermediate (XXX). Final compound (XXXI) is then obtained by following the synthetic sequence previously outlined in Scheme 1.

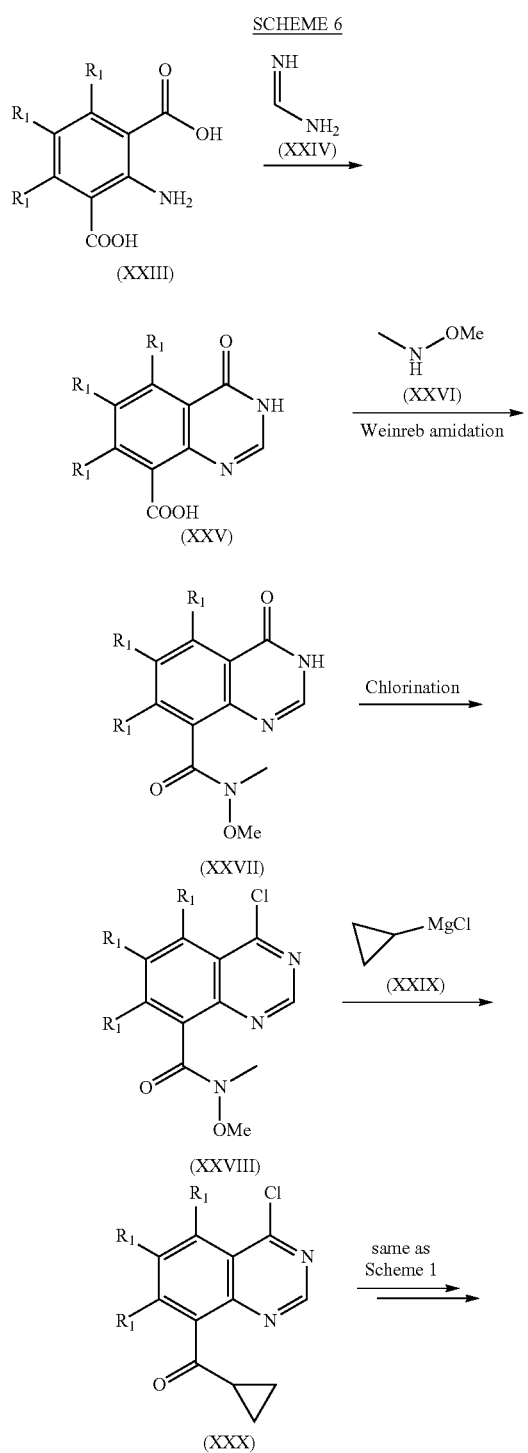

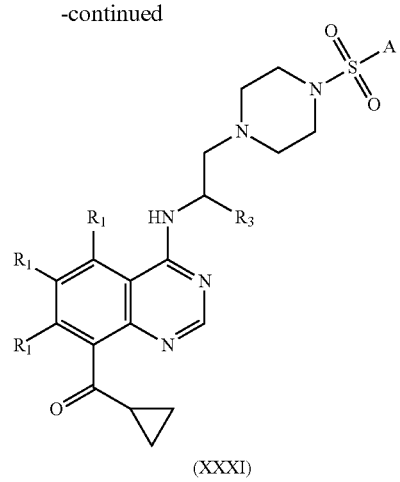

(XXXI)

The compounds of formula (I) of the present invention have surprisingly been found to effectively inhibit receptor LPA2. Advantageously, the inhibition of LPA2 may result in efficacious treatment of the diseases or condition wherein the LPA receptor is involved.

In this respect, it has now been found that the compounds of formula (I) of the present invention have an antagonist drug potency expressed as half maximal inhibitory concentration ($IC_{50}$) on LPA2 lesser or equal than 1000 nM as shown in the present experimental part.

Preferably, the compounds of the present invention have an $IC_{50}$ on LPA2 lesser or equal than 100 nM.

More preferably, the compounds of the present invention have an $IC_{50}$ on LPA2 lesser or equal than 10 nM.

In one aspect, the present invention refers to a compound of formula (I) for use as a medicament.

In a preferred embodiment, the invention refers to a compound of formula (I) for use in the treatment of disorders associated with LPA receptors mechanism.

In a further embodiment, the present invention refers to a compound of formula (I) for use in the treatment of a disease, disorder or condition associated with dysregulation of lysophosphatidic acid receptor 2 (LPA2).

In one embodiment, the present invention refers to a compound of formula (I) useful for the prevention and/or treatment of fibrosis and/or diseases, disorders, or conditions that involve fibrosis.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Preferably, the compounds of formula (I) of the present invention are useful for the treatment and/or prevention of fibrosis such as pulmonary fibrosis, idiopathic pulmonary fibrosis (IPF), hepatic fibrosis, renal fibrosis, ocular fibrosis, cardiac fibrosis, arterial fibrosis and systemic sclerosis.

More preferably, the compounds of formula (I) of the present invention are useful for the treatment of idiopathic pulmonary fibrosis (IPF).

In one aspect, the invention also refers to a method for the prevention and/or treatment of disorders associated with LPA receptors mechanisms, said method comprises administering to a patient in need of such treatment a therapeutically effective amount of a compound of formula (I).

In one aspect, the invention refers to the use of a compound of formula (I) in the preparation of a medicament for the treatment of disorders associated with LPA receptors mechanism.

In a further aspect, the invention refers to a method for the prevention and/or treatment of disorder or condition associated with dysregulation of lysophosphatidic acid receptor 2 (LPA2) administering a patient in need of such treatment a therapeutically effective amount of a compound of formula (I).

In a further aspect, the invention refers to the use of a compound of formula (I) according to the invention for the treatment of disorders associated with LPA receptors mechanism.

In a further aspect, the present invention refers to the use of a compound of formula (I) for the treatment of a disease, disorder or condition associated with dysregulation of receptor 2 (LPA2).

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan.

The compounds of formula (I) may be administered once or according to a dosing regimen wherein a number of doses are administered at varying intervals of time for a given period of time. Typical daily dosages may vary depending upon the route of administration chosen.

The present invention also refers to a pharmaceutical composition comprising a compound of formula (I) thereof in admixture with at least one or more pharmaceutically acceptable carrier or excipient.

In one embodiment, the invention refers to a pharmaceutical composition of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably, the compounds of the present invention are administered orally or by inhalation.

More preferably, the compounds of the present invention are administered orally.

In one preferred embodiment, the pharmaceutical composition comprising the compound of formula (I) is a solid oral dosage form such as tablets, gelcaps, capsules, caplets, granules, lozenges and bulk powders.

In one embodiment, the pharmaceutical composition comprising the compound of formula (I) is a tablet.

The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. In a further embodiment, the pharmaceutical composition comprising a compound of formula (I) is a liquid oral dosage forms such as aqueous and non-aqueous solutions, emulsions, suspensions, syrups, and elixirs. Such liquid dosage forms can also contain suitable known inert diluents such as water and suitable known excipients such as preservatives, wetting agents, sweeteners, flavorants, as well as agents for emulsifying and/or suspending the compounds of the invention.

In a further embodiment, the pharmaceutical composition comprising the compound of formula (I) is an inhalable preparation such as inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

The compounds of the invention can be administered as the sole active agent or in combination with other pharmaceutical active ingredients.

The dosages of the compounds of the invention depend upon a variety of factors including among others the particular disease to be treated, the severity of the symptoms, the route of administration and the like.

The invention is also directed to a device comprising a pharmaceutical composition comprising a compound of Formula (I) according to the invention, in form of a single- or multi-dose dry powder inhaler or a metered dose inhaler.

All preferred groups or embodiments described above for compounds of formula I may be combined among each other and apply as well mutatis mutandis.

The various aspects of the invention described in this application are illustrated by the following examples which are not meant to limit the invention in any way.

Preparations of Intermediates and Examples

Chemical Names of the compounds were generated with Structure To Name Enterprise 10.0 Cambridge Software.

All reagents, for which the synthesis is not described in the experimental part, are either commercially available, or are known compounds or may be formed from known compounds by known methods by a person skilled in the art.

Abbreviation—Meaning $AC_2O$=Acetic anhydride
$BBr_3$=Boron tribromide
$BH_3$=Borane
$CCl_4$=Carbon tetrachloride
$Cs_2CO_3$=Cesium carbonate
CuI=Copper iodide
DCM=Dichloromethane
DIPEA=N,N-diisopropylethylamine DMAP=4-Dimethylaminopyridine
DMF=N,N-Dimethylformamide
DMSO=Dimethylsulfoxide
EtOAc=Ethyl acetate
EtOH=Ethanol
$Fe^0$=Metallic iron
h=hour
HATU=1-[Bis(dimethylamino)methylene]-1H-1,2,3-triazolo[4,5-b]pyridinium 3-oxid hexafluorophosphate
$H_2O$=Water
HCOOH=Formic acid
$K_2CO_3$=Potassium carbonate
LC-MS=liquid chromatography/mass spectrometry
MeCN=Acetonitrile
MeOH=Methanol
MW=Microwave
$NaHCO_3$=Sodium hydrogen carbonate
$Na_2SO_4$=Sodium sulfate
NBS=N-Bromosuccinimide
$NH_4Cl$=Ammonium chloride
$NH_4HCO_3$=Ammonium hydrogen carbonate
$NH_4OH$=Ammonium hydroxide
$NH_3$=Ammonia
$Pd_2(dba)_3$=Tris(dibenzylideneacetone)dipalladium(O)
$POCl_3$=Phosphorus(V) oxychloride
r.t.=room temperature
SCX=strong cation exchange
STAB=Sodium triacetoxyborohydride
TFA=Trifluoroacetic acid
UPLC=ultra-performance liquid chromatography
Xantphos=4,5-Bis(diphenylphosphino)-9,9-dimethylxanthene

GENERAL EXPERIMENTAL DETAILS AND METHODS

Analytical Method
Instruments, Materials and Methods Employed for Analyses $^1$H-NMR spectra were performed on a Varian MR-400 spectrometer operating at 400 MHZ (proton frequency), equipped with: a self-shielded Z-gradient coil 5 mm 1H/nX broadband probe head for reverse detection, deuterium digital lock channel unit, quadrature digital detection unit with trans mitter offset frequency shift, or on AgilentVNMRS-500 or on a Bruker Avance 400 or on a Bruker Avance 300 spectrometers. Chemical shift are reported as δ values in ppm relative to trimethylsilane (TMS) as an internal standard. Coupling constants (J values) are given in hertz (Hz) and multiplicities are reported using the following abbreviation (s=singlet, d=doublet, t=triplet, q=quartet, m=multiplet, br. s=broad singlet, nd=not determined).

LC/UV/MS Analytical Methods

LC/MS retention times are estimated to be affected by an experimental error of ±0.5 min. LCMS may be recorded under the following conditions: diode array DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative electron spray ES ionization mode and/or Fractionlynx system used in analytical mode coupled with ZQ™ single quadrupole operated in positive and/or negative ES ionisation mode or on a Waters Alliance e2695 with Photodiode Detector 2998 coupled with Column Oven and Mass Spectrometer ZQ operated in positive and/or negative ES ionisation mode. Quality Control methods used operated under low pH conditions or under high pH conditions:

Method 1, low pH conditions column: Acquity CSH C18 2.1×50 mm 1.7 um, the column temperature was 40° C.; mobile phase solvent A was milliQ water+0.1% HCOOH, mobile phase solvent B MeCN+0.1% HCOOH. The flow rate was 1 mL/min.

The gradient table was t=0 min 97% A 3% B, t=1.5 min 0.1% A 99.9% B, t=1.9 min 0.1% A 99.9% B and t=2 min 97% A 3% B. The UV detection range was 210-350 nm and ES+/ES− range was 100 to 1500 AMU.

Method 2, high pH conditions: column: Acquity Kinetex 1.7 um EVO C18 100A, 2.1×50 mm, the column temperature was 40° C.; mobile phase solvent A was 10 mM aqueous solution of NH4HCO3 adjusted to pH=10 with ammonia, mobile phase solvent B MeCN. The flow rate was 1 mL/min. The gradient table was t=0 min 97% A 3% B, t=1.5 min 0.1% A 99.9% B, t=1.9 min 0.1% A 99.9% B and t=2 min 97% A 3% B. The UV detection range was 210-350 nm and ES+/ES−range was 100 to 1500 AMU.

Method 3, low pH conditions: column: Acquity CSH C18 2.1×50 mm 1.7 μm, the column temperature was 40° C.; mobile phase solvent A was milliQ water/MeCN 95:5+0.05% HCOOH, mobile phase solvent B MeCN/milliQ water 95:5+0.05% HCOOH. The flow rate was 1 mL/min. The gradient table was t=0 min 99% A 1% B, t=1.5 min 0.1% A 99.9% B, t=1.9 min 0.1% A 99.9% B and t=2 min 99% A 1% B. The UV detection range was 210-400 nm and ES+/ES− range was 100 to 1200 AMU.

Method 4, low pH conditions: column: Phenomenex Gemini-NX C18, 150×2.0 mm, 3 μm with security guard Gemini-NX C18, 4×2.0 mm, 3 μm, the column temperature was 25° C.; mobile phase solvent A was water+0.1% Formic acid filtered with 0.22 μm nylon filter, mobile phase solvent B Acetonitrile+0.1% Formic acid filtered with 0.22 μm nylon filter. The flow rate was 0.2 mL/min. The gradient table was t=0 min 95% A 5% B, t=10 min 20% A 80% B, t=30 min 20% A 80 B. The UV detection λ, was 210 nm and ES+/ES-range was 50 to 900 Da.

Method 5 (Chiesi), low pH conditions: column: Acquity CSH C18 2.1×50 mm 1.7 μm, the column temperature was 40° C.; mobile phase solvent A was milliQ water/MeCN 95:5+0.05% HCOOH, mobile phase solvent B MeCN/milliQ water 95:5+0.05% HCOOH. The flow rate was 1 mL/min. The gradient table was t=0 min 99% A 1% B, t=3.5 min 0.1% A 99.9% B, t=3.9 min 0.1% A 99.9% B and t=4 min 99% A 1% B. The UV detection range was 210-400 nm and ES+/ES− range was 100 to 1200 AMU.

Example 1

Methyl N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate

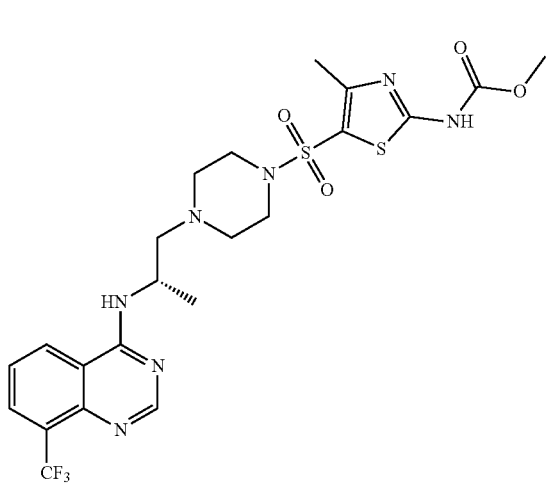 [SMILES: COC(=O)Nc1nc(C)c(S(=O)(=O)N2CCN(C[C@H](C)Nc3ncnc4c(C(F)(F)F)cccc34)CC2)s1]

Step 1: Preparation of tert-butyl 4-[(2S)-2-{[8-(trifluoromethyl)quinazolin-4-yl]amino}propyl]piperazine-1-carboxylate (Intermediate 1)

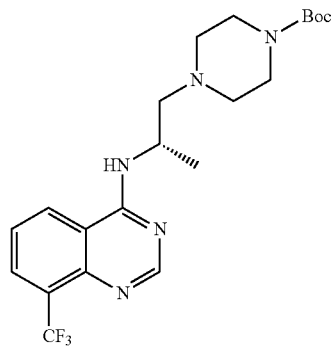 [SMILES: C[C@@H](CN1CCN(C(=O)OC(C)(C)C)CC1)Nc1ncnc2c(C(F)(F)F)cccc12]

To a solution of 4-chloro-8-(trifluoromethyl)quinazoline (232 mg, 1 mmol) in MeCN (7 mL), tert-butyl 4-[(2S)-2-aminopropyl]piperazine-1-carboxylate (267 mg, 1.1 mmol) and DIPEA (0.260 mL, 1.5 mmol) were added and the solution was heated under stirring at 85° C. for 4 h. The mixture was partitioned between $H_2O$ and EtOAc. The aqueous phase was extracted again with EtOAc and the combined organic phases were concentrated under vacuum to afford Intermediate 1 (473 mg, crude).

LC-MS (ESI): m/z (M+1): 440.3 (Method 1)

Step 2: Preparation of N-[(2S)-1-piperazin-1-ylpropan-2-yl]-8-(trifluoromethyl)quinazolin-4-amine Hydrochloride (Intermediate 2)

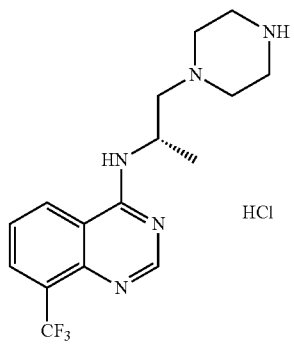 [SMILES: C[C@@H](CN1CCNCC1)Nc1ncnc2c(C(F)(F)F)cccc12 ; Cl]

To a solution of Intermediate 1 (473 mg, crude) in 1,4-dioxane (3 mL), HCl 4M in dioxane (1.33 mL, 5.35 mmol) was added. The reaction mixture was stirred at 25° C. for 6 h. The crude was then concentrated under reduced pressure to provide Intermediate 2 (400 mg, crude)

LC-MS (ESI): m/z (M+1): 340.2. (Method 1)

Step 3: Preparation of methyl N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate (Example 1)

Intermediate 2 (100 mg, 0.26 mmol) was dissolved in DCM/Pyridine 1:4 (5 mL) then methyl N[5-(chlorosulfonyl)-4-methyl-1,3-thiazol-2-yl]carbamate (81 mg, 0.30 mmol) was added and the reaction was stirred at rt for 1 hour. The solvent was removed under vacuum and the crude product was purified by flash chromatography eluting with MeOH in DCM from 0% to 10% to provide the title compound (30 mg, 0.05 mmol, 20% yield) as a white solid.

LC-MS (ESI): m/z (M+1): 574.2 (Method 1)

$^1$H NMR (500 MHz, DMSO-d6) δ ppm 1.21 (d, J=6.31 Hz, 3H), 2.39-2.65 (m, 2H), 2.42 (s, 3H), 2.53-2.59 (m, 4H), 2.98 (br. s., 4H), 3.75 (s, 3H), 4.61 (spt, J=6.91 Hz, 1H), 7.60 (t, J=7.82 Hz, 1H), 8.01-8.25 (m, 2H), 8.44-8.66 (m, 2H), 12.33 (br. s., 1H)

The Examples in the following table were prepared from commercially available reagents by using methods analogous to Example 1.

| Example No. | Structure & Name | Analytical data |
|---|---|---|
| 5 | 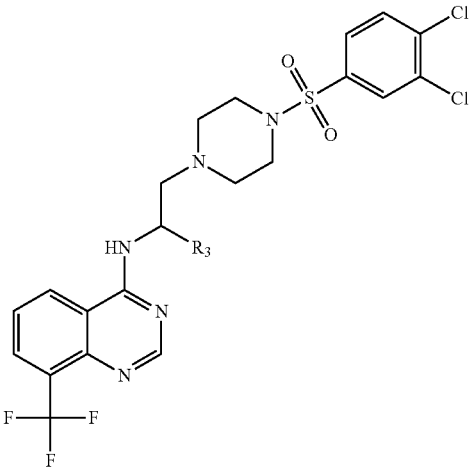<br>N-[(2S)-1-[4-(3,4-dichlorobenzenesulfonyl)piperazin-1-yl]propan-2-yl]-8-(trifluoromethyl)quinazolin-4-amine | LC-MS (ESI): m/z (M + 1): 548 (Method 1)<br>$^1$H NMR (400 MHz, DMSO-d$_6$) δ ppm 8.50-8.56 (m, 2 H), 8.08-8.16 (m, 2 H), 7.90 (d, J = 2.10 Hz, 1 H), 7.88 (d, J = 8.40 Hz, 1 H), 7.67 (dd, J = 8.41, 2.13 Hz, 1 H), 7.59 (t, J = 7.91 Hz, 1 H), 4.56-4.66 (m, 1 H), 2.87-2.96 (m, 4 H), 2.56-2.64 (m, 1 H), 2.51-2.55 (m, 4 H), 2.36-2.44 (m, 1 H), 1.19 (d, J = 6.53 Hz, 3 H) |
| 6 | 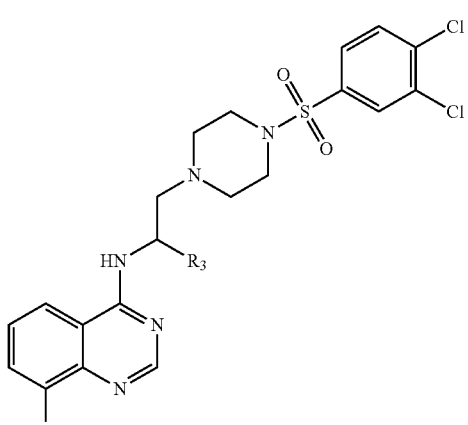<br>8-chloro-N-[(2S)-1-[4-(3,4-dichlorobenzenesulfonyl)piperazin-1-yl]propan-2-yl]quinazolin-4-amine | LC-MS (ESI): m/z (M + 1): 516.1 (Method 1)<br>$^1$H NMR (500 MHz, DMSO-d$_6$) δ ppm 8.50 (s, 1 H), 8.21 (d, J = 8.31 Hz, 1 H), 8.00 (d, J = 8.07 Hz, 1 H), 7.85-7.94 (m, 3 H), 7.67 (dd, J = 8.44, 2.08 Hz, 1 H), 7.44 (t, J = 7.95 Hz, 1 H), 4.59 (dt, J = 13.63, 7.00 Hz, 1 H), 2.84-2.95 (m, 4 H), 2.55-2.62 (m, 1 H), 2.49-2.56 (m, 4 H), 2.34-2.43 (m, 1 H), 1.18 (d, J = 6.60 Hz, 3 H) |
| 7 | 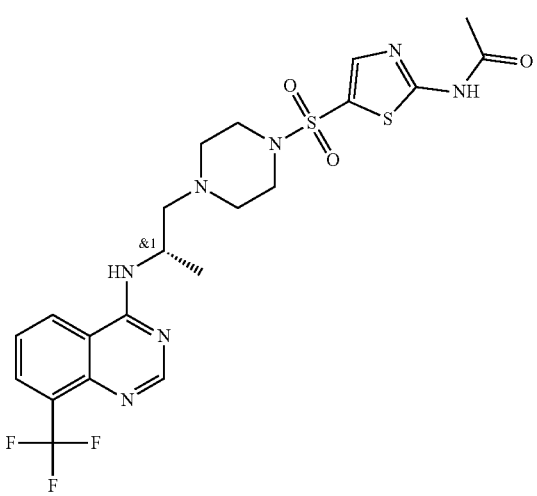 [SMILES: CC(=O)Nc1ncc(S(=O)(=O)N2CCN(C[C@H](C)Nc3ncnc4c(C(F)(F)F)cccc34)CC2)s1] | LC-MS (ESI): m/z (M + 1): 544.1 (Method 1)<br>$^1$H NMR (400 MHz, DMSO-d$_6$) δ ppm 1.20 (d, J = 6.58 Hz, 3 H), 2.18 (s, 3 H), 2.36-2.66 (m, 2 H), 2.57 (br. s., 4 H), 2.91 (br. s., 4 H), 4.61 (dt, J = 13.92, 6.85 Hz, 1 H), 7.60 (t, J = 7.89 Hz, 1 H), 7.93 (s, 1 H), 8.13 (d, J = 7.23 Hz, 2 H), 8.46-8.64 (m, 2 H), 12.67 (br. s., 1 H) |

| Example No. | Structure & Name | Analytical data |
|---|---|---|
| 8 | N-[5-({4-[(2S)-2-{[8-(trifluoromethyl)quinazolin-4-yl]amino}propyl]piperazin-1-yl}sulfonyl)-1,3-thiazol-2-yl]acetamide<br>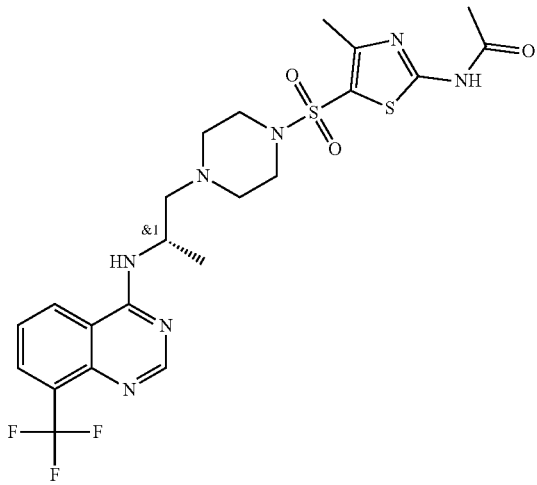 [SMILES: CC(=O)Nc1nc(C)c(S(=O)(=O)N2CCN(C[C@H](C)Nc3ncnc4c(C(F)(F)F)cccc34)CC2)s1]<br>N-[5-({4-[(2S)-2-{[8-(trifluoromethyl)quinazolin-4-yl]amino}propyl]piperazin-1-yl}sulfonyl)-1,3-thiazol-2-yl]acetamide | LC-MS (ESI): m/z (M + 1): 558.2 (Method 1)<br>$^1$H NMR (400 MHz, DMSO-$d_6$) δ ppm 12.60 (br. s., 1 H), 8.43-8.63 (m, 2 H), 8.13 (d, J = 7.24 Hz, 2 H), 7.60 (t, J = 7.89 Hz, 1 H), 4.61 (dt, J = 13.87, 6.99 Hz, 1 H), 2.97 (br. s., 4 H), 2.60-2.66 (m, 1 H), 2.56 (br. s., 4 H), 2.45 (s, 3 H), 2.37-2.43 (m, 1 H), 2.16 (s, 3 H), 1.20 (d, J = 6.58 Hz, 3 H) |
| 9 | 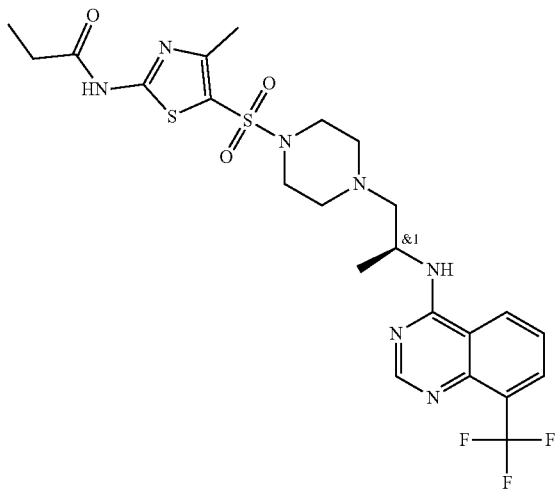 [SMILES: CCC(=O)Nc1nc(C)c(S(=O)(=O)N2CCN(C[C@H](C)Nc3ncnc4c(C(F)(F)F)cccc34)CC2)s1]<br>N-[4-methyl-5-({4-[(2S)-2-{[8-(trifluoromethyl)quinazolin-4-yl]amino}propyl]piperazin-1-yl}sulfonyl)-1,3-thiazol-2-yl]propanamide | LC-MS (ESI): m/z (M + 1): 572.2 (Method 1)<br>$^1$H NMR (500 MHz, DMSO-$d_6$) δ ppm 1.07 (t, J = 7.55 Hz, 3 H), 1.20 (d, J = 6.59 Hz, 3 H), 2.37-2.66 (m, 2 H), 2.40-2.48 (m, 2 H), 2.45 (s, 3 H), 2.52-2.59 (m, 4 H), 2.97 (br. s., 4 H), 4.61 (spt, J = 6.91 Hz, 1 H), 7.60 (t, J = 7.96 Hz, 1H), 8.03-8.17 (m, 2H), 8.47-8.62 (m, 2 H), 12.58 (br. s., 1 H) |

| Example No. | Structure & Name | Analytical data |
|---|---|---|
| 10 | 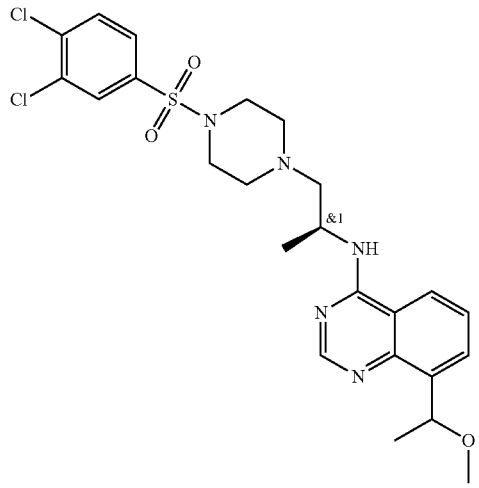 [SMILES: COC(C)c1cccc2c(N[C@@H](C)CN3CCN(S(=O)(=O)c4ccc(Cl)c(Cl)c4)CC3)ncnc12]<br>methyl 4-{[(2S)-1-[4-(3,4-dichlorobenzenesulfonyl)piperazin-1-yl]propan-2-yl]amino}quinazoline-8-carboxylate | LC-MS (ESI): m/z (M + 1): 538.1 (Method 1)<br>$^1$H NMR (500 MHz, DMSO-$d_6$) δ ppm 1.18 (d, J = 6.60 Hz, 3 H), 2.34-2.63 (m, 2 H), 2.48-2.55 (m, 4 H), 2.92 (br. s., 4H), 3.86 (s, 3 H), 4.59 (spt, J = 6.89 Hz, 1 H), 7.51 (dd, J = 8.07, 7.34 Hz, 1 H), 7.67 (dd, J = 8.31, 2.20 Hz, 1 H), 7.86-7.92 (m, 3 H), 7.99 (d, J = 8.07 Hz, 1 H), 8.37 (dd, J = 8.31, 1.22 Hz, 1 H), 8.44 (s, 1H) |
| 11 | 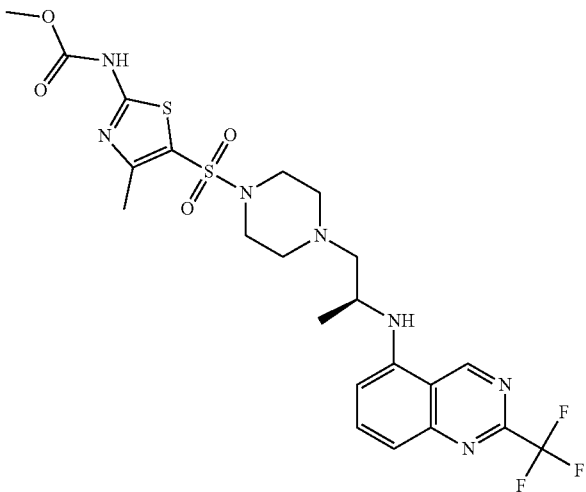 [SMILES: COC(=O)Nc1nc(C)c(S(=O)(=O)N2CCN(C[C@H](C)Nc3cccc4nc(C(F)(F)F)ncc34)CC2)s1]<br>methyl N-[4-methyl-5-({4-[(2S)-2-{[2-(trifluoromethyl)quinazolin-4-yl]amino}propyl]piperazin-1-yl}sulfonyl)-1,3-thiazol-2-yl]carbamate | LC-MS (ESI): m/z (M + 1): 574.2 (Method 1)<br>$^1$H NMR (500 MHz, DMSO-$d_6$) δ ppm 1.24 (d, J = 6.59 Hz, 3 H), 2.31-2.46 (m, 4 H), 2.46-2.53 (m, 2 H), 2.54-2.68 (m, 3 H), 2.74-3.03 (m, 4 H), 3.77 (s, 3 H), 4.54-4.67 (m, 1 H), 7.59-7.73 (m, 1 H), 7.77-7.81 (m, 1 H), 7.81-7.86 (m, 1 H), 8.29-8.38 (m, 2 H), 12.28 (br. s., 1 H) |

-continued

| Example No. | Structure & Name | Analytical data |
|---|---|---|
| 12 | 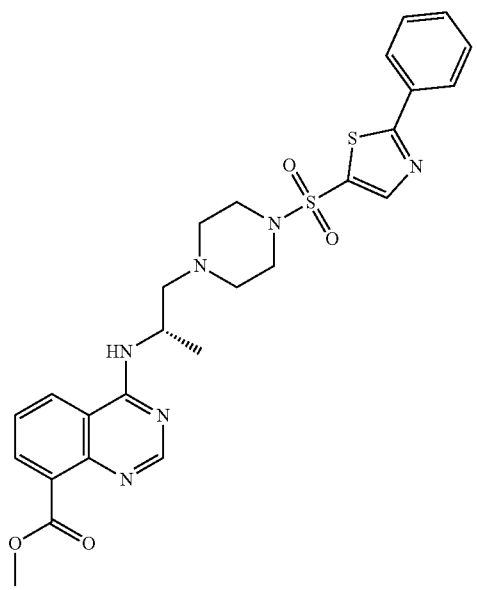 [SMILES: COC(=O)c1cccc2c(N[C@@H](C)CN3CCN(S(=O)(=O)c4cnc(-c5ccccc5)s4)CC3)ncnc12]<br><br>methyl 4-{[(2S)-1-{4-[(2-phenyl-1,3-thiazol-5-yl)sulfonyl]piperazin-1-yl}propan-2-yl]amino}quinazoline-8-carboxylate | LC-MS (ESI): m/z (M + 1): 553.2 (Method 2)<br>$^1$H NMR (400 MHz, DMSO-$d_6$) δ ppm 1.20 (d, J = 6.53 Hz, 3 H), 2.40-2.47 (m, 1 H), 2.58-2.67 (m, 5 H), 2.94-3.11 (m, 4 H), 3.85 (s, 3 H), 4.53-4.69 (m, 1 H), 7.50 (dd, J = 8.28, 7.28 Hz, 1 H), 7.53-7.63 (m, 3 H), 7.87 (dd, J = 7.28, 1.25 Hz, 1 H), 7.97-8.06 (m, 3 H), 8.35 (s, 1 H), 8.38 (dd, J = 8.41, 1.13 Hz, 1 H), 8.46 (s, 1 H) |
| 14 | 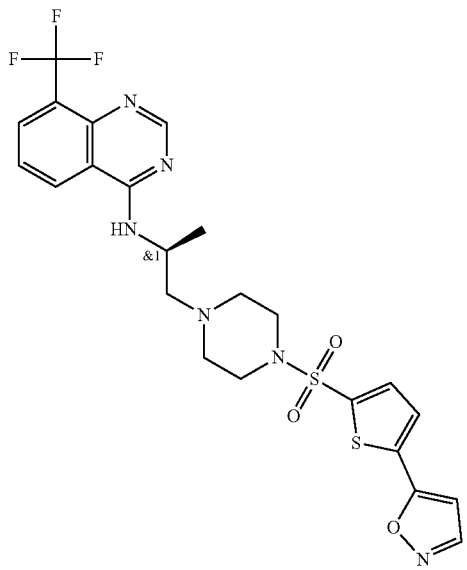 [SMILES: C[C@@H](CN1CCN(S(=O)(=O)c2ccc(-c3ccno3)s2)CC1)Nc1ncnc2c(C(F)(F)F)cccc12]<br><br>N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 553.2 (Method 2)<br>$^1$H NMR (500 MHz, DMSO-$d_6$) δ ppm 1.19 (d, J = 6.59 Hz, 3 H), 2.39-2.46 (m, 1 H), 2.54-2.63 (m, 5 H), 2.88-3.06 (m, 4 H), 4.61 (dt, J = 14.00, 7.00 Hz, 1 H), 7.12 (d, J = 1.92 Hz, 1 H), 7.58 (t, J = 7.82 Hz, 1 H), 7.71 (d, J = 3.84 Hz, 1 H), 7.81 (d, J = 4.12 Hz, 1 H), 8.09-8.16 (m, 2H), 8.50-8.57 (m, 2 H), 8.74 (d, J = 1.92 Hz, 1 H) |

| Example No. | Structure & Name | Analytical data |
|---|---|---|
| 15 | 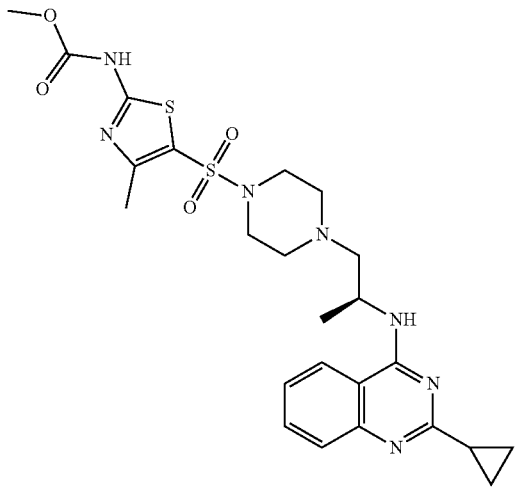 [SMILES: COC(=O)Nc1nc(C)c(S(=O)(=O)N2CCN(C[C@H](C)Nc3nc(C4CC4)nc4ccccc34)CC2)s1]<br><br>methyl N-[5-({4-[(2S)-2-[(2-cyclopropylquinazolin-4-yl)amino]propyl]piperazin-1-yl}sulfonyl)-4-methyl-1,3-thiazol-2-yl]carbamate | LC-MS (ESI): m/z (M + 1): 546.3 (Method 2)<br>$^1$H NMR (400 MHz, DMSO-d$_6$) δ ppm 0.74-1.07 (m, 4 H), 1.11-1.32 (m, 3 H), 1.93-2.06 (m, 1 H), 2.29-2.63 (m, 6 H), 2.43 (s, 3 H), 2.96 (br. s., 4 H), 3.77 (s, 3 H), 4.49 (dt, J = 13.99, 6.93 Hz, 1 H), 7.33 (td, J = 7.59, 1.13 Hz, 1H), 7.41-8.25 (m, 4 H), 12.37 (br. s., 1 H) |
| 16 | 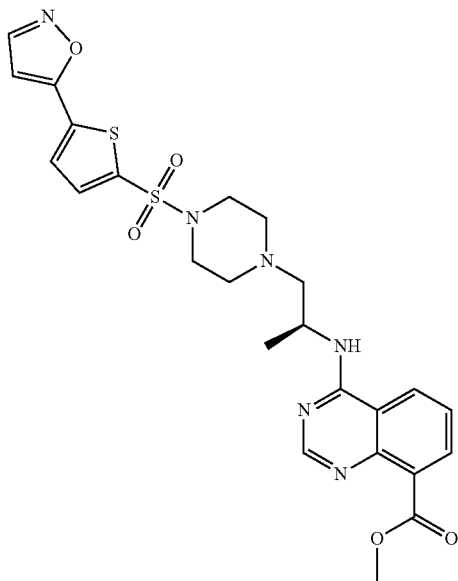 [SMILES: COC(=O)c1cccc2c(N[C@@H](C)CN3CCN(S(=O)(=O)c4ccc(-c5ccno5)s4)CC3)ncnc12]<br><br>methyl 4-{[(2S)-1-(4-{[5-(1,2-oxazol-5-yl)thiophen-2-yl]sulfonyl}piperazin-1-yl)propan-2-yl]amino}quinazoline-8-carboxylate | LC-MS (ESI): m/z (M + 1): 543.2 (Method 2)<br>$^1$H NMR (400 MHz, DMSO-d$_6$) δ ppm 1.17 (d, J = 6.65 Hz, 3 H), 2.35-2.62 (m, 6 H), 2.96 (br. s., 4H), 3.84 (s, 3 H), 4.53-4.64 (m, 1 H), 7.11 (d, J = 1.96 Hz, 1 H), 7.49 (t, J = 7.83 Hz, 1 H), 7.69 (d, J = 3.91 Hz, 1 H), 7.80 (d, J = 3.91 Hz, 1 H), 7.86 (d, J = 6.26 Hz, 1 H), 7.98 (d, J = 7.83 Hz, 1 H), 8.36 (d, J = 7.43 Hz, 1 H), 8.43 (s, 1 H), 8.72 (d, J = 1.96 Hz, 1 H) |

| Example No. | Structure & Name | Analytical data |
|---|---|---|
| 17 | 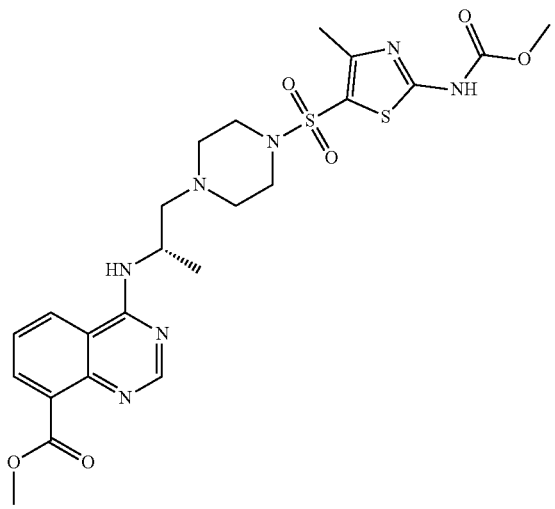 [SMILES: COC(=O)Nc1nc(C)c(S(=O)(=O)N2CCN(C[C@H](C)Nc3ncnc4c(C(=O)OC)cccc34)CC2)s1]<br>methyl 4-{[(2S)-1-[4-({2-[(methoxycarbonyl)amino]-4-methyl-1,3-thiazol-5-yl}sulfonyl)piperazin-1-yl]propan-2-yl]amino}quinazoline-8-carboxylate | LC-MS (ESI): m/z (M + 1): 564.9 (Method 1)<br>$^1$H NMR (400 MHz, DMSO-$d_6$) δ ppm 1.20 (d, J = 6.53 Hz, 3 H), 2.37-2.66 (m, 2 H), 2.43 (s, 3 H), 2.53-2.60 (m, 4 H), 2.99 (br. s., 4H), 3.76 (s, 3 H), 3.86 (s, 3 H), 4.54-4.65 (m, 1 H), 7.52 (dd, J = 8.28, 7.28 Hz, 1 H), 7.90 (dd, J = 7.28, 1.25 Hz, 1 H), 8.00 (d, J = 8.28 Hz, 1 H), 8.39 (dd, J = 8.41, 1.13 Hz, 1 H), 8.45 (s, 1 H), 12.32 (br. s., 1 H) |
| 20 | 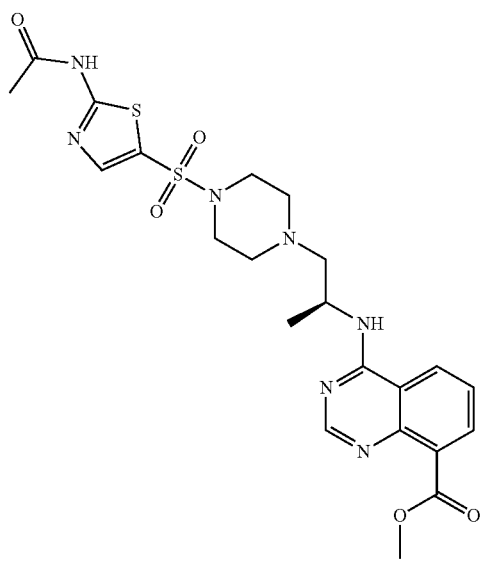 [SMILES: COC(=O)c1cccc2c(N[C@@H](C)CN3CCN(S(=O)(=O)c4cnc(NC(C)=O)s4)CC3)ncnc12]<br>methyl 4-{[(2S)-1-{4-[(2-acetamido-1,3-thiazol-5-yl)sulfonyl]piperazin-1-yl}propan-2-yl]amino}quinazoline-8-carboxylate | LC-MS (ESI): m/z (M + 1): 534.8 (Method 1)<br>$^1$H NMR (400 MHz, DMSO-$d_6$) δ ppm 1.20 (d, J = 6.53 Hz, 3 H), 2.19 (s, 3 H), 2.35-2.44 (m, 1 H), 2.54-2.65 (m, 5 H), 2.85-3.02 (m, 4 H), 3.87 (s, 3 H), 4.52-4.70 (m, 1 H), 7.54 (t, J = 7.65 Hz, 1 H), 7.88-8.28 (m, 3 H), 8.40 (d, J = 8.53 Hz, 1 H), 8.43-8.50 (m, 1 H), 12.66-12.75 (m, 1 H) |

-continued

| Example No. | Structure & Name | Analytical data |
|---|---|---|
| 28 | 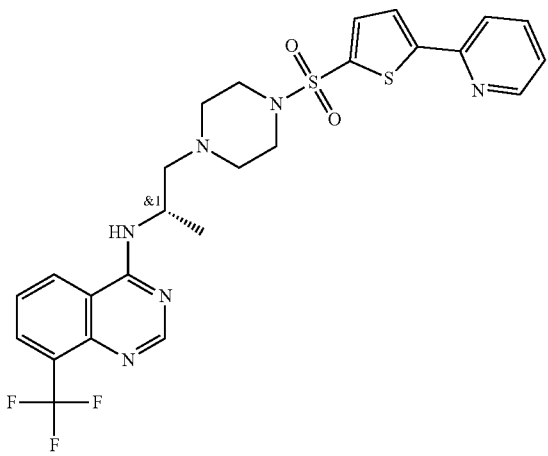 [SMILES: C[C@@H](CN1CCN(S(=O)(=O)c2ccc(-c3ccccn3)s2)CC1)Nc1ncnc2c(C(F)(F)F)cccc12]<br><br>N-[(2S)-1-(4-{[5-(pyridin-2-yl)thiophen-2-yl]sulfonyl}piperazin-1-yl)propan-2-yl]-8-(trifluoromethyl)quinazolin-4-amine | LC-MS (ESI): m/z (M + 1): 563.2 (Method 2)<br>$^1$H NMR (400 MHz, DMSO-d$_6$) δ ppm 1.19 (d, J = 6.6 Hz, 3 H), 2.42 (dd, J = 12.5, 6.8 Hz, 1 H), 2.55-2.64 (m, 5 H), 2.95 (br s, 4 H), 4.60 (dt, J = 14.0, 6.9 Hz, 1 H), 7.40 (ddd, J = 7.5, 4.8, 0.9 Hz, 1 H), 7.56 (t, J = 7.7 Hz, 1 H), 7.62 (d, J = 4.0 Hz, 1 H), 7.87-7.95 (m, 2 H), 8.02-8.15 (m, 3 H), 8.49-8.54 (m, 2 H), 8.57 (d, J = 4.8 Hz, 1 H) |
| 29 | 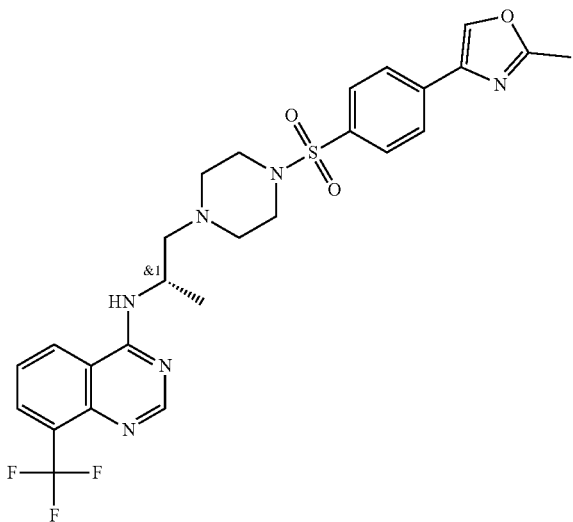 [SMILES: Cc1nc(-c2ccc(S(=O)(=O)N3CCN(C[C@H](C)Nc4ncnc5c(C(F)(F)F)cccc45)CC3)cc2)co1]<br><br>N-[(2S)-1-{4-[4-(2-methyl-1,3-oxazol-4-yl)benzenesulfonyl]piperazin-1-yl}propan-2-yl]-8-(trifluoromethyl)quinazolin-4-amine | LC-MS (ESI): m/z (M + 1): 561.3 (Method 2)<br>$^1$H NMR (500 MHz, DMSO-d$_6$) δ ppm 1.17 (d, J = 6.59 Hz, 3 H), 2.36-2.43 (m, 1 H), 2.48 (s, 3 H), 2.49-2.55 (m, 4 H), 2.55-2.62 (m, 1 H), 2.87 (br. s., 4 H), 4.58 (dt, J = 14.13, 6.93 Hz, 1 H), 7.57 (t, J = 7.82 Hz, 1 H), 7.73 (d, J = 8.23 Hz, 2 H), 7.96 (d, J = 8.51 Hz, 2 H), 8.07-8.14 (m, 2 H), 8.47-8.55 (m, 2 H), 8.66 (s, 1 H) |

| Example No. | Structure & Name | Analytical data |
|---|---|---|
| 30 | 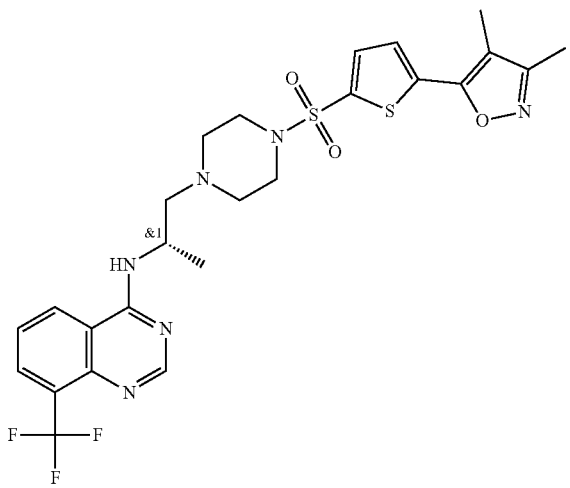 [SMILES: Cc1noc(-c2ccc(S(=O)(=O)N3CCN(C[C@H](C)Nc4ncnc5c(C(F)(F)F)cccc45)CC3)s2)c1C]<br>N-[(2S)-1-(4-{[5-(3,4-dimethyl-1,2-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 581.3 (Method 2)<br>$^1$H NMR (500 MHz, DMSO-d$_6$) δ ppm 1.19 (d, J = 6.59 Hz, 3 H), 2.14 (s, 3 H), 2.24 (s, 3 H), 2.38-2.45 (m, 1 H), 2.56-2.60 (m, 4 H), 2.60-2.63 (m, 1 H), 2.89-3.08 (m, 4 H), 4.62 (quin, J = 7.00 Hz, 1 H), 7.58 (t, J = 7.82 Hz, 1 H), 7.65 (d, J = 4.12 Hz, 1 H), 7.70 (d, J = 3.84 Hz, 1 H), 8.08-8.16 (m, 2 H), 8.50-8.55 (m, 2 H) |
| 31 | 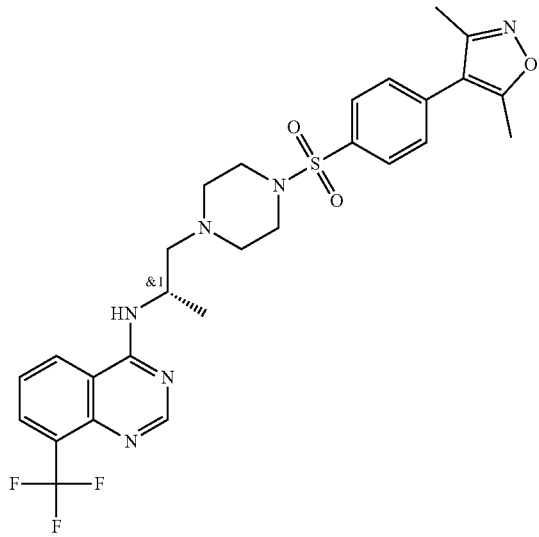 [SMILES: Cc1noc(C)c1-c1ccc(S(=O)(=O)N2CCN(C[C@H](C)Nc3ncnc4c(C(F)(F)F)cccc34)CC2)cc1]<br>N-[(2S)-1-{4-[4-(3,5-dimethyl-1,2-oxazol-4-yl)benzenesulfonyl]piperazin-1-yl}propan-2-yl]-8-(trifluoromethyl)quinazolin-4-amine | LC-MS (ESI): m/z (M + 1): 575.3 (Method 2)<br>$^1$H NMR (500 MHz, DMSO-d$_6$) δ ppm 1.18 (d, J = 6.59 Hz, 3 H), 2.24 (s, 3 H), 2.37-2.41 (m, 1 H), 2.42 (s, 3 H), 2.53-2.62 (m, 5 H), 2.89 (br. s., 4 H), 4.62 (dt, J = 13.86, 7.07 Hz, 1 H), 7.59 (t, J = 7.82 Hz, 1 H), 7.64 (d, J = 8.23 Hz, 2 H), 7.76 (d, J = 8.23 Hz, 2 H), 8.12 (d, J = 7.41 Hz, 2 H), 8.47-8.57 (m, 2H) |

| Example No. | Structure & Name | Analytical data |
|---|---|---|
| 32 | 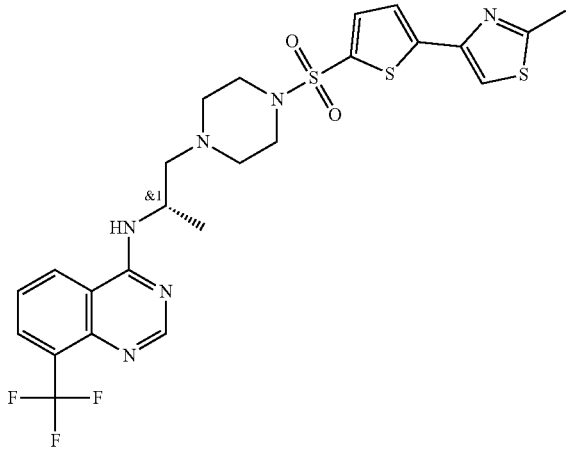 [SMILES: Cc1nc(-c2ccc(S(=O)(=O)N3CCN(C[C@H](C)Nc4ncnc5c(C(F)(F)F)cccc45)CC3)s2)cs1]<br><br>N-[(2S)-1-(4-{[5-(2-methyl-1,3-thiazol-4-yl)thiophen-2-yl]sulfonyl}piperazin-1-yl)propan-2-yl]-8-(trifluoromethyl)quinazolin-4-amine | LC-MS (ESI): m/z (M + 1): 583.3 (Method 2)<br>$^1$H NMR (400 MHz, DMSO-d$_6$) δ ppm 8.49-8.55 (m, 2 H), 8.05-8.15 (m, 3 H), 7.66 (d, J = 3.95 Hz, 1 H), 7.53-7.61 (m, 2 H), 4.60 (dt, J = 13.98, 6.71 Hz, 1 H), 2.87-3.01 (m, 4 H), 2.69 (s, 3 H), 2.55-2.63 (m, 5 H), 2.44 (s, 1 H), 1.19 (d, J = 6.50 Hz, 3 H) |
| 33 | 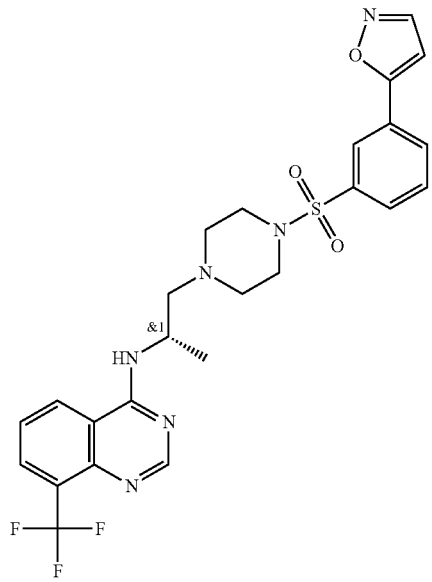 [SMILES: C[C@@H](CN1CCN(S(=O)(=O)c2cccc(-c3ccno3)c2)CC1)Nc1ncnc2c(C(F)(F)F)cccc12]<br><br>N-[(2S)-1-{4-[3-(1,2-oxazol-5-yl)benzenesulfonyl]piperazin-1-yl}propan-2-yl]-8-(trifluoromethyl)quinazolin-4-amine | LC-MS (ESI): m/z (M + 1): 547.3 (Method 2)<br>$^1$H NMR (400 MHz, DMSO-d$_6$) δ ppm 8.73 (d, J = 1.97 Hz, 1 H), 8.45-8.54 (m, 2 H), 8.20 (dt, J = 6.80, 1.86 Hz, 1 H), 8.06-8.14 (m, 3 H), 7.75-7.85 (m, 2 H), 7.56 (t, J = 1.89 Hz, 1 H), 7.26 (d, J = 1.97 Hz, 1 H), 4.58 (dt, J = 14.09, 6.88 Hz, 1 H), 2.91 (br. s., 4 H), 2.52-2.62 (m, 5 H), 2.35-2.43 (m, 1 H), 1.16 (d, J = 6.58 Hz, 3 H) |

| Example No. | Structure & Name | Analytical data |
|---|---|---|
| 34 | 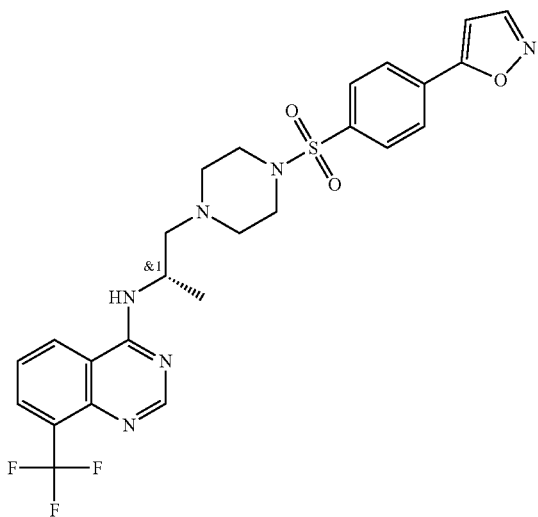 [SMILES: C[C@@H](CN1CCN(S(=O)(=O)c2ccc(-c3ccno3)cc2)CC1)Nc1ncnc2c(C(F)(F)F)cccc12]<br>N-[(2S)-1-{4-[4-(1,2-oxazol-5-yl)benzenesulfonyl]piperazin-1-yl}propan-2-yl]-8-(trifluoromethyl)quinazolin-4-amine | LC-MS (ESI): m/z (M + 1): 547.3 (Method 2)<br>$^1$H NMR (400 MHz, DMSO-d$_6$) δ ppm 1.17 (d, J = 6.36 Hz, 3 H), 2.34-2.65 (m, 6 H), 2.89 (br. s., 4 H), 4.49-4.78 (m, 1 H), 7.23 (d, J = 1.75 Hz, 1 H), 7.57 (t, J = 7.78 Hz, 1 H), 7.84 (d, J = 8.55 Hz, 2 H), 8.01-8.20 (m, 4 H), 8.45-8.57 (m, 2 H), 8.74 (d, J = 1.97 Hz, 1 H) |
| 35 | 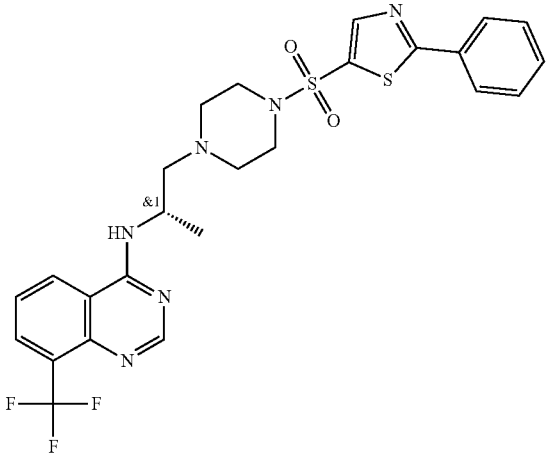 [SMILES: C[C@@H](CN1CCN(S(=O)(=O)c2cnc(-c3ccccc3)s2)CC1)Nc1ncnc2c(C(F)(F)F)cccc12]<br>N-[(2S)-1-{4-[(2-phenyl-1,3-thiazol-5-yl)sulfonyl]piperazin-1-yl}propan-2-yl]-8-(trifluoromethyl)quinazolin-4-amine | LC-MS (ESI): m/z (M + 1): 563.3 (Method 2)<br>$^1$H NMR (400 MHz, DMSO-d$_6$) δ ppm 1.20 (d, J = 6.58 Hz, 3 H), 2.40-2.46 (m, 1 H), 2.55-2.66 (m, 5 H), 3.02 (br. s., 4H ), 4.52-4.71 (m, 1 H), 7.49-7.64 (m, 4 H), 7.95-8.03 (m, 2 H), 8.05-8.18 (m, 2 H), 8.34 (s, 1 H), 8.48-8.59 (m, 2 H) |

-continued

| Example No. | Structure & Name | Analytical data |
|---|---|---|
| 36 | 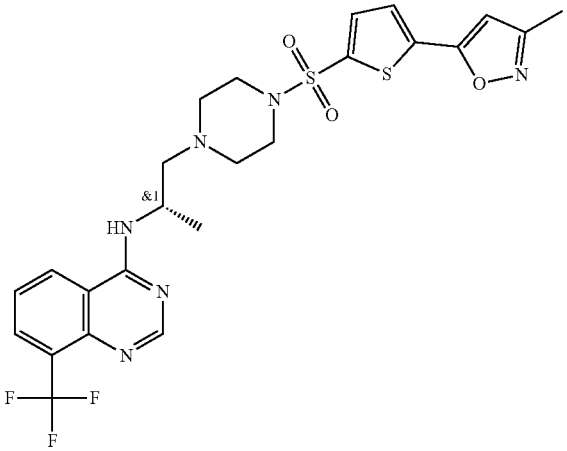 [SMILES: Cc1cc(-c2ccc(S(=O)(=O)N3CCN(C[C@H](C)Nc4ncnc5c(C(F)(F)F)cccc45)CC3)s2)on1]<br>N-[(2S)-1-(4-{[5-(3-methyl-1,2-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 567.3 (Method 2)<br>$^1$H NMR (400 MHz, DMSO-$d_6$) δ ppm 1.19 (d, J = 6.58 Hz, 3 H), 2.29 (s, 3 H), 2.36-2.69 (m, 6 H), 2.96 (br. s., 4 H), 4.53-4.73 (m, 1 H), 6.96 (s, 1 H), 7.58 (t, J = 7.89 Hz, 1 H), 7.69 (d, J = 3.95 Hz, 1 H), 7.75 (d, J = 3.95 Hz, 1 H), 8.05-8.23 (m, 2 H), 8.46-8.59 (m, 2 H) |
| 37 | 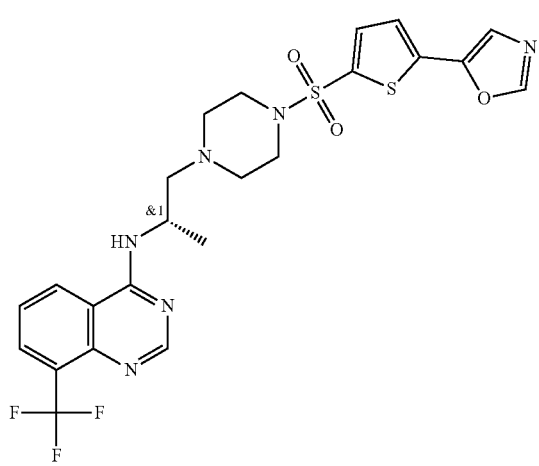 [SMILES: C[C@@H](CN1CCN(S(=O)(=O)c2ccc(-c3cnco3)s2)CC1)Nc1ncnc2c(C(F)(F)F)cccc12]<br>N-[(2S)-1-(4-{[5-(1,3-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 553.3 (Method 2)<br>$^1$H NMR (400 MHz, DMSO-$d_6$) δ ppm 1.19 (d, J = 6.58 Hz, 3 H), 2.38-2.45 (m, 1 H), 2.54-2.65 (m, 5 H), 2.94 (br. s., 4 H), 4.62 (dt, J = 13.76, 6.82 Hz, 1 H), 7.53-7.61 (m, 2 H), 7.62-7.66 (m, 1 H), 7.77 (s, 1 H), 8.07-8.18 (m, 2 H), 8.47-8.60 (m, 3 H) |
| 41 | 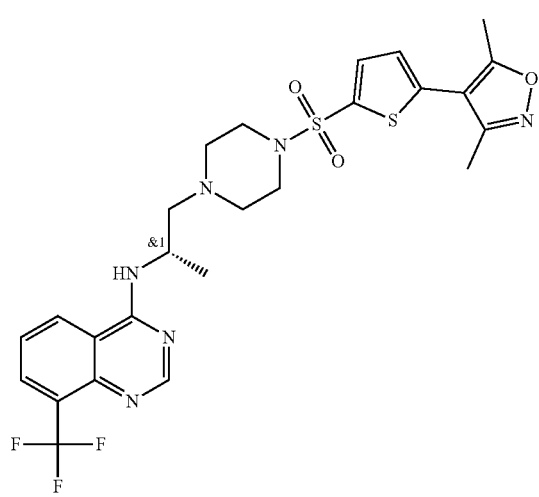 [SMILES: Cc1noc(C)c1-c1ccc(S(=O)(=O)N2CCN(C[C@H](C)Nc3ncnc4c(C(F)(F)F)cccc34)CC2)s1] | LC-MS (ESI): m/z (M + 1): 581.3 (Method 1)<br>$^1$H NMR (400 MHz, DMSO-$d_6$) δ ppm 1.10-1.31 (m, 3 H), 2.31 (s, 3 H), 2.36-2.66 (m, 9 H), 2.94 (br. s., 4 H), 4.63 (dt, J = 13.98, 7.15 Hz, 1 H), 7.34 (d, J = 3.95 Hz, 1 H), 7.59 (t, J = 7.89 Hz, 1 H), 7.64 (d, J = 3.95 Hz, 1 H), 8.05-8.22 (m, 2 H), 8.47-8.59 (m, 2 H) |

| Example No. | Structure & Name | Analytical data |
|---|---|---|
| 42 | 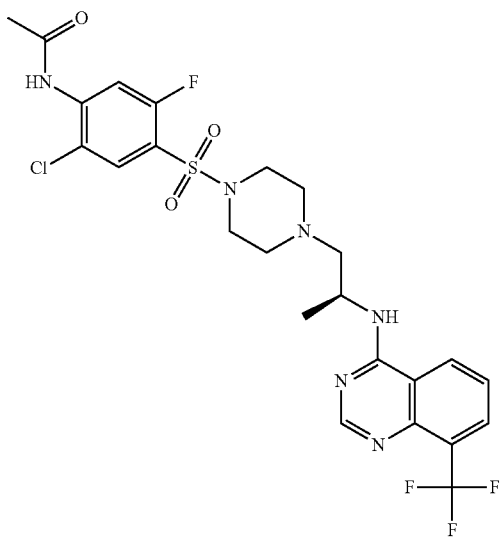 [SMILES: CC(=O)Nc1cc(F)c(S(=O)(=O)N2CCN(C[C@H](C)Nc3ncnc4c(C(F)(F)F)cccc34)CC2)cc1Cl]<br>N-[(2S)-1-(4-{[5-(3,5-dimethyl-1,2-oxazol-4-yl)thiophen-2-yl]sulfonyl}piperazin-1-yl)propan-2-yl]-8-(trifluoromethyl)quinazolin-4-amine | LC-MS (ESI): m/z (M + 1): 589.1 (Method 5)<br>$^1$H NMR (400 MHz, ACETONE-d6) δ ppm 8.98 (br s, 1 H) 8.55 (s, 1 H) 8.32-8.44 (m, 2 H) 8.06-8.13 (m, 1 H) 7.75 (d, J = 7.02 Hz, 1 H) 7.55 (t, J = 7.89 Hz, 1 H) 7.44 (br s, 1 H) 4.64-4.76 (m, 1 H) 3.14 (br s, 4 H) 2.45-2.75 (m, 6 H) 2.28 (s, 3 H) 1.31 (d, J = 6.36 Hz, 3 H) |
|   | N-[2-chloro-5-fluoro-4-({4-[(2S)-2-{[8-(trifluoromethyl)quinazolin-4-yl]amino}propyl]piperazin-1-yl}sulfonyl)phenyl]acetamide |   |
| 50 | 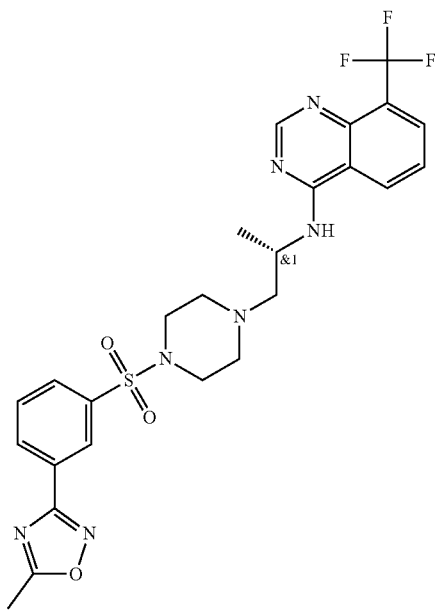 [SMILES: Cc1nc(-c2cccc(S(=O)(=O)N3CCN(C[C@H](C)Nc4ncnc5c(C(F)(F)F)cccc45)CC3)c2)no1]<br>N-[(2S)-1-{4-[3-(5-methyl-1,2,4-oxadiazol-3-yl)benzenesulfonyl]piperazin-1-yl}propan-2-yl]-8-(trifluoromethyl)quinazolin-4-amine | LC-MS (ESI): m/z (M + 1): 562.3 (Method 1)<br>$^1$H NMR (500 MHz, DMSO-d$_6$) δ ppm 1.16 (d, J = 6.59 Hz, 3 H), 2.39 (dd, J = 12.62, 6.59 Hz, 1 H), 2.51-2.55 (m, 4H), 2.56-2.62 (m, 1 H), 2.69 (s, 3 H), 2.82-3.00 (m, 4 H), 4.54-4.64 (m, 1 H), 7.56 (t, J = 7.82 Hz, 1 H), 7.82 (t, J = 7.80 Hz, 1 H), 7.89-7.93 (m, 1 H), 8.07-8.13 (m, 2H), 8.20 (t, J = 1.65 Hz, 1 H), 8.28 (dt, J = 7.96, 1.37 Hz, 1 H), 8.47-8.53 (m, 2 H) |

-continued

| Example No. | Structure & Name | Analytical data |
|---|---|---|
| 52 | 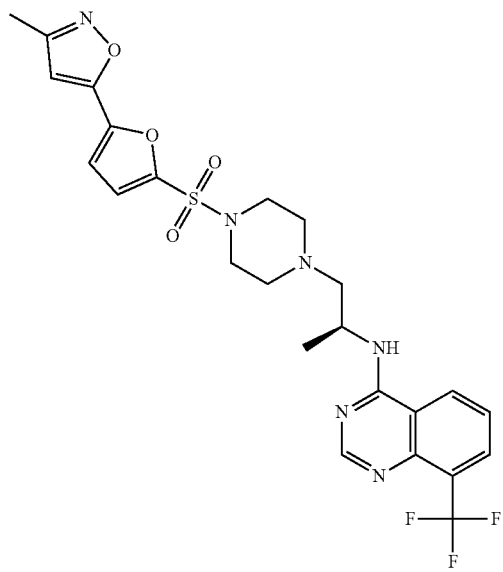 [SMILES: Cc1cc(-c2ccc(S(=O)(=O)N3CCN(C[C@H](C)Nc4ncnc5c(C(F)(F)F)cccc45)CC3)o2)on1]<br>N-[(2S)-1-(4-{[5-(3-methyl-1,2-oxazol-5-yl)furan-2-yl]sulfonyl}piperazin-1-yl)propan-2-yl]-8-(trifluoromethyl)quinazolin-4-amine | LC-MS (ESI): m/z (M + 1): 550.8 (Method 3)<br>$^1$H NMR (400 MHz, ACETONE-d6) δ ppm 8.55 (s, 1 H), 8.35 (d, J = 8.33 Hz, 1 H), 8.08 (d, J = 7.45 Hz, 1 H), 7.51 (t, J = 7.89 Hz, 1 H), 7.42 (br d, J = 7.02 Hz, 1 H), 7.22 (d, J = 3.51 Hz, 1 H), 7.13 (d, J = 3.95 Hz, 1 H), 6.70 (s, 1 H), 4.63-4.73 (m, 1 H), 3.14-3.25 (m, 4 H), 2.43-2.74 (m, 6 H), 2.32 (s, 3 H), 1.30 (d, J = 6.58 Hz, 3 H) |
| 53 | 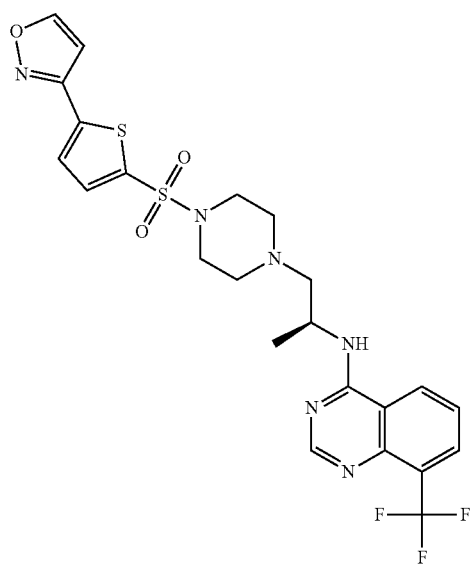 [SMILES: C[C@@H](CN1CCN(S(=O)(=O)c2ccc(-c3ccon3)s2)CC1)Nc1ncnc2c(C(F)(F)F)cccc12]<br>N-[(2S)-1-(4-{[5-(1,2-oxazol-3-yl)thiophen-2-yl]sulfonyl}piperazin-1-yl)propan-2-yl]-8-(trifluoromethyl)quinaizolin-4-amine | LC-MS (ESI): m/z (M + 1): 552.7 (Method 3)<br>$^1$H NMR (400 MHz, ACETONE-d6) δ ppm 8.48-8.58 (m, 2 H), 8.32 (d, J = 8.11 Hz, 1 H), 8.06 (d, J = 7.23 Hz, 1 H), 7.71 (d, J = 3.95 Hz, 1 H), 7.60 (d, J = 3.95 Hz, 1 H), 7.49 (t, J = 7.89 Hz, 1 H), 7.38 (br d, J = 7.02 Hz, 1 H), 6.92 (d, J = 1.97 Hz, 1 H), 4.60-4.75 (m, 1 H), 3.07 (br s, 4 H), 2.51-2.83 (m, 6 H), 1.28 (d, J = 6.36 Hz, 3 H) |

| Example No. | Structure & Name | Analytical data |
|---|---|---|
| 54 | 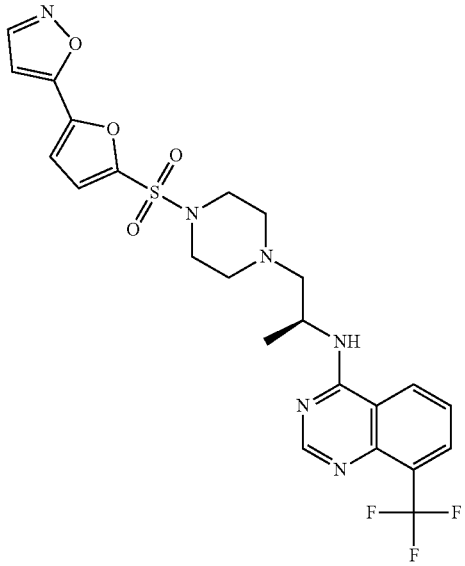 [SMILES: C[C@@H](CN1CCN(S(=O)(=O)c2ccc(-c3ccno3)o2)CC1)Nc1ncnc2c(C(F)(F)F)cccc12]<br><br>N-[(2S)-1-(4-{[5-(1,2-oxazol-5-yl)furan-2-yl]sulfonyl}piperazin-1-yl)propan-2-yl]-8-(trifluoromethyl)quinazolin-4-amine | LC-MS (ESI): m/z (M + 1): 536.8 (Method 3)<br>$^1$H NMR (400 MHz, ACETONE-d6) δ ppm 8.55 (s, 2 H) 8.36 (br d, J = 8.33 Hz, 1 H) 8.08 (d, J = 7.45 Hz, 1 H) 7.51 (t, J = 7.89 Hz, 1 H) 7.45 (br s, 1 H) 7.25 (d, J = 3.51 Hz, 1 H) 7.19 (d, J = 3.51 Hz, 1 H) 6.85 (d, J = 1.75 Hz, 1 H) 4.73 (s, 1 H) 3.24 (br s, 4 H) 2.33-2.68 (m, 6 H) 1.32 (br d, J = 6.36 Hz, 3 H) |
| 55 | 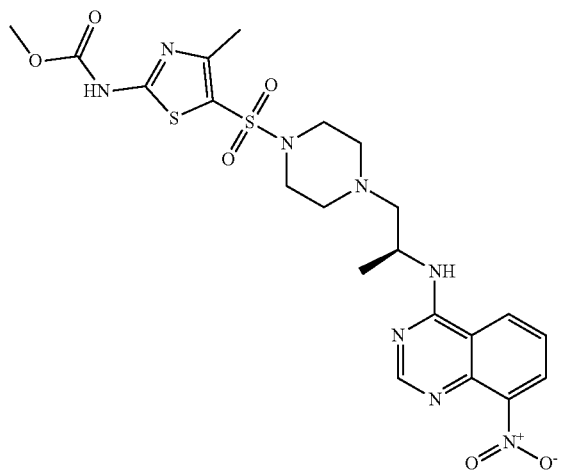 [SMILES: COC(=O)Nc1nc(C)c(S(=O)(=O)N2CCN(C[C@H](C)Nc3ncnc4c([N+](=O)[O-])cccc34)CC2)s1]<br><br>methyl N-[4-methyl-5-({4-[(2S)-2-[(8-nitroquinazolin-4-yl)amino]propyl]piperazin-1-yl}sulfonyl)-1,3-thiazol-2-yl]carbamate | LC-MS (ESI): m/z (M + 1): 551.2 (Method 5)<br>$^1$H NMR (400 MHz, ACETONE-d6) δ ppm 10.87 (br s, 1 H) 8.51 (s, 1 H) 8.31 (d, J = 8.33 Hz, 1 H) 8.07 (d, J = 7.28 Hz, 1 H) 7.55 (t, J = 8.00 Hz, 2 H) 4.74 (spt, J = 6.80 Hz, 1 H) 3.84 (s, 3 H) 3.04-3.15 (m, 4 H) 2.68-2.77 (m, 3 H) 2.60-2.68 (m, 2 H) 2.52 (dd, J = 12.50, 5.92 Hz, 1 H) 2.41 (s, 3 H) 1.32 (d, J = 6.58 Hz, 3 H) |

| Example No. | Structure & Name | Analytical data |
|---|---|---|
| 56 | 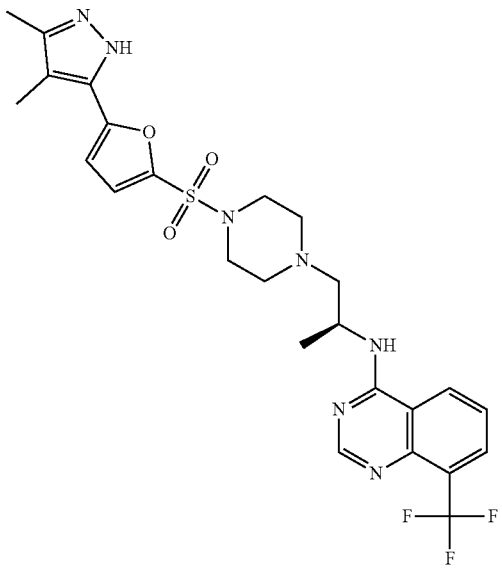 [SMILES: Cc1n[nH]c(-c2ccc(S(=O)(=O)N3CCN(C[C@H](C)Nc4ncnc5c(C(F)(F)F)cccc45)CC3)o2)c1C]<br>N-[(2S)-1-(4-{[5-(3,4-dimethyl-1H-pyrazol-5-yl)furan-2-yl]sulfonyl}piperazin-1-yl)propan-2-yl]-8-(trifluoromethyl)quinazolin-4-amine | LC-MS (ESI): m/z (M + 1): 563.8 (Method 3)<br>$^1$H NMR (400 MHz, ACETONE-d6) δ ppm 8.55 (s, 1 H) 8.33 (d, J = 8.33 Hz, 1 H) 8.06 (d, J = 7.23 Hz, 1 H) 7.48 (t, J = 7.89 Hz, 1 H) 7.41 (br d, J = 6.14 Hz, 1 H) 7.12 (d, J = 3.73 Hz, 1 H) 6.74 (d, J = 3.51 Hz, 1 H) 4.63-4.72 (m, 1 H) 3.11-3.24 (m, 4 H) 2.59-2.72 (m, 5 H) 2.51 (dd, J = 12.50, 6.14 Hz, 1 H) 2.23 (s, 3 H) 2.11 (s, 3 H) 1.30 (d, J = 6.36 Hz, 3 H) |
| 57 | 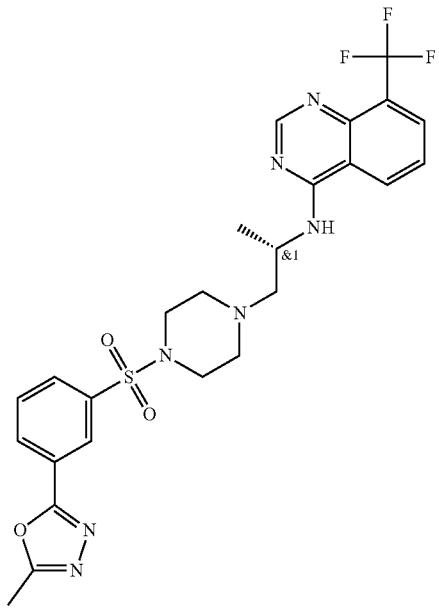 [SMILES: Cc1nnc(-c2cccc(S(=O)(=O)N3CCN(C[C@H](C)Nc4ncnc5c(C(F)(F)F)cccc45)CC3)c2)o1]<br>N-[(2S)-1-{4-[3-(5-methyl-1,3,4-oxadiazol-2-yl)benzenesulfonyl]piperazin-1-yl}propan-2-yl]-8-(trifluoromethyl)quinazolin-4-amine | LC-MS (ESI): m/z (M + 1): 562.2 (Method 1)<br>$^1$H NMR (400 MHz, DMSO-d$_6$) δ ppm 1.16 (d, J = 6.58 Hz, 3 H), 2.35-2.44 (m, 1 H), 2.52-2.56 (m, 4 H), 2.55-2.59 (m, 1 H), 2.60 (s, 3 H), 2.91 (br. s., 4 H), 4.59 (dt, J = 13.81, 6.69 Hz, 1 H), 7.57 (t, J = 7.89 Hz, 1 H), 7.84 (t, J = 7.90 Hz, 1 H), 7.90-7.95 (m, 1 H), 8.07-8.13 (m, 2 H), 8.14 (t, J = 1.53 Hz, 1 H), 8.25 (dd, J = 7.78, 1.21 Hz, 1 H), 8.46-8.54 (m, 2 H) |

| Example No. | Structure & Name | Analytical data |
|---|---|---|
| 59 | 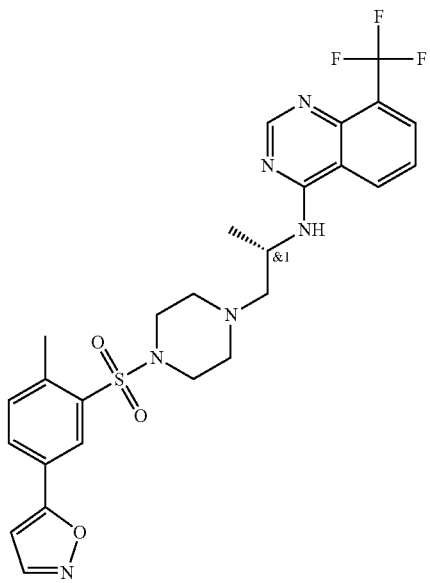 [SMILES: Cc1ccc(-c2ccno2)cc1S(=O)(=O)N1CCN(C[C@H](C)Nc2ncnc3c(C(F)(F)F)cccc23)CC1]<br>N-[(2S)-1-{4-[2-methyl-5-(1,2-oxazol-5-yl)benzenesulfonyl]piperazin-1-yl}propan-2-yl]-8-(trifluoromethyl)quinazolin-4-amine | LC-MS (ESI): m/z (M + 1): 561.2 (Method 2)<br>$^1$H NMR (400 MHz, DMSO-$d_6$) δ ppm 1.20 (d, J = 6.58 Hz, 3 H), 2.38-2.45 (m, 1 H), 2.51-2.55 (m, 4 H), 2.58 (s, 3 H), 2.60-2.65 (m, 1 H), 3.05 (br. s., 4 H), 4.53-4.72 (m, 1 H), 7.16 (d, J = 1.97 Hz, 1 H), 7.60 (d, J = 7.89 Hz, 2 H), 8.06 (dd, J = 8.00, 1.86 Hz, 1 H), 8.13 (d, J = 7.45 Hz, 2 H), 8.17 (d, J = 1.75 Hz, 1 H), 8.49-8.57 (m, 2 H), 8.70 (d, J = 1.97 Hz, 1 H) |
| 60 | 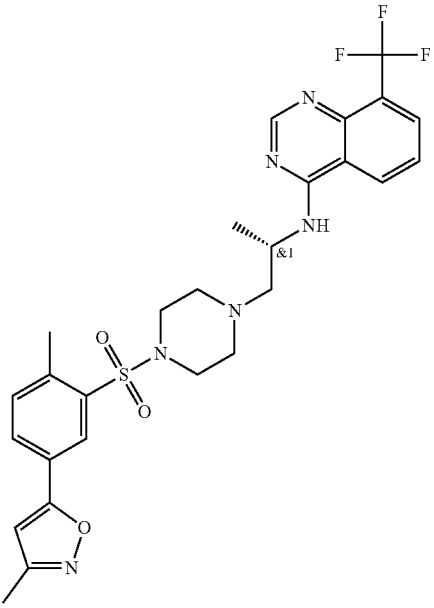 [SMILES: Cc1cc(-c2ccc(C)c(S(=O)(=O)N3CCN(C[C@H](C)Nc4ncnc5c(C(F)(F)F)cccc45)CC3)c2)on1]<br>N-[(2S)-1-{4-[2-methyl-5-(3-methyl-1,2-oxazol-5-yl)benzenesulfonyl]piperazin-1-yl}propan-2-yl]-8-(trifluoromethyl)quinazolin-4-amine | LC-MS (ESI): m/z (M + 1): 575.3 (Method 2)<br>$^1$H NMR (400 MHz, DMSO-$d_6$) δ ppm 1.20 (d, J = 6.58 Hz, 3 H), 2.29 (s, 3 H), 2.38-2.46 (m, 1 H), 2.51-2.54 (m, 4 H), 2.57 (s, 3 H), 2.60-2.65 (m, 1 H), 3.04 (br. s., 4 H), 4.62 (dt, J = 13.81, 6.91 Hz, 1 H), 7.00 (s, 1H), 7.52-7.66 (m, 2 H), 7.99 (dd, J = 8.00, 1.86 Hz, 1 H), 8.08-8.16 (m, 3H), 8.48-8.59 (m, 2H) |

| Example No. | Structure & Name | Analytical data |
|---|---|---|
| 62 | 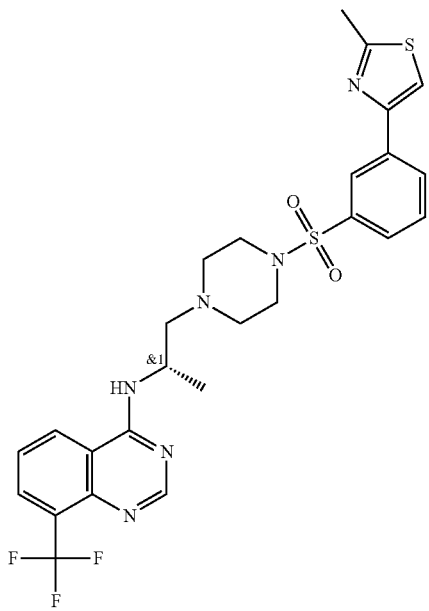 [SMILES: Cc1nc(-c2cccc(S(=O)(=O)N3CCN(C[C@H](C)Nc4ncnc5c(C(F)(F)F)cccc45)CC3)c2)cs1]<br>N-[(2S)-1-{4-[3-(2-methyl-1,3-thiazol-4-yl)benzenesulfonyl]piperazin-1-yl}propan-2-yl]-8-(trifluoromethyl)quinazolin-4-amine | LC-MS (ESI): m/z (M + 1): 577.3 (Method 2)<br>$^1$H NMR (400 MHz, DMSO-d$_6$) δ ppm 1.16 (d, J = 6.65 Hz, 3H), 2.36-2.44 (m, 1 H), 2.51-2.62 (m, 5 H), 2.73 (s, 3 H), 2.89 (br. s., 4 H), 4.57 (dt, J = 14.18, 6.99 Hz, 1 H), 7.56 (t, J = 7.92 Hz, 1 H), 7.60-7.74 (m, 2 H), 8.10 (t, J = 6.46 Hz, 2 H), 8.16 (s, 1 H), 8.19-8.27 (m, 2 H), 8.44-8.57 (m, 2 H) |
| 67 | 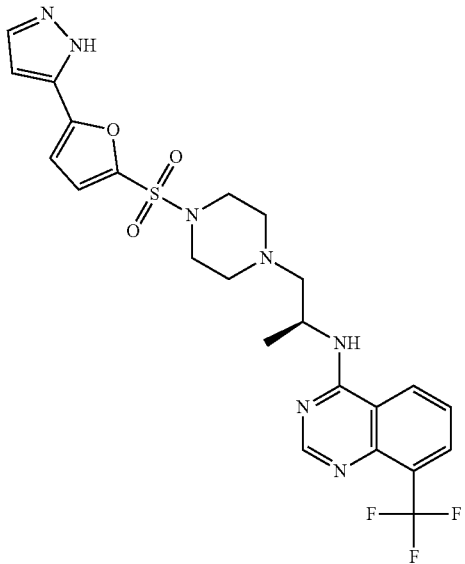 [SMILES: C[C@@H](CN1CCN(S(=O)(=O)c2ccc(-c3ccn[nH]3)o2)CC1)Nc1ncnc2c(C(F)(F)F)cccc12]<br>N-[(2S)-1-(4-{[5-(1H-pyrazol-5-yl)furan-2-yl]sulfonyl(piperazin-1-yl)propan-2-yl]-8-(trifluoromethyl)quinazolin-4-amine | LC-MS (ESI): m/z (M + 1): 535.8 (Method 3)<br>$^1$H NMR (400 MHz, ACETONE-d6) δ ppm 8.54 (s, 1 H) 8.31 (d, J = 8.33 Hz, 1 H) 8.05 (d, J = 7.23 Hz, 1 H) 7.79 (d, J = 2.41 Hz, 1 H) 7.46 (t, J = 7.89 Hz, 1 H) 7.39 (br d, J = 7.31 Hz, 1 H) 7.11 (d, J = 3.73 Hz, 1 H) 6.83 (d, J = 2.19 Hz, 1 H) 4.65 (spt, J = 6.76 Hz, 1 H) 3.10-3.22 (m, 4 H) 2.67 (br d, J = 7.89 Hz, 1 H) 2.58-2.66 (m, 4 H) 2.49 (dd, J = 12.50, 6.36 Hz, 1 H) 1.29 (d, J = 6.58 Hz, 3 H) |

| Example No. | Structure & Name | Analytical data |
|---|---|---|
| 68 | 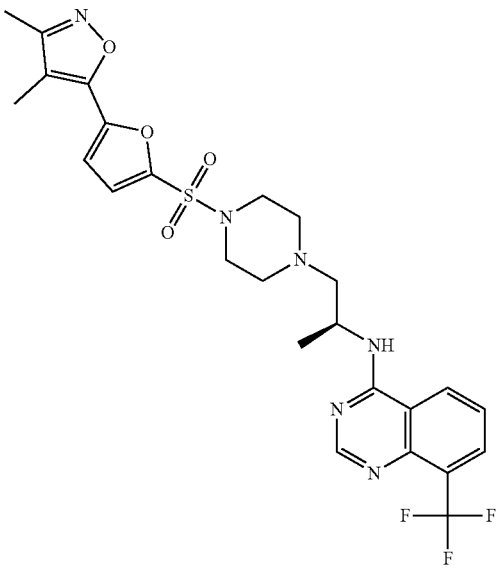 [SMILES: Cc1noc(-c2ccc(S(=O)(=O)N3CCN(C[C@H](C)Nc4ncnc5c(C(F)(F)F)cccc45)CC3)o2)c1C]<br>N-[(2S)-1-(4-{[5-(3,4-dimethyl-1,2-oxazol-5-yl)furan-2-yl]sulfonyl}piperazin-1-yl)propan-2-yl]-8-(trifluoromethyl)quinazolin-4-amine | LC-MS (ESI): m/z (M + 1): 564.7 (Method 3)<br>$^1$H NMR (400 MHz, ACETONE-d6) δ ppm 8.53 (s, 1 H) 8.33 (d, J = 8.33 Hz, 1 H) 8.06 (d, J = 7.23 Hz, 1 H) 7.50 (t, J = 7.89 Hz, 1 H) 7.40 (br d, J = 6.58 Hz, 1 H) 7.21 (d, J = 3.73 Hz, 1 H) 7.02 (d, J = 3.73 Hz, 1 H) 4.69 (spt, J = 6.83 Hz, 1 H) 3.12-3.25 (m, 4 H) 2.61-2.71 (m, 5 H) 2.50 (dd, J = 12.50, 6.14 Hz, 1 H) 2.23 (s, 3 H) 2.15 (s, 3 H) 1.29 (d, J = 6.58 Hz, 3 H) |
| 71 | 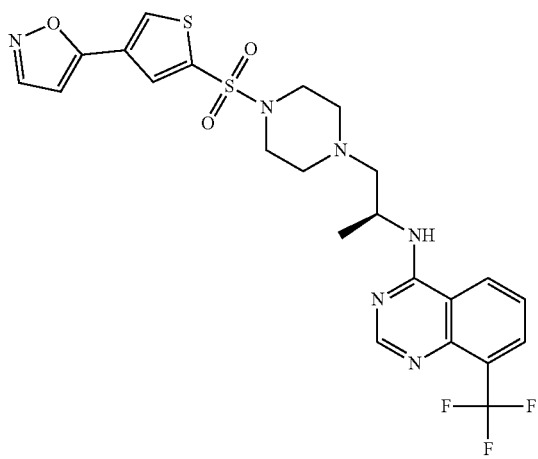 [SMILES: C[C@@H](CN1CCN(S(=O)(=O)c2cc(-c3ccno3)cs2)CC1)Nc1ncnc2c(C(F)(F)F)cccc12]<br>N-[(2S)-1-(4-{[4-(1,2-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 552.7 (Method 3)<br>$^1$H NMR (400 MHz, ACETONE-d6) δ ppm 8.54 (s, 1 H), 8.30-8.48 (m, 2 H), 8.04-8.10 (m, 2 H), 7.96 (bs, 1 H), 7.37-7.57 (m, 1 H), 6.85 (d, J = 1.75 Hz, 1 H), 4.47-4.89 (m, 1 H), 3.08 (br s, 4 H), 2.77 (br s, 6 H), 1.31 (br s, 3 H) |

| Example No. | Structure & Name | Analytical data |
| --- | --- | --- |
| 73 | 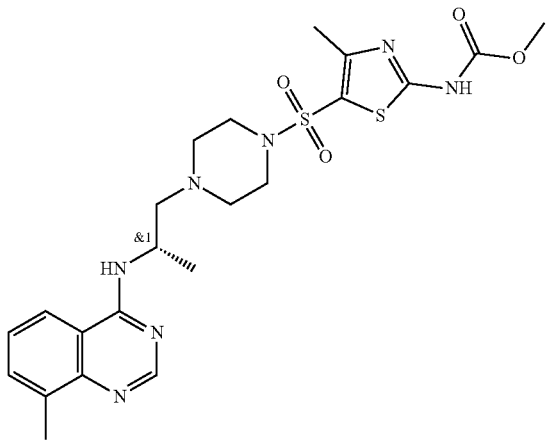 [SMILES: COC(=O)Nc1nc(C)c(S(=O)(=O)N2CCN(C[C@H](C)Nc3ncnc4c(C)cccc34)CC2)s1]<br><br>methyl N-[4-methyl-5-({4-[(2S)-2-[(8-methylquinazolin-4-yl)amino]propyl]piperazin-1-yl}sulfonyl)-1,3-thiazol-2-yl]carbamate | LC-MS (ESI): m/z (M + 1): 520.2 (Method 2)<br>$^1$H NMR (400 MHz, DMSO-d$_6$) δ ppm 1.19 (d, J = 6.6 Hz, 3 H), 2.37-2.45 (m, 4 H), 2.53-2.64 (m, 8 H), 2.88-3.05 (m, 4 H), 3.76 (s, 3 H), 4.59 (spt, J = 6.8 Hz, 1 H), 7.28-7.39 (m, 1 H), 7.59 (d, J = 7.0 Hz, 1 H), 7.72 (d, J = 8.1 Hz, 1 H), 8.06 (d, J = 8.3 Hz, 1 H), 8.46 (s, 1 H), 12.32 (br s, 1 H) |
| 90 | 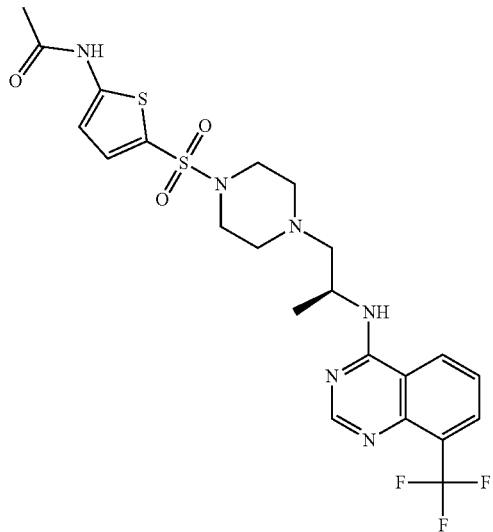 [SMILES: CC(=O)Nc1ccc(S(=O)(=O)N2CCN(C[C@H](C)Nc3ncnc4c(C(F)(F)F)cccc34)CC2)s1]<br><br>N-[5-({4-[(2S)-2-{[8-(trifluoromethyl)quinazolin-4-yl]amino}propyl]piperazin-1-yl}sulfonyl)thiophen-2-yl]acetamide | LC-MS (ESI): m/z (M + 1): 543.1 (Method 4)<br>$^1$H NMR (300 MHz, DMSO-d$_6$) δ ppm 11.76 (s, 1 H), 8.50-8.60 (m, 2 H), 8.08-8.20 (m, 2 H), 7.60 (t, 1 H), 7.36 (d, J = 4.19 Hz, 1 H), 6.68 (d, J = 4.19 Hz, 1 H), 4.52-4.70 (m, 1 H), 2.75-2.96 (m, 4 H), 2.52-2.67 (m, 5 H), 2.31-2.48 (m, 1 H), 2.12 (s, 3 H), 1.19 (d, J = 6.48 Hz, 3 H) |

-continued

| Example No. | Structure & Name | Analytical data |
|---|---|---|
| 93 | 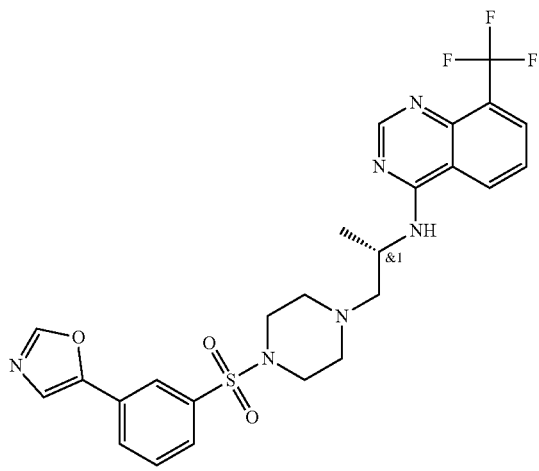 [SMILES: C[C@@H](CN1CCN(S(=O)(=O)c2cccc(-c3cnco3)c2)CC1)Nc1ncnc2c(C(F)(F)F)cccc12]<br>N-[(2S)-1-{4-[3-(1,3-oxazol-5-yl)benzenesulfonyl]piperazin-1-yl}propan-2-yl]-8-(trifluoromethyl)quinazolin-4-amine | LC-MS (ESI): m/z (M + 1): 547.4 (Method 1)<br>$^1$H NMR (400 MHz, DMSO-$d_6$) δ ppm 1.16 (d, J = 6.6 Hz, 3 H), 2.39 (dd, J = 12.3, 6.6 Hz, 1 H), 2.51-2.63 (m, 5 H), 2.89 (br s, 4 H), 4.58 (dt, J = 14.0, 7.0 Hz, 1 H), 7.56 (t, J = 1.9 Hz, 1 H), 7.65-7.80 (m, 2 H), 7.90 (s, 1 H), 7.92-7.97 (m, 1 H), 8.04 (dt, J = 7.7, 1.4 Hz, 1 H), 8.07-8.16 (m, 2 H), 8.45-8.57 (m, 3 H) |
| 97 | 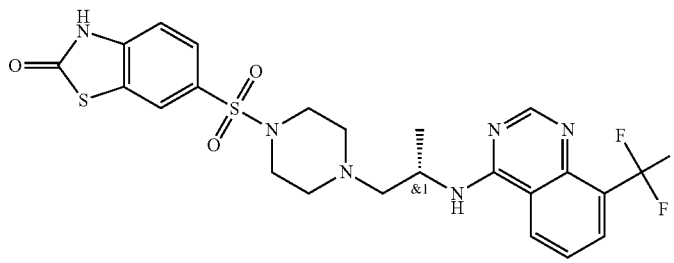<br>({4-[(2S)-2-{[8-(trifluoromethyl)quinazolin-4-yl]amino}propyl]piperazin-1-yl]sulfonyl)-2,3-dihydro-1,3-benzothiazol-2-one | LC-MS (ESI): m/z (M + 1): 553.1 (Method 2)<br>$^1$H NMR (400 MHz, DMSO-$d_6$) δ ppm 1.17 (d, J = 6.6 Hz, 3 H), 2.35-2.44 (m, 1 H), 2.52 (br s, 4 H), 2.55-2.66 (m, 1 H), 2.83 (br s, 4 H), 4.59 (dt, J = 13.8, 6.7 Hz, 1 H), 7.23 (d, J = 8.6 Hz, 1 H), 7.51-7.64 (m, 2 H), 7.96 (d, J = 1.5 Hz, 1 H), 8.08-8.17 (m, 2 H), 8.48-8.55 (m, 2 H), 12.35 (br s, 1 H) |
| 99 | 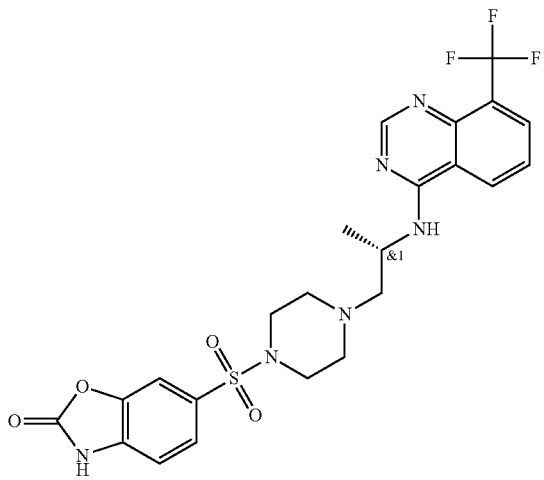 [SMILES: C[C@@H](CN1CCN(S(=O)(=O)c2ccc3[nH]c(=O)oc3c2)CC1)Nc1ncnc2c(C(F)(F)F)cccc12]<br>6-({4-[(2S)-2-{[8-(trifluoromethyl)quinazolin-4-yl]amino}propyl]piperazin-1-yl}sulfonyl)-2,3-dihydro-1,3-benzoxazol-2-one | LC-MS (ESI): m/z (M + 1): 537.1 (Method 2)<br>$^1$H NMR (500 MHz, DMSO-$d_6$) δ ppm 1.16 (d, J = 6.6 Hz, 3 H), 2.33-2.42 (m, 1 H), 2.51-2.55 (m, 4 H), 2.59 (dd, J = 12.5, 7.6 Hz, 1 H), 2.82 (br s, 4 H), 4.51-4.65 (m, 1 H), 7.24 (d, J = 8.2 Hz, 1 H), 7.48 (dd, J = 8.2, 1.6 Hz, 1 H), 7.56 (d, J = 1.5 Hz, 1 H), 7.58 (t, J = 7.9 Hz, 1 H), 8.06-8.16 (m, 2H), 8.47-8.55 (m, 2 H), 12.15 (br s, 1 H) |

| Example No. | Structure & Name | Analytical data |
|---|---|---|
| 100 | 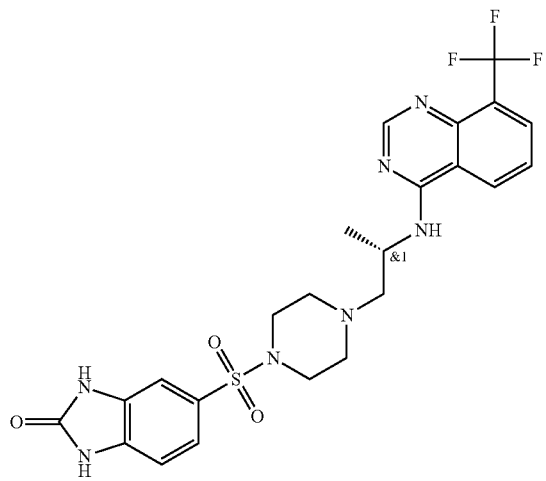 [SMILES: C[C@@H](CN1CCN(S(=O)(=O)c2ccc3[nH]c(=O)[nH]c3c2)CC1)Nc1ncnc2c(C(F)(F)F)cccc12]

5-({4-[(2S)-2-{[8-(trifluoromethyl)quinazolin-4-yl]amino}propyl]piperazin-1-yl}sulfonyl)-2,3-dihydro-1H-1,3-benzodiazol-2-one | LC-MS (ESI): m/z (M + 1): 536.1 (Method 2)<br>$^1$H NMR (500 MHz, DMSO-$d_6$) δ ppm 1.16 (d, J = 6.6 Hz, 3 H), 2.32-2.42 (m, 1 H), 2.44-2.54 (m, 4 H), 2.57 (dd, J = 12.5, 7.2 Hz, 1 H), 2.81 (br s, 4 H), 4.49-4.65 (m, 1 H), 7.08 (d, J = 8.2 Hz, 1 H), 7.14 (d, J = 1.6 Hz, 1 H), 7.28 (dd, J = 8.2, 1.6 Hz, 1 H), 7.58 (t, J = 7.9 Hz, 1 H), 8.03-8.17 (m, 2H), 8.46-8.56 (m, 2H), 11.03 (br s, 2 H) |
| 101 | 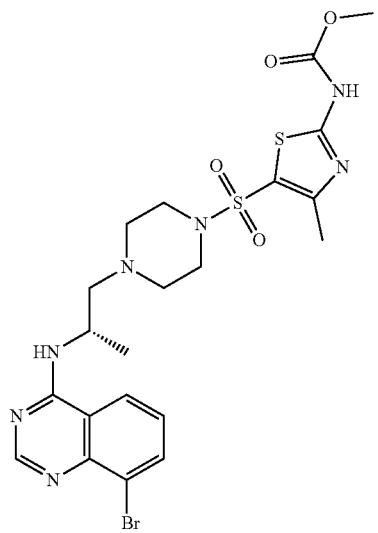 [SMILES: COC(=O)Nc1nc(C)c(S(=O)(=O)N2CCN(C[C@H](C)Nc3ncnc4c(Br)cccc34)CC2)s1]

methyl N-[5-({4-[(2S)-2-[(8-bromoquinazolin-4-yl)amino]propyl]piperazin-1-yl}sulfonyl)-4-methyl-1,3-thiazol-2-yl]carbamate | LC-MS (ESI): m/z (M + 1): 586.1 (Method 2)<br>$^1$H NMR (400 MHz, DMSO-$d_6$) δ ppm 1.20 (d, J = 6.6 Hz, 3 H), 2.37-2.47 (m, 4 H), 2.53-2.64 (m, 5 H), 2.97 (br s, 4 H), 3.75 (s, 3 H), 4.53-4.66 (m, 1 H), 7.39 (t, J = 1.9 Hz, 1 H), 8.02 (d, J = 7.9 Hz, 1 H), 8.07-8.13 (m, 1 H), 8.27 (d, Hz, 1 H), 8.51 (s, 1 H), 12.33 (br s, 1 H) |

Example 2

Methyl N-[4-methyl-5-({4-[(2S)-2-{[2-methyl-8-(trifluoromethyl)quinazolin-4-yl]amino}propyl]piperazin-1-yl}sulfonyl)-1,3-thiazol-2-yl]carbamate

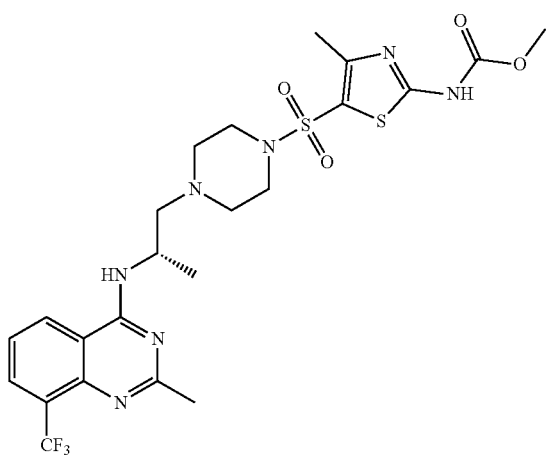 [SMILES: COC(=O)Nc1nc(C)c(S(=O)(=O)N2CCN(C[C@H](C)Nc3nc(C)nc4c(C(F)(F)F)cccc34)CC2)s1]

Step 1: Preparation of 2-methyl-8-(trifluoromethyl)-3,4-dihydroquinazolin-4-one (Intermediate 3)

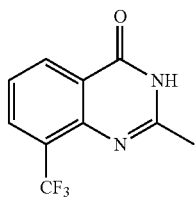 [SMILES: Cc1nc2c(C(F)(F)F)cccc2c(=O)[nH]1]

A solution of 2-amino-3-(trifluoromethyl)benzoic acid (1.2 g, 5.85 mmol) in Ac$_2$O (12 mL) was heated at reflux for 12 hours and the mixture was concentrated under vacuum to obtain the crude material as a solid. The crude was dissolved in a mixture of EtOH (12 mL) and conc. NH$_4$OH (12 mL) and the mixture was stirred at 80° C. for 5 hours. The reaction mixture was cooled to room temperature, filtered and washed with water. The solid residue was dried under vacuum to obtain Intermediate 3 (706 mg, 3 mmol, 53% yield) as a yellowish solid.

LC-MS (ESI): m/z (M+1): 229 (Method 1)

$^1$H NMR (400 MHz, DMSO-d$_6$) δ ppm 12.55-12.50 (m, 1H), 8.35 (dd, J=8.1, 1.5 Hz, 1H), 8.14 (dd, J=7.6, 1.5 Hz, 1H), 7.58 (t, J=7.8 Hz, 1H), 2.40 (s, 3H)

Step 2: Preparation of 4-chloro-2-methyl-8-(trifluoromethyl)quinazoline (Intermediate 4)

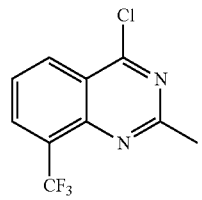 [SMILES: Cc1nc(Cl)c2cccc(C(F)(F)F)c2n1]

A suspension of Intermediate 3 (706 mg, 3 mmol) in toluene (20 mL) was added with POCl$_3$ (1.15 mL, 12.36 mmol) followed by DIPEA (1 mL, 6 mmol). The reaction was heated to 90° C. for 5 h then cooled to r.t. and the solution was concentrated under reduced pressure. The solid was taken up in DCM and concentrated again. The crude material was purified by flash chromatography eluting with a gradient from 0 to 5% of acetonitrile in water (0.1% HCOOH), yielding Intermediate 4 (418 mg, 1.7 mmol. 55% yield) as a white solid.

LC-MS (ESI): m/z (M+1): 247 (Method 1)

$^1$H NMR (400 MHz, DMSO-d$_6$) δ ppm 8.56 (dd, J=8.5, 1.4 Hz, 1H), 8.53-8.46 (m, 1H), 7.93 (t, J=7.9 Hz, 1H), 2.81 (s, 3H)

Step 3: Preparation of tert-butyl 4-[(2S)-2-{[2-methyl-8-(trifluoromethyl)quinazolin-4-yl]amino}propyl]piperazine-1-carboxylate (Intermediate 5)

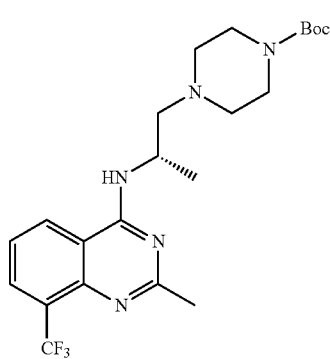 [SMILES: Cc1nc(N[C@@H](C)CN2CCN(C(=O)OC(C)(C)C)CC2)c2cccc(C(F)(F)F)c2n1]

Title compound was prepared following the procedure used for the synthesis of Intermediate 1, starting from Intermediate 4 (418 mg, 1.7 mmol) to afford Intermediate 5 (700 mg, 1.54 mmol, 91% yield) as a yellowish solid.

LC-MS (ESI): m/z (M+1): 454.29 (Method 1)

$^1$H NMR (400 MHz, DMSO-d$_6$) δ ppm 8.53 (dd, J=8.4, 1.4 Hz, 1H), 8.09 (d, J=7.3 Hz, 1H), 8.01 (d, J=8.0 Hz, 1H), 7.54 (t, J=7.9 Hz, 1H), 4.71-4.64 (m, 1H), 3.28-3.21 (m, 4H), 2.61-2.56 (m, 1H), 2.49-2.31 (m, 8H), 1.38 (s, 9H), 1.25 (d, J=6.6 Hz, 3H)

Step 4: Preparation of 2-methyl-N-[(2S)-1-(piperazin-1-yl)propan-2-yl]-8-(trifluoromethyl)quinazolin-4-amine (Intermediate 6)

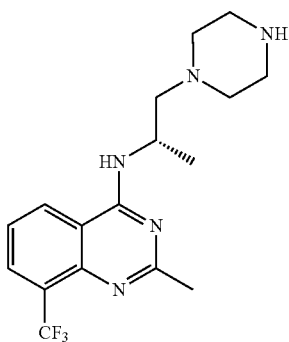 [SMILES: Cc1nc(N[C@@H](C)CN2CCNCC2)c2cccc(C(F)(F)F)c2n1]

To a solution of Intermediate 5 (700 mg, 1.54 mmol) in DCM (15 mL), TFA (2.4 mL, 30.8 mmol) was added. The reaction mixture was stirred at room temperature overnight. The mixture was concentrated under reduced pressure to obtain the crude target material. This was purified on a SCX cartridge eluting with 2N $NH_3$ in methanol to provide 2-methyl-N-[(2S)-1-(piperazin-1-yl)propan-2-yl]-8-(trifluoromethyl)quinazolin-4-amine (0.539 g, 1.52 mmol) as a yellow foam.

LC-MS (ESI): m/z (M+1): 354.25 (Method 2)

$^1$H NMR (400 MHz, Chloroform-d) δ ppm 8.03 (d, J=7.4 Hz, 1H), 7.94-7.87 (m, 1H), 7.43 (t, J=7.8 Hz, 1H), 6.56 (d, J=4.3 Hz, 1H), 4.35-4.29 (m, 1H), 2.96-2.83 (m, 4H), 2.61-251 (m, 4H), 2.46 (br. s., 2H), 1.68 (br. s., 4H), 1.40 (d, J=6.2 Hz, 3H)

Step 5: Preparation of methyl N-[4-methyl-5-({4-[(2S)-2-{[2-methyl-8-(trifluoromethyl)quinazolin-4-yl]amino}propyl]piperazin-1-yl}sulfonyl)-1,3-thiazol-2-yl]carbamate (Example 2)

Title compound was prepared following the procedure used for the synthesis of Example 1, starting from 2-methyl-N-[(2S)-1-(piperazin-1-yl)propan-2-yl]-8-(trifluoromethyl)quinazolin-4-amine (Intermediate 6, 100 mg, 0.28 mmol) to afford the title compound (135.1 mg, 0.23 mmol, 56% yield) as a white solid.

LC-MS (ESI): m/z (M+1): 588.23 (Method 1)

$^1$H NMR (400 MHz, DMSO-d6) δ ppm 1.21 (d, J=6.58 Hz, 3H), 2.44 (d, J=10.52 Hz, 7H), 2.58 (br. s., 5H), 2.98 (br. s., 4H), 3.76 (s, 3H), 4.58 (br. s., 1H), 7.50 (t, J=7.67 Hz, 1H), 7.97 (d, J=7.45 Hz, 1H), 8.07 (d, J=7.02 Hz, 1H), 8.49 (d, J=8.33 Hz, 1H), 12.32 (br. s., 1H)

The Examples in the following table were prepared from commercially available reagents by using methods analogous to Example 2.

| Example No. | Structure & Name | Analytical data |
| --- | --- | --- |
| 13 | ![structure] N-[5-({4-[(2S)-2-{[2-methyl-8-(trifluoromethyl)quinazolin-4-yl]amino}propyl]piperazin-1-yl}sulfonyl)-1,3-thiazol-2-yl]acetamide | LC-MS (ESI): m/z (M + 1): 558.2 (Method 1) <br> $^1$H NMR (400 MHz, DMSO-d$_6$) δ ppm 1.18 (d, J = 6.58 Hz, 3 H), 2.17 (s, 3 H), 2.33-2.41 (m, 1 H), 2.43 (s, 3 H), 2.53-2.64 (m, 5 H), 2.90 (br. s., 4 H), 4.56 (dt, J = 13.70, 6.96 Hz, 1 H), 7.48 (t, J = 7.89 Hz, 1 H), 7.92 (s, 1 H), 7.95 (d, J = 7.45 Hz, 1 H), 8.05 (d, J = 7.45 Hz, 1 H), 8.46 (d, J = 8.33 Hz, 1 H), 12.70 (s, 1 H) |

| Example No. | Structure & Name | Analytical data |
|---|---|---|
| 23 | 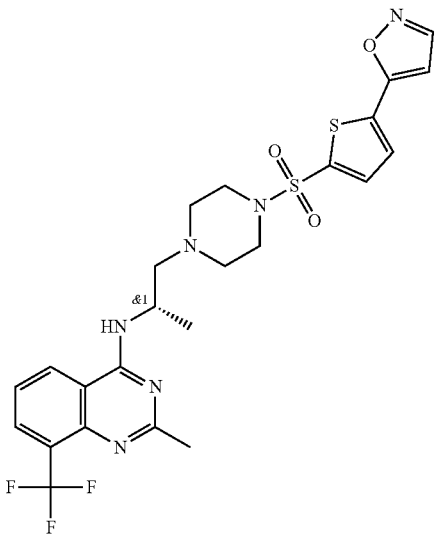<br>2-methyl-N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine | LC-MS (ESI): m/z (M + 1): 567.2 (Method 1)<br>$^1$H NMR (400 MHz, DMSO-$d_6$) δ ppm 1.16 (d, J = 6.58 Hz, 3 H), 2.31-2.39 (m, 1 H), 2.41 (s, 3 H), 2.51-2.62 (m, 5 H), 2.93 (br. s., 3 H), 4.55 (dt, J = 14.03, 7.02 Hz, 1 H), 7.08 (d, J = 1.97 Hz, 1 H), 7.45 (t, J = 7.89 Hz, 1 H), 7.67 (d, J = 3.95 Hz, 1 H), 7.78 (d, J = 3.95 Hz, 1 H), 7.93 (d, J = 7.89 Hz, 1 H), 8.00 (d, J = 7.45 Hz, 1 H), 8.43 (d, J = 7.89 Hz, 1 H), 8.71 (d, J = 1.97 Hz, 1 H) |

Example 3

Methyl N-[4-methyl-5-({4-[(2S)-2-{[8-(trifluoromethoxy)quinazolin-4-yl]amino}propyl]piperazin-1-yl}sulfonyl)-1,3-thiazol-2-yl]carbamate

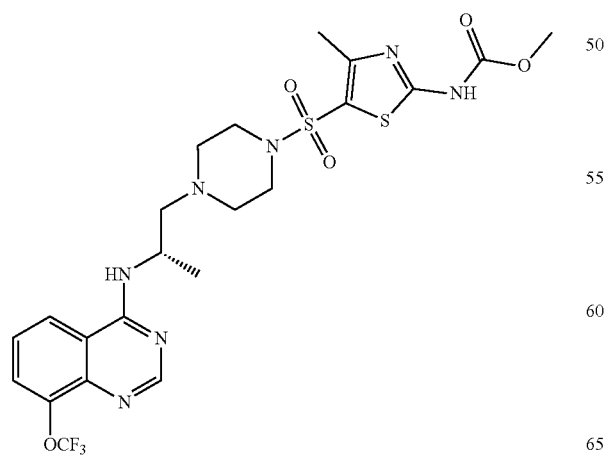

Step 1: Preparation of 8-(trifluoromethoxy)quinazolin-4-ol (Intermediate 7)

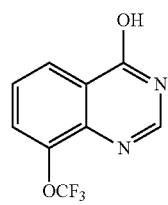

A solution of 2-amino-3-(trifluoromethoxy)benzoic acid (500 mg, 2.26 mmol) and formamidine acetate (259 mg, 2.5 mmol) in EtOH (5 mL) was heated at 85° C. for 16 hours. The solvent was removed under vacuum and the crude was added with DCM, causing the precipitation of a white solid. The solid was filtered-off and the filtrate was concentrated under reduced pressure to provide crude 8-(trifluoromethoxy)quinazolin-4-ol that was used in the next step without further purification (276 mg, 1.2 mmol, 53% yield).

LC-MS (ESI): m/z (M+1): 231.1 (Method 1)

Step 2: Preparation of 4-chloro-8-(trifluoromethoxy)quinazoline (Intermediate 8)

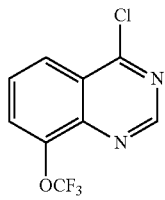 [SMILES: FC(F)(F)Oc1cccc2c(Cl)ncnc12]

Title compound was prepared following the procedure used for the synthesis of Intermediate 4, starting from 8-(trifluoromethoxy)quinazolin-4-ol (Intermediate 7, 276 mg, 1.2 mmol) to afford Intermediate 8 (65 mg, 0.261 mmol, 22% yield) LC-MS (ESI): m/z (M+1): 249.1 (Method 1)

Step 3: Preparation of tert-butyl 4-[(2S)-2-[[8-(trifluoromethoxy)quinazolin-4-yl]amino]propyl]piperazine-1-carboxylate (Intermediate 9)

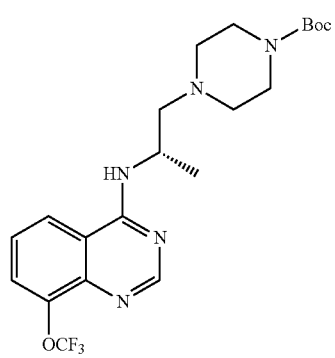 [SMILES: C[C@@H](CN1CCN(C(=O)OC(C)(C)C)CC1)Nc1ncnc2c(OC(F)(F)F)cccc12]

Title compound was prepared following the procedure used for the synthesis of Intermediate 1, starting from 4-chloro-8-(trifluoromethoxy)quinazoline (Intermediate 8, 65 mg, 0.261 mmol) to afford Intermediate 9 (180 mg, 0.4 mmol, crude) that was used in the next step without further purification.

LC-MS (ESI): m/z (M+1): 456.3 (Method 1)

Step 4: Preparation of N-[(2S)-1-piperazin-1-ylpropan-2-yl]-8-(trifluoromethoxy)quinazolin-4-amine Hydrochloride (Intermediate 10)

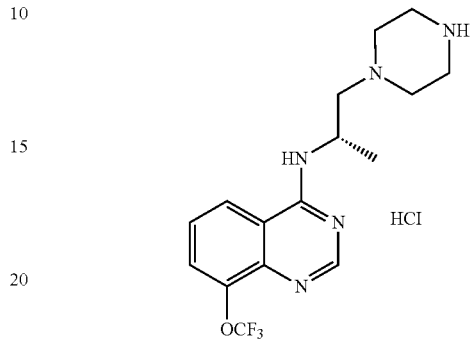

Title compound was prepared following the procedure used for the synthesis of Intermediate 2, starting from tert-butyl 4-[(2S)-2-[[8-(trifluoromethoxy)quinazolin-4-yl]amino]propyl]piperazine-1-carboxylate (Intermediate 9, 180 mg, 0.4 mmol) to afford Intermediate 10 (202 mg, crude) that was used in the next step without further purification.

LC-MS (ESI): m/z (M+1): 356.2 (Method 2)

Step 5: Preparation of methyl N-[4-methyl-5-({4-[(2S)-2-{[8-(trifluoromethoxy)quinazolin-4-yl]amino}propyl]piperazin-1-yl}sulfonyl)-1,3-thiazol-2-yl]carbamate (Example 3)

Title compound was prepared following the procedure used for the synthesis of Example 1, starting from N-[(2S)-1-piperazin-1-ylpropan-2-yl]-8-(trifluoromethoxy)quinazolin-4-amine hydrochloride (Intermediate 10, 100 mg, 0.25 mmol) to afford the title compound (55 mg, 0.093 mmol, 40% yield) as a white solid.

LC-MS (ESI): m/z (M+1): 590.33 (Method 2)

$^1$H NMR (400 MHz, DMSO-$d_6$) δ ppm 1.20 (d, J=6.6 Hz, 3H), 2.38-2.45 (m, 4H), 2.56 (br s, 5H), 2.97 (br s, 4H), 3.72 (br s, 3H), 4.55-4.66 (m, 1H), 7.54 (t, J=8.1 Hz, 1H), 7.76-7.82 (m, 1H), 8.08 (d, J=8.0 Hz, 1H), 8.29 (dd, J=8.5, 1.1 Hz, 1H), 8.50 (s, 1H), 12.30 (br s, 1H)

The Examples in the following table were prepared from commercially available reagents by using methods analogous to Example 3.

| Example No. | Structure & Name | Analytical data |
|---|---|---|
| 75 | 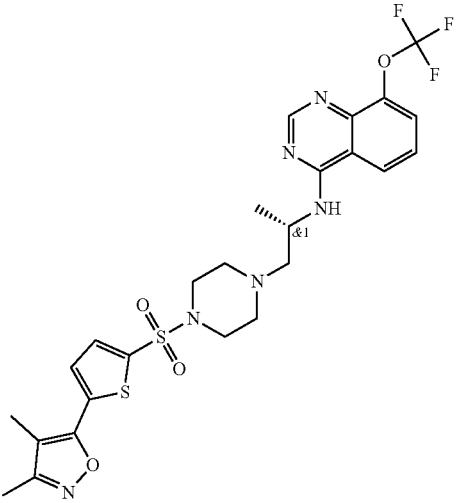<br><br>N-[(2S)-1-(4-{[5-(3,4-dimethyl-1,2-oxazol-5-yl)thiophen-2-yl]sulfonyl}piperazin-1-yl)propan-2-yl]-8-(trifluoromethoxy)quinazolin-4-amine | LC-MS (ESI): m/z (M + 1): 597.36 (Method 2)<br>$^1$H NMR (400 MHz, DMSO-d$_6$) δ ppm 1.19 (d, J = 6.6 Hz, 3 H), 2.15 (s, 3 H), 2.24 (s, 3 H), 2.41 (dd, J = 12.4, 6.7 Hz, 1 H), 2.54-2.65 (m, 5 H), 2.89-3.04 (m, 4 H), 4.61 (spt, J = 6.9 Hz, 1 H), 7.52 (t, J = 8.1 Hz, 1 H), 7.64 (d, J = 3.9 Hz, 1 H), 7.70 (d, J = 3.9 Hz, 1 H), 7.75 (d, J = 7.9 Hz, 1 H), 8.06 (d, J = 7.9 Hz, 1 H), 8.27 (d, J = 7.7 Hz, 1 H), 8.49 (s, 1 H) |
| | 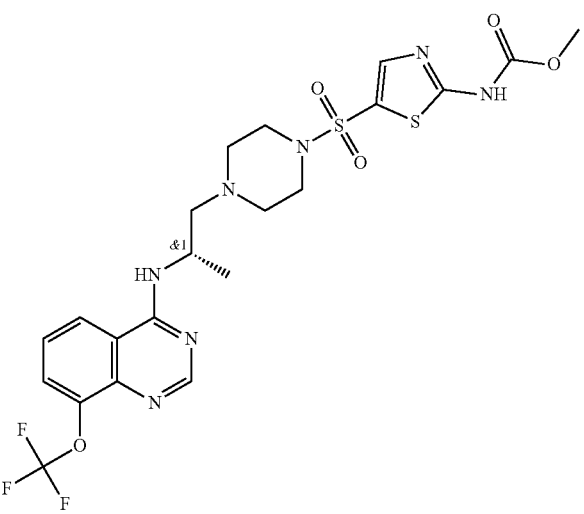<br><br>methyl N-[5-({4-[(2S)-2-{[8-(trifluoromethoxy)quinazolin-4-yl]amino}propyl]piperazin-1-yl}sulfonyl)-1,3-thiazol-2-yl]carbamate | LC-MS (ESI): m/z (M + 1): 576 (Method 2)<br>$^1$H NMR (400 MHz, DMSO-d$_6$) δ ppm 1.20 (d, J = 6.6 Hz, 3 H), 2.41 (dd, J = 12.5, 6.8 Hz, 1 H), 2.58 (br d, J = 4.6 Hz, 5 H), 2.92 (br s, 4 H), 3.76 (s, 3 H), 4.60 (dt, J = 14.0, 6.8 Hz, 1 H), 7.53 (t, J = 8.1 Hz, 1 H), 7.78 (d, J = 7.9 Hz, 1 H), 7.85 (s, 1 H), 8.08 (d, J = 7.9 Hz, 1 H), 8.29 (d, J = 7.9 Hz, 1 H), 8.50 (s, 1 H), 12.47 (br s, 1 H) |

Example 4

8-(difluoromethoxy)-N-[(2S)-1-(4-{[5-(3,4-dimethyl-1,2-oxazol-5-yl)thiophen-2-yl]sulfonyl}piperazin-1-yl)propan-2-yl]quinazolin-4-amine

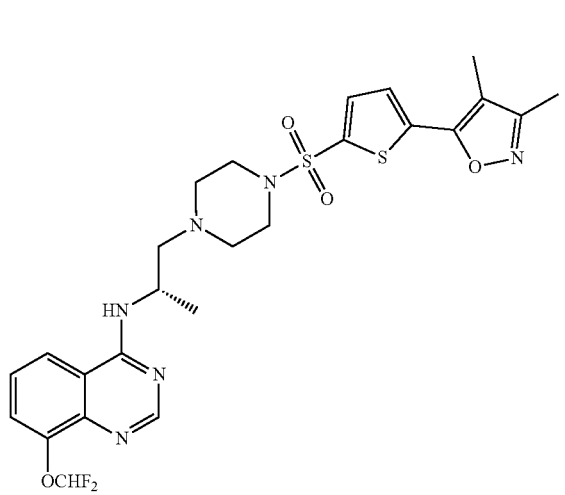 [SMILES: Cc1noc(-c2ccc(S(=O)(=O)N3CCN(C[C@H](C)Nc4ncnc5c(OC(F)F)cccc45)CC3)s2)c1C]

Step 1: Preparation of 4-chloroquinazolin-8-ol (Intermediate 11)

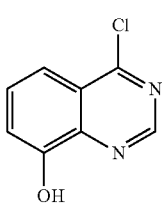 [SMILES: Oc1cccc2c(Cl)ncnc12]

To a solution of 4-chloro-8-methoxyquinazoline (300.0 mg, 1.54 mmol) in dry DCM (1.5 mL), BBr$_3$ 1 M in DCM (9.25 mL, 9.25 mmol) was added at 0° C. and the solution was stirred at room temperature for 12 hour. The solution was cooled to 0° C. and ice/water was added. After stirring for 15 min., DCM and water were added. The organic solvent was separated and removed under vacuum to provide Intermediate 11 (385 mg, crude).

LC-MS (ESI): m/z (M+1): 180.9 (Method 1)

H NMR (400 MHz, DMSO-d$_6$) δ 8.60 (s, 1H), 7.59 (dd, J=7.9, 1.3 Hz, 1H), 7.46 (t, J=7.9 Hz, 1H), 7.33 (dd, J=8.0, 1.4 Hz, 1H)

Step 2: Preparation of 8-(difluoromethoxy)quinazolin-4-ol (Intermediate 12)

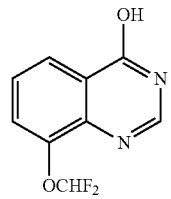

To a solution of Intermediate 11 (94 mg, 0.52 mmol) in DCM (1.5 mL), potassium hydroxide 2M aqueous solution (0.1 mL, 0.100 mmol) and then [bromo(difluoro)methyl]-trimethylsilane (0.16 mL, 1.04 mmol) were added at r.t. The reaction was stirred at r.t. for 8 h. Additional [bromo(difluoro)methyl]-trimethylsilane (0.16 mL, 1.04 mmol) and 2M potassium hydroxide (0.1 mL, 0.100 mmol) were added and the reaction was stirred at r.t. for 24 h. The solvent was removed under vacuum to provide Intermediate 12 (156 mg, crude) that was used in the next step without further purification.

LC-MS (ESI): m/z (M+1): 213 (Method 1)

Step 3: Preparation of 4-chloro-8-(difluoromethoxy)quinazoline (Intermediate 13)

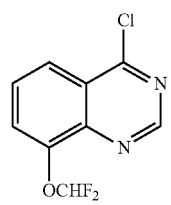 [SMILES: FC(F)Oc1cccc2c(Cl)ncnc12]

Title compound was prepared following the procedure used for the synthesis of Intermediate 4 starting from 8-(difluoromethoxy)quinazolin-4-ol (Intermediate 12, 110 mg, 0.52 mmol) to afford Intermediate 13 (84 mg, 0.36 mmol, 70% yield). LC-MS (ESI): m/z (M+1): 231 (Method 1)

Step 4: Preparation of tert-butyl 4-[(2S)-2-[[8-(difluoromethoxy)quinazolin-4-yl]amino]propyl]piperazine-1-carboxylate (Intermediate 14)

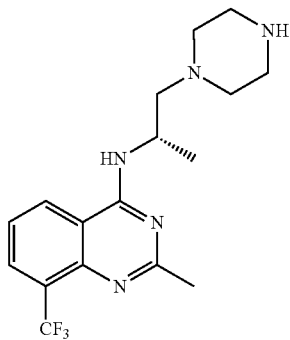 [SMILES: Cc1nc(N[C@@H](C)CN2CCNCC2)c2cccc(C(F)(F)F)c2n1]

Title compound was prepared following the procedure used for the synthesis of Intermediate 1 starting from 4-chloro-8-(difluoromethoxy)quinazoline (Intermediate 13, 84 mg, 0.36 mmol) to afford Intermediate 14 (14 mg, 0.032 mmol, 9% yield).

LC-MS (ESI): m/z (M+1): 438.2 (Method 2)

Step 5: Preparation of 8-(difluoromethoxy)-N-[(2S)-1-piperazin-1-ylpropan-2-yl]quinazolin-4-amine hydrochloride (Intermediate 15)

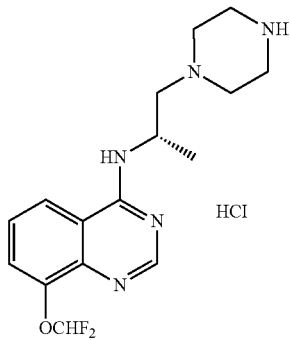

Title compound was prepared following the procedure used for the synthesis of Intermediate 2, starting from tert-butyl 4-[(2S)-2-[[-8-(difluoromethoxy)quinazolin-4-yl]amino]propyl]piperazine-1-carboxylate (Intermediate 14, 14 mg, 0.032 mmol) to afford Intermediate 15 (22 mg, crude) that was used in the next step without further purification.

LC-MS (ESI): m/z (M+1): 338.2 (Method 2)

Step 6: Preparation of 8-(difluoromethoxy)-N-[(2S)-1-(4-{[5-(3,4-dimethyl-1,2-oxazol-5-yl)thiophen-2-yl]sulfonyl}piperazin-1-yl)propan-2-yl]quinazolin-4-amine Example 4

Title compound was prepared following the procedure used for the synthesis of Example 1, starting from 8-(difluoromethoxy)-N-[(2S)-1-piperazin-1-ylpropan-2-yl]quinazolin-4-amine hydrochloride (Intermediate 15, 22 mg, crude) and 5-(3,4-dimethyl-1,2-oxazol-5-yl)thiophene-2-sulfonyl chloride (9.8 mg, 0.04 mmol) to afford the title compound (6 mg, 0.010 mmol, 32% yield) as a yellowish solid.

LC-MS (ESI): m/z (M+1): 579.13 (Method 2)

1H NMR (500 MHz, DMSO-$d_6$) δ ppm 1.18 (d, J=6.6 Hz, 3H), 2.15 (s, 3H), 2.24 (s, 3H), 2.39-2.45 (m, 1H), 2.55-2.63 (m, 5H), 2.96 (br s, 4H), 4.54-4.70 (m, 1H), 7.35 (t, J=75.5 Hz, 1H), 7.41-7.49 (m, 1H), 7.54 (d, J=7.7 Hz, 1H), 7.65 (d, J=4.1 Hz, 1H), 7.71 (d, J=4.1 Hz, 1H), 8.00 (br d, J=8.0 Hz, 1H), 8.13 (d, J=8.2 Hz, 1H), 8.47 (s, 1H)

Example 18 methyl N-[5-({4-[(2S)-2-[(2-cyclopropyl-8-methylquinazolin-4-yl)amino]propyl]piperazin-1-yl}sulfonyl)-4-methyl-1,3-thiazol-2-yl]carbamate

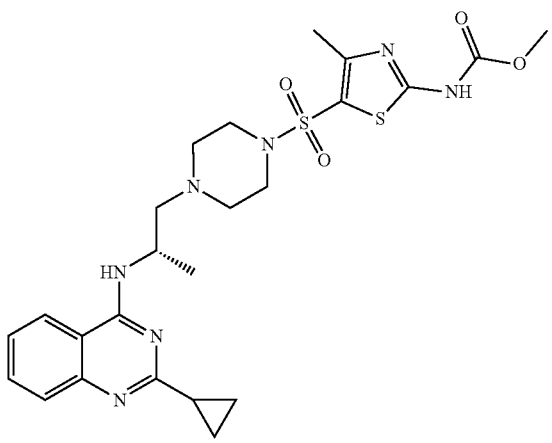 [SMILES: COC(=O)Nc1nc(C)c(S(=O)(=O)N2CCN(C[C@H](C)Nc3nc(C4CC4)nc4ccccc34)CC2)s1]

Step 1: Preparation of 2-cyclopropyl-8-methyl-3,4-dihydroquinazolin-4-one (Intermediate 16)

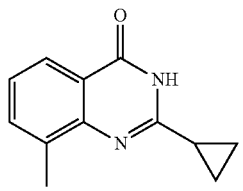

To a solution of 2-bromo-3-methylbenzoic acid (500 mg, 2.33 mmol) in dry DMF (6 mL), cyclopropanecarboximidamide hydrochloride (416 mg, 3.45 mmol), CuI (222 mg, 1.165 mmol), $Cs_2CO_3$ (1.518 g, 4.66 mmol) were added in a sealed tube under nitrogen atmosphere and the suspension was stirred at room temperature for 12 hour. The mixture was then partitioned between DCM and water, the organic solvent was separated and removed under vacuum to provide crude Intermediate 16 (240 mg, 1.2 mmol, 52% yield) that was used in the next step without further purifications.

LC-MS (ESI): m/z (M+1): 201.1 (Method 1)

Step 2: Preparation of 4-chloro-2-cyclopropyl-8-methylquinazoline (Intermediate 17)

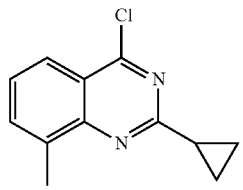

Title compound was prepared following the procedure used for the synthesis of Intermediate 4 starting from 2-cyclopropyl-8-methyl-3,4-dihydroquinazolin-4-one (Intermediate 16, 240 mg, 1.2 mmol) to afford Intermediate 17 as a crude (1.2 mmol) that was used in the next step without further purifications.

LC-MS (ESI): m/z (M+1): 219.3 (Method 1)

Step 3: Preparation of tert-butyl 4-[(2S)-2-[(2-cyclopropyl-8-methyl quinazolin-4-yl)amino]propyl] piperazine-1-carboxylate (Intermediate 18)

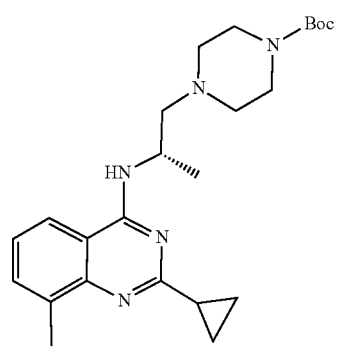 [SMILES: Cc1cccc2c(N[C@@H](C)CN3CCN(C(=O)OC(C)(C)C)CC3)nc(C3CC3)nc12]

Title compound was prepared following the procedure used for the synthesis of Intermediate 1 starting from 4-chloro-2-cyclopropyl-8-methylquinazoline (Intermediate 17, 1.2 mmol, crude) to afford Intermediate 18 (181 mg, 0.43 mmol, 36% yield).

LC-MS (ESI): m/z (M+1): 426.3 (Method 1)

Step 4: Preparation of 2-cyclopropyl-8-methyl-N-[(2S)-1-(piperazin-1-yl)propan-2-yl]quinazolin-4-amine hydrochloride (Intermediate 19)

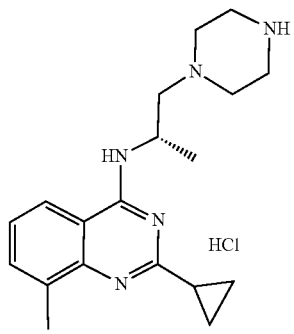 [SMILES: Cc1cccc2c(N[C@@H](C)CN3CCNCC3)nc(C3CC3)nc12 ; Cl]

Title compound was prepared following the procedure used for the synthesis of Intermediate 2, starting from tert-butyl 4-[(2S)-2-[(2-cyclopropyl-8-methylquinazolin-4-yl)amino]propyl]piperazine-1-carboxylate (Intermediate 18, 181 mg, 0.43 mmol) to afford Intermediate 19 as a crude (0.43 mmol) that was used in the next step without further purification.

LC-MS (ESI): m/z (M+1): 326.3 (Method 2)

Step 5: Preparation of methyl N-[5-({4-[(2S)-2-[(2-cyclopropyl-8-methylquinazolin-4-yl)amino]propyl]piperazin-1-yl}sulfonyl)-4-methyl-1,3-thiazol-2-yl]carbamate (Example 18)

Title compound was prepared following the procedure used for the synthesis of Example 1, starting from 2-cyclopropyl-8-methyl-N-[(2S)-1-(piperazin-1-yl)propan-2-yl]quinazolin-4-amine hydrochloride (Intermediate 19, 0.215 mmol, crude) and 5-(3,4-dimethyl-1,2-oxazol-5-yl)thiophene-2-sulfonyl chloride (68 mg, 0.25 mmol) to afford the title compound (90 mg, 0.16 mmol, 75% yield) as a white solid.

LC-MS (ESI): m/z (M+1): 560.2 (Method 1)

$^1$H NMR (400 MHz, DMSO-d$_6$) ppm 0.84-0.93 (m, 2H), 0.94-1.08 (m, 2H), 1.20 (d, J=6.58 Hz, 3H), 1.94-2.11 (m, 1H), 2.33-2.38 (m, 1H), 2.43 (s, 3H), 2.46-2.53 (m, 3H), 2.53-2.63 (m, 5H), 2.98 (br. s., 4H), 3.76 (s, 3H), 4.48 (dt, J=13.81, 6.91 Hz, 1H), 7.02-7.31 (m, 1H), 7.39-7.64 (m, 2H), 7.97 (d, J=8.11 Hz, 1H), 12.33 (br. s., 1H)

The Examples in the following table were prepared from commercially available reagents by using methods analogous to Example 18.

| Example No. | Structure & Name | Analytical data |
|---|---|---|
| 19 | 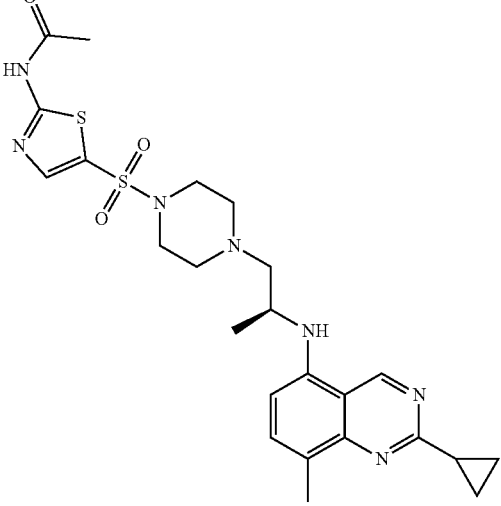<br>N-[5-({4-[(2S)-2-[(2-cyclopropyl-8-methylquinazolin-4-yl)amino]propyl]piperazin-1-yl}sulfonyl)-1,3-thiazol-2-yl]acetamide | LC-MS (ESI): m/z (M + 1): 530.2 (Method 1)<br>$^1$H NMR (400 MHz, DMSO-$d_6$) δ ppm 0.77-1.09 (m, 4 H), 1.19 (d, J = 6.58 Hz, 3 H), 1.95-2.09 (m, 1 H), 2.19 (s, 3 H), 2.27-2.64 (m, 9 H), 2.92 (br. s., 4 H), 4.47 (dt, J = 13.92, 6.85 Hz, 1 H), 7.20 (t, J = 7.67 Hz, 1 H), 7.41-7.64 (m, 2 H), 7.82-8.10 (m, 2 H), 12.73 (br. s., 1 H) |
| 21 | 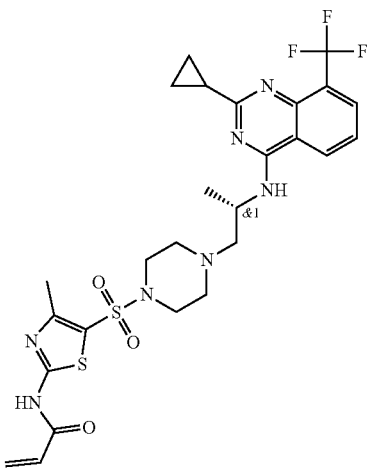<br>methyl N-[5-({4-[(2S)-2-{[2-cyclopropyl-8-(trifluoromethyl)quinazolin-4-yl]amino}propyl]piperazin-1-yl}sulfonyl)-4-methyl-1,3-thiazol-2-yl]carbamate | LC-MS (ESI): m/z (M + 1): 614.3 (Method 1)<br>$^1$H NMR (500 MHz, DMSO-$d_6$) δ ppm 0.86-1.11 (m, 4 H), 1.21 (d, J = 6.59 Hz, 3 H), 1.97-2.05 (m, 1 H), 2.34-2.39 (m, 1 H), 2.43 (s, 3 H), 2.57 (d, J = 6.31 Hz, 5 H), 2.98 (br. s., 4 H), 3.76 (s, 3 H), 4.52 (dt, J = 13.86, 6.79 Hz, 1 H), 7.45 (t, J = 7.82 Hz, 1 H), 7.94 (d, J = 7.68 Hz, 1 H), 8.04 (d, J = 7.41 Hz, 1 H), 8.45 (d, J = 8.51 Hz, 1 H), 11.85-12.48 (m, 1 H) |

| Example No. | Structure & Name | Analytical data |
|---|---|---|
| 22 | 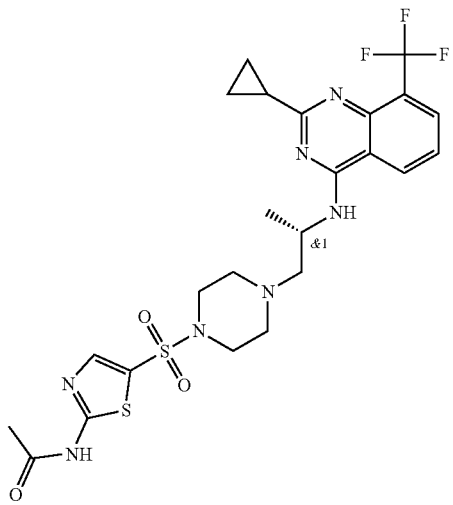  N-[5-({4-[(2S)-2-{[2-cyclopropyl-8-(trifluoromethy)quinazolin-4-yl]amino}propyl]piperazin-1-yl}sulfonyl)-1,3-thiazol-2-yl]acetamide | LC-MS (ESI): m/z (M + 1): 584.2 (Method 1)<br>$^1$H NMR (400 MHz, DMSO-$d_6$) δ ppm 0.89-1.05 (m, 4 H), 1.20 (d, J = 6.53 Hz, 3 H), 1.96-2.06 (m, 1 H), 2.16 (s, 3 H), 2.34-2.40 (m, 1 H), 2.54-2.64 (m, 5 H), 2.92 (br. s., 4 H), 4.51 (dt, J = 13.87, 6.74 Hz, 1 H), 7.44 (t, J = 7.91 Hz, 1 H), 7.86-7.96 (m, 2 H), 8.03 (d, J = 7.03 Hz, 1 H), 8.44 (d, J = 7.78 Hz, 1 H), 12.71 (br. s., 1 H) |

Example 24

2-methoxy-N-[5-({4-[(2S)-2-{[8-(trifluoromethyl)quinazolin-4-yl]amino}propyl]piperazin-1-yl}sulfonyl)-1,3-thiazol-2-yl]acetamide

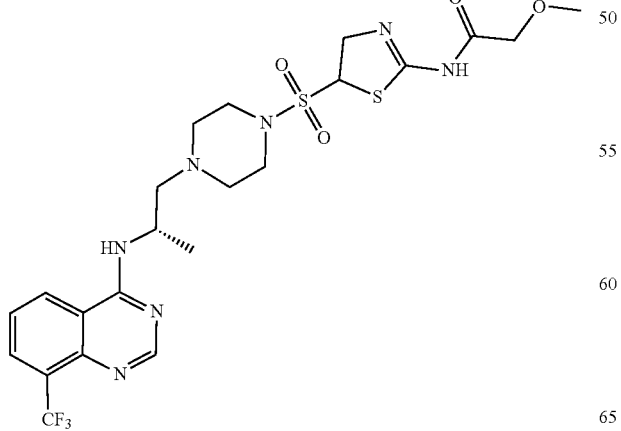

Step 1: Preparation of N-[(2S)-1-{4-[(2-amino-1,3-thiazol-5-yl)sulfonyl]piperazin-1-yl}propan-2-yl]-8-(trifluoromethyl)quinazolin-4-amine (Intermediate 20)

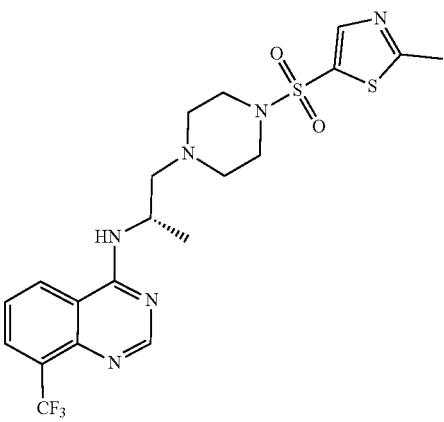 [SMILES: Cc1ncc(S(=O)(=O)N2CCN(C[C@H](C)Nc3ncnc4c(C(F)(F)F)cccc34)CC2)s1]

Compound of Example 7 (2.5 g 4.60, mmol) was dissolved in 10 g of 50% $H_2SO_4$, the solution was stirred 5 hr at 70° C., then the crude was refrigerated to 0° C. and cautiously poured into a flask containing water (25 g) and ice (25 g). To the cold mixture 2N NaOH was cautiously added until neutral pH. The precipitate was filtered, washed with water and dried under vacuum.

N-[(2S)-1-{4-[(2-amino-1,3-thiazol-5-yl)sulfonyl]piperazin-1-yl}propan-2-yl]-8-(trifluoromethyl)quinazolin-4-amine (1.8 g, 3.59 mmol, 78% yield) was obtained as a light brown solid LC-MS (ESI): rt=0.37 min; m/z (M+1): 502.5 (Method 3 Chiesi)

$^1$H NMR (400 MHz, DMSO-d6) δ ppm 8.52-8.60 (m, 2H) 8.08-8.25 (m, 2H) 7.92 (s, 2H) 7.62 (t, J=7.89 Hz, 1H) 7.43 (s, 1H) 4.66 (br s, 1H) 2.94 (br s, 4H) 2.53-2.83 (m, 5H) 1.23 (d, J=6.58 Hz, 3H)

Step 2: Preparation of 2-methoxy-N-[5-({4-[(2S)-2-{[8-(trifluoromethyl)quinazolin-4-yl]amino}propyl]piperazin-1-yl}sulfonyl)-1,3-thiazol-2-yl]acetamide (Example 24)

To a stirred solution of Intermediate 20 (89.5 mg, 0.178 mmol) and triethylamine (0.050 mL, 0.357 mmol) in DMA (2 mL) at 0° C., 2-methoxyacetyl chloride (0.020 mL, 0.214 mmol) was added, then the mixture was heated to 45° C. and stirred overnight. The solvent was evaporated under vacuum and the crude was purified by flash chromatography (30 g column KP-C18 ultra gradient A:B from 100:0 to 60:40 with 10 CV Eluent A: Water:ACN:HCOOH 95:5:0.1 B:Water:ACN:HCOOH 5:95:0.1). Appropriate fractions were combined and evaporated to give 2-methoxy-N-[5-({4-[(2S)-2-{[8-(trifluoromethyl)quinazolin-4-yl]amino}propyl]piperazin-1-yl}sulfonyl)-1,3-thiazol-2-yl]acetamide (61.1 mg, 0.107 mmol, 59.7% yield) as an off-white solid LC-MS (ESI): m/z (M+1): 574.2 (Method 5)

$^1$H NMR (400 MHz, ACETONE-d6) δ ppm 11.12 (br s, 1H), 8.55 (s, 1H), 8.40 (br d, J=8.11 Hz, 1H), 8.10 (br d, J=7.45 Hz, 1H), 7.84 (s, 1H), 7.60 (br s, 1H), 7.52 (br t, J=7.89 Hz, 1H), 4.66-4.83 (m, 1H), 4.25 (s, 2H), 3.48 (s, 3H), 3.02-3.26 (m, 4H), 2.46-3.00 (m, 6H), 1.31 (d, J=6.58 Hz, 3H)

The Example in the following table was prepared from commercially available reagents by using methods analogous to Example 24.

Example 25

2-methoxy-N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide

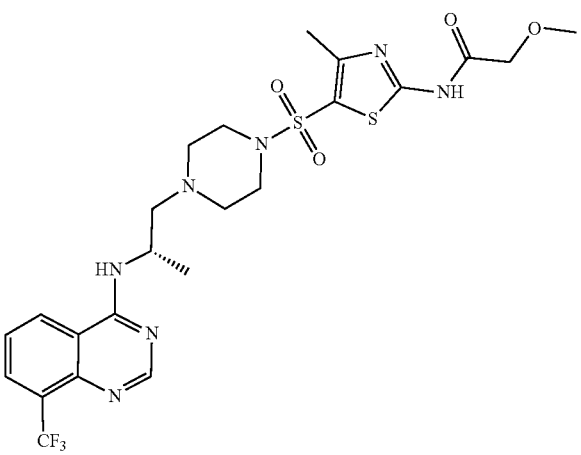 [SMILES: COCC(=O)Nc1nc(C)c(S(=O)(=O)N2CCN(C[C@H](C)Nc3ncnc4c(C(F)(F)F)cccc34)CC2)s1]

| Example No. | Structure & Name | Analytical data |
| --- | --- | --- |
| 26 | 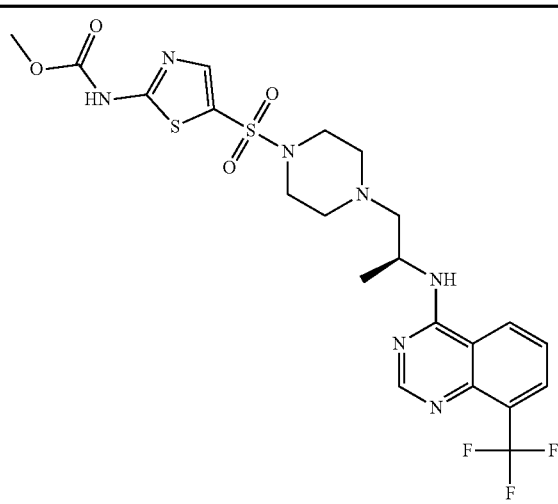<br>methyl N-[5-({4-[(2S)-2-{[8-(trifluoromethyl)quinazolin-4-yl]amino}propyl]piperazin-1-yl}sulfonyl)-1,3-thiazol-2-yl]carbamate | LC-MS (ESI): m/z (M + 1): 560.1 (Method 5)<br>$^1$H NMR (400 MHz, ACETONEd$_6$) δ ppm 10.90-11.18 (bs, 1 H), 8.56 (d, J = 3.73 Hz, 1 H), 8.37 (br d, J = 7.67 Hz, 1 H), 8.07-8.13 (m, 1 H), 7.75 (d, J = 3.73 Hz, 1 H), 7.44-7.58 (m, 2 H), 4.72 (br s, 1 H), 3.86 (s, 3 H), 3.07 (br s, 4 H), 2.59-2.77 (m, 6 H), 1.28-1.32 (m, 3 H) |

Step 1: Preparation of N-[(2S)-1-{4-[(2-amino-4-methyl-1,3-thiazol-5-yl)sulfonyl]piperazin-1-yl}propan-2-yl]-8-(trifluoromethyl)quinazolin-4-amine (Intermediate 21)

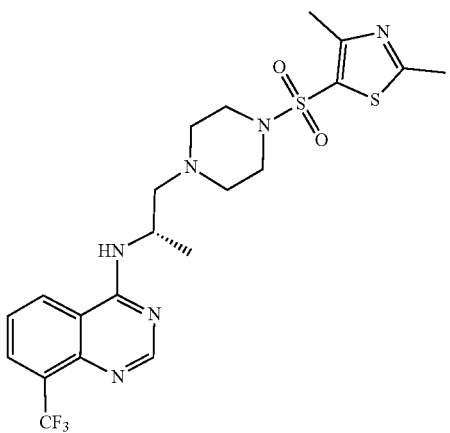 [SMILES: Cc1nc(C)c(S(=O)(=O)N2CCN(C[C@H](C)Nc3ncnc4c(C(F)(F)F)cccc34)CC2)s1]

Title compound was prepared following the procedure used for the synthesis of Intermediate 20, starting from Example 8 (5 g, 8.97 mmol), to afford N-[(2S)-1-{4-[(2-amino-4-methyl-1,3-thiazol-5-yl)sulfonyl]piperazin-1-yl}propan-2-yl]-8-(trifluoromethyl)quinazolin-4-amine (2.0 g, 3.88 mmol, 43% yield) as a white solid LC-MS (ESI): rt=0.37 min; m/z (M+1) (Method 3)

$^1$H NMR (400 MHz, DMSO-d$_6$) δ ppm 8.47-8.64 (m, 2H) 8.08-8.21 (m, 2H) 7.74 (s, 2H) 7.61 (t, J=7.89 Hz, 1H) 4.55-4.72 (m, 1H) 2.95 (br s, 4H) 2.58-2.67 (m, 1H) 2.56 (br s, 4H) 2.35-2.47 (m, 1H) 2.27 (s, 3H) 1.23 (d, J=6.58 Hz, 3H)

Step 2: Preparation of] 2-methoxy-N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide (Example 25)

To a stirred solution of Intermediate 21 (95.1 mg, 0.184 mmol) and triethylamine (0.051 mL, 0.369 mmol) in DMA (2 mL) at 0° C. 2-methoxyacetyl chloride (0.020 mL, 0.221 mmol) was added, then the mixture was heated to 45° C. and stirred overnight. The solvent was evaporated under vacuum and the residue was purified by flash chromatography (30 g column KP-C18 ultra gradient A:B from 100:0 to 60:40 with 10 CV Eluent A: Water:ACN:HCOOH 95:5:0.1 B:Water:ACN:HCOOH 5:95:0.1). Appropriate fractions were combined and evaporated to give 2-methoxy-N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide (56.5 mg, 0.096 mmol, 52.1% yield) as white solid.

LC-MS (ESI): m/z (M+1): 588.2 (Method 5)

$^1$H NMR (400 MHz, ACETONE-d6) δ ppm 10.74-11.02 (bs, 1H), 8.54 (s, 1H), 8.39 (br d, J=8.33 Hz, 1H), 8.08 (d, J=6.80 Hz, 1H), 7.58 (br s, 1H), 7.50 (t, J=7.89 Hz, 1H), 4.69-4.80 (m, 1H), 4.20 (s, 2H), 3.47 (s, 3H), 3.07-3.20 (m, 4H), 2.62-3.03 (m, 6H), 2.45 (s, 3H), 1.30 (d, J=6.36 Hz, 3H)

The Examples in the following table were prepared from commercially available reagents by using methods analogous to Example 25.

| Example No. | Structure & Name | Analytical data |
|---|---|---|
| 72 | N-[4-methyl-5-({4-[(2S)-2-{[8-(trifluoromethyl)quinazolin-4-yl]amino}propyl]piperazin-1-yl}sulfonyl)-1,3-thiazol-2-yl]cyclohexanecarboxamide | LC-MS (ESI): m/z (M + 1): 626.3 (Method 2)<br>$^1$H NMR (400 MHz, DMSO-d$_6$) δ ppm 1.08-1.44 (m, 8 H), 1.52-1.86 (m, 5 H), 2.37-2.48 (m, 5 H), 2.52-2.66 (m, 5 H), 2.97 (br. s., 4 H), 4.61 (spt, J = 6.94 Hz, 1 H), 7.60 (t, J = 7.89 Hz, 1 H), 8.13 (d, J = 7.45 Hz, 2 H), 8.49-8.58 (m, 2 H), 12.35-12.77 (m, 1 H) |

| Example No. | Structure & Name | Analytical data |
|---|---|---|
| 81 | 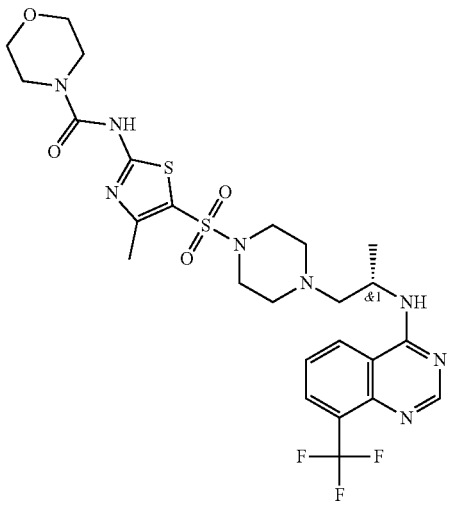<br>N-[4-methyl-5-({4-[(2S)-2-{[8-(trifluoromethyl)quinazolin-4-yl]amino}propyl]piperazin-1-yl}sulfonyl)-1,3-thiazol-2-yl]morpholine-4-carboxamide | LC-MS (ESI): m/z (M + 1): 629.3 (Method 1)<br>$^1$H NMR (500 MHz, DMSO-$d_6$) δ ppm 1.21 (d, J = 6.6 Hz, 3 H), 2.38-2.45 (m, 1 H), 2.41 (s, 3 H), 2.56 (br s, 4 H), 2.57-2.68 (m, 1 H), 2.87-3.08 (m, 4 H), 3.43-3.53 (m, 4 H), 3.53-3.63 (m, 4 H), 4.61 (spt, J = 6.9 Hz, 1 H), 7.61 (t, J = 7.8 Hz, 1 H), 8.04-8.24 (m, 2 H), 8.44-8.64 (m, 2 H), 9.88-12.97 (m, 1 H) |
| 88 | 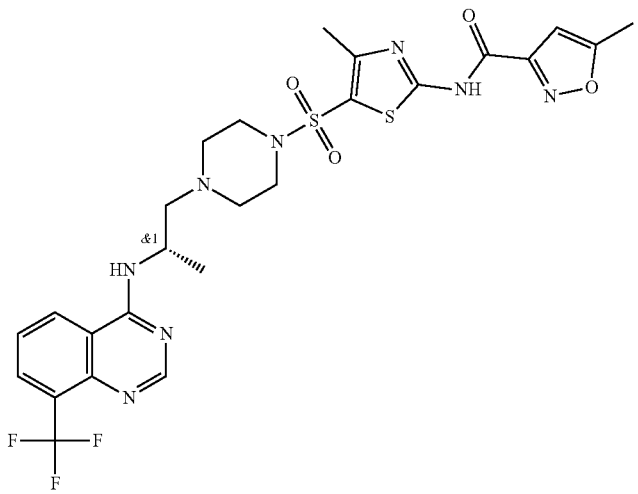<br>5-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]-1,2-oxazole-3-carboxamide | LC-MS (ESI): m/z (M + 1): 625.41 (Method 1)<br>$^1$H NMR (500 MHz, DMSO-$d_6$) δ ppm 1.20 (d, J = 6.6 Hz, 3 H), 2.39-2.46 (m, 1 H), 2.48 (s, 3 H), 2.49-2.52 (m, 3 H), 2.55-2.66 (m, 5 H), 3.00 (br s, 4 H), 4.60 (dt, J = 14.1, 6.9 Hz, 1 H), 6.74 (br s, 1 H), 7.59 (t, J = 8.0 Hz, 1 H), 8.10-8.17 (m, 2 H), 8.50-8.57 (m, 2 H), 11.73-14.45 (m, 1 H) |

| Example No. | Structure & Name | Analytical data |
|---|---|---|
| 95 | 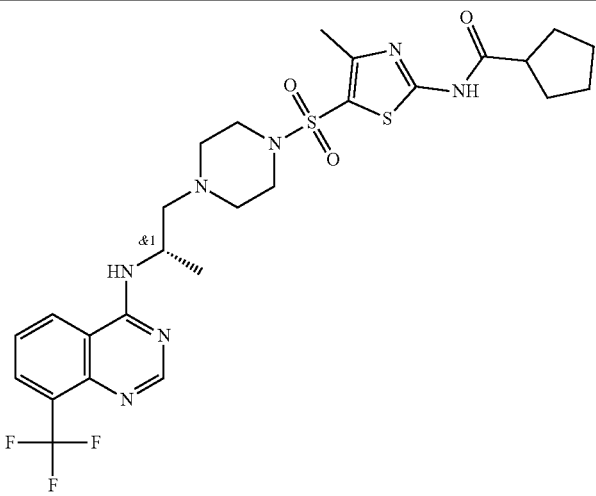<br>N-[4-methyl-5-({4-[(2S)-2-{[8-(trifluoromethyl)quinazolin-4-yl]amino}propyl]piperazin-1-yl}sulfonyl)-1,3-thiazol-2-yl]cyclopentanecarboxamide | LC-MS (ESI): m/z (M + 1): 612.1 (Method 2)<br>$^1$H NMR (400 MHz, DMSO-d$_6$) δ ppm 1.10-1.29 (m, 3 H), 1.44-1.94 (m, 8 H), 2.35-2.45 (m, 1 H), 2.45 (s, 3 H), 2.52-2.65 (m, 5 H), 2.81-3.06 (m, 5 H), 4.61 (spt, J = 6.8 Hz, 1 H), 7.48-7.70 (m, 1 H), 8.13 (d, J = 7.5 Hz, 2 H), 8.47-8.62 (m, 2 H), 12.60 (br s, 1 H) |

Example 43

4-{[(2S)-1-(4-{[5-(3,4-dimethyl-1,2-oxazol-5-yl)thiophen-2-yl]sulfonyl}piperazin-1-yl)propan-2-yl]amino}-N,N-dimethylquinazoline-8-carboxamide

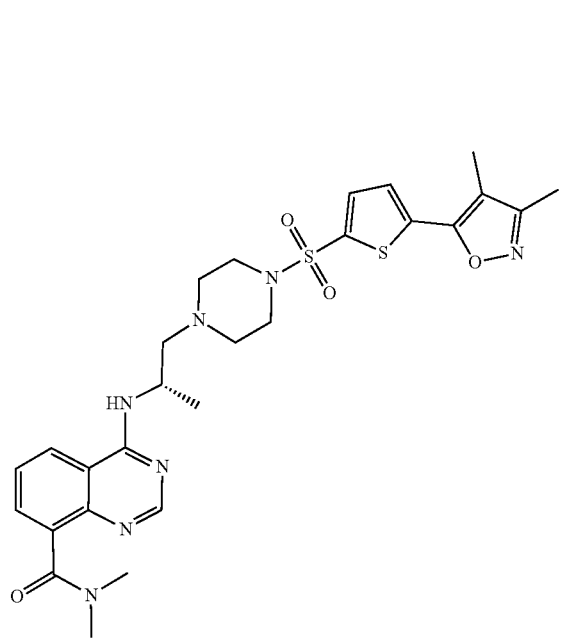 [SMILES: Cc1noc(-c2ccc(S(=O)(=O)N3CCN(C[C@H](C)Nc4ncnc5c(C(=O)N(C)C)cccc45)CC3)s2)c1C]

Step 1: Preparation of methyl 4-[[(2S)-1-[4-[(2-methylpropan-2-yl)oxycarbonyl]piperazin-1-yl]propan-2-yl]amino]quinazoline-8-carboxylate (Intermediate 22)

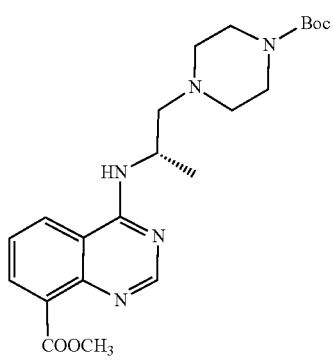 [SMILES: COC(=O)c1cccc2c(N[C@@H](C)CN3CCN(C(=O)OC(C)(C)C)CC3)ncnc12]

Title compound was prepared following the procedure used for the synthesis of Intermediate 1, starting from methyl 4-chloroquinazoline-8-carboxylate (500 mg, 2.25 mmol) to afford Intermediate 22 (772 mg, 1.8 mmol, 80% yield) as a yellow foam. LC-MS (ESI): m/z (M+1): 430 (Method 1)

Step 2: Preparation of 4-[[(2S)-1-[4-[(2-methylpropan-2-yl)oxycarbonyl]piperazin-1-yl]propan-2-yl]amino]quinazoline-8-carboxylic acid (Intermediate 23)

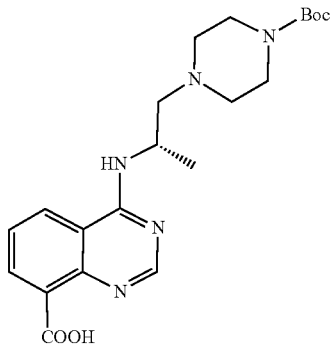 [SMILES: C[C@@H](CN1CCN(C(=O)OC(C)(C)C)CC1)Nc1ncnc2c(C(=O)O)cccc12]

To a solution of Intermediate 22 (772 mg, 1.78 mmol) in Methanol (3 mL), sodium hydroxide 3M solution in water (2.97 mL, 8.9 mmol) was added. The yellow solution was stirred at rt for 2 h. The solvent was removed under vacuum to afford title compound (1.08 g, 2.6 mmol, crude) that was used in the next step without further purifications.

LC-MS (ESI): m/z (M+1): 416 (Method 1)

Step 3: Preparation of tert-butyl 4-[(2S)-2-[[8-(dimethylcarbamoyl)quinazolin-4-yl]amino]propyl]piperazine-1-carboxylate (Intermediate 24)

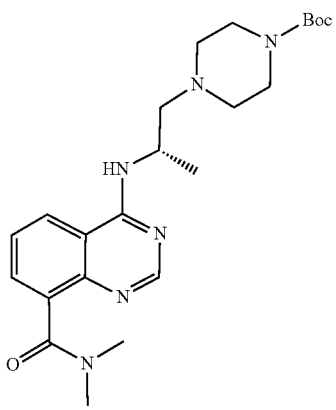 [SMILES: C[C@@H](CN1CCN(C(=O)OC(C)(C)C)CC1)Nc1ncnc2c(C(=O)N(C)C)cccc12]

To a solution of Intermediate 23 (200 mg, 0.48 mmol) in DMF (1 mL), HATU (219.63 mg, 0.58 mmol), N-methylmethanamine 2M solution in THF (0.24 mL, 0.48 mmol) and DIPEA (0.12 mL, 0.72 mmol) were added and the mixture was stirred overnight at room temperature. The mixture was evaporated to dryness to obtain the crude material that was purified by reverse phase flash chromatography eluting with acetonitrile (from 5% to 40%) in basic water (+0.1% NH₃) to afford title compound (80 mg, 0.181 mmol, 37.55% yield) as a yellowish solid.

LC-MS (ESI): m/z (M+1): 443 (Method 1)

Step 4: Preparation of N,N-dimethyl-4-[[(2S)1-piperazin-1-ylpropan-2-yl]amino]quinazoline-8-carboxamide hydrochloride (Intermediate 25)

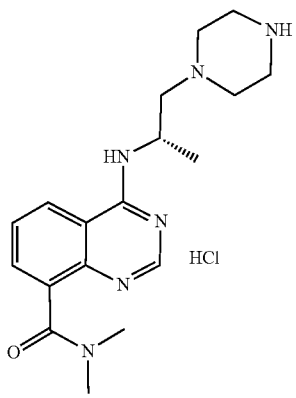 [SMILES: C[C@@H](CN1CCNCC1)Nc1ncnc2c(C(=O)N(C)C)cccc12 ; Cl]

Title compound was prepared following the procedure used for the synthesis of Intermediate 2, starting from tert-butyl 4-[(2S)-2-[[8-(dimethylcarbamoyl)quinazolin-4-yl]amino]propyl]piperazine-1-carboxylate (Intermediate 24, 80 mg, 0.18 mmol) to afford Intermediate 25 (62 mg, 0.18 mmol, crude) that was used in the next step without further purification.

LC-MS (ESI): m/z (M+1): 343 (Method 2)

Step 5: Preparation of 4-{[(2S)-1-(4-{[5-(3,4-dimethyl-1,2-oxazol-5-yl)thiophen-2-yl]sulfonyl}piperazin-1-yl)propan-2-yl]amino}-N,N-dimethylquinazoline-8-carboxamide (Example 43)

Title compound was prepared following the procedure used for the synthesis of Example 1, starting from N,N-dimethyl-4-[[(2S)1-piperazin-1-ylpropan-2-yl]amino]quinazoline-8-carboxamide (Intermediate 25, 30 mg, 0.09 mmol) and 5-(3,4-dimethyl-1,2-oxazol-5-yl)thiophene-2-sulfonyl chloride (24.33 mg, 0.09 mmol) to afford the title compound (21.8 mg, 0.037 mmol, 43% yield) as a white solid.

LC-MS (ESI): m/z (M+1): 584.4 (Method 2)

¹H NMR (400 MHz, DMSO-d₆) δ ppm 1.19 (d, J=6.58 Hz, 3H), 2.15 (d, J=1.53 Hz, 3H), 2.24 (s, 3H), 2.37-2.45 (m, 1H), 2.54-2.66 (m, 8H), 2.97 (br.s., 4H), 3.00-3.05 (m, 3H), 4.60 (dq, J=13.92, 6.98 Hz, 1H), 7.44-7.52 (m, 1H), 7.59 (dd, J=7.13, 0.99 Hz, 1H), 7.63-7.68 (m, 1H), 7.68-7.73 (m, 1H), 7.94 (dd, J=7.67, 4.82 Hz, 1H), 8.26 (dd, J=8.33, 1.10 Hz, 1H), 8.42 (s, 1H)

The Examples in the following table were prepared from commercially available reagents by using methods analogous to Example 43.

| Example No. | Structure & Name | Analytical data |
|---|---|---|
| 27 | 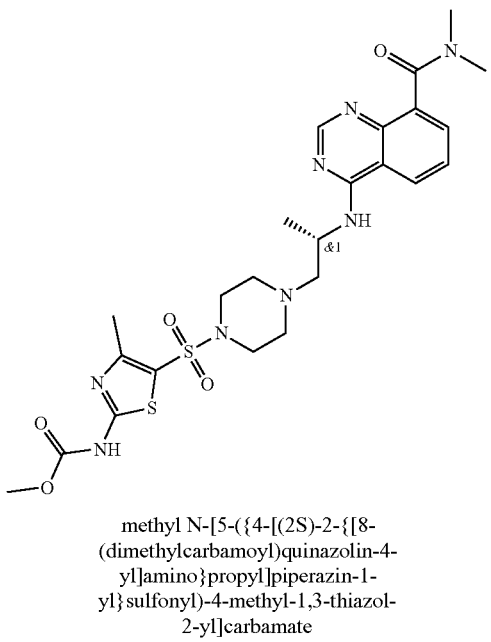<br>methyl N-[5-({4-[(2S)-2-{[8-(dimethylcarbamoyl)quinazolin-4-yl]amino}propyl]piperazin-1-yl}sulfonyl)-4-methyl-1,3-thiazol-2-yl]carbamate | LC-MS (ESI): m/z (M + 1): 577.3 (Method 2)<br>$^1$H NMR (500 MHz, DMSO-$d_6$) δ ppm 1.20 (d, J = 6.31 Hz, 3 H), 2.37-2.62 (m, 6 H), 2.41 (s, 3 H), 2.62-3.12 (m, 6 H), 2.98 (br. s., 4 H), 3.74 (br. s., 3 H), 4.52-4.70 (m, 1 H), 7.50 (t, J = 7.68 Hz, 1 H), 7.61 (d, J = 6.59 Hz, 1 H), 7.95 (t, J = 7.82 Hz, 1 H), 8.28 (d, J = 8.51 Hz, 1 H), 8.43 (s, 1 H), 12.34 (br. s., 1 H) |
| 38 | 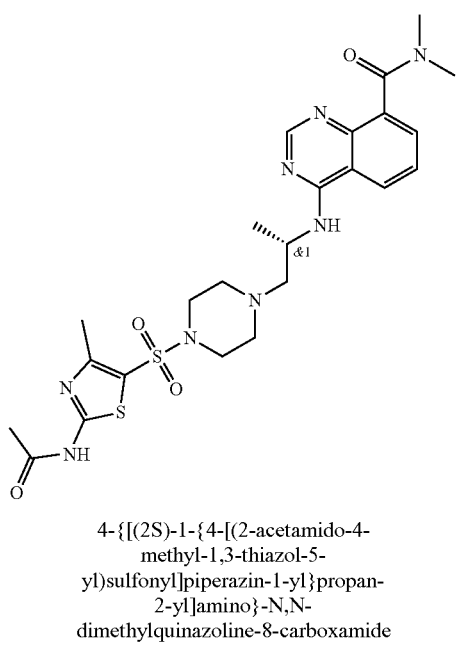 [SMILES: CC(=O)Nc1nc(C)c(S(=O)(=O)N2CCN(C[C@H](C)Nc3ncnc4c(C(=O)N(C)C)cccc34)CC2)s1]<br>4-{[(2S)-1-{4-[(2-acetamido-4-methyl-1,3-thiazol-5-yl)sulfonyl]piperazin-1-yl}propan-2-yl]amino}-N,N-dimethylquinazoline-8-carboxamide | LC-MS (ESI): m/z (M + 1): 561.3 (Method 2)<br>$^1$H NMR (400 MHz, DMSO-$d_6$) δ ppm 1.20 (d, J = 6.78 Hz, 3 H), 2.15 (s, 3 H), 2.37-2.71 (m, 5 H), 2.42-3.06 (m, 6 H), 2.56 (br. s., 4 H), 2.97 (br. s., 4 H), 4.51-4.68 (m, 1 H), 7.46-7.53 (m, 1 H), 7.61 (d, J = 6.53 Hz, 1 H), 7.90-7.98 (m, 1 H), 8.25-8.30 (m, 1 H), 8.43 (s, 1 H), 12.55 (br. s., 1 H) |

-continued

| Example No. | Structure & Name | Analytical data |
|---|---|---|
| 39 | 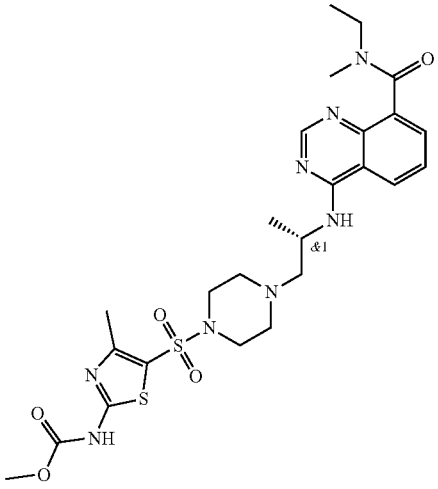methyl N-[5-({4-[(2S)-2-({8-[ethyl(methyl)carbamoyl]quinazolin-4-yl}amino)propyl]piperazin-1-yl}sulfonyl)-4-methyl-1,3-thiazol-2-yl]carbamate | LC-MS (ESI): m/z (M + 1): 591.3 (Method 2)<br>$^1$H NMR (500 MHz, DMSO-d$_6$) δ ppm 0.87-1.18 (m, 3 H), 1.20 (d, J = 6.31 Hz, 3 H), 2.37-2.71 (m, 6 H), 2.38-2.45 (m, 3 H), 2.59-3.02 (m, 3 H), 2.89-3.07 (m, 5 H), 3.39-3.66 (m, 1 H), 3.74 (br. s., 3 H), 4.48-4.76 (m, 1 H), 7.49 (t, J = 7.68 Hz, 1 H), 7.55-7.67 (m, 1 H), 7.83-8.03 (m, 1 H), 8.27 (d, J = 8.23 Hz, 1 H), 8.36-8.49 (m, 1 H), 11.83-13.01 (m, 1 H) |
| 40 | 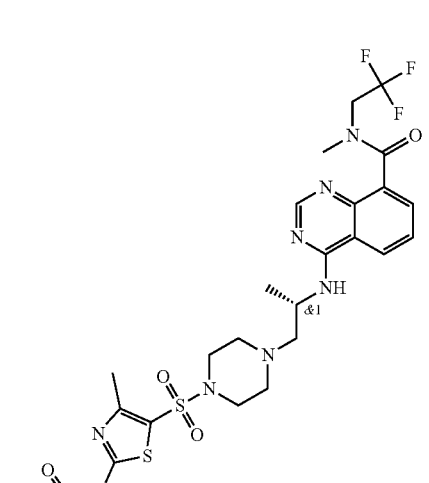methyl N-[4-methyl-5-({4-[(2S)-2-({8-[methyl(2,2,2-trifluoroethyl)carbamoyl]quinazolin-4-yl}amino)propyl]piperazin-1-yl}sulfonyl)-1,3-thiazol-2-yl]carbamate | LC-MS (ESI): m/z (M + 1): 645.3 (Method 2)<br>$^1$H NMR (400 MHz, DMSO-d$_6$) δ ppm 1.11-1.34 (m, 3 H), 2.34-2.64 (m, 6 H), 2.41 (s, 3 H), 2.72-3.22 (m, 3 H), 2.98 (br. s., 4 H), 3.73 (br. s., 3 H), 4.15-4.80 (m, 3 H), 7.44-7.57 (m, 1 H), 7.58-7.71 (m, 1 H), 7.92-8.10 (m, 1 H), 8.33 (d, J = 8.41 Hz, 1 H), 8.44 (s, 1 H), 11.72-12.65 (m, 1 H) |

| Example No. | Structure & Name | Analytical data |
|---|---|---|
| 44 | 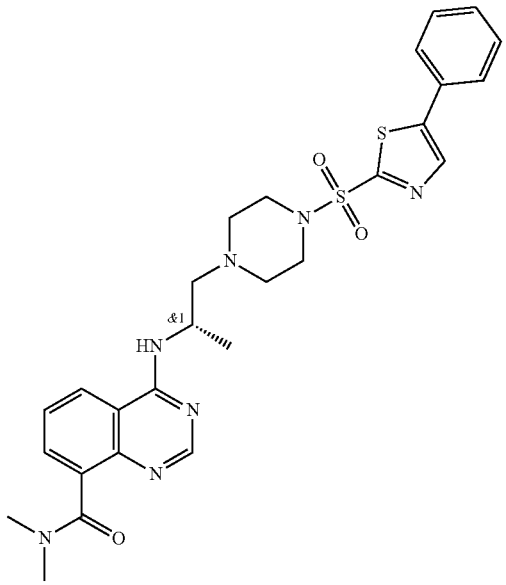

N,N-dimethyl-4-{[(2S)-1-{4-[(2-phenyl-1,3-thiazol-5-yl)sulfonyl]piperazin-1-yl}propan-2-yl]amino}quinazolin-8-carboxamide | LC-MS (ESI): m/z (M + 1): 566.42 (Method 2)<br>$^1$H NMR (500 MHz, DMSO-$d_6$) δ ppm 1.19 (d, J = 6.6 Hz, 3 H), 2.42 (ddd, J = 12.1, 6.8, 4.9 Hz, 1 H), 2.54-2.68 (m, 8 H), 2.91-3.12 (m, 7 H), 4.52-4.71 (m, 1 H), 7.47 (t, J = 7.7 Hz, 1 H), 7.52-7.64 (m, 4 H), 7.88-7.97 (m, 1 H), 7.98-8.06 (m, 2 H), 8.21-8.29 (m, 1 H), 8.35 (s, 1 H), 8.39-8.45 (m, 1 H) |
| 45 | 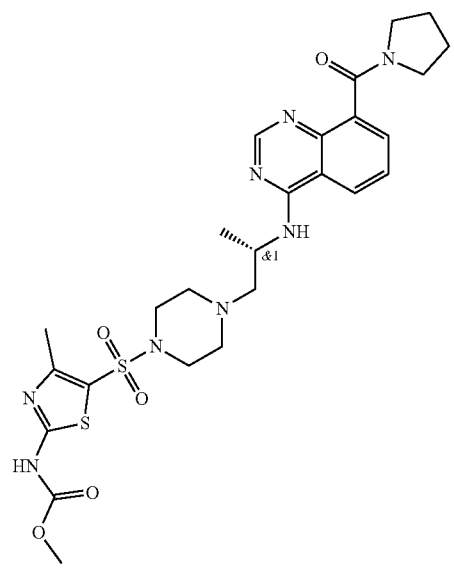

methyl N-[4-methyl-5-({4-[(2S)-2-{[8-(pyrrolidine-1-carbonyl)quinazolin-4-yl]amino}propyl]piperazin-1-yl}sulfonyl)-1,3-thiazol-2-yl]carbamate | LC-MS (ESI): m/z (M + 1): 603.3 (Method 1)<br>$^1$H NMR (400 MHz, DMSO-$d_6$) δ ppm 1.20 (d, J = 6.58 Hz, 3 H), 1.63-1.99 (m, 4 H), 2.35-2.46 (m, 1 H), 2.42 (s, 3 H), 2.53-2.65 (m, 5 H), 2.77-3.20 (m, 66 H), 3.51 (br. s., 2 H), 3.75 (s, 3 H), 3.59 (dquin, J = 13.59, 6.80, 6.80, 6.80, 6.80 Hz, 1 H), 7.50 (t, J = 7.57 Hz, 1 H), 7.63 (dd, J = 7.13, 0.99 Hz, 1 H), 7.94 (d, J = 7.89 Hz, 1 H), 8.28 (d, J = 7.45 Hz, 1 H), 8.44 (s, 1 H), 12.33 (br. s., 1 H) |

| Example No. | Structure & Name | Analytical data |
|---|---|---|
| 47 | 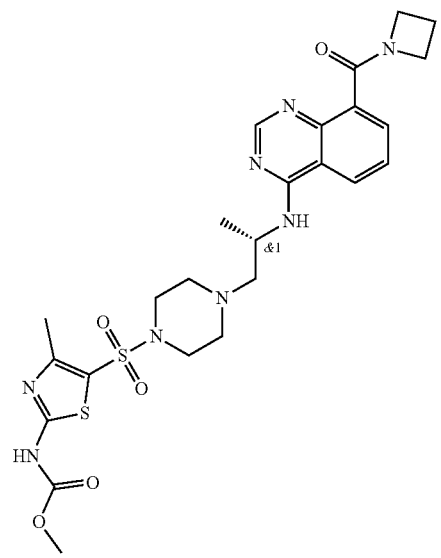<br>methyl N-[5-({4-[(2S)-2-{[8-(azetidine-1-carbonyl)quinazolin-4-yl]amino}propyl]piperazin-1-yl}sulfonyl)-4-methyl-1,3-thiazol-2-yl]carbamate | LC-MS (ESI): m/z (M + 1): 589.3 (Method 1)<br>$^1$H NMR (400 MHz, METHANOL-d4) d ppm 1.29 (d, J = 6.58 Hz, 3 H), 2.33 (quin, J = 7.73 Hz, 2 H), 2.44 (s, 3 H), 2.49 (dd, J = 12.61, 5.59 Hz, 1 H), 2.57-2.77 (m, 5 H), 3.00-3.15 (m, 4 H), 3.82 (s, 3 H), 3.87 (t, J = 7.78 Hz, 2 H), 4.27 (t, J = 7.89 Hz, 2 H), 4.72 (dd, J = 14.69, 6.36 Hz, 1 H), 7.52 (t, J = 8.10 Hz, 1 H), 7.74 (dd, J = 7.23, 1.10 Hz, 1 H), 8.21 (dd, J = 8.33, 1.10 Hz, 1 H), 8.46 (s, 1 H) |
| 48 | 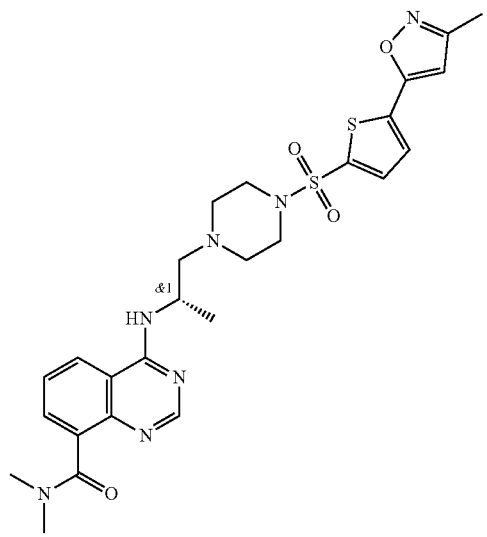<br>N,N-dimethyl-4-{[(2S)-1-(4-{[5-(3-methyl-1,2-oxazol-5-yl)thiophen-2-yl]sulfonyl}piperazin-1-yl)propan-2-yl]amino}quinazoline-8-carboxamide | LC-MS (ESI): m/z (M + 1): 570.3 (Method 2)<br>$^1$H NMR (500 MHz, METHANOL-d4) d ppm 1.28 (d, J = 6.59 Hz, 3 H), 2.33 (s, 3 H), 2.48 (dd, J = 12.62, 5.49 Hz, 1 H), 2.57-2.66 (m, 2 H), 2.67-2.80 (m, 6 H), 2.95-3.12 (m, 4 H), 3.15-3.20 (m, 3 H), 4.67-4.78 (m, 1 H), 6.69 (s, 1 H), 7.50 (t, J = 7.68 Hz, 1 H), 7.52-7.57 (m, 1 H), 7.59 (d, J = 4.12 Hz, 1 H), 7.64 (d, J = 6.86 Hz, 1 H), 8.17 (dd, J = 8.23, 1.10 Hz, 1 H), 8.40 (s, 1 H) |

| Example No. | Structure & Name | Analytical data |
|---|---|---|
| 49 | 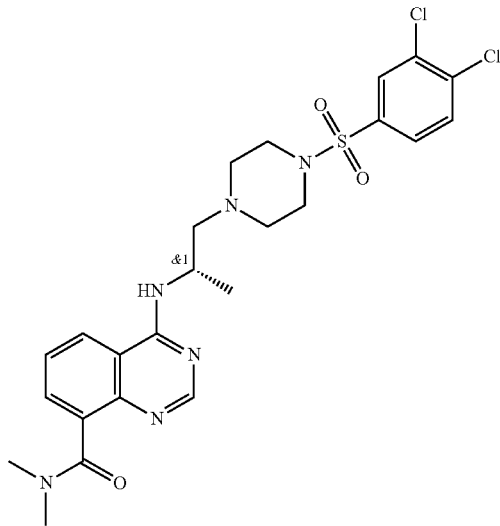<br>4-{[(2S)-1-[4-(3,4-dichlorobenzenesulfonyl)piperazin-1-yl]propan-2-yl]amino}-N,N-dimethylquinazoline-8-carboxamide | LC-MS (ESI): m/z (M + 1): 551.3 (Method 2)<br>$^1$H NMR (500 MHz, METHANOL-d4) d ppm 1.27 (d, J = 6.59 Hz, 3 H), 2.45 (d, J = 5.76 Hz, 1 H), 2.55-2.71 (m, 4 H), 2.70 (dd, J = 12.60, 8.51 Hz, 2 H), 2.74-2.81 (m, 3 H), 2.88-3.10 (m, 4 H), 3.19 (s, 3 H), 4.65-4.77 (m, 1 H), 7.52 (dd, J = 8.23, 7.14 Hz, 1 H), 7.61-7.66 (m, 1 H), 7.68 (dd, J = 7.27, 1.24 Hz, 1 H), 7.75 (d, J = 8.51 Hz, 1 H), 7.88 (d, J = 2.20 Hz, 1 H), 8.17 (dd, J = 8.23, 1.37 Hz, 1 H), 8.40 (s, 1 H) |
| 51 | 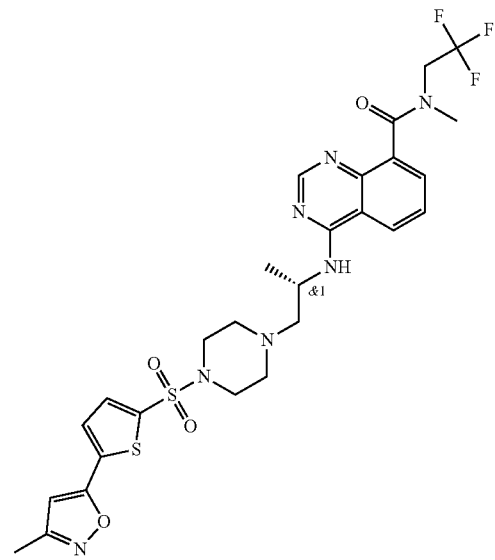<br>N-methyl-4-{[(2S)-1-(4-{[5-(3-methyl-1,2-oxazol-5-yl)thiophen-2-yl]sulfonyl}piperazin-1-yl)propan-2-yl]amino}-N-(2,2,2-trifluoroethyl)quinazoline-8-carboxamide | LC-MS (ESI): m/z (M + 1): 638.2 (Method 2)<br>$^1$H NMR (400 MHz, DMSO-d$_6$) δ ppm 1.19 (d, J = 6.58 Hz, 3 H), 2.29 (s, 3 H), 2.35-2.46 (m, 1 H), 2.52-2.66 (m, 5 H), 2.68-3.20 (m, 3 H), 2.97 (br. s., 4 H), 3.58-4.70 (m, 2 H), 4.53-4.70 (m, 1 H), 6.94-7.08 (m, 1 H), 7.45-7.56 (m, 1 H), 7.58-7.65 (m, 1 H), 7.65-7.72 (m, 1 H), 7.73-7.80 (m, 1 H), 7.93-8.08 (m, 1 H), 8.22-8.36 (m, 1 H), 8.43 (s, 1H) |

| Example No. | Structure & Name | Analytical data |
|---|---|---|
| 58 | 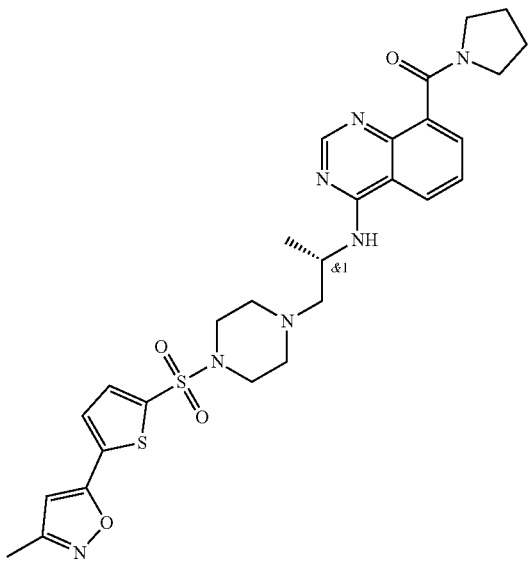<br>N-[(2S)-1-(4-{[5-(3-methyl-1,2-oxazol-5-yl)thiophen-2-yl]sulfonyl}piperazin-1-yl)propan-2-yl]-8-(pyrrolidine-1-carbonyl)quinazolin-4-amine | LC-MS (ESI): m/z (M + 1): 596.3 (Method 2)<br>$^1$H NMR (400 MHz, DMSO-d$_6$) δ ppm 1.15 (d, J = 6.58 Hz, 3 H), 1.64-1.90 (m, 4 H), 2.26 (s, 3 H), 2.33-2.43 (m, 1 H), 2.51-2.62 (m, 5 H), 2.77-3.15 (m, 6 H), 3.48 (br. s., 2 H), 4.56 (br. s., 1 H), 6.94 (s, 1 H), 7.45 (t, J = 7.67 Hz, 1 H), 7.56-7.61 (m, 1 H), 7.62-7.69 (m, 1 H), 7.73 (d, J = 3.95 Hz, 1 H), 7.90 (d, J = 7.89 Hz, 1 H), 8.23 (d, J = 8.33 Hz, 1 H), 8.40 (s, 1 H) |
| 64 | 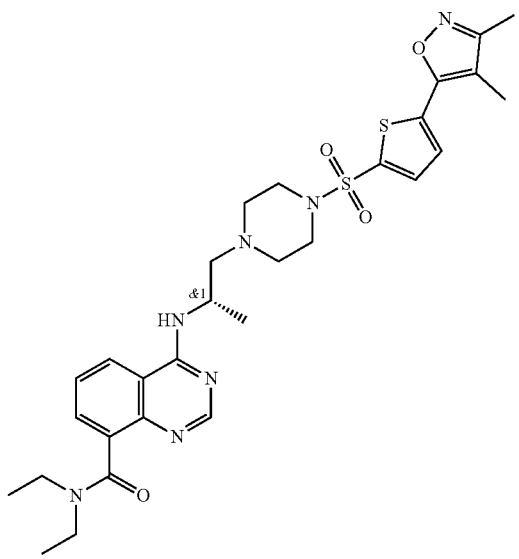<br>4-{[(2S)-1-(4-{[5-(3,4-dimethyl-1,2-oxazol-5-yl)thiophen-2-yl]sulfonyl}piperazin-1-yl)propan-2-yl]amino}-N,N-diethylquinazoline-8-carboxamide | LC-MS (ESI): m/z (M + 1): 612.3 (Method 2)<br>$^1$H NMR (400 MHz, DMSO-d$_6$) δ ppm 0.83-0.94 (m, 3 H), 1.14-1.22 (m, 6 H), 2.13-2.18 (m, 3 H), 2.24 (s, 3 H), 2.41 (dt, J = 11.93, 6.16 Hz, 1 H), 2.53-2.65 (m, 5 H), 2.86-3.06 (m, 6 H), 3.41-3.56 (m, 2 H), 4.60 (dq, J = 14.11, 7.10 Hz, 1 H), 7.43-7.51 (m, 1 H), 7.54-7.59 (m, 1 H), 7.64-7.68 (m, 1 H), 7.68-7.74 (m, 1 H), 7.92 (dd, J = 7.83, 2.93 Hz, 1 H), 8.25 (dd, J = 8.41, 1.57 Hz, 1 H), 8.41 (s, 1 H) |

| Example No. | Structure & Name | Analytical data |
|---|---|---|
| 65 | 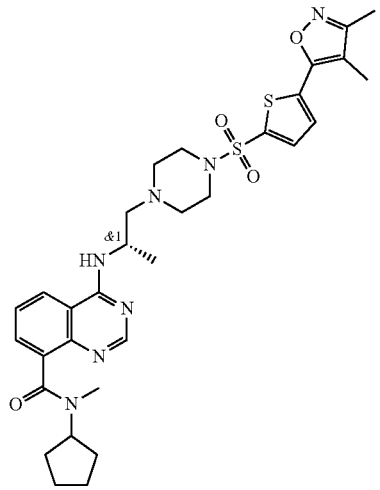<br>N-cyclopentyl-4-{[(2S)-1-(4-{[5-(3,4-dimethyl-1,2-oxazol-5-yl)thiophen-2-yl]sulfonyl}piperazin-1-yl)propan-2-yl]amino}-N-methylquinazoline-8-carboxamide | LC-MS (ESI): m/z (M + 1): 638.3 (Method 2)<br>$^1$H NMR (500 MHz, DMSO-$d_6$) δ ppm 1.19 (br d, J = 6.6 Hz, 3 H), 1.20-1.92 (m, 8 H), 2.11-2.17 (m, 3 H), 2.21-2.28 (m, 3 H), 2.37-2.44 (m, 1 H), 2.44-2.93 (m, 3 H), 2.54-2.68 (m, 5 H), 2.92-3.11 (m, 4 H), 3.54-5.14 (m, 1 H), 4.47-4.75 (m, 1 H), 7.42-7.51 (m, 1 H), 7.52-7.59 (m, 1 H), 7.62-7.68 (m, 1 H), 7.68-7.77 (m, 1 H), 7.83-8.03 (m, 1 H), 8.16-8.32 (m, 1 H), 8.36-8.46 (m, 1 H) |
| 66 | 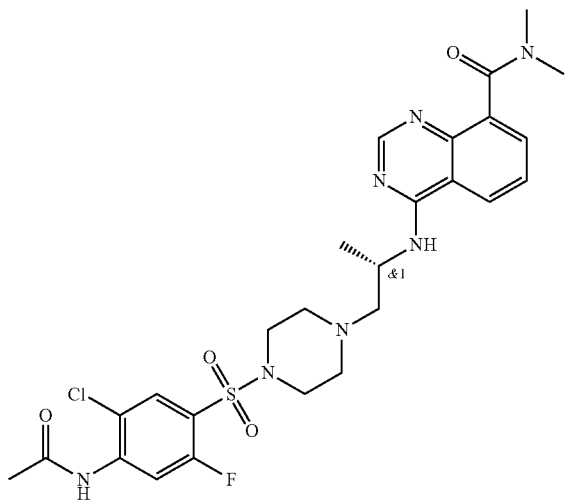<br>4-{[(2S)-1-[4-(5-chloro-4-acetamido-2-fluorobenzenesulfonyl)piperazin-1-yl]propan-2-yl]amino}-N,N-dimethylquinazoline-8-carboxamide | LC-MS (ESI): m/z (M + 1): 592.3 (Method 2)<br>$^1$H NMR (500 MHz, DMSO-$d_6$) δ ppm 1.20 (d, J = 6.04 Hz, 3 H), 2.20 (s, 3 H), 2.36-2.45 (m, 1 H), 2.52-2.62 (m, 5 H), 2.62-2.67 (m, 3 H), 2.95-3.12 (m, 7 H), 4.60 (dq, J = 14.41, 7.27 Hz, 1 H), 7.50 (t, J = 7.68 Hz, 1 H), 7.58-7.64 (m, 1 H), 7.74 (t, J = 6.59 Hz, 1 H), 7.94 (t, J = 7.14 Hz, 1 H), 8.13 (dd, J = 12.62, 6.59 Hz, 1 H), 8.27 (d, J = 8.23 Hz, 1 H), 8.42 (s, 1 H), 9.82 (br. s., 1 H) |

| Example No. | Structure & Name | Analytical data |
|---|---|---|
| 69 | 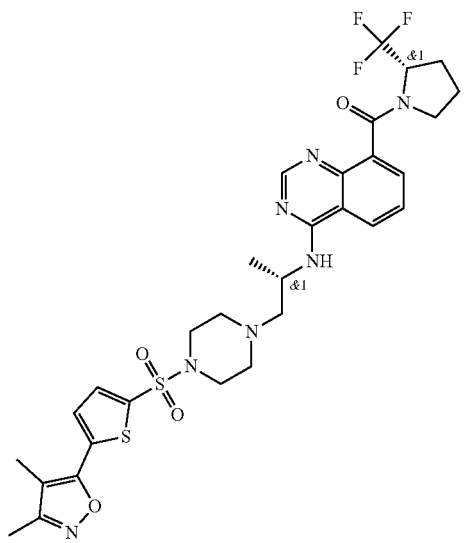<br>N-[(2S)-1-(4-{[5-(3,4-dimethyl-1,2-oxazol-5-yl)thiophen-2-yl]sulfonyl}piperazin-1-yl)propan-2-yl]-8-[(2S)-2-(trifluoromethyl)pyrrolidine-1-carbonyl]quinazolin-4-amine | LC-MS (ESI): m/z (M + 1): 678.41 (Method 2)<br>$^1$H NMR (400 MHz, DMSO-$d_6$) δ ppm 1.19 (d, J = 6.6 Hz, 3 H), 1.75-2.22 (m, 4 H), 2.15 (s, 3 H), 2.24 (s, 3 H), 2.36-2.45 (m, 1 H), 2.59 (m, J = 2.6 Hz, 4 H), 2.62 (br d, J = 5.3 Hz, 1 H), 2.92-3.03 (m, 4 H), 2.97-3.97 (m, 2 H), 4.06-5.11 (m, 1 H), 4.53-4.69 (m, 1 H), 7.46-7.55 (m, 1 H), 7.57-7.75 (m, 3 H), 7.90-8.09 (m, 1 H), 8.31 (d, J = 8.3 Hz, 1 H), 8.39-8.48 (m, 1 H) |
| 70 | 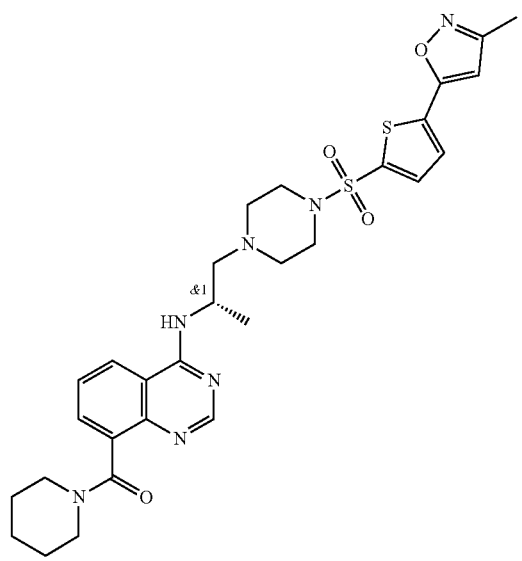<br>N-[(2S)-1-(4-{[5-(3-methyl-1,2-oxazol-5-yl)thiophen-2-yl]sulfonyl}piperazin-1-yl)propan-2-yl]-8-(piperidine-1-carbonyl)quinazolin-4-amine | LC-MS (ESI): m/z (M + 1): 601.3 (Method 2)<br>$^1$H NMR (400 MHz, DMSO-$d_6$) δ ppm 1.19 (d, J = 5.9 Hz, 3 H), 1.22-1.68 (m, 6 H), 2.29 (s, 3 H), 2.35-2.46 (m, 1 H), 2.54-2.66 (m, 5 H), 2.88-3.07 (m, 6 H), 3.45-3.59 (m, 1 H), 3.78 (br dd, J = 12.8, 3.6 Hz, 1 H), 4.59 (dt, J = 10.7, 7.0 Hz, 1 H), 6.97 (d, J = 1.5 Hz, 1 H), 7.44-7.52 (m, 1 H), 7.59 (dd, J = 7.1, 1.0 Hz, 1 H), 7.65-7.73 (m, 1 H), 7.76 (dd, J = 3.9, 1.5 Hz, 1 H), 7.93 (br d, J = 6.6 Hz, 1 H), 8.25 (d, J = 8.3 Hz, 1 H), 8.41 (s, 1 H) |

| Example No. | Structure & Name | Analytical data |
|---|---|---|
| 76 | 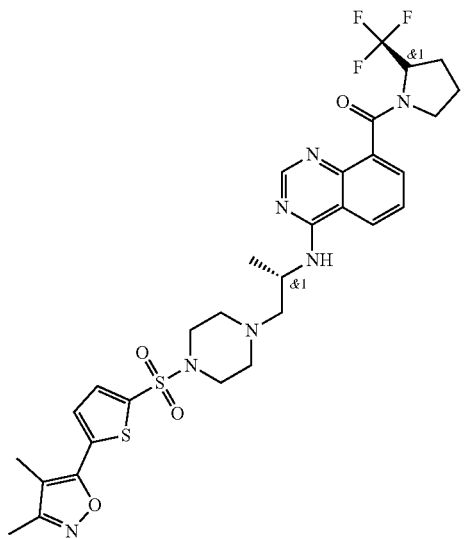<br>N-[(2S)-1-(4-{[5-(3,4-dimethyl-1,2-oxazol-5-yl)thiophen-2-yl]sulfonyl}piperazin-1-yl)propan-2-yl]-8-[(2R)-2-(trifluoromethyl)pyrrolidine-1-carbonyl]quinazolin-4-amine | LC-MS (ESI): m/z (M + 1): 678.3 (Method 1)<br>$^1$H NMR (500 MHz, DMSO-$d_6$) δ ppm 1.19 (d, J = 6.6 Hz, 3 H), 1.71-2.30 (m, 4 H), 2.15 (s, 3 H), 2.24 (s, 3 H), 2.38-2.46 (m, 1 H), 2.53-2.68 (m, 5 H), 2.93-3.05 (m, 4 H), 3.03-3.99 (m, 2 H), 4.06-5.10 (m, 1 H), 4.51-4.68 (m, 1 H), 7.51 (t, J = 7.8 Hz, 1 H), 7.57-7.78 (m, 3 H), 7.90-8.12 (m, 1 H), 8.27-8.36 (m, 1 H), 8.38-8.50 (m, 1 H) |
| 77 | 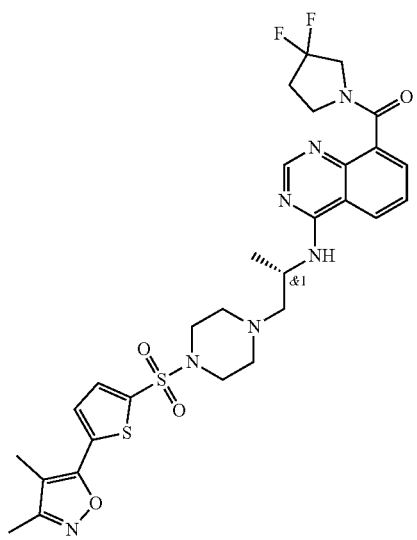<br>8-(3,3-difluoropyrrolidine-1-carbonyl)-N-[(2S)-1-(4-{[5-(3,4-dimethyl-1,2-oxazol-5-yl)thiophen-2-yl]sulfonyl}piperazin-1-yl)propan-2-yl]quinazolin-4-amine | LC-MS (ESI): m/z (M + 1): 646.3 (Method 1)<br>$^1$H NMR (400 MHz, DMSO-$d_6$) δ ppm 1.19 (d, J = Hz, 3 H) 2.16 (s, 3 H), 2.25 (s, 3 H), 2.35-2.46 (m, 2 H), 2.47-2.54 (m, 1 H), 2.55-2.66 (m, 5 H), 2.99 (br s, 4 H), 3.10-3.65 (m, 2 H), 3.77 (br t, J = 7.5 Hz, 1 H), 3.95 (t, J = 13.4 Hz, 1 H), 4.49-4.69 (m, 1H), 7.52 (td, J = 7.7, 3.3 Hz, 1 H), 7.62-7.79 (m, 3 H), 8.00 (br d, J = 7.8 Hz, 1 H), 8.24-8.39 (m, 1 H), 8.45 (s, 1 H) |

| Example No. | Structure & Name | Analytical data |
|---|---|---|
| 78 | 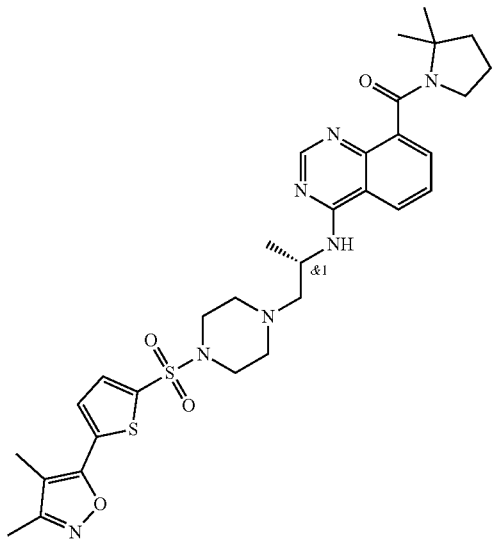<br>N-[(2S)-1-(4-{[5-(3,4-dimethyl-1,2-oxazol-5-yl)thiophen-2-yl]sulfonyl}piperazin-1-yl)propan-2-yl]-8-(2,2-dimethylpyrrolidine-1-carbonyl)quinazolin-4-amine | LC-MS (ESI): m/z (M + 1): 638.3 (Method 2)<br>$^1$H NMR (500 MHz, DMSO-$d_6$) δ ppm 1.18 (dd, J = 6.3, 3.3 Hz, 3 H), 1.49-1.57 (m, 6 H), 1.60-1.72 (m, 2 H), 1.79 (td, J = 6.8, 1.5 Hz, 2 H), 2.15 (d, J = 2.2 Hz, 3 H), 2.24 (s, 3 H), 2.34-2.46 (m, 1 H), 2.54-2.68 (m, 5 H), 2.85-3.13 (m, 6 H), 4.53-4.67 (m, 1 H), 7.46 (td, J = 7.7, 3.8 Hz, 1 H), 7.54 (br d, J = 7.4 Hz, 1 H), 7.66 (d, J = 4.1 Hz, 1 H), 7.71 (dd, J = 12.6, 4.1 Hz, 1 H), 7.90 (d, J = 7.7 Hz, 1 H), 8.22 (d, J = 8.2 Hz, 1 H), 8.41-8.46 (m, 1 H) |
| 79 | 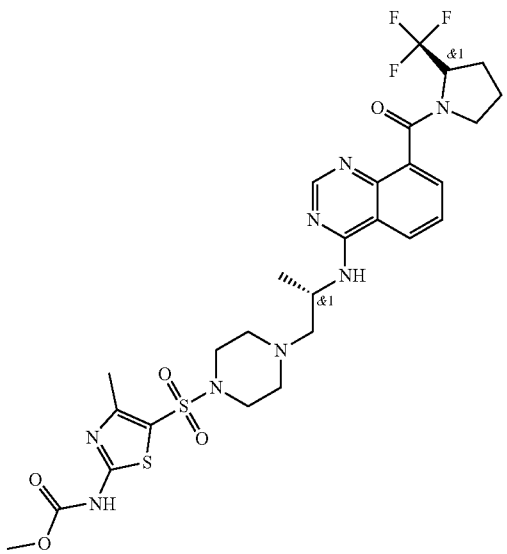<br>methyl N-[4-methyl-5-({4-[(2S)-2-({8-[(2R)-2-(trifluoromethyl)pyrrolidine-1-carbonyl]quinazolin-4-yl}amino)propyl]piperazin-1-yl}sulfonyl)-1,3-thiazol-2-yl]carbamate | LC-MS (ESI): m/z (M + 1): 671.2 (Method 1)<br>$^1$H NMR (500 MHz, DMSO-$d_6$) δ ppm 1.20 (d, J = 6.6 Hz, 3 H), 1.76-2.30 (m, 4 H), 2.37-2.46 (m, 4 H), 2.53-2.69 (m, 5 H), 2.91-3.04 (m, 4 H), 3.02-3.99 (m, 2 H), 3.74 (s, 3 H), 4.02-5.22 (m, 1 H), 4.60 (dt, J = 13.9, 6.9 Hz, 1 H), 7.53 (t, J = 7.7 Hz, 1 H), 7.58-7.74 (m, 1 H), 7.90-8.12 (m, 1 H), 8.33 (br d, J = 8.3 Hz, 1 H), 8.43 (s, 1 H), 12.17-12.49 (m, 1 H) |

| Example No. | Structure & Name | Analytical data |
|---|---|---|
| 80 | 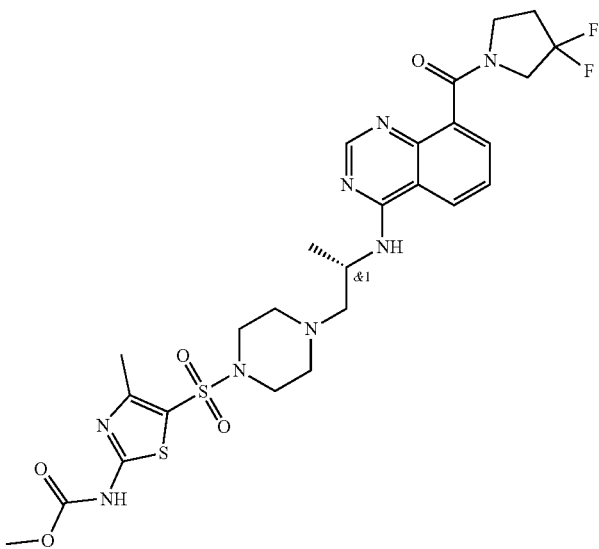<br>methyl N-[5-({4-[(2S)-2-{[8-(3,3-difluoropyrrolidine-1-carbonyl)quinazolin-4-yl]amino}propyl]piperazin-1-yl}sulfonyl)-4-methyl-1,3-thiazol-2-yl]carbamate | LC-MS (ESI): m/z (M + 1): 639.3 (Method 1)<br>$^1$H NMR (500 MHz, DMSO-$d_6$) δ ppm 1.20 (d, J = 6.4 Hz, 3 H), 2.38-2.53 (m, 3 H), 2.42 (s, 3 H), 2.53-2.66 (m, 5 H), 2.99 (br s, 4 H), 3.11-3.57 (m, 2 H), 3.71-3.81 (m, 4 H), 3.95 (t, J = 13.3 Hz, 1 H), 4.54-4.66 (m, 1 H), 7.49-7.57 (m, 1 H), 7.67-7.73 (m, 1 H), 7.98-8.05 (m, 1 H), 8.33 (d, J = 8.6 Hz, 1 H), 8.46 (s, 1 H), 12.33 (br s, 1 H) |
| 82 | 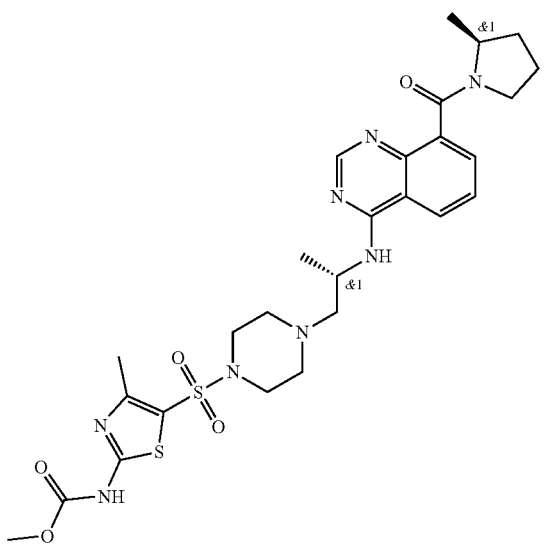<br>methyl N-[4-methyl-5-({4-[(2S)-2-({8-[(2S)-2-methylpyrrolidine-1-carbonyl]quinazolin-4-yl}amino)propyl]piperazin-1-yl}sulfonyl)-1,3-thiazol-2-yl]carbamate | LC-MS (ESI): m/z (M + 1): 617.3 (Method 1)<br>$^1$H NMR (500 MHz, DMSO-$d_6$) δ ppm 0.59-1.39 (m, 3 H), 1.17-1.23 (m, 3 H), 1.44-2.14 (m, 4 H), 2.40 (s, 3 H), 2.41-2.46 (m, 1 H), 2.54-2.62 (m, 5 H), 2.91-3.03 (m, 4 H), 3.04-3.64 (m, 2 H), 3.52-4.27 (m, 1 H), 3.71 (br s, 3 H), 4.59 (dt, J = 14.1, 6.9 Hz, 1 H), 7.44-7.54 (m, 1 H), 7.56-7.73 (m, 1 H), 7.86-8.03 (m, 1 H), 8.24-8.32 (m, 1 H), 8.43 (s, 1 H), 12.33 (br s, 1 H) |

| Example No. | Structure & Name | Analytical data |
|---|---|---|
| 83 | 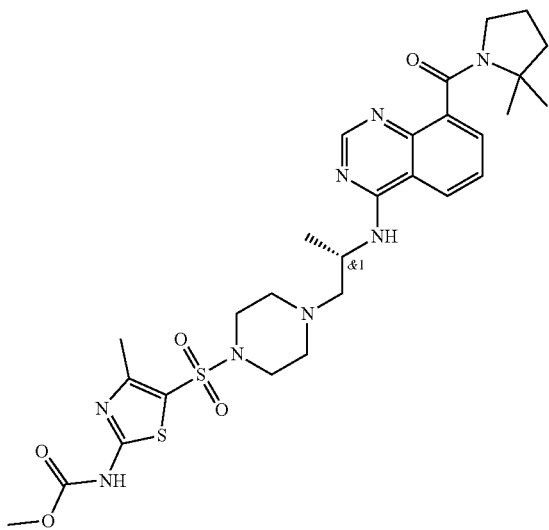

methyl N-[5-({4-[(2S)-2-{[8-(2,2-dimethylpyrrolidine-1-carbonyl)quinazolin-4-yl]amino}propyl]piperazin-1-yl}sulfonyl)-4-methyl-1,3-thiazol-2-yl]carbamate | LC-MS (ESI): m/z (M + 1): 631.3 (Method 1)<br>$^1$H NMR (500 MHz, DMSO-$d_6$) δ ppm 1.20 (dd, J = 6.5, 2.3 Hz, 3 H), 1.50-1.59 (m, 6 H), 1.60-1.86 (m, 4 H), 2.38-2.46 (m, 4 H), 2.52-2.66 (m, 5 H), 2.86-3.18 (m, 2 H), 2.95-3.06 (m, 4 H), 3.74 (s, 3 H), 4.53-4.68 (m, 1 H), 7.46-7.50 (m, 1 H), 7.56 (dd, J = 7.1, 1.2 Hz, 1 H), 7.91 (d, J = 8.1 Hz, 1 H), 8.24 (dd, J = 8.3, 1.2 Hz, 1 H), 8.44 (s, 1 H), 12.33 (br s, 1 H) |
| 84 | 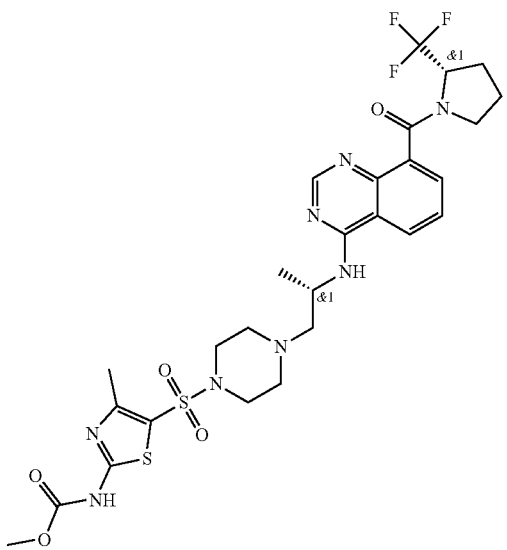

methyl N-[4-methyl-5-({4-[(2S)-2-({8-[(2S)-2-(trifluoromethyl)pyrrolidine-1-carbonyl]quinazolin-4-yl}amino)propyl]piperazin-1-yl}sulfonyl)-1,3-thiazol-2-yl]carbamate | LC-MS (ESI): m/z (M + 1): 671.3 (Method 1)<br>$^1$H NMR (500 MHz, DMSO-$d_6$) δ ppm 1.20 (d, J = 6.6 Hz, 3 H), 1.76-2.30 (m, 4 H), 2.37-2.46 (m, 4 H), 2.53-2.69 (m, 5 H), 2.91-3.04 (m, 4 H), 3.02-3.99 (m, 2 H), 3.74 (s, 3 H), 4.02-5.22 (m, 1 H), 4.60 (dt, J = 13.9, 6.9 Hz, 1 H), 7.53 (t, J = 7.7 Hz, 1 H), 7.58-7.74 (m, 1 H), 7.90-8.12 (m, 1 H), 8.33 (br d, J = 8.3 Hz, 1 H), 8.43 (s, 1 H), 12.17-12.49 (m, 1 H) |

| Example No. | Structure & Name | Analytical data |
|---|---|---|
| 85 | 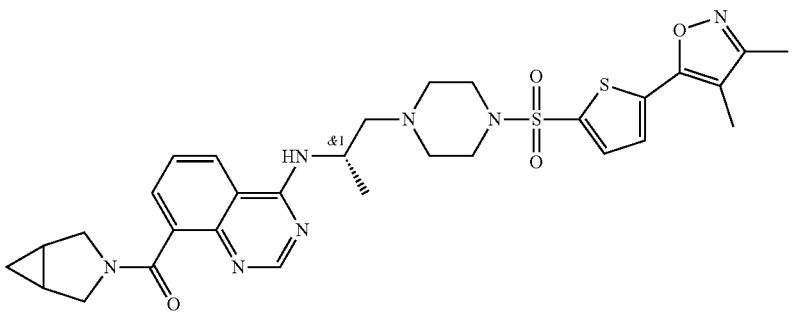<br>8-{3-azabicyclo[3.1.0]hexane-3-carbonyl}-N-[(2S)-1-(4-{[5-(3,4-dimethyl-1,2-oxazol-5-yl)thiophen-2-yl]sulfonyl}piperazin-1-yl)propan-2-yl]quinazolin-4-amine | LC-MS (ESI): m/z (M + 1): 622.3 (Method 1)<br>$^1$H NMR (400 MHz, DMSO-$d_6$) δ ppm 0.09-0.49 (m, 1 H), 0.55-0.68 (m, 1 H), 1.19 (d, J = 6.4 Hz, 3 H), 1.34-1.46 (m, 1 H), 1.51-1.63 (m, 1 H), 2.15 (s, 3 H), 2.24 (s, 3 H), 2.41 (br dd, J = 11.8, 6.8 Hz, 1 H), 2.54-2.66 (m, 5 H), 2.78-2.90 (m, 1 H), 2.98 (br s, 4 H), 3.15-3.48 (m, 2 H), 3.81-3.96 (m, 1 H), 4.51-4.67 (m, 1 H), 7.43-7.51 (m, 1 H), 7.54-7.63 (m, 1 H), 7.64-7.76 (m, 2 H), 7.90-7.98 (m, 1 H), 8.26 (d, J = 8.3 Hz, 1 H), 8.39-8.44 (m, 1 H) |
| 86 | 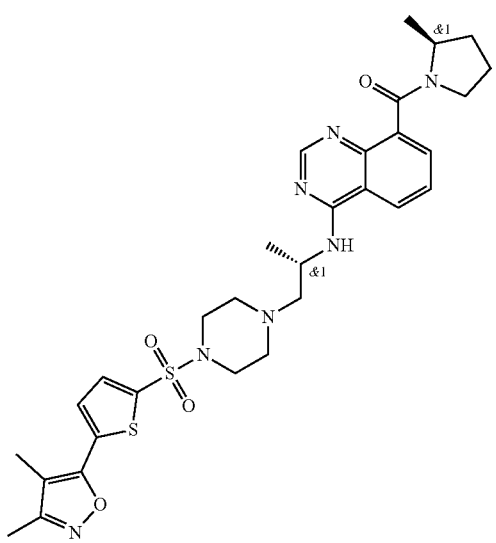<br>N-[(2S)-1-(4-{[5-(3,4-dimethyl-1,2-oxazol-5-yl)thiophen-2-yl]sulfonyl}piperazin-1-yl)propan-2-yl]-8-[(2S)-2-methylpyrrolidine-1-carbonyl]quinazolin-4-amine | LC-MS (ESI): m/z (M + 1): 624.3 (Method 1)<br>$^1$H NMR (500 MHz, DMSO-$d_6$) δ ppm 0.59-1.36 (m, 3 H), 1.16-1.23 (m, 3 H), 1.41-2.08 (m, 4 H), 2.15 (s, 3 H), 2.24 (s, 3 H), 2.37-2.44 (m, 1 H), 2.53-2.70 (m, 5 H), 2.98 (br s, 5 H), 3.41-4.33 (m, 2 H), 4.49-4.68 (m, 1 H), 7.44-7.68 (m, 3 H), 7.68-7.75 (m, 1 H), 7.88-8.00 (m, 1 H), 8.20-8.31 (m, 1 H), 8.35-8.50 (m, 1 H) |
| 87 | 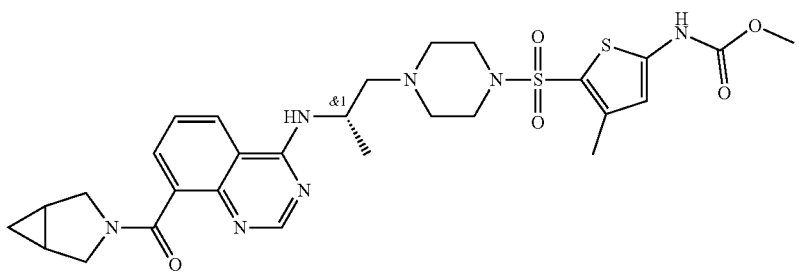<br>methyl N-[5-({4-[(2S)-2-[(8-{3-azabicyclo[3.1.0]hexane-3-carbonyl}quinazolin-4-yl)amino]propyl]piperazin-1-yl}sulfonyl)-4-methyl-1,3-thiazol-2-yl]carbamate | LC-MS (ESI): m/z (M + 1): 615.2 (Method 1)<br>$^1$H NMR (400 MHz, DMSO-$d_6$) δ ppm 0.08-0.51 (m, 1 H), 0.57-0.70 (m, 1 H), 1.20 (d, J = 6.4 Hz, 3 H), 1.34-1.47 (m, 1 H), 1.52-1.63 (m, 1 H), 2.36-2.46 (m, 4 H), 2.53-2.65 (m, 5 H), 2.78-2.90 (m, 1 H), 2.99 (br s, 4 H), 3.12-3.51 (m, 2 H), 3.73 (s, 3 H), 3.82-3.98 (m, 1 H), 4.49-4.70 (m, 1 H), 7.42-7.53 (m, 1 H), 7.54-7.65 (m, 1 H), 7.95 (br d, J = 8.1 Hz, 1 H), 8.27 (d, J = 8.6 Hz, 1 H), 8.43 (br s, 1 H), 12.33 (br s, 1 H) |

Example 46 methyl N-[5-({4-[(2S)-2-[(8-cyclopropanecarbonylquinazolin-4-yl)amino]propyl]piperazin-1-yl}sulfonyl)-4-methyl-1,3-thiazol-2-yl]carbamate

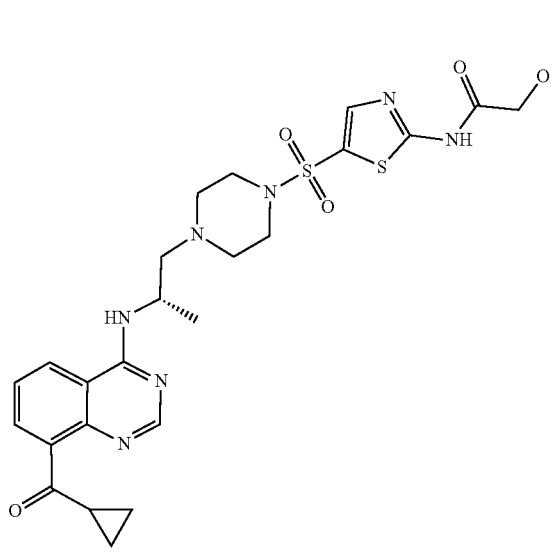 [SMILES: C[C@@H](CN1CCN(S(=O)(=O)c2cnc(NC(=O)CO)s2)CC1)Nc1ncnc2c(C(=O)C3CC3)cccc12]

Step 1: Preparation of 4-hydroxyquinazoline-8-carboxylic acid (Intermediate 26)

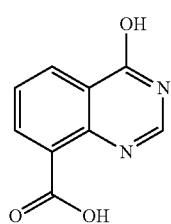 [SMILES: O=C(O)c1cccc2c(O)ncnc12]

A mixture of 2-aminobenzene-1,3-dicarboxylic acid (2.5 g, 13.8 mmol) and formamide (8.22 mL, 207 mmol) was heated at 150° C. for 2 hour under MW irradiation. After cooling down the temperature, formation of a precipitate was observed. The reaction mixture was diluted with MeOH and filtered on a buchner funnel. Solid precipitate was washed with MeOH and dried under vacuum to afford title compound (1.59 g, 8.36 mmol, 30% yield) that was used in the next step without further purification.

LC-MS (ESI): m/z (M+1): 190.9 (Method 1)

Step 2: Preparation of 4-hydroxy-N-methoxy-N-methylquinazoline-8-carboxamide (Intermediate 27)

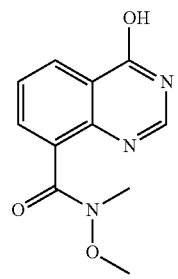 [SMILES: CON(C)C(=O)c1cccc2c(Cl)ncnc12]

Title compound was prepared following the procedure used for the synthesis of Intermediate 24, starting from 4-hydroxyquinazoline-8-carboxylic acid (Intermediate 26, 1.59 g, 8.36 mmol) and N-methoxymethanamine hydrochloride (815 mg, 8.36 mmol) to afford the title compound (1.19 g, 5.4 mmol, 65% yield).

LC-MS (ESI): m/z (M+1): 234 (Method 1)

Step 3: Preparation of 4-chloro-N-methoxy-N-methylquinazoline-8-carboxamide (Intermediate 28)

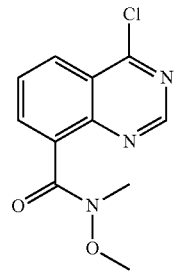

Title compound was prepared following the procedure used for the synthesis of Intermediate 4 starting from 4-hydroxy-N-methoxy-N-methylquinazoline-8-carboxamide (Intermediate 27, 919 mg, 3.9 mmol) to afford Intermediate 28 (350 mg, 1.4 mmol, 36% yield).

LC-MS (ESI): m/z (M+1): 252 (Method 1)

Step 4: Preparation of (4-chloroquinazolin-8-yl)-cyclopropylmethanone (Intermediate 29)

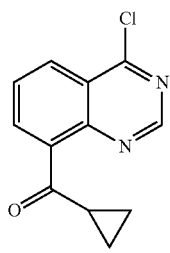 [SMILES: O=C(c1cccc2c(Cl)ncnc12)C1CC1]

To a solution of Intermediate 28 (100 mg, 0.39 mmol) in THF (5 mL) at 0° C., cyclopropylmagnesium bromide 1M solution in THF (68.58 mg, 0.470 mmol) was added dropwise and the reaction mixture was stirred at 0° C. for 2 hours. Then a saturated solution of ammonium chloride in water was added and the mixture was extracted with EtOAc (2 times). The collected organic layers were dried over $Na_2SO_4$ and concentrated under reduced pressure. The crude product was purified by flash chromatography eluting with EtOAc in Cyclohexane from 0% to 20% to afford title compound (82 mg, 0.345 mmol, 90% yield).

LC-MS (ESI): m/z (M+1): 233 (Method 1)

Step 5: Preparation of tert-butyl 4-[(2S)-2-[[8-(cyclopropanecarbonyl)quinazolin-4-yl]amino]propyl]piperazine-1-carboxylate (Intermediate 30)

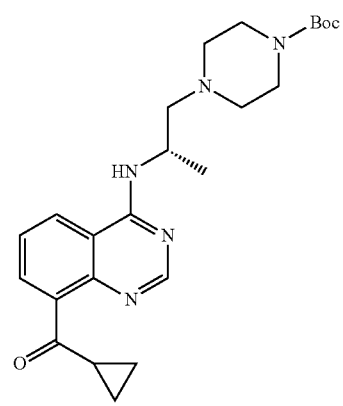 [SMILES: C[C@@H](CN1CCN(C(=O)OC(C)(C)C)CC1)Nc1ncnc2c(C(=O)C3CC3)cccc12]

Title compound was prepared following the procedure used for the synthesis of Intermediate 1, starting from (4-chloroquinazolin-8-yl)-cyclopropylmethanone (Intermediate 29, 82 mg, 0.345 mmol) to afford Intermediate 30 (150 mg, 0.341 mmol, 99% yield).

LC-MS (ESI): m/z (M+1): 440 (Method 1)

Step 6: Preparation of cyclopropyl-[4-[[(2S)-1-piperazin-1-ylpropan-2-yl]amino]quinazolin-8-yl]methanone (Intermediate 31)

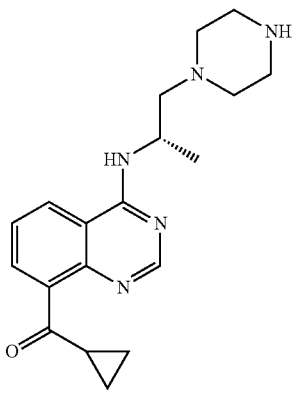 [SMILES: C[C@@H](CN1CCNCC1)Nc1ncnc2c(C(=O)C3CC3)cccc12]

To a solution of Intermediate 30 (930 mg, 2.12 mmol), in DCM (25 mL), TFA (2.43 mL, 32 mmol) was added. The reaction was stirred at room temperature overnight. The mixture was then concentrated under reduced pressure and the residue was purified using a SCX cartridge eluting with a solution of $NH_3$ 2M in methanol to afford title compound (600 mg, 1.768 mmol, 83.55% yield) as a white off foam.

LC-MS (ESI): m/z (M+1): 340 (Method 2)

Step 7: Preparation of methyl N-[5-({4-[(2S)-2-[(8-cyclopropanecarbonylquinazolin-4-yl)amino]propyl]piperazin-1-yl}sulfonyl)-4-methyl-1,3-thiazol-2-yl]carbamate (Example 46)

Title compound was prepared following the procedure used for the synthesis of Example 1, starting from cyclopropyl[4-[[(2S)-1-piperazin-1-ylpropan-2-yl]amino]quinazolin-8-yl]methanone (Intermediate 31, 100 mg, 0.29 mmol) and N-[5-(chlorosulfonyl)-4-methyl-1,3-thiazol-2-yl]carbamate (96 mg, 0.35 mmol) to afford the title compound (98 mg, 0.17 mmol, 56% yield) as white solid.

LC-MS (ESI): m/z (M+1): 574.1 (Method 1)

$^1$H NMR (400 MHz, DMSO-$d_6$) δ ppm 1.01-1.12 (m, 4H), 1.21 (d, J=6.60 Hz, 3H), 2.38-2.47 (m, 4H), 2.54-2.66 (m, 5H), 2.88-3.07 (m, 5H), 3.68-3.80 (m, 3H), 4.55-4.69 (m, 1H), 7.53 (t, J=7.50 Hz, 1H), 7.77 (dd, J=7.48, 1.32 Hz, 1H), 8.02 (d, J=7.92 Hz, 1H), 8.41 (dd, J=8.36, 1.32 Hz, 1H), 8.51 (s, 1H), 12.31 (br. s., 1H)

The Example in the following table was prepared from commercially available reagents by using methods analogous to Example 46.

| Example No. | Structure & Name | Analytical data |
|---|---|---|
| 92 | 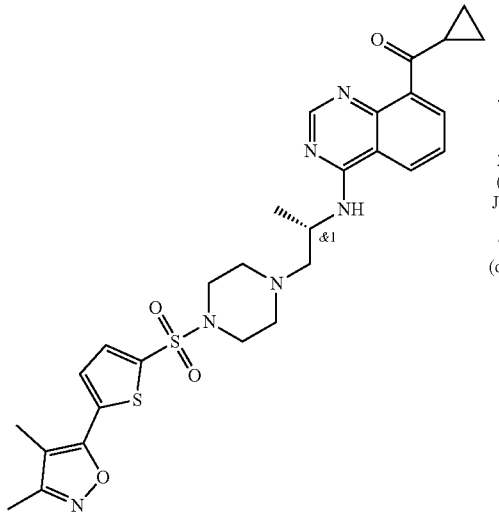<br>8-cyclopropanecarbonyl-N-[(2S)-1-(4-{[5-(3,4-dimethyl-1,2-oxazol-5-yl)thiophen-2-yl]sulfonyl}piperazin-1-yl)propan-2-yl]quinazolin-4-amine | LC-MS (ESI): m/z (M + 1): 581.6 (Method 1)<br>$^1$H NMR (400 MHz, DMSO-d$_6$) δ ppm 0.96-1.11 (m, 4 H), 1.20 (d, J = 6.4 Hz, 3 H), 2.14 (s, 3 H), 2.24 (s, 3 H), 2.43 (dd, J = 12.4, 6.5 Hz, 1 H), 2.55-2.66 (m, 5 H), 2.87-2.96 (m, 1 H), 2.98 (br s, 4 H), 4.62 (dt, J = 13.9, 7.0 Hz, 1 H), 7.51 (dd, J = 8.1, 7.5 Hz, 1 H), 7.65 (d, J = 4.2 Hz, 1 H), 7.70 (d, J = 4.2 Hz, 1 H), 7.74 (dd, J = 7.3, 1.3 Hz, 1 H), 8.01 (d, J = 8.1 Hz, 1 H), 8.39 (dd, J = 8.4, 1.3 Hz, 1 H), 8.50 (s, 1 H) |

Example 61

N-[(2S)-1-(4-{[5-(3,4-dimethyl-1,2-oxazol-5-yl)thiophen-2-yl]sulfonyl}piperazin-1-yl)propan-2-yl]-2-(methoxymethyl)-8-(trifluoromethyl)quinazolin-4-amine

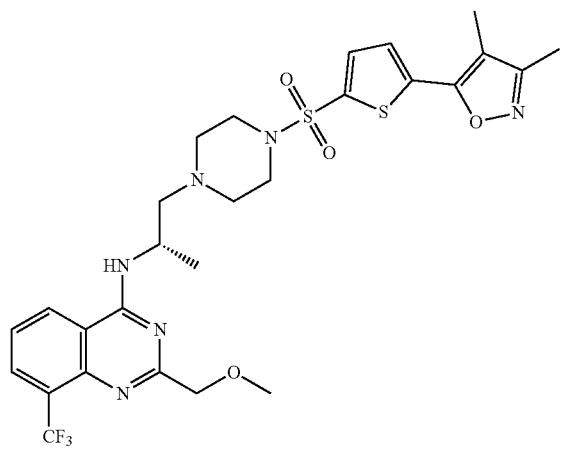 [SMILES: COCc1nc(N[C@@H](C)CN2CCN(S(=O)(=O)c3ccc(-c4onc(C)c4C)s3)CC2)c2cccc(C(F)(F)F)c2n1]

Step 1: Preparation of 2-(bromomethyl)-8-(trifluoromethyl)quinazolin-4-ol (Intermediate 32)

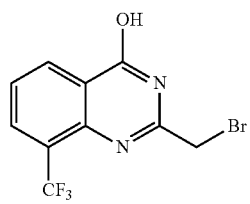 [SMILES: Oc1nc(CBr)nc2c(C(F)(F)F)cccc12]

To a solution of 4-chloro-2-methyl-8-(trifluoromethyl)quinazoline (Intermediate 4, 123 mg, 0.5 mmol) in CCl4 (1 mL) NBS (52 mg, 0.29 mmol) was added followed by benzoyl peroxide (6 mg, 0.02 mmol). The reaction was heated at 80° C. for 12 h. The solvent was removed under vacuum and the crude was purified by flash column chromatography eluting with a gradient of EtOAc in cyclohexane from 0% to 50% affording Intermediate 32 (15 mg, 0.05 mmol, 10% yield).

$^1$H NMR (400 MHz, DMSO-d$_6$) δ 4.55 (s, 3H), 7.93-7.96 (m, 1H), 8.17 (d, J=7.92 Hz, 1H), 8.35-8.42 (m, 1H), 12.94 (s, 1H).

Step 2: Preparation of 2-(methoxymethyl)-8-(trifluoromethyl)quinazolin-4-ol (Intermediate 33)

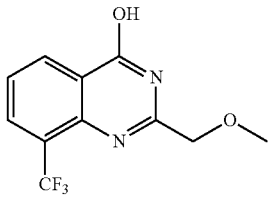 [SMILES: COCc1nc(Cl)c2cccc(C(F)(F)F)c2n1]

2-(bromomethyl)-8-(trifluoromethyl)quinazolin-4-ol (Intermediate 32, 15.0 mg, 0.05 mmol) was dissolved in Methanol (1 mL), followed by the addition of $K_2CO_3$ (6.75 mg, 0.05 mmol). The reaction was heated at 65° C. for 24 h, then warmed up to r.t. and solvent was removed under reduced pressure. $H_2O$ was added and the mixture was extracted with EtOAc for 3 times. The combined organic layer was further washed with water and brine, dried over $Na_2SO_4$, and the solvent was removed under vacuum to provide Intermediate 33 (6 mg, 0.02 mmol, 48% yield) that was used in the next step without further purification.

LC-MS (ESI): m/z (M+1): 259.1 (Method 1)

Step 3: Preparation of 4-chloro-2-(methoxymethyl)-8-(trifluoromethyl)quinazoline (Intermediate 34)

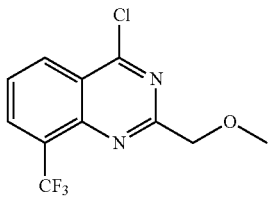

Title compound was prepared following the procedure used for the synthesis of Intermediate 4 starting from 2-(methoxymethyl)-8-(trifluoromethyl)quinazolin-4-ol (Intermediate 33, 6 mg, 0.02 mmol) to afford Intermediate 34 (5 mg, 0.02 mmol) that was used in the next step without further purification.

LC-MS (ESI): m/z (M+1): 277.1 (Method 1)

Step 4: Preparation of tert-butyl 4-[(2S)-2-[[2-(methoxymethyl)-8-(trifluoromethyl)quinazolin-4-yl]amino]propyl]piperazine-1-carboxylate (Intermediate 35)

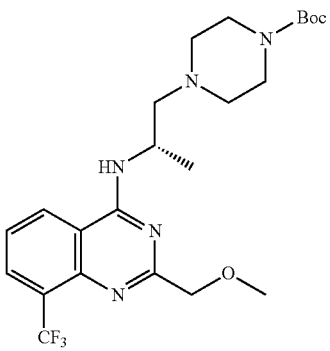 [SMILES: COCc1nc(N[C@@H](C)CN2CCN(C(=O)OC(C)(C)C)CC2)c2cccc(C(F)(F)F)c2n1]

Title compound was prepared following the procedure used for the synthesis of Intermediate 1, starting from 4-chloro-2-(methoxymethyl)-8-(trifluoromethyl)quinazoline (Intermediate 34, 5 mg, 0.02 mmol) to afford Intermediate 35 (8.7 mg, 0.02 mmol) that was used in the next step without further purification.

LC-MS (ESI): m/z (M+1): 484.3 (Method 2)

Step 5: Preparation of 2-(methoxymethyl)-N-[(2S)-1-piperazin-1-ylpropan-2-yl]-8-(trifluoromethyl)quinazolin-4-amine hydrochloride (Intermediate 36)

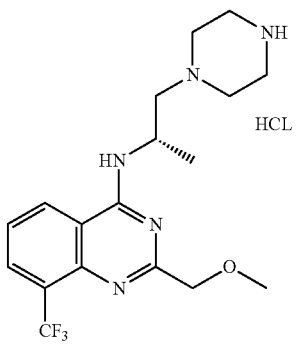 [SMILES: COCc1nc(N[C@@H](C)CN2CCNCC2)c2cccc(C(F)(F)F)c2n1]

Title compound was prepared following the procedure used for the synthesis of Intermediate 2, starting from tert-butyl 4-[(2S)-2-[[2-(methoxymethyl)-8-(trifluoromethyl)quinazolin-4-yl]amino]propyl]piperazine-1-carboxylate (Intermediate 35, 8.7 mg, 0.02 mmol) to afford Intermediate 36 (8.2 mg, crude) that was used in the next step without further purification.

LC-MS (ESI): m/z (M+1): 384.2 (Method 1)

Step 6: Preparation of N-[(2S)-1-(4-{[5-(3,4-dimethyl-1,2-oxazol-5-yl)thiophen-2-yl]sulfonyl}piperazin-1-yl)propan-2-yl]-2-(methoxymethyl)-8(trifluoromethyl)quinazolin-4-amine (Example 61)

Title compound was prepared following the procedure used for the synthesis of Example 1, starting from 2-(methoxymethyl)-N-[(2S)-1-piperazin-1-ylpropan-2-yl]-8-(trifluoromethyl)quinazolin-4-amine hydrochloride (Intermediate 36, 8.2 mg, crude) and 5-(3,4-dimethyl-1,2-oxazol-5-yl)thiophene-2-sulfonyl chloride (6 mg, 0.02 mmol) to afford the title compound (5 mg, 0.008 mmol, 44.5% yield) as a yellow solid.

LC-MS (ESI): m/z (M+1): 625.3 (Method 2)

$^1H$ NMR (400 MHz, DMSO-$d_6$) δ ppm 1.21 (d, J=6.65 Hz, 3H), 2.14 (s, 3H), 2.24 (s, 3H), 2.36-2.43 (m, 1H), 2.55-2.66 (m, 5H), 2.87-3.04 (m, 4H), 3.42 (s, 3H), 4.38 (s, 2H), 4.55-4.66 (m, 1H), 7.55 (t, J=7.83 Hz, 1H), 7.64 (d, J=4.11 Hz, 1H), 7.69 (d, J=3.91 Hz, 1H), 8.03-8.14 (m, 2H), 8.51 (d, J=8.22 Hz, 1H)

Example 63

N-[(2S)-1-(4-{[2-(3-methyl-1,2-oxazol-5-yl)-1,3-thiazol-5-yl]sulfonyl}piperazin-1-yl)propan-2-yl]-8-(trifluoromethyl)quinazolin-4-amine

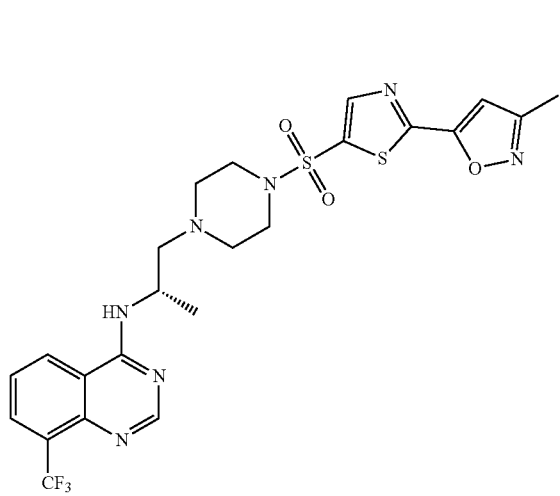 [SMILES: Cc1cc(-c2ncc(S(=O)(=O)N3CCN(C[C@H](C)Nc4ncnc5c(C(F)(F)F)cccc45)CC3)s2)on1]

Step 1: Preparation of (E)-3-(dimethylamino)-1-(4-methyl-1,3-thiazol-2-yl)prop-2-en-1-one (Intermediate 37)

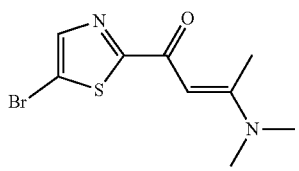

To a solution of 1-(5-bromo-1,3-thiazol-2-yl)ethanone (400 mg, 1.94 mmol) in anhydrous THF (4 mL) N,N-Dimethylacetamide dimethyl acetal (0.43 mL, 2.91 mmol) was added and the resulting mixture was stirred at 65° C. for 12 h. Solvent was removed under vacuum to provide Intermediate 37 (1.94 mmol theoric) that was used in the next step without further purification.

LC-MS (ESI): m/z (M+1): 277 (Method 1)

Step 2: Preparation of 5-(5-bromo-1,3-thiazol-2-yl)-3-methyl-1,2-oxazole (Intermediate 38)

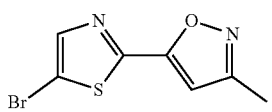

To a solution of Intermediate 37 (381 mg, 1.94 mmol) in Ethanol (2.854 mL) hydroxylamine hydrochloride (134.88 mg, 1.94 mmol) was added and the orange solution was stirred at 80° C. for 3 h. Solvent was removed under vacuum and the crude was purified by flash column chromatography eluting with a gradient of MeOH in DCM from 0% to 1% to afford title compound (90 mg, 0.36 mmol, 19% yield).

LC-MS (ESI): m/z (M+1): 247.1 (Method 1)

Step 3: Preparation of 5-(5-benzylsulfanyl-1,3-thiazol-2-yl)-3-methyl-1,2-oxazole (Intermediate 39)

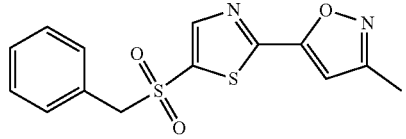 [SMILES: Cc1cc(-c2ncc(S(=O)(=O)Cc3ccccc3)s2)on1]

A mixture of Intermediate 38 (34 mg, 0.14 mmol), phenylmethanethiol (0.02 mL, 0.14 mmol) and DIPEA (0.05 mL, 0.280 mmol) in 1,4-Dioxane (1.2 mL) was degassed under nitrogen atmosphere for 5 min. Pd2(dba)3 (2.52 mg, 0 mmol) and Xantphos (6.37 mg, 0.01 mmol) were then added and the reaction was heated at 100° C. for 90 min. After cooling the mixture was diluted with DCM and washed with sat. aqueous NaHCO$_3$. The organic layer was concentrated under reduced pressure to provide Intermediate 39 (58.5 mg, 0.14 mmol) that was used in the next step without further purification.

LC-MS (ESI): m/z (M+1): 289.1 (Method 1)

Step 4: Preparation of 2-(3-methyl-1,2-oxazol-5-yl)-1,3-thiazole-5-sulfonyl chloride (Intermediate 40)

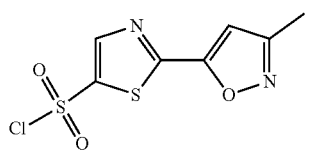

To a solution of Intermediate 39 (58.5 mg, 0.14 mmol) in MeCN (0.8 mL), Acetic acid (0.042 mL) and H$_2$O (0.021 mL) were added. After cooling at 0° C. under nitrogen atmosphere, 1,3-dichloro-5,5-dimethylimidazolidine-2,4-dione (27.19 mg, 0.14 mmol) was added dropwise. The mixture was stirred at 0° C. for 1 h. Solvent was removed under vacuum to afford title compound (36.5 mg, 0.14 mmol) that was used in the next step without purification.

LC-MS (ESI): m/z (M+1): 265 (Method 1)

Step 5: Preparation of N-[(2S)-1-(4-{[2-(3-methyl-1,2-oxazol-5-yl)-1,3-thiazol-5-yl]sulfonyl}piperazin-1-yl)propan-2-yl]-8-(trifluoromethyl)quinazolin-4-amine)

Example 63

Title compound was prepared following the procedure used for the synthesis of Example 1, starting from N-[(2S)-1-piperazin-1-ylpropan-2-yl]-8-(trifluoromethyl)quinazolin-4-amine hydrochloride (Intermediate 2, 45 mg, 0.12 mmol) and 2-(3-methyl-1,2-oxazol-5-yl)-1,3-thiazole-5-sulfonyl chloride (Intermediate 40, 36.5 mg, 0.14 mmol) to afford title compound (13 mg, 0.023 mmol, 17% yield) as a whitenish solid.

LC-MS (ESI): m/z (M+1): 568.2 (Method 2)

$^1$H NMR (400 MHz, DMSO-d$_6$) δ ppm 1.20 (d, J=6.46 Hz, 3H), 2.34 (s, 3H), 2.38-2.65 (m, 6H), 3.03 (br. s., 4H), 4.62 (dt, J=13.79, 6.80 Hz, 1H), 7.21 (s, 1H), 7.59 (t, J=7.83 Hz, 1H), 8.06-8.20 (m, 2H), 8.42-8.62 (m, 3H)

Example 74

N-[(2S)-1-(4-{[5-(3,4-dimethyl-1,2-oxazol-5-yl)thiophen-2-yl]sulfonyl}piperazin-1-yl)propan-2-yl]-8-[(dimethylamino)methyl]quinazolin-4-amine

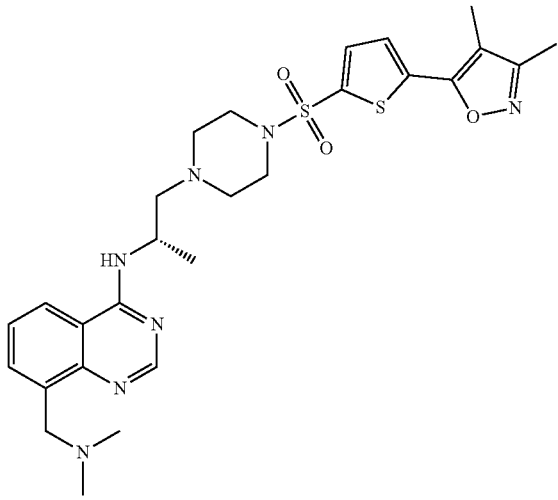 [SMILES: Cc1noc(-c2ccc(S(=O)(=O)N3CCN(C[C@H](C)Nc4ncnc5c(CN(C)C)cccc45)CC3)s2)c1C]

Step 1: Preparation of N-[(2S)-1-(4-{[5-(3,4-dimethyl-1,2-oxazol-5-yl)thiophen-2-yl]sulfonyl}piperazin-1-yl)propan-2-yl]-8-[(dimethylamino)methyl]-1,2-dihydroquinazolin-4-amine (Intermediate 41)

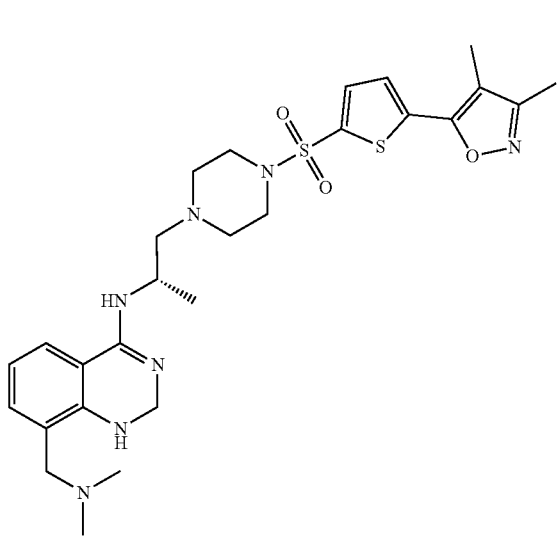 [SMILES: Cc1noc(-c2ccc(S(=O)(=O)N3CCN(C[C@H](C)NC4=NCNc5c(CN(C)C)cccc54)CC3)s2)c1C]

To a solution of Example 43 (40 mg, 0.07 mmol) in THF (1 mL) BH₃ 1 M in THF (0.07 mL, 0.07 mmol) was added dropwise at 0° C. The reaction was allowed to reach rt in 1 h and then stirred overnight. Solvent was removed under vacuum and H₂O was added and the solution was acidified with aqueous HCl 6M till pH<2. MeOH was then added and the reaction was refluxed at 65° C. for 2.5 h allowing the de-complexation of the compound. NaOH 5M in H₂O was finally added till pH=7 and then solvent was removed under reduced pressure to afford the crude product (120 mg, crude) that was used in the next step without further purification.

LC-MS (ESI): m/z (M+1): 572.3 (Method 2)

Step 2: Preparation of N-[(2S)-1-(4-{[5-(3,4-dimethyl-1,2-oxazol-5-yl)thiophen-2-yl]sulfonyl}piperazin-1-yl)propan-2-yl]-8-[(dimethylamino)methyl]quinazolin-4-amine

Example 74

To a solution of Intermediate 41 (120 mg, crude) in DCM (2 mL) Manganese (IV) oxide (91.4 mg, 1.05 mmol) was added and the mixture was stirred at r.t. for 2 h. Solvent was removed under reduced pressure and the crude was purified by flash column chromatography eluting with a gradient of MeCN in basic H₂O (10 mM ammonium bicarbonate aqueous solution adjusted to pH 10 with ammonia) from 5% to 55% to afford title compound (4.5 mg, 0.008 mmol, 7% yield).

LC-MS (ESI): m/z (M+1): 570.42 (Method 2)

¹H NMR ((500 MHz, METHANOL-d₄) δ ppm 1.28 (d, J=6.6 Hz, 3H), 2.19 (s, 3H), 2.29 (s, 3H), 2.40 (br s, 6H), 2.49 (dd, J=12.8, 5.6 Hz, 1H), 2.59-2.65 (m, 2H), 2.67-2.76 (m, 3H), 2.95-3.12 (m, 4H), 3.94-4.24 (m, 2H), 4.66-4.75 (m, 1H), 7.44 (dd, 7.1 Hz, 1H), 7.54 (d, J=4.0 Hz, 1H), 7.59 (d, J=4.0 Hz, 1H), 7.74 (d, J=7.1 Hz, 1H), 8.08 (br d, J=8.2 Hz, 1H), 8.46 (s, 1H)

Example 89 methyl N-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate

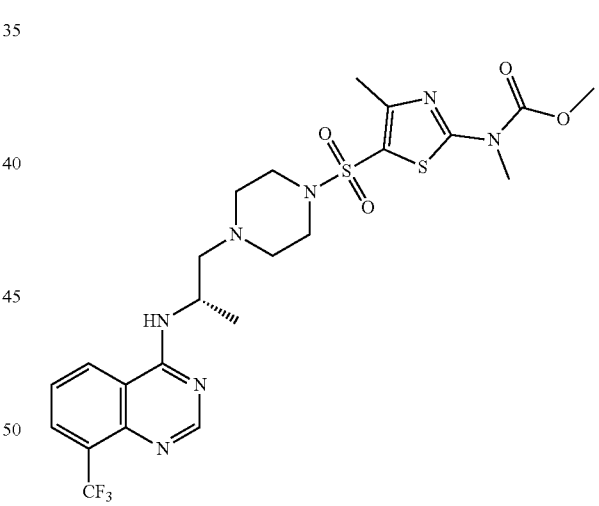

Step 1: Preparation of 4-methyl-2-(methylamino)-1,3-thiazole-5-sulfonyl chloride (Intermediate 42)

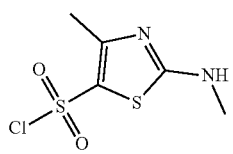

219

To a solution of N,4-dimethyl-1,3-thiazol-2-amine (250 mg, 1.95 mmol) in DCM (2.5 mL), sulfurochloridic acid (1.95 mL, 29.25 mmol) was slowly added at 25° C. The reaction was then stirred at 25° C. for 2 h and then quenched with cold water and extracted with DCM (twice). The solvent was removed under vacuum and the crude product 4-methyl-2-(methylamino)-1,3-thiazole-5-sulfonyl chloride (53 mg, 0.23 mmol, 12% yield) was used in the next step without any further purification.

LC-MS (ESI): m/z (M+1): 223 (Method 1)

Step 2: Preparation of N,4-dimethyl-5-[4-[(2S)-2-[[8-(trifluoromethyl)quinazolin-4-yl]amino]propyl]piperazin-1-yl]sulfonyl-1,3-thiazol-2-amine (Intermediate 42)

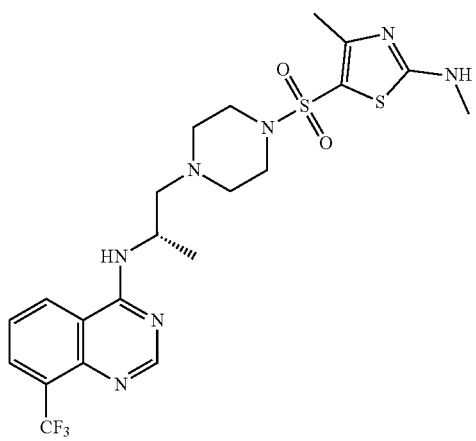 [SMILES: CNc1nc(C)c(S(=O)(=O)N2CCN(C[C@H](C)Nc3ncnc4c(C(F)(F)F)cccc34)CC2)s1]

Title compound was prepared following the procedure used for the synthesis of Example 1, starting from N-[(2S)-1-piperazin-1-ylpropan-2-yl]-8-(trifluoromethyl)quinazolin-4-amine hydrochloride (Intermediate 2, mg, mmol) and 4-methyl-2-(methylamino)-1,3-thiazole-5-sulfonyl chloride (Intermediate 41, 53 mg, 0.23 mmol) to afford the title compound (35 mg, 0.07 mmol, 38% yield).

LC-MS (ESI): m/z (M+1): 530.2 (Method 2)

Step 3: Preparation of methyl N-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate (Example 89)

To a solution of Intermediate 42 (35 mg, 0.07 mmol) in DCM (1.7 mL) at 0° C. was added N,N-dimethyl-4-pyridinamine (40 mg, 0.33 mmol), followed by Chloroformic acid methyl ester (0.01 mL, 0.130 mmol) and the mixture was stirred at room temperature for 1.5 h. Solvent was removed under reduced pressure and the crude was purified by flash chromatography eluting with a gradient of MeCN in basic H₂O (10 mM NH₄HCO₃ aqueous solution adjusted to pH 10 with NH₄) from 5% to 95% to afford title compound as a white solid (34 mg, 0.06 mmol, 86% yield)

LC-MS (ESI): m/z (M+1): 588.2 (Method 2)

¹H NMR (400 MHz, DMSO-d₆) δ ppm 1.20 (d, J=6.4 Hz, 3H), 2.41 (dd, J=12.5, 6.6 Hz, 1H), 2.46 (s, 3H), 2.54-2.59 (m, 4H), 2.63 (dd, J=12.5, 7.5 Hz, 1H), 2.90-3.05 (m, 4H), 3.46 (s, 3H), 3.85 (s, 3H), 4.62 (spt, J=6.9 Hz, 1H), 7.60 (t, J=7.9 Hz, 1H), 8.10-8.15 (m, 2H), 8.51-8.57 (m, 2H)

Example 91

4-{[(2S)-1-(4-{[5-(3-methyl-1,2-oxazol-5-yl)thiophen-2-yl]sulfonyl}piperazin-1-yl)propan-2-yl]amino}quinazolin-8-yl N,N-dimethylcarbamate

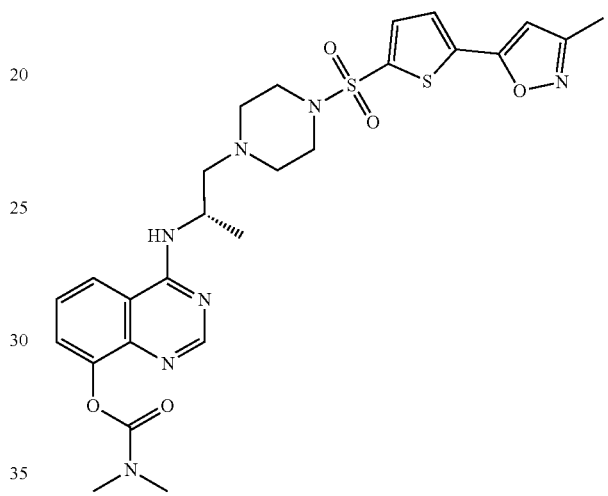

Step 1: Preparation of tert-butyl 4-[(2S)-2-[(8-hydroxyquinazolin-4-yl)amino]propyl]piperazine-1-carboxylate (Intermediate 43)

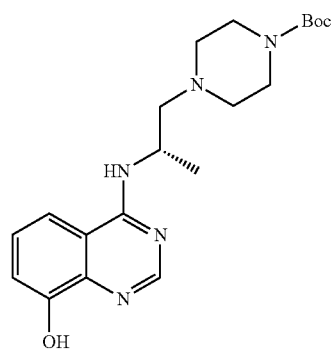 [SMILES: C[C@@H](CN1CCN(C(=O)OC(C)(C)C)CC1)Nc1ncnc2c(O)cccc12]

Title compound was prepared following the procedure used for the synthesis of Intermediate 1, starting from 4-chloroquinazolin-8-ol (Intermediate 11, 50 mg, 0.277 mmol) to afford Intermediate 43 (99 mg, 0.25 mmol, 92% yield).

LC-MS (ESI): m/z (M+1): 388.2 (Method 2)

Step 2: Preparation of tert-butyl 4-[(2S)-2-[[8-(dimethylcarbamoyloxy)quinazolin-4-yl]amino]propyl]piperazine-1-carboxylate (Intermediate 44)

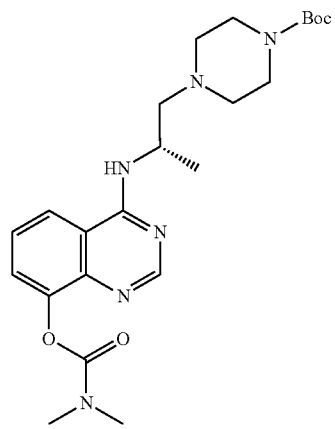 [SMILES: C[C@@H](CN1CCN(C(=O)OC(C)(C)C)CC1)Nc1ncnc2c(OC(=O)N(C)C)cccc12]

To a solution of tert-butyl 4-[(2S)-2-[(8-hydroxyquinazolin-4-yl)amino]propyl]piperazine-1-carboxylate (Intermediate 43, 99 mg, 0.25 mmol) in DCM (5 mL) at 0° C. DMAP (101 mg, 0.8 mmol) was added, followed by N,N-dimethylcarbamoyl chloride (0.12 mL, 1.32 mmol). The mixture was stirred at room temperature for 24 h. The solvent was removed under vacuum and the crude was purified by flash chromatograpy using a gradient of MeCN in basic H$_2$O (10 mM ammonium bicarbonate aqueous solution adjusted to pH 10 with ammonia) from 5% to 45% affording title compound (42 mg, 0.09 mmol, 36% yield) as a white solid.

LC-MS (ESI): m/z (M+1): 459.3 (Method 1)

Step 3: Preparation of [4-[[(2S)-1-piperazin-1-ylpropan-2-yl]amino]quinazolin-8-yl]N,N-dimethylcarbamate hydrochloride (Intermediate 45)

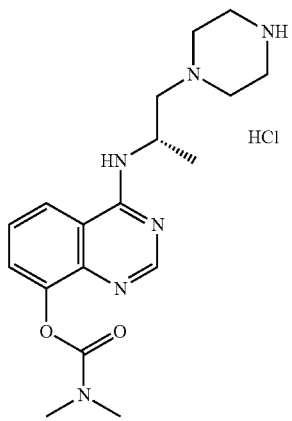 [SMILES: C[C@@H](CN1CCNCC1)Nc1ncnc2c(OC(=O)N(C)C)cccc12 ; Cl]

Title compound was prepared following the procedure used for the synthesis of Intermediate 2, starting from tert-butyl 4-[(2S)-2-[[8-(dimethylcarbamoyloxy)quinazolin-4-yl]amino]propyl]piperazine-1-carboxylate (Intermediate 44, 42 mg, 0.09 mmol) to afford Intermediate 45 (46 mg, crude) that was used in the next step without further purification.

LC-MS (ESI): m/z (M+1): 359.2 (Method 1)

Step 4: Preparation of 4-{[(2S)-1-(4-{[5-(3-methyl-1,2-oxazol-5-yl)thiophen-2-yl]sulfonyl}piperazin-1-yl)propan-2-yl]amino}quinazolin-8-yl N,N-dimethylcarbamate

Example 91

Title compound was prepared following the procedure used for the synthesis of Example 1, starting from [4-[[(2S)-1-piperazin-1-ylpropan-2-yl]amino]quinazolin-8-yl]N,N-dimethylcarbamate hydrochloride (Intermediate 45, 40 mg, 0.1 mmol) and 5-(3-methyl-1,2-oxazol-5-yl)thiophene-2-sulfonyl chloride (27 mg, 0.11 mmol) to afford title compound (26 mg, 0.04 mmol, 48% yield) as a white solid.

LC-MS (ESI): m/z (M+1): 586.12 (Method 2)

$^1$H NMR (400 MHz, DMSO-d$_6$) δ ppm 1.18 (d, J=6.4 Hz, 3H), 2.29 (s, 3H), 2.41 (dd, J=12.4, 6.7 Hz, 1H), 2.54-2.65 (m, 5H), 2.91 (s, 3H), 2.98 (br s, 4H), 3.13 (s, 3H), 4.59 (dquin, J=13.9, 6.8, 6.8, 6.8, 6.8 Hz, 1H), 6.96 (s, 1H), 7.42 (t, J=7.9 Hz, 1H), 7.45-7.49 (m, 1H), 7.69 (d, J=4.0 Hz, 1H), 7.75 (d, J=4.0 Hz, 1H), 7.90 (d, J=8.1 Hz, 1H), 8.09 (dd, J=8.1, 1.5 Hz, 1H), 8.41 (s, 1H)

Example 96

N8,N8-dimethyl-N4-[(2S)-1-(4-{[5-(3-methyl-1,2-oxazol-5-yl)thiophen-2-yl]sulfonyl}piperazin-1-yl)propan-2-yl]quinazoline-4,8-diamine

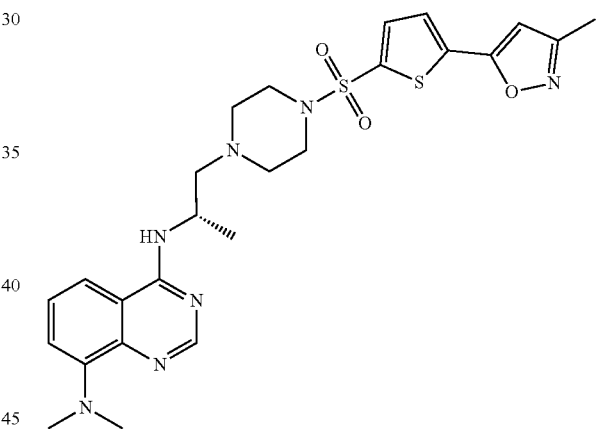

Step 1: Preparation of tert-butyl 4-[(2S)-2-[(8-hydroxyquinazolin-4-yl)amino]propyl]piperazine-1-carboxylate (Intermediate 46)

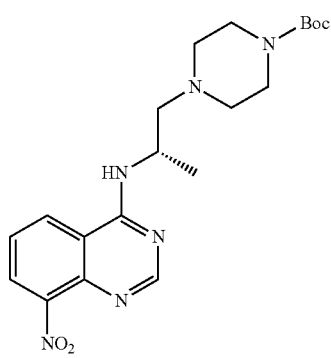 [SMILES: C[C@@H](CN1CCN(C(=O)OC(C)(C)C)CC1)Nc1ncnc2c([N+](=O)[O-])cccc12]

Title compound was prepared following the procedure used for the synthesis of Intermediate 1, starting from 4-chloro-8-nitroquinazoline (350 mg, 1.67 mmol) to afford Intermediate 46 (485 mg, 1.17 mmol, 70% yield).

LC-MS (ESI): m/z (M+1): 417.1 (Method 2)

Step 2: Preparation of tert-butyl 4-[(2S)-2-[(8-aminoquinazolin-4-yl)amino]propyl]piperazine-1-carboxylate (Intermediate 47)

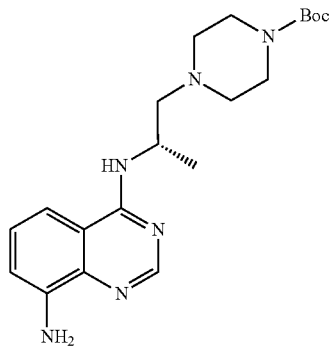

To a solution of tert-butyl 4-[(2S)-2-[(8-nitroquinazolin-4-yl)amino]propyl]piperazine-1-carboxylate (Intermediate 46, 485 mg, 1.17 mmol) in Ethanol (6 mL) Fe$^0$ (651 mg, 11.6 mmol) was added followed by NH$_4$Cl (499 mg, 9.33 mmol). The reaction was stirred at 75° C. for 48 h. The solvent was removed under vacuum and the crude was dissolved in DCM, washed with NaHCO$_3$ sat. sol. and the organic layer was concentrated under reduced pressure to afford Intermediate 47 (1.17 mmol theoric) that was used in the next step without further purification.

LC-MS (ESI): m/z (M+1): 387.1 (Method 2)

Step 3: Preparation of tert-butyl 4-[(2S)-2-{[8-(dimethylamino)quinazolin-4-yl]amino}propyl]piperazine-1-carboxylate (Intermediate 48)

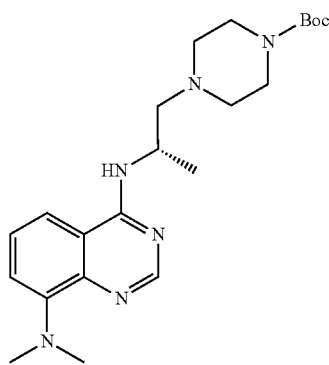 [SMILES: C[C@@H](CN1CCN(C(=O)OC(C)(C)C)CC1)Nc1ncnc2c(N(C)C)cccc12]

To a solution of tert-butyl 4-[(2S)-2-[(8-aminoquinazolin-4-yl)amino]propyl]piperazine-1-carboxylate (Intermediate 47, 100 mg, 0.26 mmol) in DCM (1 mL) and Acetic acid (0.05 mL) formaldehyde (0.02 mL, 0.57 mmol) was added followed by STAB (222 mg, 0.390 mmol). NaHCO$_3$ sat. sol. was added and the aqueous layer was extracted with DCM. The organic layer was separated and concentrated under reduced pressure to afford title compound (0.26 mmol theoric) that was used in the following step without further purification.

LC-MS (ESI): m/z (M+1): 415.2 (Method 2)

Step 4: N8,N8-dimethyl-N4-[(2S)-1-(piperazin-1-yl)propan-2-yl]quinazoline-4,8-diamine hydrochloride (Intermediate 49)

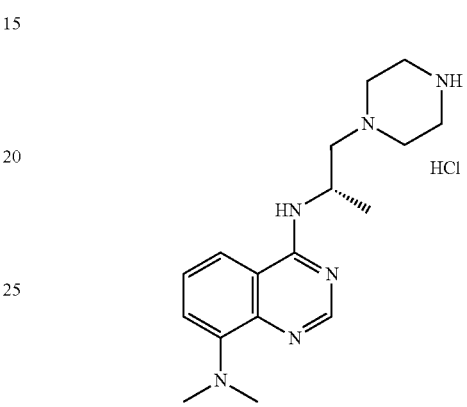

Title compound was prepared following the procedure used for the synthesis of Intermediate 2, starting from Intermediate 48 (107 mg, 0.26 mmol) to afford Intermediate 49 (120 mg, crude) that was used in the next step without further purification.

LC-MS (ESI): m/z (M+1): 315.2 (Method 2)

Step 4: Preparation of N8,N8-dimethyl-N4-[(2S)-1-(4-{[5-(3-methyl-1,2-oxazol-5-yl)thiophen-2-yl]sulfonyl}piperazin-1-yl)propan-2-yl]quinazoline-4,8-diamine Example 96

Title compound was prepared following the procedure used for the synthesis of Example 1, starting from [4-[[(2S)-1-piperazin-1-ylpropan-2-yl]amino]quinazolin-8-yl]N,N-dimethylcarbamate hydrochloride (Intermediate 45, 100 mg, 0.26 mmol) and 5-(3-methyl-1,2-oxazol-5-yl)thiophene-2-sulfonyl chloride (68 mg, 0.26 mmol) to afford title compound (8 mg, 0.015 mmol, 5% yield) as a whitenish solid.

LC-MS (ESI): m/z (M+1): 542.1 (Method 2)

$^1$H NMR (500 MHz, DMSO-d$_6$) δ ppm 1.17 (d, J=6.6 Hz, 3H), 2.29 (s, 3H), 2.40 (br dd, J=12.4, 6.9 Hz, 1H), 2.54-2.62 (m, 5H), 2.96 (br s, 4H), 2.94 (s, 6H), 4.50-4.63 (m, 1H), 6.97 (s, 1H), 7.04 (d, J=7.7 Hz, 1H), 7.28 (t, J=8.1 Hz, 1H), 7.59 (d, J=8.0 Hz, 1H), 7.65 (d, J=8.2 Hz, 1H), 7.69 (d, J=3.8 Hz, 1H), 7.76 (d, J=3.8 Hz, 1H), 8.38 (s, 1H)

The Example in the following table was prepared from commercially available reagents by using methods analogous to Example 96.

| Example No. | Structure & Name | Analytical data |
|---|---|---|
| 98 | 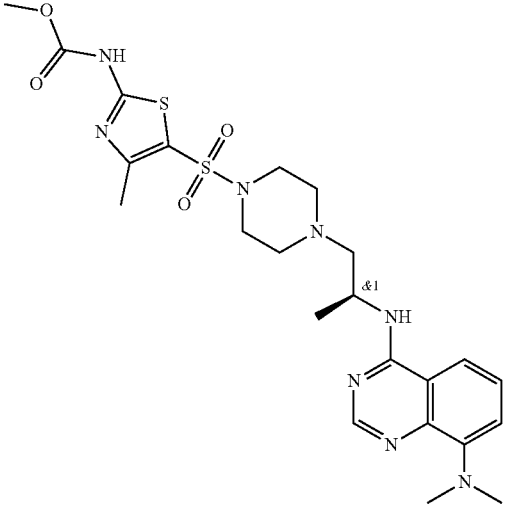<br>methyl N-[5-({4-[(2S)-2-{[8-(dimethylamino)quinazolin-4-yl]amino}propyl]piperazin-1-yl}sulfonyl)-4-methyl-1,3-thiazol-2-yl]carbamate | LC-MS (ESI): m/z (M + 1): 549.2 (Method 2)<br>$^1$H NMR (500 MHz, DMSO-$d_6$) δ ppm 1.18 (d, J = 6.6 Hz, 3 H), 2.37-2.41 (m, 1 H), 2.42 (s, 3 H), 2.53-2.62 (m, 5 H), 2.93-3.06 (m, 10 H), 3.75 (s, 3 H), 4.57 (dt, J = 13.9, 6.9 Hz, 1 H), 7.06 (d, J = 7.7 Hz, 1 H), 7.30 (t, J = 8.0 Hz, 1 H), 7.60 (d, J = 8.0 Hz, 1 H), 7.67 (d, J = 8.2 Hz, 1 H), 8.39 (s, 1 H), 12.33 (br s, 1 H) |

Pharmacological Activity of the Compounds of the Invention

In Vitro Assays

The effectiveness of compounds of the present invention as LPA2 antagonist can be determined at the human recombinant LPA2 expressed in CHO cells, using a FLIPR assay in 384 well format.

CHO-hLPA2 cell lines are cultured in a humidified incubator at 5% CO2 in DMEM/F-12 (1:1) MIXTURE with 2 mM Glutamax, supplemented with 10% of Foetal Bovine Serum, 1 mM Sodium Pyruvate, 11 mM Hepes and 1× Penicillin/Streptomycin. CHO hLPA2 cells are seeded into black walled clear-bottom 384-well plates (#781091, Greiner Bio-One GmbH) at a density of 7,500 cells per well in 50 µl culture media and grown overnight in a 37° C. humidified CO2-incubator. Serial dilutions (1:3 or 1:4, 11 points CRC) of compounds are performed in 100% DMSO at 200× the final concentration. The compounds are diluted 1:50 prior to the experiment with Assay Buffer (20 mM HEPES, 145 mM NaCl, 5 mM KCl, 5.5 mM glucose, 1 mM MgCl2 and 2 mM CaCl2, pH 7.4 containing 0.01% Pluronic F-127) to obtain a solution corresponding to 5-fold the final concentration in the assay (4×, 2% DMSO). The final concentration of DMSO in the assay will be 0.5% in each well. Medium is removed by aspiration and cells are then incubated with 30 µl of a loading solution containing 5 µM of the cytoplasmic Ca2+ indicator Cal-520 AM in Assay Buffer containing 2.5 mM probenecid for 30 min at 37° C. incubator (cell loading). The loaded cell plates are transferred into the FLIPR instrument and calcium responses are monitored during the on-line addition protocols. For testing of compounds, after the cell loading, 10 µl/well of 4× antagonists' solution was added onto the cells. After 30 min pre-incubation (at 37° C.), 10 µl/well of 5× concentrated LPA EC80 was added and Ca2+ mobilization responses was followed during the on-line addition protocol. Intracellular peak fluorescence values subtracted by baseline fluorescence are exported and analysed to determine $IC_{50}$ values, respectively. The calcium response is expressed as percentage of the maximal inhibition of the EC80 agonist response.

The raw data obtained in unstimulated controls (DMSO, no LPA) are set as "100% inhibition", while the raw data obtained in negative controls, i.e. in the absence of compounds and stimulating with LPA EC80, are set as "0% inhibition".

The raw data (peak height expressed as relative fluorescence units) are normalized and transformed into "percent of inhibition". Curve fitting and $pIC_{50}$ ($-Log\ IC_{50}$) estimations are carried out using a four-parameter logistic model using XLfit Software.

The results for individual compounds are provided below in Table 2 wherein the compounds are classified in term of potency with respect to their inhibitory activity on LPA2 isoform, according to the following classification criterion:

TABLE 2

| Example No. | LPA2 IC50 |
|---|---|
| 5 | + |
| 11 | + |
| 6 | + |
| 100 | + |
| 24 | + |
| 74 | + |
| 73 | + |
| 7 | + |
| 15 | + |
| 99 | + |
| 57 | + |
| 49 | + |
| 19 | + |
| 81 | + |
| 41 | + |
| 38 | + |
| 22 | + |
| 26 | + |
| 27 | + |
| 34 | + |
| 25 | + |
| 31 | + |

TABLE 2-continued

| Example No. | LPA2 IC50 |
|---|---|
| 8 | + |
| 62 | + |
| 39 | + |
| 66 | + |
| 9 | + |
| 61 | + |
| 40 | + |
| 90 | + |
| 23 | + |
| 59 | + |
| 29 | + |
| 21 | + |
| 35 | + |
| 55 | + |
| 60 | + |
| 84 | + |
| 93 | + |
| 54 | + |
| 47 | + |
| 10 | + |
| 42 | + |
| 72 | + |
| 67 | + |
| 88 | + |
| 13 | ++ |
| 37 | ++ |
| 101 | ++ |
| 97 | ++ |
| 33 | ++ |
| 20 | ++ |
| 16 | ++ |
| 50 | ++ |
| 83 | ++ |
| 17 | ++ |
| 4 | ++ |
| 44 | ++ |
| 12 | ++ |
| 52 | ++ |
| 1 | ++ |
| 56 | ++ |
| 32 | ++ |
| 80 | ++ |
| 18 | ++ |
| 28 | ++ |
| 94 | ++ |
| 79 | ++ |
| 82 | ++ |
| 2 | ++ |
| 71 | ++ |
| 46 | ++ |
| 89 | ++ |
| 63 | ++ |
| 45 | ++ |
| 53 | ++ |
| 14 | ++ |
| 98 | ++ |
| 3 | ++ |
| 91 | ++ |
| 68 | ++ |
| 95 | ++ |
| 87 | ++ |
| 75 | ++ |
| 69 | +++ |
| 65 | +++ |
| 36 | +++ |
| 48 | +++ |
| 30 | +++ |
| 64 | +++ |
| 77 | +++ |
| 78 | +++ |
| 76 | +++ |
| 51 | +++ |
| 43 | +++ |
| 70 | +++ |
| 86 | +++ |

TABLE 2-continued

| Example No. | LPA2 IC50 |
|---|---|
| 85 | +++ |
| 96 | +++ |
| 58 | +++ |
| 92 | +++ |

LPA receptor 2 (LPA2)

+: LPA2 IC$_{50}$ less than 1000 nM

++: LPA2 IC$_{50}$ comprised between about 100 nM and 10 nm

+++: LPA2 IC$_{50}$ less than about 10 nM.

As it can be appreciated in Table 2, the compounds of the present invention show a good activity as antagonist of LPA2 receptor.

Comparative Example A

Methyl (S)-(4-methyl-5-((4-(2-(pyrido[2,3-d]pyrimidin-4 ylamino)propyl)piperazin-1-yl)sulfonyl)thiazol-2-yl)carbamate

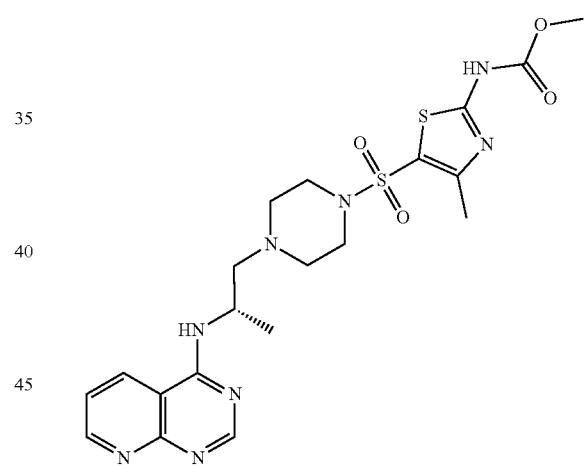

The activity of comparative Example A as has been tested in the in vitro assay for the determination of activity on LPA2 receptor as described above.

Differently from the compounds of formula (I) of the present invention, the comparative Example A shows an IC$_{50}$ greater than 1 μm, even greater than 3 μm, and thus the compound is inactive on receptor LPA2.

The above results demonstrate that the scaffold of the compounds of formula (I) of the invention comprising a quinazoline moiety linked to the piperazine through an aminoalkyl linker leads unexpectedly to a series of compounds that is active on receptor LPA2.

The invention claimed is:

1. A compound of formula (I)

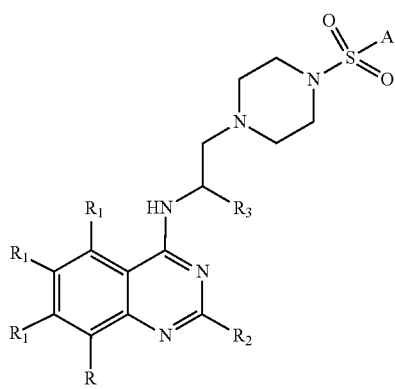

wherein
R is selected from the group consisting of H, $(C_1-C_4)$ alkyl, halo, $(C_1-C_4)$haloalkyl, —$NO_2$, —C(O)$OR_1$, —$OR_1$, —O$(C_1-C_4)$haloalkyl, —$NR_AR_B$, —OC(O) $NR_AR_B$, —C(O)$R_C$, —C(O)$NR_AR_B$, and —$(C_1-C_4)$ alkylene-$NR_AR_B$;

$R_1$ is H or $(C_1-C_4)$alkyl;

$R_2$ is selected from the group consisting of H, $(C_1-C_4)$ alkyl, $(C_1-C_4)$haloalkyl, —$(C_1-C_4)$alkylene-$OR_1$ and $(C_3-C_8)$cycloalkyl;

$R_3$ is selected from the group consisting of H and $(C_1-C_4)$alkyl;

A is selected from the group consisting of 5-6 membered heteroaryl and aryl wherein each of said heteroaryl and aryl is optionally substituted by one or more groups selected from $(C_1-C_4)$alkyl, —C(O)$R_1$, —C(O)$OR_1$, —C(O)$R_1$, $(C_1-C_4)$haloalkyl, halo, —$NR_AC(O)R_1$, —$NR_AC(O)OR_1$, —$NR_AC(O)$—$(C_1-C_4)$alkylene-$OR_1$, —$NR_AC(O)R_C$, —$NR_AC(O)$ $NR_AR_B$, —N$(C_1-C_4)$alkylene-$NR_AR_B$, aryl and heteroaryl optionally substituted by one or more $(C_1-C_4)$alkyl and $(C_1-C_4)$haloalkyl, or when A is aryl it is optionally fused to a second saturated or unsaturated ring optionally containing one or more heteroatoms selected from N, O and S to form a bicyclic ring system optionally substituted by one or more groups selected from —C(O)$R_1$, $(C_1-C_4)$alkyl and oxo;

$R_C$ is selected from of from heteroaryl, aryl, $(C_3-C_8)$cycloalkyl and $(C_4-C_8)$heterocycloalkyl wherein said heteroaryl, aryl, heterocycloalkyl and cycloalkyl is optionally substituted by one or more $(C_1-C_4)$alkyl and —C(O)$OR_1$;

$R_A$ and $R_B$ are at each occurrence independently selected from the group consisting of H, $(C_1-C_4)$alkyl, $(C_3-C_8)$ cycloalkyl, $(C_1-C_6)$haloalkyl and halo, or $R_A$ and $R_B$ may form together with the nitrogen atom to which they are attached a 4-6 membered saturated heterocyclic ring system optionally containing a further heteroatom selected from N, S and O, wherein said heterocyclic ring system is optionally substituted by one or more groups selected from $(C_1-C_4)$alkyl, $(C_1-C_4)$haloalkyl and halo, with the proviso that when $R_2$ is H, R is not H.

2. The compound of formula (I) according to claim 1, wherein
R is selected from the group consisting of H, $(C_1-C_4)$ alkyl, halo, $(C_1-C_4)$haloalkyl, —$NO_2$, —C(O)$OR_1$, —$OR_1$, —O$(C_1-C_4)$haloalkyl, —$NR_AR_B$, —OC(O) $NR_AR_B$, —C(O)$R_C$, —C(O) $NR_AR_B$ and —$(C_1-C_4)$ alkylene-$NR_AR_B$;

$R_1$ is H or $(C_1-C_4)$alkyl, $R_2$ is selected from the group consisting of H, $(C_1-C_4)$ alkyl, $(C_1-C_4)$haloalkyl,-$(C_1-C_4)$alkylene-$OR_1$ and $(C_3-C_8)$cycloalkyl;

$R_3$ is $(C_1-C_4)$alkyl;

A is selected from the group consisting of 5-6 membered heteroaryl and aryl wherein each of said heteroaryl and aryl is optionally substituted by one or more groups selected from $(C_1-C_4)$alkyl, halo, —$NR_AC(O)R_1$, —$NR_AC(O)OR_1$, —$NR_AC(O)$—$(C_1-C_4)$alkylene-$OR_1$, —$NR_AC(O)R_C$, —$NR_AC(O)$ $NR_AR_B$, aryl and heteroaryl optionally substituted by one or more $(C_1-C_4)$ alkyl, or when A is aryl it is optionally fused to a second saturated ring optionally containing one or more heteroatoms selected from N, S and O, to form a bicyclic ring system optionally substituted by one or more oxo;

$R_C$ is selected from $(C_3-C_8)$cycloalkyl and 5-6 membered heteroaryl optionally substituted by one or more $(C_1-C_4)$alkyl;

$R_A$ and $R_B$ are at each occurrence independently selected from the group consisting of H, $(C_1-C_4)$alkyl, $(C_3-C_8)$ cycloalkyl, $(C_1-C_6)$haloalkyl and halo, or $R_A$ and $R_B$ may form together with the nitrogen atom to which they are attached a 4-6 membered saturated heterocyclic ring system optionally containing a further heteroatom selected from N, S and O, wherein said heterocyclic ring system is optionally substituted by one or more groups selected from $(C_1-C_4)$alkyl, $(C_1-C_4)$haloalkyl and halo, with the proviso that when $R_2$ is H, R is not H.

3. The compound of formula (I) according to claim 1, wherein A is selected from the group consisting of 5-6 membered heteroaryl and aryl wherein each of said heteroaryl and aryl is optionally substituted by one or more groups selected from $(C_1-C_4)$alkyl, —C(O)$R_1$, —C(O)$OR_1$, —C(O)$R_1$, $(C_1-C_4)$haloalkyl, halo, —$NR_AC(O)R_1$, —$NR_AC$ (O)$OR_1$, —$NR_AC(O)$—$(C_1-C_4)$alkylene-$OR_1$, —$NR_AC(O)$ $R_C$, —$NR_AC(O)$ $NR_AR_B$, —N$(C_1-C_4)$alkylene-$NR_AR_B$, aryl and heteroaryl optionally substituted by one or more $(C_1-C_4)$alkyl and $(C_1-C_4)$haloalkyl selected from the group consisting of isoxazole, pyridine, thiazole, oxazole, 1,2,4-oxadiazole, 1,3,4-oxadiazole and pyrazole; or when A is aryl it is optionally fused to a second saturated or unsaturated ring optionally containing one or more heteroatoms selected from N, O and S to form a bicyclic ring system optionally substituted by one or more groups selected from —C(O)$R_1$, $(C_1-C_4)$alkyl and oxo.

4. The compound of formula (I) according to claim 1, wherein A is a 5-6 membered heteroaryl selected from the group consisting of thiazole, thiophene and furan.

5. The compound of formula (I) according to claim 1, wherein $R_C$ is isoxazole optionally substituted by one or more groups selected from $(C_1-C_4)$alkyl and —C(O)$OR_1$.

6. The compound of formula (I) according to claim 1 selected from:
methyl N-[4-methyl-5-({4-[(2S)-2-{[8-(trifluoromethyl) quinazolin-4-yl]amino}propyl]piperazin-1-yl}sulfonyl)-1,3-thiazol-2-yl]carbamate, methyl N-[4-methyl-5-({4-[(2S)-2-{[2-methyl-8-(trifluoromethyl)quinazolin-4-yl]amino}propyl]piperazin-1-yl}sulfonyl)-1,3-thiazol-2-yl]carbamate,
methyl N-[4-methyl-5-({4-[(2S)-2-{[8-(trifluoromethoxy)quinazolin-4-yl]amino}propyl]piperazin-1-yl}sulfonyl)-1,3-thiazol-2-yl]carbamate,
8-(difluoromethoxy)—N-[(2S)-1-(4-{[5-(3,4-dimethyl-1,2-oxazol-5-yl)thiophen-2-yl]sulfonyl}piperazin-1-yl)propan-2-yl]quinazolin-4-amine,
N-[(2S)-1-[4-(3,4-dichlorobenzenesulfonyl)piperazin-1-yl]propan-2-yl]-8-(trifluoromethyl)quinazolin-4-amine,
8-chloro-N-[(2S)-1-[4-(3,4-dichlorobenzenesulfonyl)piperazin-1-yl]propan-2-yl]quinazolin-4-amine,
N-[5-({4-[(2S)-2-{[8-(trifluoromethyl)quinazolin-4-yl]amino}propyl]piperazin-1-yl}sulfonyl)-1,3-thiazol-2-yl]acetamide,
N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide,
N-[4-methyl-5-({4-[(2S)-2-{[8-(trifluoromethyl)quinazolin-4-yl]amino}propyl]piperazin-1-yl}sulfonyl)-1,3-thiazol-2-yl]propanamide,
methyl 4-{[(2S)-1-[4-(3,4-dichlorobenzenesulfonyl)piperazin-1-yl]propan-2-yl]amino}quinazoline-8-carboxylate,
methyl N-[4-methyl-5-({4-[(2S)-2-{[2-(trifluoromethyl)quinazolin-4-yl]amino}propyl]piperazin-1-yl}sulfonyl)-1,3-thiazol-2-yl]carbamate,
methyl 4-{[(2S)-1-{4-[(2-phenyl-1,3-thiazol-5-yl)sulfonyl]piperazin-1-yl}propan-2-yl]amino}quinazoline-8-carboxylate,
N-[5-({4-[(2S)-2-{[2-methyl-8-(trifluoromethyl)quinazolin-4-yl]amino}propyl]piperazin-1-yl}sulfonyl)-1,3-thiazol-2-yl]acetamide,
N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine,
methyl N-[5-({4-[(2S)-2-[(2-cyclopropylquinazolin-4-yl)amino]propyl]piperazin-1-yl}sulfonyl)-4-methyl-1,3-thiazol-2-yl]carbamate,
methyl 4-{[(2S)-1-(4-{[5-(1,2-oxazol-5-yl)thiophen-2-yl]sulfonyl}piperazin-1-yl)propan-2-yl]amino}quinazoline-8-carboxylate,
methyl 4-{[(2S)-1-[4-({2-[(methoxycarbonyl)amino]-4-methyl-1,3-thiazol-5-yl}sulfonyl)piperazin-1-yl]propan-2-yl]amino}quinazoline-8-carboxylate,
methyl N-[5-({4-[(2S)-2-[(2-cyclopropyl-8-methylquinazolin-4-yl)amino]propyl]piperazin-1-yl}sulfonyl)-4-methyl-1,3-thiazol-2-yl]carbamate,
N-[5-({4-[(2S)-2-[(2-cyclopropyl-8-methylquinazolin-4-yl)amino]propyl]piperazin-1-yl}sulfonyl)-1,3-thiazol-2-yl]acetamide,
methyl 4-{[(2S)-1-{4-[(2-acetamido-1,3-thiazol-5-yl)sulfonyl]piperazin-1-yl}propan-2-yl]amino}quinazoline-8-carboxylate,
methyl N-[5-({4-[(2S)-2-{[2-cyclopropyl-8-(trifluoromethyl)quinazolin-4-yl]amino}propyl]piperazin-1-yl}sulfonyl)-4-methyl-1,3-thiazol-2-yl]carbamate,
N-[5-({4-[(2S)-2-{[2-cyclopropyl-8-(trifluoromethyl)quinazolin-4-yl]amino}propyl]piperazin-1-yl}sulfonyl)-1,3-thiazol-2-yl]acetamide,
2-methyl-N-[(2S)-1-(4-{[5-(1,2-oxazol-5-yl)thiophen-2-yl]sulfonyl}piperazin-1-yl)propan-2-yl]-8-(trifluoromethyl)quinazolin-4-amine,
2-methoxy-N-[5-({4-[(2S)-2-{[8-(trifluoromethyl)quinazolin-4-yl]amino}propyl]piperazin-1-yl}sulfonyl)-1,3-thiazol-2-yl]acetamide,
2-methoxy-N-[4-methyl-5-({4-[(2S)-2-{[8-(trifluoromethyl)quinazolin-4-yl]amino}propyl]piperazin-1-yl}sulfonyl)-1,3-thiazol-2-yl]acetamide,
methyl N-[5-({4-[(2S)-2-{[8-(trifluoromethyl)quinazolin-4-yl]amino}propyl]piperazin-1-yl}sulfonyl)-1,3-thiazol-2-yl]carbamate,
methyl N-[5-({4-[(2S)-2-{[8-(dimethylcarbamoyl)quinazolin-4-yl]amino}propyl]piperazin-1-yl}sulfonyl)-4-methyl-1,3-thiazol-2-yl]carbamate,
N-[(2S)-1-(4-{[5-(pyridin-2-yl)thiophen-2-yl]sulfonyl}piperazin-1-yl)propan-2-yl]-8-(trifluoromethyl)quinazolin-4-amine,
N-[(2S)-1-{4-[4-(2-methyl-1,3-oxazol-4-yl)benzenesulfonyl]piperazin-1-yl}propan-2-yl]-8-(trifluoromethyl)quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-(trifluoromethyl)quinazolin-4-amine,
N-[(2S)-1-{4-[4-(3,5-dimethyl-1,2-oxazol-4-yl)benzenesulfonyl]piperazin-1-yl}propan-2-yl]-8-(trifluoromethyl)quinazolin-4-amine,
N-[(2S)-1-(4-{[5-(2-methyl-1,3-thiazol-4-yl)thiophen-2-yl]sulfonyl}piperazin-1-yl)propan-2-yl]-8-(trifluoromethyl)quinazolin-4-amine,
N-[(2S)-1-{4-[3-(1,2-oxazol-5-yl)benzenesulfonyl]piperazin-1-yl}propan-2-yl]-8-(trifluoromethyl)quinazolin-4-amine,
N-[(2S)-1-{4-[4-(1,2-oxazol-5-yl)benzenesulfonyl]piperazin-1-yl}propan-2-yl]-8-(trifluoromethyl)quinazolin-4-amine,
N-[(2S)-1-{4-[(2-phenyl-1,3-thiazol-5-yl)sulfonyl]piperazin-1-yl}propan-2-yl]-8-(trifluoromethyl)quinazolin-4-amine,
N-[(2S)-1-(4-{[5-(3-methyl-1,2-oxazol-5-yl)thiophen-2-yl]sulfonyl}piperazin-1-yl)propan-2-yl]-8-(trifluoromethyl)quinazolin-4-amine,
N-[(2S)-1-(4-{[5-(1,3-oxazol-5-yl)thiophen-2-yl]sulfonyl}piperazin-1-yl)propan-2-yl]-8-(trifluoromethyl)quinazolin-4-amine,
4-{[(2S)-1-{4-[(2-acetamido-4-methyl-1,3-thiazol-5-yl)sulfonyl]piperazin-1-yl}propan-2-yl]amino}-N,N-dimethylquinazoline-8-carboxamide,
methyl N-[5-({4-[(2S)-2-({8-[ethyl(methyl)carbamoyl]quinazolin-4-yl}amino)propyl]piperazin-1-yl}sulfonyl)-4-methyl-1,3-thiazol-2-yl]carbamate,
methyl N-[4-methyl-5-({4-[(2S)-2-({8-[methyl(2,2,2-trifluoroethyl)carbamoyl]quinazolin-4-yl}amino)propyl]piperazin-1-yl}sulfonyl)-1,3-thiazol-2-yl]carbamate,
N-[(2S)-1-(4-{[5-(3,5-dimethyl-1,2-oxazol-4-yl)thiophen-2-yl]sulfonyl}piperazin-1-yl)propan-2-yl]-8-(trifluoromethyl)quinazolin-4-amine,
N-[2-chloro-5-fluoro-4-({4-[(2S)-2-{[8-(trifluoromethyl)quinazolin-4-yl]amino}propyl]piperazin-1-yl}sulfonyl)phenyl]acetamide,
4-{[(2S)-1-(4-{[5-(3,4-dimethyl-1,2-oxazol-5-yl)thiophen-2-yl]sulfonyl}piperazin-1-yl)propan-2-yl]amino}-N,N-dimethylquinazoline-8-carboxamide,
N,N-dimethyl-4-{[(2S)-1-{4-[(2-phenyl-1,3-thiazol-5-yl)sulfonyl]piperazin-1-yl}propan-2-yl]amino}quinazoline-8-carboxamide,
methyl N-[4-methyl-5-({4-[(2S)-2-{[8-(pyrrolidine-1-carbonyl)quinazolin-4-yl]amino}propyl]piperazin-1-yl}sulfonyl)-1,3-thiazol-2-yl]carbamate, methyl N-[5-({4-[(2S)-2-[(8-cyclopropanecarbonylquinazolin-4-yl)amino]propyl]piperazin-1-yl}sulfonyl)-4-methyl-1,3-thiazol-2-yl]carbamate,
methyl N-[5-({4-[(2S)-2-{[8-(azetidine-1-carbonyl)quinazolin-4-yl]amino}propyl]piperazin-1-yl}sulfonyl)-4-methyl-1,3-thiazol-2-yl]carbamate,
N,N-dimethyl-4-{[(2S)-1-(4-{[5-(3-methyl-1,2-oxazol-5-yl)thiophen-2-yl]sulfonyl}piperazin-1-yl)propan-2-yl]amino}quinazoline-8-carboxamide,
4-{[(2S)-1-[4-(3,4-dichlorobenzenesulfonyl)piperazin-1-yl]propan-2-yl]amino}-N,N-dimethylquinazoline-8-carboxamide,
N-[(2S)-1-{4-[3-(5-methyl-1,2,4-oxadiazol-3-yl)benzenesulfonyl]piperazin-1-yl}propan-2-yl]-8-(trifluoromethyl)quinazolin-4-amine,
N-methyl-4-{[(2S)-1-(4-{[5-(3-methyl-1,2-oxazol-5-yl)thiophen-2-yl]sulfonyl}piperazin-1-yl)propan-2-yl]amino}-N-(2,2,2-trifluoroethyl)quinazoline-8-carboxamide,
N-[(2S)-1-(4-{[5-(3-methyl-1,2-oxazol-5-yl)furan-2-yl]sulfonyl}piperazin-1-yl)propan-2-yl]-8-(trifluoromethyl)quinazolin-4-amine, N-[(2S)-1-(4-{[5-(1,2-oxazol-3-yl)thiophen-2-yl]sulfonyl}piperazin-1-yl)propan-2-yl]-8-(trifluoromethyl)quinazolin-4-amine,
N-[(2S)-1-(4-{[5-(1,2-oxazol-5-yl)furan-2-yl]sulfonyl}piperazin-1-yl)propan-2-yl]-8-(trifluoromethyl)quinazolin-4-amine, methyl N-[4-methyl-5-({4-[(2S)-2-[(8-nitroquinazolin-4-yl)amino]propyl]piperazin-1-yl}sulfonyl)-1,3-thiazol-2-yl]carbamate,
N-[(2S)-1-(4-{[5-(3,4-dimethyl-1H-pyrazol-5-yl)furan-2-yl]sulfonyl}piperazin-1-yl)propan-2-yl]-8-(trifluoromethyl)quinazolin-4-amine, N-[(2S)-1-{4-[3-(5-methyl-1,3,4-oxadiazol-2-yl)benzenesulfonyl]piperazin-1-yl}propan-2-yl]-8-(trifluoromethyl)quinazolin-4-amine,
N-[(2S)-1-(4-{[5-(3-methyl-1,2-oxazol-5-yl)thiophen-2-yl]sulfonyl}piperazin-1-yl)propan-2-yl]-8-(pyrrolidine-1-carbonyl)quinazolin-4-amine,
N-[(2S)-1-{4-[2-methyl-5-(1,2-oxazol-5-yl)benzenesulfonyl]piperazin-1-yl}propan-2-yl]-8-(trifluoromethyl)quinazolin-4-amine,
N-[(2S)-1-{4-[2-methyl-5-(3-methyl-1,2-oxazol-5-yl)benzenesulfonyl]piperazin-1-yl}propan-2-yl]-8-(trifluoromethyl)quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-2-(methoxymethyl)-8-(trifluoromethyl)quinazolin-4-amine,
N-[(2S)-1-{4-[3-(2-methyl-1,3-thiazol-4-yl)benzenesulfonyl]piperazin-1-yl}propan-2-yl]-8-(trifluoromethyl)quinazolin-4-amine,
N-[(2S)-1-(4-{[2-(3-methyl-1,2-oxazol-5-yl)-1,3-thiazol-5-yl]sulfonyl}piperazin-1-yl)propan-2-yl]-8-(trifluoromethyl)quinazolin-4-amine,
4-{[(2S)-1-(4-{[5-(3,4-dimethyl-1,2-oxazol-5-yl)thiophen-2-yl]sulfonyl}piperazin-1-yl)propan-2-yl]amino}-N,N-diethylquinazoline-8-carboxamide,
N-cyclopentyl-4-{[(2S)-1-(4-{[5-(3,4-dimethyl-1,2-oxazol-5-yl)thiophen-2-yl]sulfonyl}piperazin-1-yl)propan-2-yl]amino}-N-methylquinazoline-8-carboxamide,
4-{[(2S)-1-[4-(5-chloro-4-acetamido-2-fluorobenzenesulfonyl)piperazin-1-yl]propan-2-yl]amino}-N,N-dimethylquinazoline-8-carboxamide,
N-[(2S)-1-(4-{[5-(1H-pyrazol-5-yl)furan-2-yl]sulfonyl}piperazin-1-yl)propan-2-yl]-8-(trifluoromethyl)quinazolin-4-amine,
N-[(2S)-1-(4-{[5-(3,4-dimethyl-1,2-oxazol-5-yl)furan-2-yl]sulfonyl}piperazin-1-yl)propan-2-yl]-8-(trifluoromethyl)quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-[(2S)-2-(trifluoromethyl)pyrrolidine-1-carbonyl]quinazolin-4-amine,
N-[(2S)-1-(4-{[5-(3-methyl-1,2-oxazol-5-yl)thiophen-2-yl]sulfonyl}piperazin-1-yl)propan-2-yl]-8-(piperidine-1-carbonyl)quinazolin-4-amine,
N-[(2S)-1-(4-{[4-(1,2-oxazol-5-yl)thiophen-2-yl]sulfonyl}piperazin-1-yl)propan-2-yl]-8-(trifluoromethyl)quinazolin-4-amine,
N-[4-methyl-5-({4-[(2S)-2-{[8-(trifluoromethyl)quinazolin-4-yl]amino}propyl]piperazin-1-yl}sulfonyl)-1,3-thiazol-2-yl]cyclohexanecarboxamide,
methyl N-[4-methyl-5-({4-[(2S)-2-[(8-methylquinazolin-4-yl)amino]propyl]piperazin-1-yl}sulfonyl)-1,3-thiazol-2-yl]carbamate,
N-[(2S)-1-(4-{[5-(3,4-dimethyl-1,2-oxazol-5-yl)thiophen-2-yl]sulfonyl}piperazin-1-yl)propan-2-yl]-8-[(dimethylamino)methyl]quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-(trifluoromethoxy)quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-[(2R)-2-(trifluoromethyl)pyrrolidine-1-carbonyl]quinazolin-4-amine,
8-(3,3-difluoropyrrolidine-1-carbonyl)—N-[(2S)-1-(4-{[5-(3,4-dimethyl-1,2-oxazol-5-yl)thiophen-2-yl]sulfonyl}piperazin-1-yl)propan-2-yl]quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-(2,2-dimethylpyrrolidine-1-carbonyl)quinazolin-4-amine,
methyl N-[4-methyl-5-({4-[(2S)-2-({8-[(2R)-2-(trifluoromethyl)pyrrolidine-1-carbonyl]quinazolin-4-yl}amino)propyl]piperazin-1-yl}sulfonyl)-1,3-thiazol-2-yl]carbamate,
methyl N-[5-({4-[(2S)-2-{[8-(3,3-difluoropyrrolidine-1-carbonyl)quinazolin-4-yl]amino}propyl]piperazin-1-yl}sulfonyl)-4-methyl-1,3-thiazol-2-yl]carbamate,
N-[4-methyl-5-({4-[(2S)-2-{[8-(trifluoromethyl)quinazolin-4-yl]amino}propyl]piperazin-1-yl}sulfonyl)-1,3-thiazol-2-yl]morpholine-4-carboxamide,
methyl N-[4-methyl-5-({4-[(2S)-2-({8-[(2S)-2-methylpyrrolidine-1-carbonyl]quinazolin-4-yl}amino)propyl]piperazin-1-yl}sulfonyl)-1,3-thiazol-2-yl]carbamate,
methyl N-[5-({4-[(2S)-2-{[8-(2,2-dimethylpyrrolidine-1-carbonyl)quinazolin-4-yl]amino}propyl]piperazin-1-yl}sulfonyl)-4-methyl-1,3-thiazol-2-yl]carbamate,
methyl N-[4-methyl-5-({4-[(2S)-2-({8-[(2S)-2-(trifluoromethyl)pyrrolidine-1-carbonyl]quinazolin-4-yl}amino)propyl]piperazin-1-yl}sulfonyl)-1,3-thiazol-2-yl]carbamate,
8-{3-azabicyclo[3.1.0]hexane-3-carbonyl}—N-[(2S)-1-(4-{[5-(3,4-dimethyl-1,2-oxazol-5-yl)thiophen-2-yl]sulfonyl}piperazin-1-yl)propan-2-yl]quinazolin-4-amine,
N-[(2S)-1-(4-{[5-(3,4-dimethyl-1,2-oxazol-5-yl)thiophen-2-yl]sulfonyl}piperazin-1-yl)propan-2-yl]-8-[(2S)-2-methylpyrrolidine-1-carbonyl]quinazolin-4-amine, methyl N-[5-({4-[(2S)-2-[(8-{3-azabicyclo[3.1.0]hexane-3-carbonyl}quinazolin-4-yl)amino]propyl]piperazin-1-yl}sulfonyl)-4-methyl-1,3-thiazol-2-yl]carbamate, 5-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]-1,2-oxazole-3-carboxamide, methyl N-methyl-N-[4-methyl-5-({4-[(2S)-2-{[8-(trifluoromethyl)quinazolin-4-yl]amino}propyl]piperazin-1-yl}sulfonyl)-1,3-thiazol-2-yl]carbamate, N-[5-({4-[(2S)-2-{[8-(trifluoromethyl)quinazolin-4-yl]amino}propyl]piperazin-1-yl}sulfonyl)thiophen-2-yl]acetamide, 4-{[(2S)-1-(4-{[5-(3-methyl-1,2-oxazol-5-yl)thiophen-2-yl]sulfonyl}piperazin-1-yl)propan-2-yl]amino}quinazolin-8-yl N,N-dimethylcarbamate, 8-cyclopropanecarbonyl-N-[(2S)-1-(4-{[5-(3,4-dimethyl-1,2-oxazol-5-yl)thiophen-2-yl]sulfonyl}piperazin-1-yl)propan-2-yl]quinazolin-4-amine, N-[(2S)-1-{4-[3-(1,3-oxazol-5-yl)benzenesulfonyl]piperazin-1-yl}propan-2-yl]-8-(trifluoromethyl)quinazolin-4-amine, methyl N-[5-({4-[(2S)-2-{[8-(trifluoromethoxy)quinazolin-4-yl]amino}propyl]piperazin-1-yl}sulfonyl)-1,3-thiazol-2-yl]carbamate, N-[4-methyl-5-({4-[(2S)-2-{[8-(trifluoromethyl)quinazolin-4-yl]amino}propyl]piperazin-1-yl}sulfonyl)-1,3-thiazol-2-yl]cyclopentanecarboxamide, N8,N8-dimethyl-N4-[(2S)-1-(4-{[5-(3-methyl-1,2-oxazol-5-yl)thiophen-2-yl]sulfonyl}piperazin-1-yl)propan-2-yl]quinazoline-4,8-diamine, 6-({4-[(2S)-2-{[8-(trifluoromethyl)quinazolin-4-yl]amino}propyl]piperazin-1-yl}sulfonyl)-2,3-dihydro-1,3-benzothiazol-2-one, methyl N-[5-({4-[(2S)-2-{[8-(dimethylamino)quinazolin-4-yl]amino}propyl]piperazin-1-yl}sulfonyl)-4-methyl-1,3-thiazol-2-yl]carbamate, 6-({4-[(2S)-2-{[8-(trifluoromethyl)quinazolin-4-yl]amino}propyl]piperazin-1-yl}sulfonyl)-2,3-dihydro-1,3-benzoxazol-2-one, 5-({4-[(2S)-2-{[8-(trifluoromethyl)quinazolin-4-yl]amino}propyl]piperazin-1-yl}sulfonyl)-2,3-dihydro-1H-1,3-benzodiazol-2-one, and methyl N-[5-({4-[(2S)-2-[(8-bromoquinazolin-4-yl)amino]propyl]piperazin-1-yl}sulfonyl)-4-methyl-1,3-thiazol-2-yl]carbamate.

7. A pharmaceutical composition comprising a compound of formula (I) according to claim 1, in admixture with one or more pharmaceutically acceptable carriers or excipients.

8. The pharmaceutical composition according to claim 7 for oral administration.

9. A method of treating a disease, disorder, or condition associated with dysregulation of lysophosphatidic acid receptor 2 (LPA2) comprising administering to a subject in need thereof the compound of claim 1.

10. A method of treating fibrosis and/or diseases, disorders, or conditions that involve fibrosis comprising administering to a subject in need thereof the compound of claim 1.

11. The method of claim 10, wherein the fibrosis is selected from the group consisting of pulmonary fibrosis, idiopathic pulmonary fibrosis (IPF), hepatic fibrosis, renal fibrosis, ocular fibrosis, cardiac fibrosis, arterial fibrosis and systemic sclerosis.

12. The method of claim 11, wherein the fibrosis is idiopathic pulmonary fibrosis (IPF).

13. A method of treating a disease, disorder, or condition associated with dysregulation of lysophosphatidic acid receptor 2 (LPA2) comprising administering to a subject in need thereof the pharmaceutical composition of claim 7.

14. A method of treating fibrosis and/or diseases, disorders, or conditions that involve fibrosis comprising administering to a subject in need thereof the pharmaceutical composition of claim 7.

15. The method of claim 14, wherein the fibrosis is selected from the group consisting of pulmonary fibrosis, idiopathic pulmonary fibrosis (IPF), hepatic fibrosis, renal fibrosis, ocular fibrosis, cardiac fibrosis, arterial fibrosis and systemic sclerosis.

16. The method of claim 15, wherein the fibrosis is idiopathic pulmonary fibrosis (IPF).

* * * * *